US009856254B2

(12) United States Patent
Lindstrom et al.

(10) Patent No.: US 9,856,254 B2
(45) Date of Patent: *Jan. 2, 2018

(54) ALKOXY SUBSTITUTED IMIDAZOQUINOLINES

(71) Applicant: 3M INNOVATIVE PROPERTIES COMPANY, St. Paul, MN (US)

(72) Inventors: Kyle J. Lindstrom, Houlton, WI (US); Bryon A. Merrill, River Falls, WI (US); Chad A. Haraldson, Apple Valley, MN (US); Michael J. Rice, Oakdale, MN (US); Tushar A. Kshirsagar, Woodbury, MN (US); Philip D. Heppner, Forest Lake, MN (US); Joshua R. Wurst, North St. Paul, MN (US); Shri Niwas, Maple Grove, MN (US); Sarah J. Slania, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/181,068

(22) Filed: Jun. 13, 2016

(65) Prior Publication Data

US 2016/0280707 A1    Sep. 29, 2016

Related U.S. Application Data

(63) Continuation of application No. 14/502,157, filed on Sep. 30, 2014, now Pat. No. 9,365,567, which is a continuation of application No. 10/595,230, filed as application No. PCT/US2004/032616 on Oct. 1, 2004, now Pat. No. 8,871,782.

(60) Provisional application No. 60/508,634, filed on Oct. 3, 2003.

(51) Int. Cl.
    C07D 413/14    (2006.01)
    C07D 519/00    (2006.01)
    A61K 31/4745   (2006.01)
    C07D 471/04    (2006.01)

(52) U.S. Cl.
    CPC ......... *C07D 471/04* (2013.01); *C07D 519/00* (2013.01); *A61K 31/4745* (2013.01); *C07D 413/14* (2013.01)

(58) Field of Classification Search
    CPC ............................ C07D 471/12; C07D 519/00
    USPC ..................................... 546/81, 82
    See application file for complete search history.

(56) References Cited

U.S. PATENT DOCUMENTS 3,314,941 A    4/1967   Littell et al.
4,689,338 A    8/1987   Gerster
4,698,348 A    10/1987  Gerster
4,753,951 A    6/1988   Takada et al.
4,929,624 A    5/1990   Gerster et al.
4,988,815 A    1/1991   Andre et al.
5,037,986 A    8/1991   Gerster
5,175,296 A    12/1992  Gerster
5,238,944 A    8/1993   Wick et al.
5,266,575 A    11/1993  Gerster
5,268,376 A    12/1993  Gester
5,346,905 A    9/1994   Gerster
5,352,784 A    10/1994  Nikolaides et al.
5,367,076 A    11/1994  Gerster
5,389,640 A    2/1995   Gerster et al.
5,395,937 A    3/1995   Nikolaides et al.
5,444,065 A    8/1995   Nikolaides et al.
5,446,153 A    8/1995   Lindstrom et al.
5,482,936 A    1/1996   Lindstrom
5,494,916 A    2/1996   Lindstrom et al.
5,525,612 A    6/1996   Gerster
5,627,281 A    5/1997   Nikolaides et al.
5,644,063 A    7/1997   Lindstrom et al.
5,648,516 A    7/1997   Nikolaides et al.
5,693,811 A    12/1997  Lindstrom
5,714,608 A    2/1998   Gerster
5,741,908 A    4/1998   Gerster et al.
5,756,747 A    5/1998   Gerster et al.
5,886,006 A    3/1999   Nikolaides et al.
5,939,090 A    8/1999   Beaurline et al.
6,039,969 A    3/2000   Tomai et al.
6,069,149 A    5/2000   Nanba et al.
6,083,505 A    7/2000   Miller et al.
6,110,929 A    8/2000   Gerster et al.

(Continued)

FOREIGN PATENT DOCUMENTS

| EP | 0 394 026 | 10/1990 |
|---|---|---|
| EP | 1 104 764 | 6/2001 |
| JP | 9-176116 | 7/1997 |
| JP | 9-208584 | 8/1997 |
| JP | 11-080156 | 3/1999 |
| JP | 11-222432 | 8/1999 |
| JP | 2000-247884 | 9/2000 |
| WO | WO 02/36592 | 5/2002 |
| WO | WO 2005/003064 | 1/2005 |
| WO | WO 2005/020999 | * 3/2005 |
| WO | WO 2006/028451 | 3/2006 |
| WO | WO 2006/063072 | 6/2006 |
| WO | WO 2006/121528 | 11/2006 |
| WO | WO 2007/030775 | 3/2007 |

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

(Continued)

*Primary Examiner* — Rita Desai

(57) ABSTRACT

Imidazoquinoline compounds with an alkoxy substituent at the 6, 7, 8, or 9-position, pharmaceutical compositions containing the compounds, intermediates, methods of making, and methods of use of these compounds as immunomodulators, for inducing or inhibiting cytokine biosynthesis in animals and in the treatment of diseases including viral, and neoplastic, are disclosed.

20 Claims, No Drawings

(56) References Cited

U.S. PATENT DOCUMENTS

| | | |
|---|---|---|
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |
| 6,440,992 B1 | 8/2002 | Gerster et al. |
| 6,451,810 B1 | 9/2002 | Coleman et al. |
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,225 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stoermer et al. |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 7,906,506 B2 | 3/2011 | Griesgraber et al. |
| 7,915,281 B2 | 3/2011 | Moser et al. |
| 7,939,526 B2 | 5/2011 | Radmer et al. |
| 7,943,609 B2 | 5/2011 | Griesgraber et al. |
| 7,943,610 B2 | 5/2011 | Hays et al. |
| 7,943,636 B2 | 5/2011 | Hays et al. |
| 7,968,562 B2 | 6/2011 | Skwierczynski et al. |
| 7,968,563 B2 | 6/2011 | Kshirsagar et al. |
| 7,993,659 B2 | 8/2011 | Noelle et al. |
| 8,017,779 B2 | 9/2011 | Merrill et al. |
| 8,026,366 B2 | 9/2011 | Prince et al. |
| 8,034,938 B2 | 10/2011 | Griesgraber et al. |
| 8,138,173 B2 | 3/2012 | Merrill et al. |
| 8,143,270 B2 | 3/2012 | Kshirsagar et al. |
| 8,158,794 B2 | 4/2012 | Kshirsagar et al. |
| 8,178,677 B2 | 5/2012 | Kshirsagar et al. |
| 8,263,594 B2 | 9/2012 | Lindstrom et al. |
| 8,343,993 B2 | 1/2013 | Kshirsagar et al. |
| 8,541,438 B2 | 9/2013 | Stoermer et al. |
| 8,658,666 B2 | 2/2014 | Rice et al. |
| 8,673,932 B2 | 3/2014 | Kshirsagar et al. |
| 8,691,837 B2 | 4/2014 | Krepski et al. |
| 8,697,873 B2 | 4/2014 | Krepski et al. |
| 8,735,421 B2 | 5/2014 | Bonk et al. |
| 8,802,853 B2 | 8/2014 | Bonk et al. |
| 8,846,710 B2 | 9/2014 | Kshirsager et al. |
| 8,871,782 B2 | 10/2014 | Lindstrom et al. |
| 9,006,264 B2 | 4/2015 | Stoermer et al. |
| 9,107,958 B2 | 8/2015 | Wightman |
| 9,365,567 B2 * | 6/2016 | Lindstrom ............ C07D 471/04 |

(56) References Cited

U.S. PATENT DOCUMENTS

| | | | |
|---|---|---|---|
| 9,475,804 | B2 | 10/2016 | Wightman |
| 9,550,773 | B2 | 1/2017 | Stoermer et al. |
| 2002/0055517 | A1 | 5/2002 | Smith |
| 2002/0058674 | A1 | 5/2002 | Hedenstrom et al. |
| 2002/0107262 | A1 | 8/2002 | Lindstrom |
| 2003/0133913 | A1 | 7/2003 | Tomai et al. |
| 2003/0139364 | A1 | 7/2003 | Krieg et al. |
| 2004/0014779 | A1 | 1/2004 | Gorden et al. |
| 2004/0132079 | A1 | 7/2004 | Gupta et al. |
| 2004/0171086 | A1* | 9/2004 | Fink ............ A61K 31/00 435/7.2 |
| 2004/0175336 | A1 | 9/2004 | Egging et al. |
| 2004/0176367 | A1* | 9/2004 | Griesgraber ......... C07D 471/02 514/227.8 |
| 2004/0180919 | A1 | 9/2004 | Lee et al. |
| 2004/0191833 | A1 | 9/2004 | Fink et al. |
| 2004/0197865 | A1 | 10/2004 | Gupta et al. |
| 2004/0202720 | A1 | 10/2004 | Wightman et al. |
| 2004/0214851 | A1 | 10/2004 | Birmachu et al. |
| 2004/0258698 | A1 | 12/2004 | Wightman et al. |
| 2004/0265351 | A1 | 12/2004 | Miller et al. |
| 2005/0048072 | A1 | 3/2005 | Kedl et al. |
| 2005/0059072 | A1 | 3/2005 | Birmachu et al. |
| 2005/0070460 | A1 | 3/2005 | Hammerbeck et al. |
| 2005/0096259 | A1 | 5/2005 | Tomai et al. |
| 2005/0106300 | A1 | 5/2005 | Chen et al. |
| 2005/0158325 | A1 | 7/2005 | Hammerbeck et al. |
| 2005/0165043 | A1 | 7/2005 | Miller et al. |
| 2005/0171072 | A1 | 8/2005 | Tomai et al. |
| 2005/0239735 | A1 | 10/2005 | Miller et al. |
| 2005/0245562 | A1 | 11/2005 | Garcia-Echeverria et al. |
| 2006/0045885 | A1 | 3/2006 | Kedl et al. |
| 2006/0045886 | A1 | 3/2006 | kedl |
| 2006/0051374 | A1 | 3/2006 | Miller et al. |
| 2006/0088542 | A1 | 4/2006 | Braun |
| 2006/0142202 | A1 | 6/2006 | Alkan et al. |
| 2006/0142235 | A1 | 6/2006 | Miller et al. |
| 2006/0195067 | A1 | 8/2006 | Wolter et al. |
| 2006/0216333 | A1 | 9/2006 | Miller et al. |
| 2007/0060754 | A1 | 3/2007 | Lindstrom et al. |
| 2007/0066639 | A1 | 3/2007 | Kshirsagar et al. |
| 2007/0072893 | A1 | 3/2007 | Krepski et al. |
| 2007/0099901 | A1 | 5/2007 | Krepski et al. |
| 2007/0123559 | A1 | 5/2007 | Statham et al. |
| 2007/0166384 | A1 | 7/2007 | Zarraga et al. |
| 2007/0167479 | A1 | 7/2007 | Busch et al. |
| 2007/0213355 | A1 | 9/2007 | Capraro et al. |
| 2007/0219196 | A1 | 9/2007 | Krepski et al. |
| 2007/0243215 | A1 | 10/2007 | Miller et al. |
| 2007/0259881 | A1 | 11/2007 | Dellaria et al. |
| 2007/0259907 | A1 | 11/2007 | Prince |
| 2007/0292456 | A1 | 12/2007 | Hammerbeck et al. |
| 2008/0015184 | A1 | 1/2008 | Kshirsagar et al. |
| 2008/0039533 | A1 | 2/2008 | Sahouani et al. |
| 2008/0063714 | A1 | 3/2008 | Sahouani et al. |
| 2008/0119508 | A1 | 5/2008 | Slade et al. |
| 2008/0188513 | A1 | 8/2008 | Skwierczynski et al. |
| 2008/0193468 | A1 | 8/2008 | Levy et al. |
| 2008/0193474 | A1 | 8/2008 | Griesgraber et al. |
| 2008/0207674 | A1 | 8/2008 | Stoesz et al. |
| 2008/0213308 | A1 | 9/2008 | Valiante et al. |
| 2008/0262021 | A1 | 10/2008 | Capraro et al. |
| 2008/0262022 | A1 | 10/2008 | Lee et al. |
| 2008/0306252 | A1 | 12/2008 | Crooks et al. |
| 2008/0306266 | A1 | 12/2008 | Martin et al. |
| 2008/0312434 | A1 | 12/2008 | Lindstrom et al. |
| 2008/0318998 | A1 | 12/2008 | Prince et al. |
| 2009/0005371 | A1 | 1/2009 | Rice et al. |
| 2009/0017076 | A1 | 1/2009 | Miller et al. |
| 2009/0023720 | A1 | 1/2009 | Kshirsagar et al. |
| 2009/0023722 | A1 | 1/2009 | Coleman et al. |
| 2009/0029988 | A1 | 1/2009 | Kshirsagar et al. |
| 2009/0030030 | A1 | 1/2009 | Bonk et al. |
| 2009/0030031 | A1 | 1/2009 | Kshirsagar et al. |
| 2009/0035323 | A1 | 2/2009 | Stoermer et al. |
| 2009/0062272 | A1 | 3/2009 | Bonk et al. |
| 2009/0069299 | A1 | 3/2009 | Merrill et al. |
| 2009/0069314 | A1 | 3/2009 | Kshirsagar et al. |
| 2009/0075980 | A1 | 3/2009 | Hays et al. |
| 2009/0099161 | A1 | 4/2009 | Rice et al. |
| 2009/0105295 | A1 | 4/2009 | Kshirsagar et al. |
| 2009/0124611 | A1 | 5/2009 | Hays et al. |
| 2009/0124652 | A1 | 5/2009 | Ach et al. |
| 2009/0163532 | A1 | 6/2009 | Perman et al. |
| 2009/0163533 | A1 | 6/2009 | Hays et al. |
| 2009/0176821 | A1 | 7/2009 | Kshirsagar et al. |
| 2009/0202443 | A1 | 8/2009 | Miller et al. |
| 2009/0221551 | A1 | 9/2009 | Kshirsagar et al. |
| 2009/0221556 | A1 | 9/2009 | Kshirsagar et al. |
| 2009/0240055 | A1 | 9/2009 | Krepski et al. |
| 2009/0246174 | A1 | 10/2009 | Rook et al. |
| 2009/0253695 | A1 | 10/2009 | Kshirsagar et al. |
| 2009/0270443 | A1 | 10/2009 | Stoermer et al. |
| 2009/0298821 | A1 | 12/2009 | Kshirsagar et al. |
| 2009/0306388 | A1 | 12/2009 | Zimmerman et al. |
| 2010/0028381 | A1 | 2/2010 | Gorski et al. |
| 2010/0056557 | A1 | 3/2010 | Benninghoff et al. |
| 2010/0096287 | A1 | 4/2010 | Stoesz et al. |
| 2010/0113565 | A1 | 5/2010 | Gorden et al. |
| 2010/0152230 | A1 | 6/2010 | Dellaria et al. |
| 2010/0158928 | A1 | 6/2010 | Stoermer et al. |
| 2010/0173906 | A1 | 7/2010 | Griesgraber |
| 2010/0180902 | A1 | 7/2010 | Miller et al. |
| 2010/0240693 | A1 | 9/2010 | Lundquist et al. |
| 2011/0021554 | A1 | 1/2011 | Stoesz et al. |

OTHER PUBLICATIONS

Brennan et al., "Automated Bioassay of Interferons in Micro-test Plates.", *Biotechniques*, Jun./Jul. 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).

Gerster et al. "Synthesis and Structure" *J. Med Chem.* 2005, 48, 3481-3491.

\* cited by examiner

ALKOXY SUBSTITUTED IMIDAZOQUINOLINES

CROSS-REFERENCE TO RELATED APPLICATION

This application is a continuation of application Ser. No. 14/502,157, filed Sep. 30, 2014, now U.S. Pat. No. 9,365,567, which is a continuation of application Ser. No. 10/595,230, filed Mar. 28, 2006, now U.S. Pat. No. 8,871,782, which is a National Stage filing of International Application No. PCT/US2004/032616, filed Oct. 1, 2004, which claims priority to U.S. Provisional Patent Application Ser. No. 60/508,634, filed on Oct. 3, 2003, each of which is incorporated herein by reference.

BACKGROUND

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers (IRMs), rendering them useful in the treatment of a variety of disorders.

There continues to be interest in and a need for compounds that have the ability to modulate the immune response, by induction of cytokine biosynthesis or other mechanisms.

SUMMARY

A new class of compounds useful for modulating cytokine biosynthesis has now been found. In one aspect, the present invention provides such compounds, which are of Formula I:

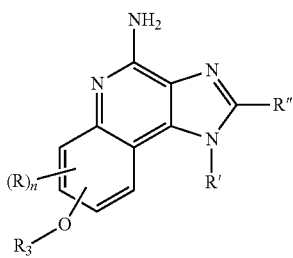

wherein R, n, R', R", and $R_3$ are as defined below; and pharmaceutically acceptable salts thereof.

The compounds of the present invention are useful as immune response modifiers (IRMs) due to their ability to induce or inhibit cytokine biosynthesis (e.g., induce or inhibit the biosynthesis or production of one or more cytokines) and otherwise modulate the immune response when administered to animals. Compounds can be tested per the test procedures described in the Examples Section. Compounds can be tested for induction of cytokine biosynthesis by incubating human peripheral blood mononuclear cells (PBMC) in a culture with the compound(s) at a concentration range of 30 to 0.014 μM and analyzing for interferon (α) or tumor necrosis factor (α) in the culture supernatant. Compounds can be tested for inhibition of cytokine biosynthesis by incubating mouse macrophage cell line Raw 264.7 in a culture with the compound(s) at a single concentration of, for example, 5 μM and analyzing for tumor necrosis factor (α) in the culture supernatant. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

In another aspect, the present invention provides pharmaceutical compositions containing the immune response modifier compounds, and methods of inducing or inhibiting cytokine biosynthesis in an animal, treating a viral disease in an animal, and treating a neoplastic disease in an animal, by administering an effective amount of one or more compounds of Formula I and/or pharmaceutically acceptable salts thereof to the animal.

In another aspect, the invention provides methods of synthesizing compounds of Formula I and intermediates useful in the synthesis of these compounds.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides such compounds of the following Formula I:

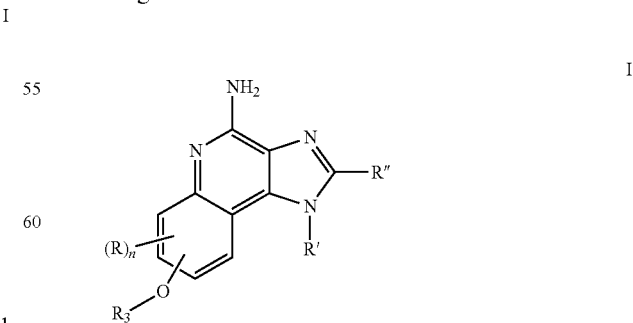

wherein R, n, R', R", and $R_3$ are as defined below; and pharmaceutically acceptable salts thereof.

Examples of compounds of Formula I are more specifically defined by the following Formulas II-VIII:

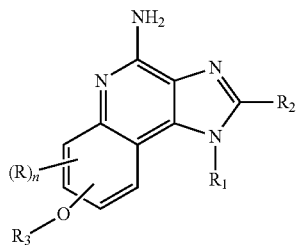
II

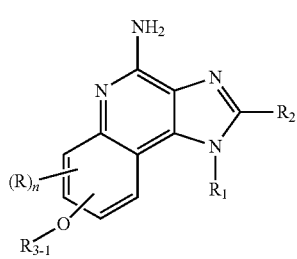
III

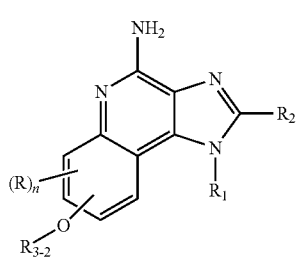
IV

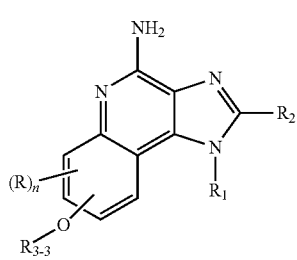
V

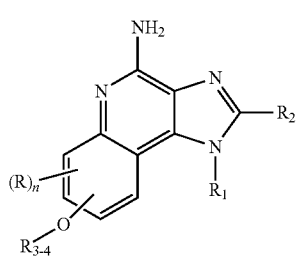
VI

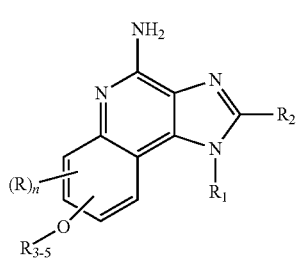
VII

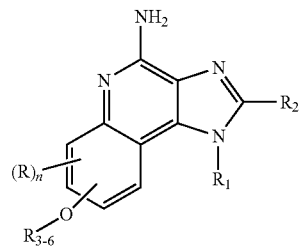
VIII wherein R, $R_1$, $R_2$, $R_{3-1}$, $R_{3-2}$, $R_{3-3}$, $R_{3-4}$, $R_{3-5}$, $R_{3-6}$, and n are as defined below; and pharmaceutically acceptable salts thereof.

The compounds of Formula VIII and salts thereof are also useful as intermediates for the preparation of compounds and salts of Formulas I-VII. The present invention also provides intermediate compounds of Formula IX:

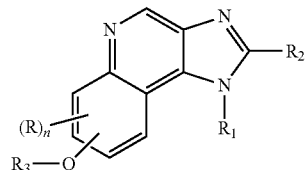
IX wherein R, $R_1$, $R_2$, $R_3$, and n are as defined below.

In one aspect, the present invention provides compounds of the formula (I):

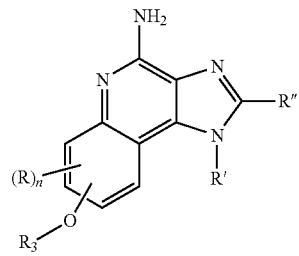
I wherein:
$R_3$ is selected from the group consisting of
—Z—Y—X—Y—$R_4$,
—Z—$R_5$,
—Z-Het,
—Z-Het'-$R_4$, and
—Z-Het'-Y—$R_4$;
Z is selected from the group consisting of alkylene, alkenylene, and alkynylene, wherein alkylene, alkenylene, and alkynylene can be optionally interrupted with one or more —O— groups;
Y is selected from the group consisting of
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,

—O—C(R$_6$)—N(R$_8$)—,
—C(R$_6$)—N(OR$_9$)—,

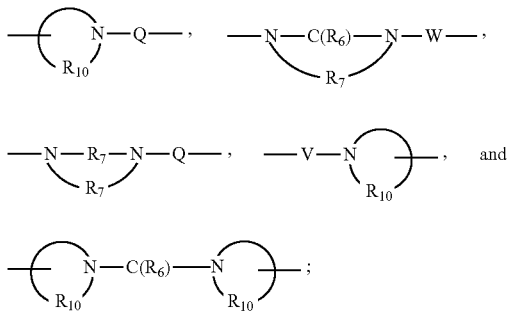

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of

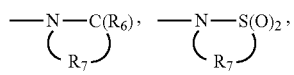

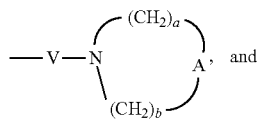

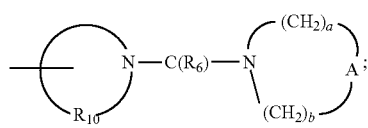

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;

A is selected from the group consisting of —O—, —C(O)—, —S(O)$_{0-2}$—, and —N(R$_4$)—;

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, mercapto, cyano, aryloxy, arylalkyleneoxy, heteroaryloxy, heteroarylalkyleneoxy, heterocyclyl, hydroxyalkyleneoxyalkylenyl, amino, alkylamino, dialkylamino, (dialkylamino)alkyleneoxy, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, mercapto, cyano, aryloxy, arylalkyleneoxy, heteroaryloxy, heteroarylalkyleneoxy, amino, alkylamino, dialkylamino, (dialkylamino)alkyleneoxy, and oxo;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

a and b are independently integers from 1 to 6 with the proviso that a+b is ≤7;

R is selected from the group consisting of alkyl, alkoxy, hydroxy, halogen, and trifluoromethyl;

n is 0 or 1; and

R' and R" are independently selected from the group consisting of hydrogen and non-interfering substitutents;

with the proviso that Z can also be a bond when:
R$_3$ is —Z-Het, —Z-Het'-R$_4$, or —Z-Het'-Y—R$_4$; or
R$_3$ is —Z—Y—R$_4$ or —Z—Y—X—Y—R$_4$, and Y is selected from —S(O)$_{0-2}$—, —S(O)$_2$—N(R$_8$)—, —C(R$_6$)—, —C(R$_6$)—O—, —C(R$_6$)—N(R$_8$)—,

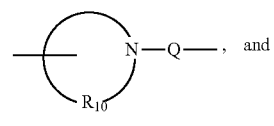

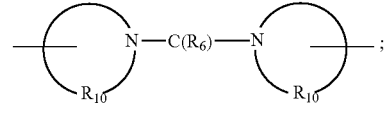

or
R$_3$ is —Z—R$_5$ and R$_5$ is

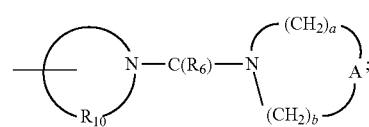

or a pharmaceutically acceptable salt thereof.

In one embodiment, the present invention provides compounds of the formula (II):

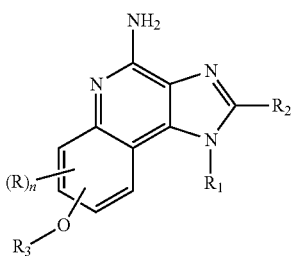

wherein:

$R_3$ is selected from the group consisting of
—Z—Y—$R_4$,
—Z—Y—X—Y—$R_4$,
—Z-Het,
—Z-Het'-$R_4$, and
—Z-Het'-Y—$R_4$;

Z is selected from the group consisting of alkylene, alkenylene, and alkynylene, wherein alkylene, alkenylene, and alkynylene can be optionally interrupted with one or more —O— groups;

R is selected from the group consisting of alkyl, alkoxy, hydroxy, halogen, and trifluoromethyl;

n is 0 or 1;

$R_1$ is selected from the group consisting of
—$R_4$,
—X—$R_4$,
—X—Y—$R_4$,
—X—Y—X—Y—$R_4$, and
—X—$R_5$;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

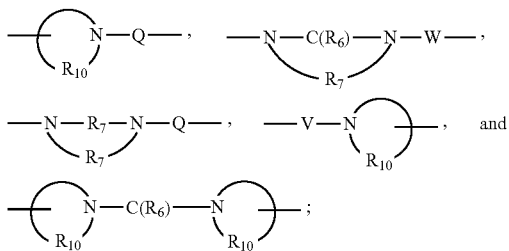

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

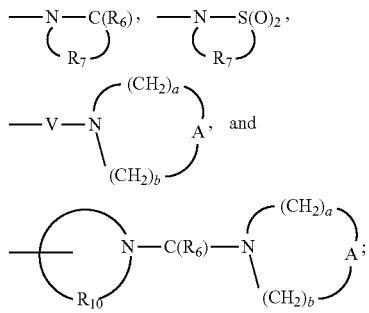

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene;

A is selected from the group consisting of —O—, —C(O)—, —S(O)$_{0-2}$—, and —N($R_4$)—;

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, mercapto, cyano, aryloxy, arylalkyleneoxy, heteroaryloxy, heteroarylalkyleneoxy, heterocyclyl, hydroxyalkyleneoxyalkylenyl, amino, alkylamino, dialkylamino, (dialkylamino)alkyleneoxy, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, mercapto, cyano, aryloxy, arylalkyleneoxy, heteroaryloxy, heteroarylalkyleneoxy, amino, alkylamino, dialkylamino, (dialkylamino)alkyleneoxy, and oxo;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;

V is selected from the group consisting of —C($R_6$)—, —O—C($R_6$)—, —N($R_8$)—C($R_6$)—, and —S(O)$_2$—;

W is selected from the group consisting of a bond, —C(O)—, and —S(O)$_2$—; and a and b are independently integers from 1 to 6 with the proviso that a+b is ≤7;

with the proviso that Z can also be a bond when:
$R_3$ is —Z-Het, —Z-Het'-$R_4$, or —Z-Het'-Y—$R_4$; or
$R_3$ is —Z—Y—$R_4$ or —Z—Y—X—Y—$R_4$, and Y is selected from —S(O)$_{0-2}$—, —S(O)$_2$—N($R_8$)—, —C($R_6$)—, —C($R_6$)—O—, —C($R_6$)—N($R_8$)—,

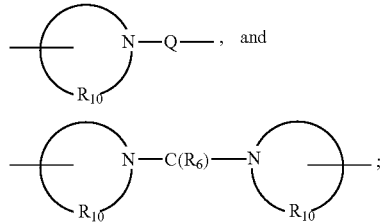

or
$R_3$ is —Z—$R_5$ and $R_5$ is

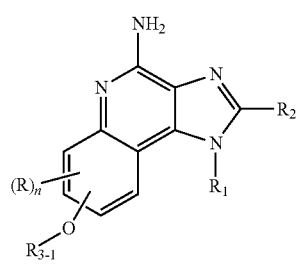

or a pharmaceutically acceptable salt thereof.

In another embodiment, the present invention provides compounds of the formula (III):

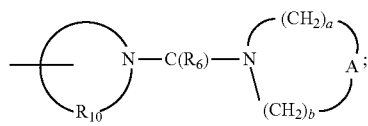

III wherein:
$R_{3-1}$ is selected from the group consisting of
—Z—N($R_8$)—C($R_6$)—$R_4$,

Z is selected from the group consisting of alkylene, alkenylene, and alkynylene, wherein alkylene, alkenylene, and alkynylene can be optionally interrupted with one or more —O— groups;
R is selected from the group consisting of alkyl, alkoxy, hydroxy, halogen, and trifluoromethyl;
n is 0 or 1;

$R_1$ is selected from the group consisting of
—$R_4$,
—X—$R_4$,
—X—Y—$R_4$,
—X—Y—X—Y—$R_4$, and
—X—$R_5$;
$R_2$ is selected from the group consisting of
—$R_4$,
—X—$R_4$,
—X—Y—$R_4$, and
—X—$R_5$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

[chemical structures showing:
—N(R$_7$)—C(R$_6$)—, —N(R$_7$)—S(O)$_2$—,
—V—N with (CH$_2$)$_a$ and (CH$_2$)$_b$ connecting to A,
and a ring structure with R$_{10}$, N—C(R$_6$)—N, (CH$_2$)$_a$, A, (CH$_2$)$_b$]

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;

with the proviso that Z can also be a bond when $R_{3-1}$ is

[chemical structure: —Z—ring with R$_{10}$, N—C(R$_6$)—R$_4$]

or a pharmaceutically acceptable salt thereof.

In another embodiment, the present invention provides compounds of the formula (IV):

[chemical structure IV showing a fused ring system with NH$_2$, N, N, R$_2$, (R)$_n$, O—R$_{3-2}$, R$_1$]

IV wherein:

$R_{3-2}$ is selected from the group consisting of
—Z—N(R$_8$)—S(O)$_2$—R$_4$,
—Z—N(R$_8$)—S(O)$_2$—N(R$_8$)—R$_4$, —Z—N(R$_7$)—S(O)$_2$—,
—Z—ring(R$_{10}$)—N—S(O)$_2$—R$_4$, and
—Z—ring(R$_{10}$)—N—S(O)$_2$—N(R$_8$)—R$_4$;

Z is selected from the group consisting of alkylene, alkenylene, and alkynylene, wherein alkylene, alkenylene, and alkynylene can be optionally interrupted with one or more —O— groups;

R is selected from the group consisting of alkyl, alkoxy, hydroxy, halogen, and trifluoromethyl;

n is 0 or 1;

$R_1$ is selected from the group consisting of
—$R_4$,
—X—$R_4$,
—X—Y—$R_4$,
—X—Y—X—Y—$R_4$, and
—X—$R_5$;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—C(R$_6$)—N(R$_8$)—,
—O—C(R$_6$)—N(R$_8$)—,
—C(R$_6$)—N(OR$_9$)—,

[chemical structures:
—ring(R$_{10}$)—N—Q—,
—N(R$_7$)—C(R$_6$)—N—W—,
—N(R$_7$)—R$_7$—N(R$_7$)—Q—,
—V—N—ring(R$_{10}$)—, and]

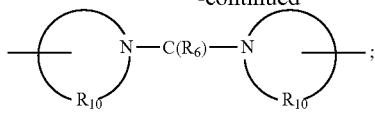

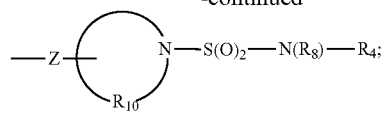

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R₅ is selected from the group consisting of

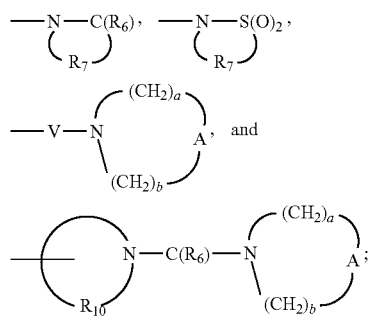

R₆ is selected from the group consisting of =O and =S;
R₇ is C₂₋₇ alkylene;
R₈ is selected from the group consisting of hydrogen, alkyl, alkoxyalkylenyl, and arylalkylenyl;
R₉ is selected from the group consisting of hydrogen and alkyl;
R₁₀ is C₃₋₈ alkylene;
A is selected from the group consisting of —O—, —C(O)—, —S(O)₀₋₂—, and —N(R₄)—;
Q is selected from the group consisting of a bond, —C(R₆)—, —C(R₆)—C(R₆)—, —S(O)₂—, —C(R₆)—N(R₈)—W—, —S(O)₂—N(R₈)—, —C(R₆)—O—, and —C(R₆)—N(OR₉)—;
V is selected from the group consisting of —C(R₆)—, —O—C(R₆)—, —N(R₈)—C(R₆)—, and —S(O)₂—;
W is selected from the group consisting of a bond, —C(O)—, and —S(O)₂—; and
a and b are independently integers from 1 to 6 with the proviso that a+b is ≤7;
with the proviso that Z can also be a bond when R₃₋₂ is

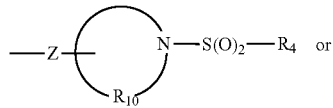

or a pharmaceutically acceptable salt thereof.

In another embodiment, the present invention provides compounds of the formula (V):

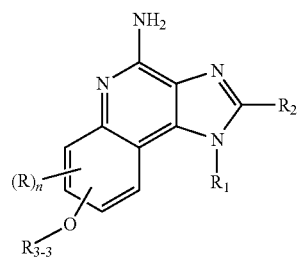

wherein:
R₃₋₃ is selected from the group consisting of
—Z—N(R₈)—C(R₆)—N(R₈)—W—R₄,

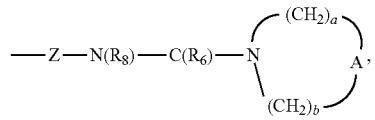

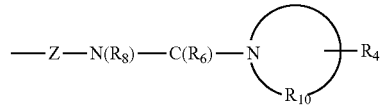

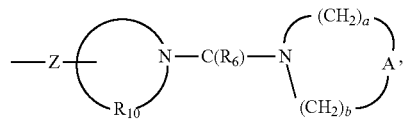

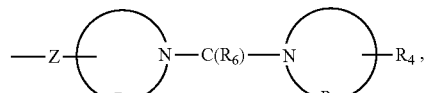

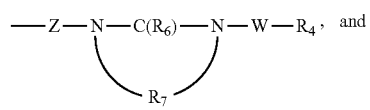

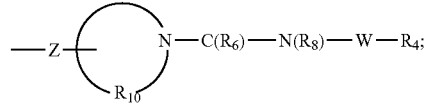

Z is selected from the group consisting of alkylene, alkenylene, and alkynylene, wherein alkylene, alkenylene, and alkynylene can be optionally interrupted with one or more —O— groups;
R is selected from the group consisting of alkyl, alkoxy, hydroxy, halogen, and trifluoromethyl;
n is 0 or 1;
R₁ is selected from the group consisting of
—R₄,
—X—R₄, —X—Y—R$_4$,
—X—Y—X—Y—R$_4$, and
—X—R$_5$;

R$_2$ is selected from the group consisting of
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

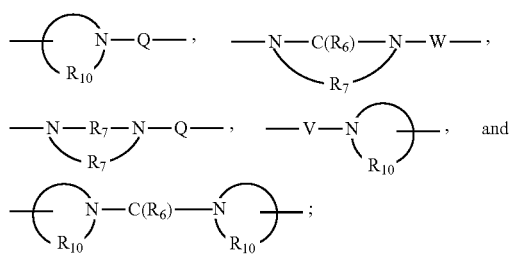

and

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of

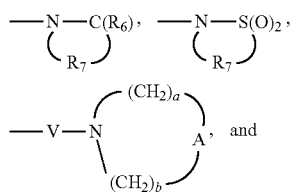

and

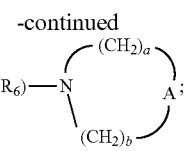

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;

with the proviso that Z can also be a bond when R$_{3-3}$ is

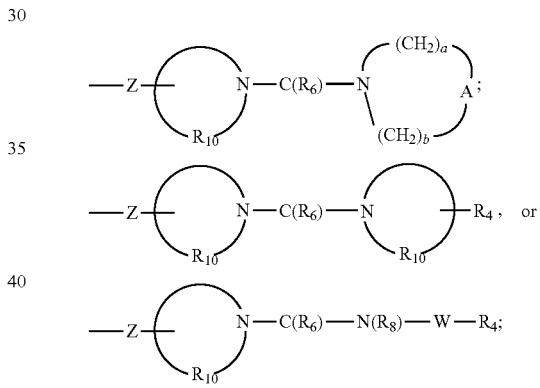

or a pharmaceutically acceptable salt thereof.

In another embodiment, the present invention provides compounds of the formula (VI):

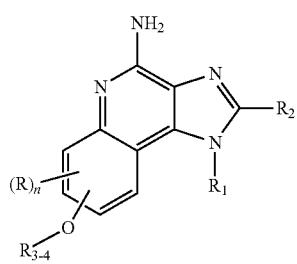

wherein:
R$_{3-4}$ is selected from the group consisting of
—Z$_a$—C(R$_6$)—R$_4$,
—Z$_a$—C(R$_6$)—O—R$_4$,
—Z$_a$—C(R$_6$)—N(R$_8$)—R$_4$, and

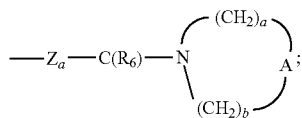

$Z_a$ is selected from the group consisting of a bond, alkylene, alkenylene, and alkynylene, wherein alkylene, alkenylene, and alkynylene can be optionally interrupted with one or more —O— groups;

R is selected from the group consisting of alkyl, alkoxy, hydroxy, halogen, and trifluoromethyl;

n is 0 or 1;

$R_1$ is selected from the group consisting of
—$R_4$,
—X—$R_4$,
—X—Y—$R_4$,
—X—Y—X—Y—$R_4$, and
—X—$R_5$;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of
—$S(O)_{0-2}$—,
—$S(O)_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

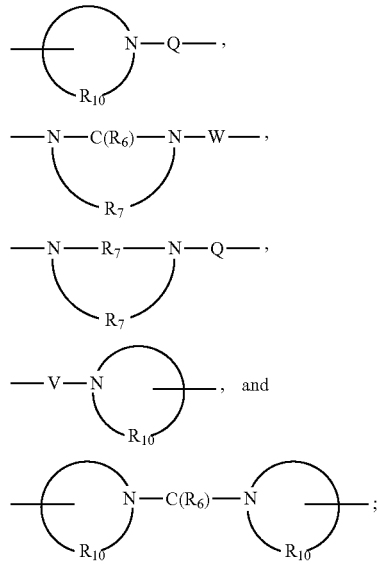

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

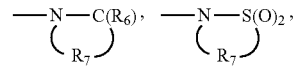

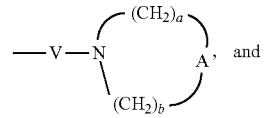

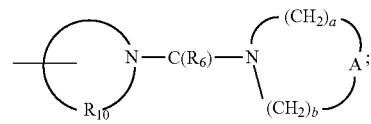

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene;

A is selected from the group consisting of —O—, —C(O)—, —$S(O)_{0-2}$—, and —N($R_4$)—;

A' is selected from the group consisting of —O—, —C(O)—, —$S(O)_{0-2}$—, —N($R_4$)—, and —$CH_2$—;

Q is selected from the group consisting of a bond, —C($R_6$)—, —C($R_6$)—C($R_6$)—, —$S(O)_2$—, —C($R_6$)—N($R_8$)—W—, —$S(O)_2$—N($R_8$)—, —C($R_6$)—O—, and —C($R_6$)—N(O$R_9$)—;

V is selected from the group consisting of —C($R_6$)—, —O—C($R_6$)—, —N($R_8$)—C($R_6$)—, and —$S(O)_2$—;

W is selected from the group consisting of a bond, —C(O)—, and —$S(O)_2$—; and a and b are independently integers from 1 to 6 with the proviso that a+b is ≤7;

or a pharmaceutically acceptable salt thereof.

In another embodiment, the present invention provides compounds of the formula (VII):

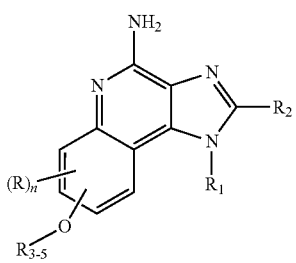

wherein:

$R_{3-5}$ is selected from the group consisting of
—Z—N($R_8$)—C($R_6$)—O—$R_4$;

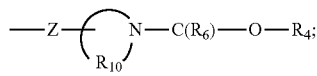

and
—Z—N($R_8$)—C($R_6$)—C($R_6$)—$R_4$;

Z is selected from the group consisting of alkylene, alkenylene, and alkynylene, wherein alkylene, alkenylene, and alkynylene can be optionally interrupted with one or more —O— groups;

R is selected from the group consisting of alkyl, alkoxy, hydroxy, halogen, and trifluoromethyl;

n is 0 or 1;

$R_1$ is selected from the group consisting of
—$R_4$,
—X—$R_4$,
—X—Y—X—Y—$R_4$, and
—X—$R_5$;

$R_2$ is selected from the group consisting of
—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

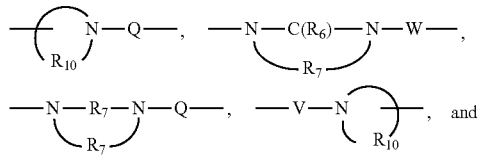

VII 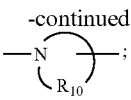

-continued

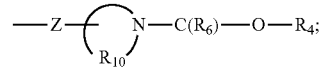

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

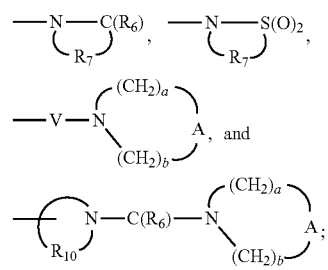

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene;

A is selected from the group consisting of —O—, —C(O)—, —S(O)$_{0-2}$—, and —N($R_4$)—;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;

V is selected from the group consisting of —C($R_6$)—, —O—C($R_6$)—, —N($R_8$)—C($R_6$)—, and —S(O)$_2$—;

W is selected from the group consisting of a bond, —C(O)—, and —S(O)$_2$—; and a and b are independently integers from 1 to 6 with the proviso that a+b is ≤7;

with the proviso that Z can also be a bond when $R_{3-5}$ is

—Z—N($R_{10}$)—C($R_6$)—O—$R_4$;

or a pharmaceutically acceptable salt thereof.

In another embodiment, the present invention provides compounds of the formula (VIII):

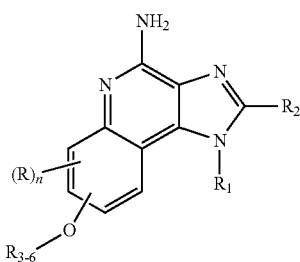

wherein:

$R_{3-6}$ is selected from the group consisting of
—Z—N($R_8$)H, and

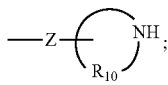

Z is selected from the group consisting of alkylene, alkenylene, and alkynylene, wherein alkylene, alkenylene, and alkynylene can be optionally interrupted with one or more —O— groups;

R is selected from the group consisting of alkyl, alkoxy, hydroxy, halogen, and trifluoromethyl;

n is 0 or 1;

$R_1$ is selected from the group consisting of
—$R_4$,
—X—$R_4$,
—X—Y—$R_4$,
—X—Y—X—Y—$R_4$, and
—X—$R_5$;

$R_2$ is selected from the group consisting of
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(OR$_9$)—,

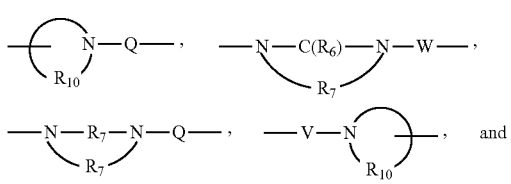

VIII

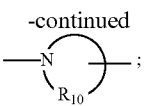

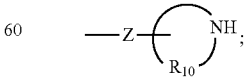

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

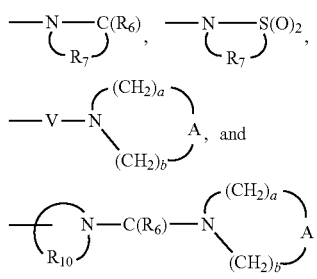

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene;

A is selected from the group consisting of —O—, —C(O)—, —S(O)$_{0-2}$—, and —N($R_4$)—;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(OR$_9$)—;

V is selected from the group consisting of —C($R_6$)—, —O—C($R_6$)—, —N($R_8$)—C($R_6$)—, and —S(O)$_2$—;

W is selected from the group consisting of a bond, —C(O)—, and —S(O)$_2$—; and a and b are independently integers from 1 to 6 with the proviso that a+b is ≤7;

with the proviso that Z can also be a bond when $R_{3-6}$ is

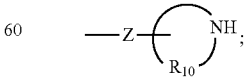

or a pharmaceutically acceptable salt thereof.

The compounds of Formula VIII and salts thereof are also useful as intermediates for the preparation of compounds and salts of Formulas I-VII.

In another aspect, the present invention provides intermediate compounds of Formula IX:

wherein:

$R_3$ is selected from the group consisting of
—Z—Y—$R_4$,
—Z—Y—X—Y—$R_4$,
—Z-Het,
—Z-Het'-$R_4$, and
—Z-Het'-Y—$R_4$;

Z is selected from the group consisting of alkylene, alkenylene, and alkynylene, wherein alkylene, alkenylene, and alkynylene can be optionally interrupted with one or more —O— groups;

R is selected from the group consisting of alkyl, alkoxy, hydroxy, halogen, and trifluoromethyl;

n is 0 or 1;

$R_1$ is selected from the group consisting of
—$R_4$,
—X—$R_4$,
—X—Y—X—Y—$R_4$, and
—X—$R_5$;

$R_2$ is selected from the group consisting of
—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

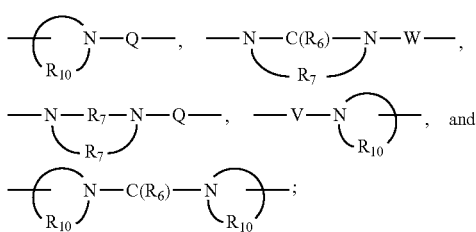

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

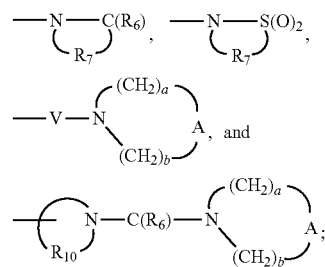

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene;

A is selected from the group consisting of —O—, —C(O)—, —S(O)$_{0-2}$—, and —N($R_4$)—;

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, mercapto, cyano, aryloxy, arylalkyleneoxy, heteroaryloxy, heteroarylalkyleneoxy, heterocyclyl, hydroxyalkyleneoxyalkylenyl, amino, alkylamino, dialkylamino, (dialkylamino)alkyleneoxy, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, mercapto, cyano, aryloxy, arylalkyleneoxy, heteroaryloxy, heteroarylalkyleneoxy, amino, alkylamino, dialkylamino, (dialkylamino)alkyleneoxy, and oxo;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;

V is selected from the group consisting of —C($R_6$)—, —O—C($R_6$)—, —N($R_8$)—C($R_6$)—, and —S(O)$_2$—;

W is selected from the group consisting of a bond, —C(O)—, and —S(O)$_2$—; and a and b are independently integers from 1 to 6 with the proviso that a+b is ≤7;

with the proviso that Z can also be a bond when:
R$_3$ is —Z-Het, —Z-Het'-R$_4$, or —Z-Het'-Y—R$_4$; or
R$_3$ is —Z—Y—R$_4$ or —Z—Y—X—Y—R$_4$, and Y is selected from —S(O)$_{0-2}$—, —S(O)$_2$—N(R$_8$)—, —C(R$_6$)—, —C(R$_6$)—O—, —C(R$_6$)—N(R$_8$)—,

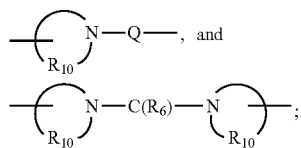

or
R$_3$ is —Z—R$_5$ and R$_5$ is

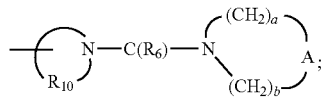

or a pharmaceutically acceptable salt thereof.

Certain embodiments of the present invention include non-interfering substituents. For example, in certain embodiments, R' and R" are independently selected from the group consisting of hydrogen and non-interfering substitutents.

Herein, "non-interfering" means that the immunomodulator activity (for example, the ability to induce the biosynthesis of one or more cytokines or the ability to inhibit the biosynthesis of one or more cytokines) of the compound or salt is not destroyed. Illustrative non-interfering R' groups include those described herein for R$_1$. Illustrative non-interfering R" groups include those described herein for R$_2$.

As used herein, the terms "alkyl", "alkenyl", "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "-alkylene-", "alkenylene", "-alkenylene-", "alkynylene", and "-alkynylene-" are the divalent forms of the "alkyl", "alkenyl", and "alkynyl" groups defined above. The terms "alkylenyl", "alkenylenyl", and "alkynylenyl" are used when "alkylene", "alkenylene", and "alkynylene", respectively, are substituted. For example, an arylalkylenyl group comprises an "alkylene" moiety to which an aryl group is attached.

The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

The term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl (azepanyl), homopiperazinyl (diazepanyl), 1,3-dioxolanyl, aziridinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and the like. When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms "arylenyl," "heteroarylenyl," and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N(R$_8$)—C(R$_6$)—N(R$_8$)— each R$_8$ group is independently selected. In another example, when an R$_2$ and an R$_3$ group both contain an R$_4$ group, each R$_4$ group is independently selected. In a further example, when more than one Y group is present (i.e., R$_2$ and R$_3$ both contain a Y group) and each Y group contains one or more R$_8$ groups, then each Y group is independently selected, and each R$_8$ group is independently selected.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

For any of the compounds presented herein, each one of the following variables (e.g., R, R', R", R$_1$, R$_2$, R$_3$, n, A, X, Z, and so on) in any of its embodiments can be combined with any one or more of the other variables in any of their embodiments as would be understood by one of skill in the art. Each of the resulting combinations of variables is an embodiment of the present invention.

In some embodiments, compounds of Formula I-VIII induce the biosynthesis of one or more cytokines.

In some embodiments, compounds of Formula I-VIII inhibit the biosynthesis of one or more cytokines (e.g., TNF-α).

In certain embodiments, R is selected from the group consisting of alkyl, alkoxy, hydroxy, halogen, and trifluoromethyl.

In some embodiments of Formula I, R' is selected from the group consisting of —$R_4$, —X—$R_4$, —X—Y—$R_4$, —X—Y—X—Y—$R_4$, and —X—$R_5$.

In some embodiments, R' is selected from the group consisting of alkyl, arylalkylenyl, aryloxyalkylenyl, hydroxyalkyl, dihydroxyalkyl, alkyl sulfonylalkylenyl, —X—Y—$R_4$, —X—$R_5$, and heterocyclylalkylenyl, wherein the heterocyclyl of the heterocyclylalkylenyl group is optionally substituted by one or more alkyl groups; wherein X is alkylene; Y is —N($R_8$)—C(O)—, —N($R_8$)—S(O)$_2$—, —N($R_8$)—C(O)—N($R_8$)—, or

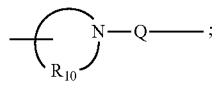

$R_4$ is alkyl, aryl, or heteroaryl; and $R_5$ is

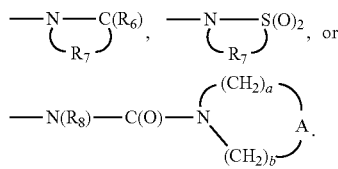

In certain embodiments, R' is selected from the group consisting of alkyl, arylalkylenyl, aryloxyalkylenyl, hydroxyalkyl, alkyl sulfonylalkylenyl, —X—Y—$R_4$, and —X—$R_5$; wherein X is alkylene; Y is —N($R_8$)—C(O)—, —N($R_8$)—S(O)$_2$—, —N($R_8$)—C(O)—N($R_8$)—, or

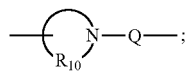

$R_4$ is alkyl, aryl, or heteroaryl; and $R_5$ is

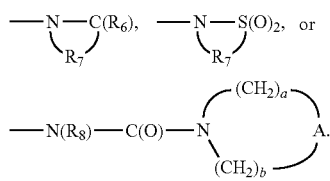

In some embodiments of Formula I, R" is selected from the group consisting of —$R_4$, —X—$R_4$, —X—Y—$R_4$, and —X—$R_5$. In some embodiments, R" is selected from the group consisting of hydrogen, alkyl, and alkoxyalkylenyl. In some embodiments, R" is selected from the group consisting of hydrogen, alkyl, alkoxyalkylenyl, and hydroxyalkyl.

In some embodiments, $R_1$ is selected from the group consisting of —$R_4$, —X—$R_4$, —X—Y—$R_4$, —X—Y—X—Y—$R_4$, and —X—$R_5$.

In some embodiments (e.g., of Formulas II-IX), $R_1$ is selected from the group consisting of alkyl, arylalkylenyl, aryloxyalkylenyl, hydroxyalkyl, dihydroxyalkyl, alkylsulfonylalkylenyl, —X—Y—$R_4$, —X—$R_5$, and heterocyclylalkylenyl, wherein the heterocyclyl of the heterocyclylalkylenyl group is optionally substituted by one or more alkyl groups; wherein X is alkylene; Y is —N($R_8$)—C(O)—, —N($R_8$)—S(O)$_2$—, —N($R_8$)—C(O)—N($R_8$)—, or

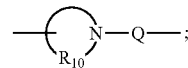

$R_4$ is alkyl, aryl, or heteroaryl; and $R_5$ is

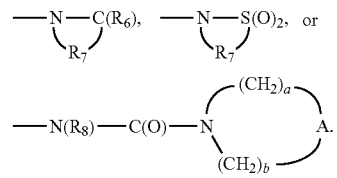

In certain embodiments, $R_1$ is selected from the group consisting of alkyl, arylalkylenyl, aryloxyalkylenyl, hydroxyalkyl, alkyl sulfonylalkylenyl, —X—Y—$R_4$, and —X—$R_5$; wherein X is alkylene; Y is —N($R_8$)—C(O)—, —N($R_8$)—S(O)$_2$—, —N($R_8$)—C(O)—N($R_8$)—, or

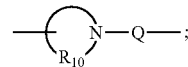

$R_4$ is alkyl, aryl, or heteroaryl; and $R_5$ is

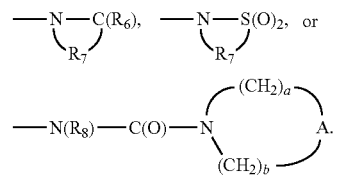

In some embodiments (e.g., of Formulas II-IX), $R_1$ is selected from the group consisting of methyl, n-propyl, 2-methylpropyl, 2-phenylethyl, 2-phenoxyethyl, benzyl, 4-(methanesulfonylamino)butyl, 2-(methanesulfonylamino)-2-methylpropyl, 4-(benzenesulfonylamino)butyl, 2-(acetamido)-2-methylpropyl, 4-(ureido)butyl, 2-hydroxy-2-methylpropyl, 5-(methanesulfonyl)pentyl, 4-aminobutyl, 4-(3-phenylureido)butyl, 4-(benzoylamino)lbutyl, 4-[(4-morpholinecarbonyl)amino]butyl, 2-(1,1-dioxidoisothiazolidin-2-yl)ethyl, 3-(1,1-dioxidoisothiazolidin-2-yl)propyl, 4-(1,1-dioxidoisothiazolidin-2-yl)butyl, 2-(benzoylamino)-2-methylpropyl, 2-(3-phenylureido)butyl, 2-(2-oxopyrrolidin-1-yl)ethyl, 3-(2-oxopyrrolidin-1-yl)propyl, 4-(2-oxopyrrolidin-1-yl)butyl.

In some embodiments (e.g., of Formulas II-IX), $R_1$ is selected from the group consisting of 2-hydroxy-2-methylpropyl, 2-methylpropyl, propyl, ethyl, methyl, 2,3-dihydroxypropyl, 2-phenoxyethyl, 4-[(methyl sulfonyl)amino]butyl, 2-methyl-2-[(methyl sulfonyl)amino]propyl, 2-(acetylamino)-2-methylpropyl, 2-{[(isopropylamino)carbonyl]amino}-2-methylpropyl, 4-{[(isopropylamino)carbonyl]amino}butyl, 4-(1,1-dioxidoisothiazolidin-2-yl)butyl, tetrahydro-2H-pyran-4-ylmethyl, and (2,2-dimethyl-1,3-dioxolan-4-yl)methyl.

In some embodiments, $R_2$ is selected from the group consisting of —$R_4$, —X—$R_4$, —X—Y—$R_4$, and —X—$R_5$.

In some embodiments (e.g., of Formulas II-IX), $R_2$ is selected from the group consisting of hydrogen, alkyl, alkoxyalkylenyl, and hydroxyalkylenyl. In some embodiments (e.g., of Formulas II-IX), $R_2$ is selected from the group consisting of hydrogen, alkyl, and alkoxyalkylenyl. In some embodiments, $R_2$ is selected from the group consisting of hydrogen, methyl, ethyl, propyl, butyl, ethoxymethyl, methoxymethyl, 2-methoxyethyl, hydroxymethyl, and 2-hydroxyethyl.

In some embodiments (e.g., of Formulas II-X), $R_2$ is selected from the group consisting of methyl, ethyl, n-propyl, n-butyl, ethoxymethyl, methoxyethyl, methoxymethyl, hydrogen, hydroxymethyl, 2-methoxy(ethoxymethyl), 4-(3-phenylureido)butyl, cyclopropylmethyl, trifluoromethyl, phenyl, and benzyl.

In certain embodiments of the present invention, $R_3$ is selected from the group consisting of —Z—Y—$R_4$, —Z—Y—X—Y—$R_4$, —Z—$R_5$, —Z-Het, —Z-Het'-$R_4$, and —Z-Het'-Y—$R_4$. In some embodiments (e.g., of Formulas I or II), $R_3$ is —Z—Y—$R_4$ or —Z—Y—X—Y—$R_4$. In some embodiments (e.g., of Formula I or II), $R_3$ is —Z—$R_5$. In some embodiments (e.g., of Formula I or II), $R_3$ is —Z-Het, —Z-Het'-$R_4$, or —Z-Het'-Y—$R_4$.

In certain embodiments, $R_3$ is —Z—Y—$R_4$ or —Z—Y—X—Y—$R_4$, wherein Y is selected from the group consisting of —S(O)$_{0-2}$—, —C(O)—, —C(O)—O—, —O—C(O)—, —C($R_6$)—N($R_8$),

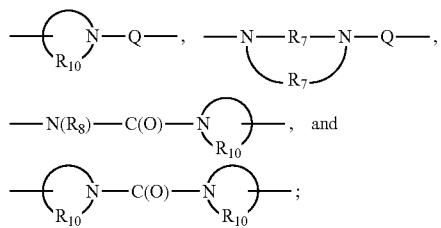

wherein Q is selected from the group consisting of a bond, —C(O)—, —C(O)—O—, —S(O)$_2$—, —C($R_6$)—N($R_8$)—W—, and —S(O)$_2$—N($R_8$)—; W is selected from the group consisting of a bond, —C(O)—, and —S(O)$_2$—; $R_6$ is selected from the group consisting of =O or =S; $R_8$ is selected from the group consisting of hydrogen, $C_{1-4}$ alkyl, and alkoxyalkylenyl; and $R_{10}$ is selected from the group consisting of $C_{4-6}$ alkylene; X is selected from the group consisting of alkylene, arylene, heterocyclylene, heteroarylene, and alkylene terminated with heteroarylene; and $R_4$ is selected from the group consisting of hydrogen, alkyl, alkenyl, aryl, arylalkylenyl, alkylheteroarylenyl, heteroarylalkylenyl, aryloxyalkylenyl, heteroaryl, and heterocyclyl, wherein alkyl is unsubstituted or substituted by one or more substituents selected from the group consisting of hydroxy, alkoxy, and heterocyclyl, and wherein arylalkylenyl and heteroarylalkylenyl are unsubstituted or substituted by one or more substituents selected from the group consisting of alkyl, halogen, and alkoxy.

In certain embodiments, $R_3$ is —Z—Y—$R_4$ or —Z—Y—X—Y—$R_4$. In certain of these embodiments, Y is selected from the group consisting of —S(O)$_{0-2}$—, —C(O)—, —C(O)—O—, —N($R_8$)-Q-, —C($R_6$)—N($R_8$),

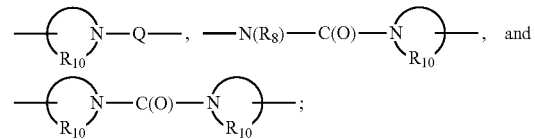

wherein Q is selected from the group consisting of a bond, —C(O)—, —C(O)—O—, —S(O)$_2$—, —C($R_6$)—N($R_8$)—W—, and —S(O)$_2$—N($R_8$)—; W is selected from the group consisting of a bond, —C(O)—, and —S(O)$_2$—; $R_6$ is selected from the group consisting of =O and =S; $R_8$ is selected from the group consisting of hydrogen, $C_{1-4}$ alkyl, and alkoxyalkylenyl; and $R_{10}$ is a $C_{4-6}$ alkylene.

In some embodiments (e.g., of Formula II), $R_3$ is —Z—$R_5$, wherein $R_5$ is selected from the group consisting of

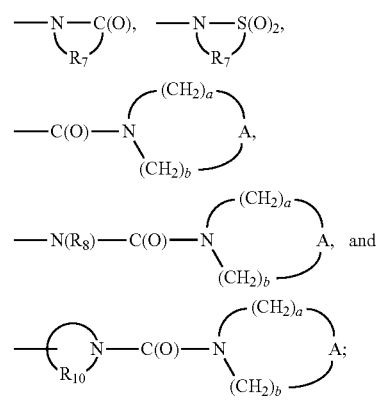

wherein
$R_7$ is $C_{3-5}$ alkylene; $R_{10}$ is $C_{4-6}$ alkylene; and a and b are each independently 1 to 3.

In some embodiments (e.g., of Formula II), $R_3$ is —Z-Het, —Z-Het'-$R_4$, or —Z-Het'-Y—$R_4$. In certain of these embodiments, Het is substituted by one or more substituents selected from the group consisting of alkyl, hydroxy, hydroxyalkyl, hydroxyalkyleneoxyalkylenyl, diakylamino, and heterocyclyl. In certain of these embodiments, Y is selected from the group consisting of —C(O)—, —C(O)—O—, —C(O)—N(H)—, and —N(H)—C(O)—. In certain embodiments, Het or Het' is selected from the group consisting of tetrahydropyranyl, tetrahydrofuranyl, 1,3-dioxolanyl, pyrrolidinyl, piperidinyl, morpholinyl, thiomorpholinyl, thiazolidinyl, aziridinyl, azepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and piperazinyl. In certain embodiments Het is selected from the group consisting of tetrahydropyranyl and tetrahydrofuranyl.

In some embodiments of Formula III, $R_{3-1}$ is selected from the group consisting of —Z—N($R_8$)—C($R_6$)—$R_4$,

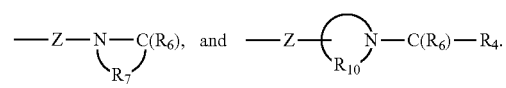

In some embodiments of Formula III, $R_{3-1}$ is —Z—N($R_8$)—C($R_6$)—$R_4$. In certain embodiments of this formula for $R_{3-1}$, Z is $C_{2-6}$ alkylene. In certain embodiments of this, $R_8$ is hydrogen, $R_6$ is =O, and $R_4$ is selected from the group consisting of alkyl, alkenyl, aryl, arylalkylenyl, aryloxyalkylenyl, and heteroaryl wherein the alkyl, alkenyl, aryl, arylalkylenyl, aryloxyalkylenyl, and heteroaryl groups can be unsubstituted or substituted by one or more substituents selected from the group consisting of alkyl, aryl, halogen, alkoxy, cyano, arylalkyleneoxy, nitro, dialkylamino, aryloxy, heterocyclyl, trifluoromethyl, trifluormethoxy, and in the case of alkyl, oxo. In certain embodiments of this, $R_8$ is hydrogen, $R_6$ is =O, and $R_4$ is selected from the group consisting of alkyl, alkenyl, aryl, arylalkylenyl, aryloxyalkylenyl, and heteroaryl, wherein aryl can be optionally substituted with halogen, methoxy, cyano, trifluoromethyl, and trifluoromethoxy. In certain embodiments, Z is ethylene or propylene, $R_8$ is hydrogen, $R_6$ is =O, and $R_4$ is $C_{1-3}$ alkyl.

In some embodiments of Formula III, $R_{3-1}$ is

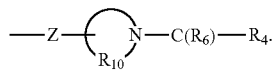

In certain embodiments of this formula for $R_{3-1}$, Z is a bond. In certain embodiments of this, $R_6$ is =O, $R_{10}$ is $C_{4-6}$ alkylene, and $R_4$ is selected from the group consisting of alkyl, alkenyl, aryl, arylalkylenyl, aryloxyalkylenyl, and heteroaryl, wherein the alkyl, alkenyl, aryl, arylalkylenyl, aryloxyalkylenyl, and heteroaryl groups can be unsubstituted or substituted by one or more substituents selected from the group consisting of alkyl, aryl, halogen, alkoxy, cyano, arylalkyleneoxy, nitro, dialkylamino, aryloxy, heterocyclyl, trifluoromethyl, trifluormethoxy, and in the case of alkyl, oxo. In certain embodiments, $R_4$ is alkyl or aryl.

In certain embodiments, $R_{3-1}$ is

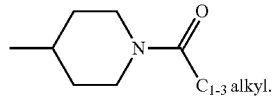

In some embodiments of Formula III, $R_{3-1}$ is

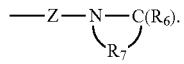

In certain embodiments of this formula for $R_{3-1}$, $R_6$ is =O, and $R_7$ is $C_{3-5}$ alkylene. In certain of these embodiments, Z is ethylene or propylene and $R_7$ is propylene.

In some embodiments of Formula IV, $R_{3-2}$ is selected from the group consisting of —Z—N($R_8$)—S(O)$_2$—$R_4$, —Z—N($R_8$)—S(O)$_2$—N($R_8$)—$R_4$,

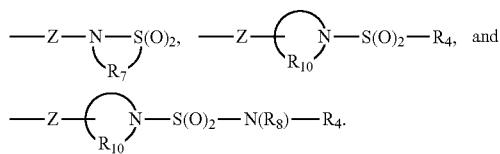

In some embodiments of Formula IV, $R_{3-2}$ is —Z—N ($R_8$)—S(O)$_2$—$R_4$. In certain embodiments of this formula for $R_{3-2}$, $R_8$ is hydrogen, and $R_4$ is selected from the group consisting of alkyl, alkenyl, aryl, arylalkylenyl, aryloxyalkylenyl, and heteroaryl, wherein the alkyl, alkenyl, aryl, arylalkylenyl, aryloxyalkylenyl, and heteroaryl groups can be unsubstituted or substituted by one or more substituents selected from the group consisting of alkyl, aryl, halogen, alkoxy, cyano, arylalkyleneoxy, nitro, dialkylamino, aryloxy, heterocyclyl, trifluoromethyl, trifluormethoxy, and in the case of alkyl, oxo. In certain embodiments, $R_4$ is selected from the group consisting of alkyl, aryl, alkenyl, heteroaryl, arylalkylenyl, and alkylheteroarylenyl; wherein aryl can be optionally substituted with halogen, methoxy, cyano, trifluoromethyl, and trifluoromethoxy. In certain embodiments, Z is ethylene or propylene, $R_8$ is hydrogen, and $R_4$ is $C_{1-3}$ alkyl.

In some embodiments of Formula IV, $R_{3-2}$ is

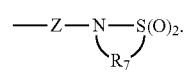

In certain embodiments of this formula for $R_{3-2}$, $R_7$ is $C_{3-5}$ alkylene.

In some embodiments of Formula IV, $R_{3-2}$ is

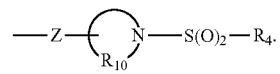

In certain embodiments of this formula for $R_{3-2}$, Z is a bond. In certain embodiments of this formula for $R_{3-2}$, $R_{10}$ is $C_{4-6}$ alkylene, and $R_4$ is selected from the group consisting of alkyl, alkenyl, aryl, arylalkylenyl, aryloxyalkylenyl, and heteroaryl, wherein the alkyl, alkenyl, aryl, arylalkylenyl, aryloxyalkylenyl, and heteroaryl groups can be unsubstituted or substituted by one or more substituents selected from the group consisting of alkyl, aryl, halogen, alkoxy, cyano, arylalkyleneoxy, nitro, dialkylamino, aryloxy, heterocyclyl, trifluoromethyl, trifluormethoxy, and in the case of alkyl, oxo. In certain of these embodiments, $R_4$ is selected from the group consisting of alkyl, aryl, heteroaryl, arylalkylenyl, and alkylheteroarylenyl, wherein aryl can be optionally substituted with halogen, methoxy, cyano, trifluoromethyl, trifluoromethoxy.

In certain embodiments, $R_{3-2}$ is

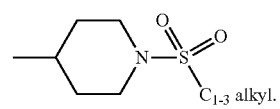

In some embodiments of Formula IV, $R_{3-2}$ is —Z—N ($R_8$)—S(O)$_2$—N($R_8$)—$R_4$ or

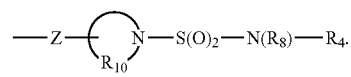

In certain embodiments of this formula for $R_{3-2}$, $R_{10}$ is $C_{4-6}$ alkylene, $R_8$ is hydrogen or $C_{1-4}$ alkyl, and $R_4$ is alkyl.

In certain embodiments $R_{3-2}$ is

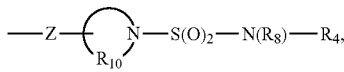

and Z is a bond.

In some embodiments, $R_{3-3}$ is selected from the group consisting of —Z—N($R_8$)—C($R_6$)—N($R_8$)—W—$R_4$,

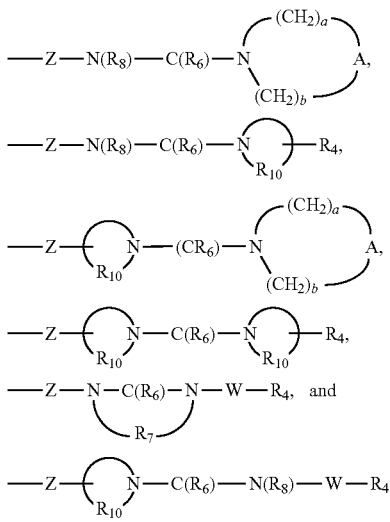

In some embodiments of Formula V, $R_{3-3}$ is —Z—N($R_8$)—C($R_6$)—N($R_8$)—W—$R_4$. In certain embodiments of this formula for $R_{3-3}$, $R_6$ is =O or =S, $R_8$ is hydrogen or $C_{1-4}$ alkyl, W is a bond, —C(O)—, or —S(O)$_2$—; and $R_4$ is selected from the group consisting of alkyl, alkenyl, aryl, arylalkylenyl, aryloxyalkylenyl, and heteroaryl, wherein the alkyl, alkenyl, aryl, arylalkylenyl, aryloxyalkylenyl, and heteroaryl groups can be unsubstituted or substituted by one or more substituents selected from the group consisting of alkyl, aryl, halogen, alkoxy, cyano, arylalkyleneoxy, nitro, dialkylamino, aryloxy, heterocyclyl, trifluoromethyl, trifluoromethoxy, and in the case of alkyl, oxo. In certain embodiments, $R_4$ is selected from the group consisting of alkyl, aryl, arylalkylenyl, and heteroaryl; wherein aryl can be optionally substituted with halogen, methoxy, cyano, trifluoromethyl, and trifluoromethoxy. In certain embodiments, Z is ethylene or propylene, each $R_8$ is hydrogen, $R_6$ is =O, and $R_4$ is isopropyl.

In some embodiments of Formula V, $R_{3-3}$ is

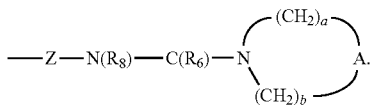

In certain embodiments of this formula for $R_{3-3}$, $R_6$ is =O, $R_8$ is hydrogen, a and b are each independently 1 to 3, and A is —O—. In certain of these embodiments, Z is ethylene or propylene, and a and b are each 2.

In some embodiments of Formula V, $R_{3-3}$ is

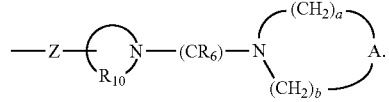

In certain embodiments of this formula for $R_{3-3}$, $R_6$ is =O, $R_{10}$ is $C_{4-6}$ alkylene, a and b are each independently 1 to 3, and A is —O—. In certain embodiments, Z is a bond.

In certain embodiments, $R_{3-3}$ is

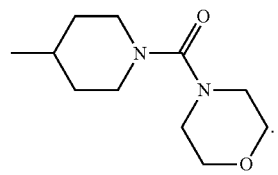

In some embodiments of Formula V, $R_{3-3}$ is

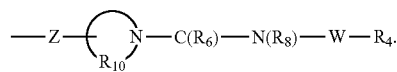

In certain embodiments of this formula for $R_{3-3}$, $R_6$ is =O or =S, $R_8$ is hydrogen or $C_{1-4}$ alkyl, $R_{10}$ is $C_{4-6}$ alkylene, W is a bond, —C(O)—, or —S(O)$_2$—, and $R_4$ is selected from the group consisting of alkyl, alkenyl, aryl, arylalkylenyl, aryloxyalkylenyl, and heteroaryl, wherein the alkyl, alkenyl, aryl, arylalkylenyl, aryloxyalkylenyl, and heteroaryl groups can be unsubstituted or substituted by one or more substituents selected from the group consisting of alkyl, aryl, halogen, alkoxy, cyano, arylalkyleneoxy, nitro, dialkylamino, aryloxy, heterocyclyl, trifluoromethyl, trifluoromethoxy, and in the case of alkyl, oxo. In certain embodiments W is a bond or —C(O)—. In certain embodiments, $R_4$ is selected from the group consisting of alkyl, aryl, arylalkylenyl, and heteroaryl; wherein aryl can be optionally substituted with halogen, methoxy, cyano, trifluoromethyl, and trifluoromethoxy. In certain embodiments, Z is a bond.

In certain embodiments, $R_{3-3}$ is

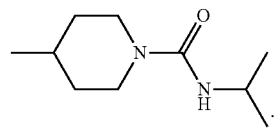

In some embodiments of Formula V, $R_{3-3}$ is

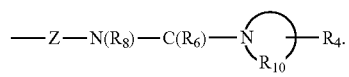

In certain embodiments of this formula for $R_{3-3}$, $R_6$ is =O or =S, $R_8$ is hydrogen or $C_{1-4}$ alkyl, $R_{10}$ is $C_{4-6}$ alkylene, and $R_4$ is hydrogen or alkyl.

In some embodiments of Formula V, $R_{3-3}$ is

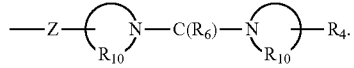

In certain embodiments of this formula for $R_{3-3}$, $R_6$ is $=O$ or $=S$, $R_{10}$ is $C_{4-6}$ alkylene, and $R_4$ is hydrogen or alkyl. In certain embodiments, Z is a bond.

In some embodiments of Formula V, $R_{3-3}$ is

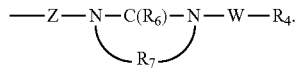

In certain embodiments of this formula for $R_{3-3}$, $R_6$ is $=O$ or $=S$, $R_7$ is $C_{2-4}$ alkylene, W is a bond, and $R_4$ is hydrogen or alkyl.

In some embodiments of Formula VI, $R_{3-4}$ is $-Z_a-C(R_6)-R_4$, $-Z_a-C(R_6)-O-R_4$, $-Z_a-C(R_6)-N(R_8)-R_4$, or

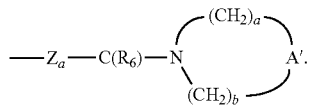

In some embodiments of Formula VI, $R_{3-4}$ is $-Z_a-C(R_6)-R_4$. In certain embodiments of this formula for $R_{3-4}$, $R_6$ is $=O$ or $=S$, and $R_4$ is alkyl, aryl, or heterocyclyl.

In some embodiments of Formula VI, $R_{3-4}$ is $-Z_a-C(R_6)-O-R_4$. In certain embodiments of this formula for $R_{3-4}$, $R_6$ is $=O$ and $R_4$ is hydrogen or alkyl.

In some embodiments of Formula VI, $R_{3-4}$ is $-Z_a-C(R_6)-N(R_8)-R_4$. In certain embodiments of this formula for $R_{3-4}$, $R_6$ is $=O$ or $=S$, $R_8$ is hydrogen, alkyl, or alkoxyalkylenyl, and $R_4$ is alkyl, aryl, or arylalkylenyl; wherein aryl can be optionally substituted with halogen, methoxy, cyano, trifluoromethyl, and trifluoromethoxy.

In some embodiments of Formula VI, $R_{3-4}$ is

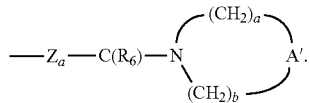

In certain embodiments of this formula for $R_{3-4}$, $R_6$ is $=O$ or $=S$, a and b are each independently 1 to 3, and A' is selected from the group consisting of $-CH_2-$, $-S(O)_2-$, and $-O-$. In certain embodiments A' is $-CH_2-$. In certain of these embodiments, $Z_a$ is methylene, $R_6$ is $=O$, a is 1 or 2, b is 2, and A' is $-CH_2-$. In certain of these embodiments, $Z_a$ is methylene, $R_6$ is $=O$, a and b are each 2, and A' is $-O-$.

In certain embodiments of Formula VI, $Z_a$ is a bond or alkylene.

In some embodiments of Formula VII, $R_{3-5}$ is $-Z-N(R_8)-C(R_6)-O-R_4$,

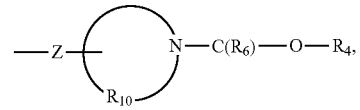

or $-Z-N(R_8)-C(R_6)-C(R_6)-R_4$.

In some embodiments of Formula VII, $R_{3-5}$ is $-Z-N(R_8)-C(R_6)-O-R_4$. In certain embodiments of this formula for $R_{3-5}$, $R_6$ is $=O$, $R_8$ is hydrogen, and $R_4$ is alkyl.

In some embodiments of Formula VII, $R_{3-5}$ is

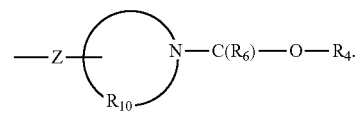

In certain embodiments of this formula for $R_{3-5}$, $R_6$ is $=O$, $R_{10}$ is $C_{4-6}$ alkylene, and $R_4$ is alkyl. In certain embodiments, Z is a bond.

In some embodiments of Formula VII, $R_{3-5}$ is $-Z-N(R_8)-C(R_6)-C(R_6)-R_4$. In certain embodiments of this formula for $R_{3-5}$, $R_6$ is $=O$ or $=S$, $R_8$ is hydrogen, and $R_4$ is alkyl, aryl, or heteroaryl; wherein aryl can be optionally substituted with halogen, methoxy, cyano, trifluoromethyl, and trifluoromethoxy.

In some embodiments of Formula VIII, $R_{3-6}$ is $-Z-N(R_8)H$ or

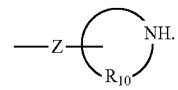

In some embodiments of Formula VIII, $R_{3-6}$ is $-Z-N(R_8)H$. In certain embodiments of this formula for $R_{3-6}$, Z is alkylene, and $R_8$ is hydrogen.

In some embodiments of Formula VIII, $R_{3-6}$ is

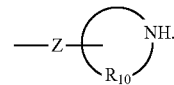

In certain embodiments of this formula for $R_{3-6}$, Z is a bond, and $R_{10}$ is $C_{4-6}$ alkylene.

In certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

In certain embodiments, $R_4$ is selected from the group consisting of alkyl, alkenyl, aryl, arylalkylenyl, aryloxyalkylenyl, and heteroaryl, wherein the alkyl, alkenyl, aryl, arylalkylenyl, aryloxyalkylenyl, and heteroaryl groups can be unsubstituted or substituted by one or more substituents selected from the group consisting of alkyl, aryl, halogen, alkoxy, cyano, arylalkyleneoxy, nitro, dialkylamino, aryloxy, heterocyclyl, trifluoromethyl, trifluormethoxy, and in the case of alkyl, oxo.

In certain embodiments, $R_4$ is selected from the group consisting of hydrogen, alkyl, alkenyl, aryl, arylalkylenyl, alkylheteroarylenyl, heteroarylalkylenyl, aryloxyalkylenyl, heteroaryl, and heterocyclyl, wherein alkyl is unsubstituted or substituted by one or more substituents selected from the group consisting of hydroxy, alkoxy, and heterocyclyl, and wherein arylalkylenyl and heteroarylalkylenyl are unsubstituted or substituted by one or more substituents selected from the group consisting of alkyl, halogen, and alkoxy.

In certain embodiments, $R_4$ is selected from the group consisting of hydrogen, alkyl, alkenyl, aryl, arylalkylenyl, alkylheteroarylenyl, heteroarylalkylenyl, aryloxyalkylenyl, heteroaryl, and heterocyclyl.

In certain embodiments, $R_4$ is selected from the group consisting of hydrogen and alkyl. In certain embodiments, $R_4$ is alkyl. In certain embodiments, $R_4$ is alkyl or aryl. In certain embodiments, $R_4$ is $C_{1-3}$ alkyl. In certain embodiments, $R_4$ is isopropyl.

In certain embodiments, $R_4$ is alkyl, aryl, or heterocyclyl. In certain embodiments, $R_4$ is alkyl, aryl, or heteroaryl, wherein aryl can be optionally substituted with halogen, methoxy, cyano, trifluoromethyl, and trifluoromethoxy.

In certain embodiments, $R_4$ is selected from the group consisting of alkyl, aryl, alkenyl, heteroaryl, arylalkylenyl, and alkylheteroarylenyl; wherein aryl can be optionally substituted with halogen, methoxy, cyano, trifluoromethyl, and trifluoromethoxy.

In certain embodiments, $R_4$ is alkyl, aryl, or arylalkylenyl; wherein aryl can be optionally substituted with halogen, methoxy, cyano, trifluoromethyl, and trifluoromethoxy.

In certain embodiments, $R_5$ is selected from the group consisting of

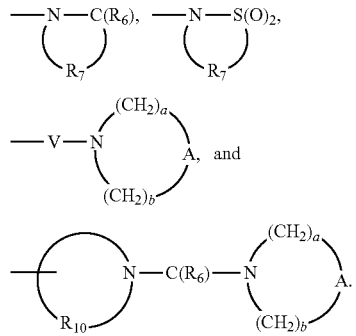

In certain embodiments, $R_5$ is selected from the group consisting of

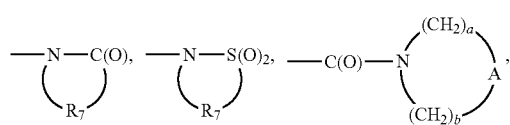

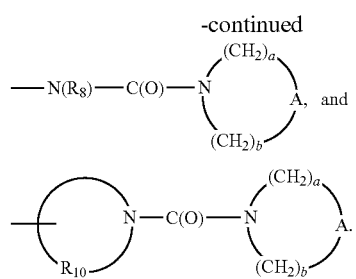

In certain of these embodiments, $R_7$ is $C_{3-5}$ alkylene; $R_{10}$ is $C_{4-6}$ alkylene; and a and b are each independently 1 to 3.

In certain embodiments, $R_6$ is selected from the group consisting of =O and =S. In certain embodiments, $R_6$ is =O.

In certain embodiments, $R_7$ is a $C_{2-7}$ alkylene. In certain embodiments, $R_7$ is $C_{3-5}$ alkylene. In certain embodiments, $R_7$ is $C_{2-4}$ alkylene. In certain embodiments, $R_7$ is propylene.

In certain embodiments, $R_8$ is selected from the group consisting of hydrogen, alkyl, alkoxyalkylenyl, and arylalkylenyl. In certain embodiments, $R_8$ is selected from the group consisting of hydrogen, $C_{1-4}$ alkyl, and alkoxyalkylenyl. In certain embodiments, $R_8$ is hydrogen or $C_{1-4}$ alkyl. In certain embodiments, $R_8$ is hydrogen.

In certain embodiments, $R_9$ is selected from the group consisting of hydrogen and alkyl.

In certain embodiments, $R_{10}$ is a $C_{3-8}$ alkylene. In certain embodiments, $R_{10}$ is a $C_{4-6}$ alkylene. In certain embodiments, $R_{10}$ is butylene.

In certain embodiments, A is selected from the group consisting of —O—, —C(O)—, —S(O)$_{0-2}$—, and —N(R$_4$)—. In certain embodiments, A is —O—.

In certain embodiments, A' is selected from the group consisting of —O—, —C(O)—, —S(O)$_{0-2}$—, —N(R$_4$)—, and —CH$_2$—. In certain embodiments, A' is selected from the group consisting of —CH$_2$—, —S(O)$_2$—, and —O—. In certain embodiments, A' is —CH$_2$—. In certain embodiments, A' is —O—.

In certain embodiments, Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—. In certain embodiments, Q is selected from the group consisting of a bond, —C(O)—, —C(O)—O—, —S(O)$_2$—, —C(R$_6$)—N(R$_8$)—W—, and —S(O)$_2$—N(R$_8$)—.

In certain embodiments, V is selected from the group consisting of —C(R$_6$)—, —O—C(R$_6$)—, —N(R$_8$)—C(R$_6$)—, and —S(O)$_2$—. In certain embodiments, V is selected from the group consisting of —C(O)— and —N(R$_8$)—C(O)—.

In certain embodiments, W is selected from the group consisting of a bond, —C(O)—, and —S(O)$_2$—. In certain embodiments, W is a bond or —C(O)—. In certain embodiments, W is a bond.

In certain embodiments, X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups.

In certain embodiments, X is selected from the group consisting of alkylene, arylene, heterocyclylene, heteroarylene, and alkylene terminated with heteroarylene. In certain embodiments, X is selected from the group consisting of alkylene, arylene, heteroarylene, and alkylene terminated with heteroarylene.

In certain embodiments, Y is selected from the group consisting of
—S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

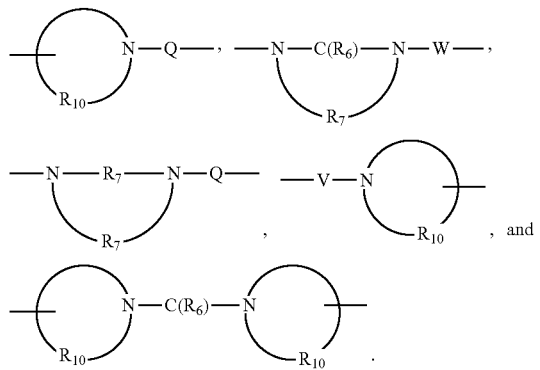

In certain embodiments, Y is selected from the group consisting of —S(O)$_{0-2}$—, —C(O)—, —C(O)—O—, —O—C(O)—, —N(R$_8$)-Q-, —C(R$_6$)—N(R$_8$)—,

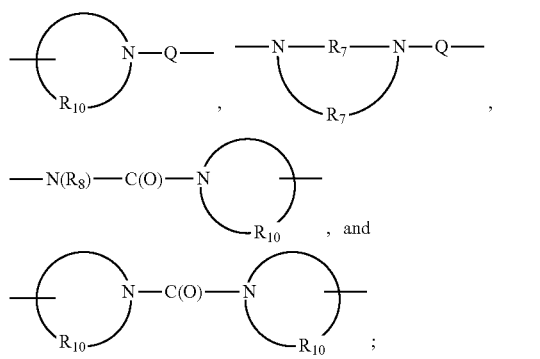

wherein Q is selected from the group consisting of a bond, —C(O)—, —C(O)—O—, —S(O)$_2$—, —C(R$_6$)—N(R$_8$)—W—, and —S(O)$_2$—N(R$_8$)—; W is selected from the group consisting of a bond, —C(O)—, and —S(O)$_2$—; R$_6$ is selected from the group consisting of =O or =S; R$_8$ is selected from the group consisting of hydrogen, C$_{1-4}$ alkyl, and alkoxyalkylenyl; and R$_{10}$ is selected from the group consisting of C$_{4-6}$ alkylene; X is selected from the group consisting of alkylene, arylene, heterocyclylene, heteroarylene, and alkylene terminated with heteroarylene; and R$_4$ is selected from the group consisting of hydrogen, alkyl, alkenyl, aryl, arylalkylenyl, alkylheteroarylenyl, heteroarylalkylenyl, aryloxyalkylenyl, heteroaryl, and heterocyclyl, wherein alkyl is unsubstituted or substituted by one or more substituents selected from the group consisting of hydroxy, alkoxy, and heterocyclyl, and wherein arylalkylenyl and heteroarylalkylenyl are unsubstituted or substituted by one or more substituents selected from the group consisting of alkyl, halogen, and alkoxy.

In certain embodiments, Y is selected from the group consisting of
—S(O)$_{0-2}$—, —C(O)—, —C(O)—O—, —O—C(O)—, —N(R$_8$)-Q-, —C(R$_6$)—N(R$_8$)—,

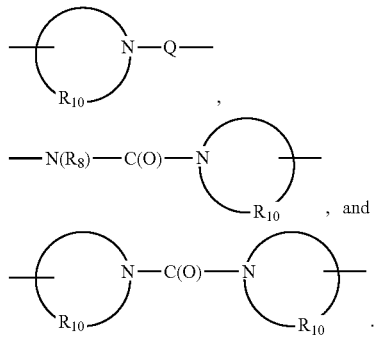

In certain of these embodiments, Q is selected from the group consisting of a bond, —C(O)—, —C(O)—O—, —S(O)$_2$—, —C(R$_6$)—N(R$_8$)—W—, and —S(O)$_2$—N(R$_8$)—; W is selected from the group consisting of a bond, —C(O)—, and —S(O)$_2$—; R$_6$ is selected from the group consisting of =O or =S; R$_8$ is selected from the group consisting of hydrogen, C$_{1-4}$ alkyl, and alkoxyalkylenyl; and R$_{10}$ is selected from the group consisting of C$_{4-6}$ alkylene.

In certain embodiments, Y is selected from the group consisting of —S(O)$_{0-2}$—, —C(O)—, —C(O)—O—, —N(R$_8$)-Q-, —C(R$_6$)—N(R$_8$)),

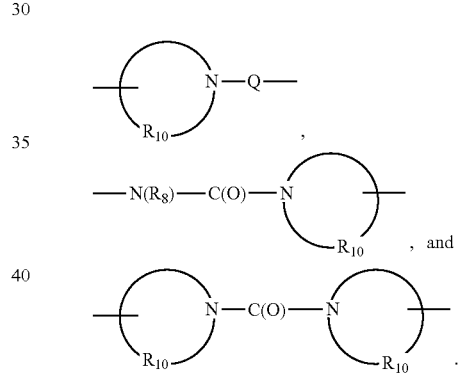

In certain embodiments, Y is selected from the group consisting of —C(O)—, —C(O)—O—, —C(O)—N(H)—, and —N(H)—C(O)—.

In certain embodiments, Z is selected from the group consisting of alkylene, alkenylene, and alkynylene, wherein alkylene, alkenylene, and alkynylene can be optionally interrupted with one or more —O— groups. Z can also be a bond. In some embodiments (e.g., of Formulas I-IX), Z is alkylene. In certain of these embodiments, Z is C$_{2-6}$ alkylene. In certain embodiments Z is ethylene or propylene.

In certain embodiments, Z is a bond. For example, Z can be a bond when: R$_3$ is —Z-Het, —Z-Het'-R$_4$, or —Z-Het'-Y—R$_4$; or R$_3$ is —Z—Y—R$_4$ or —Z—Y—X—Y—R$_4$, and Y is selected from —S(O)$_{0-2}$—, —S(O)$_2$—N(R$_8$)—, —C(R$_6$)—, —C(R$_6$)—O—, —C(R$_6$)—N(R$_8$)—,

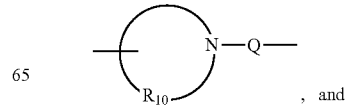

-continued

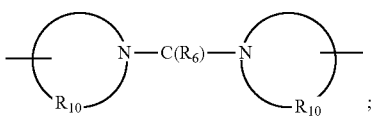

or R$_3$ is —Z—R$_5$ and R$_5$ is

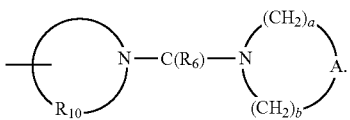

As another example, Z can be a bond when R$_{3-1}$ is

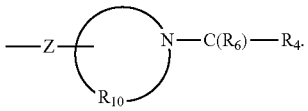

As another example, Z can be a bond when R$_{3-2}$ is

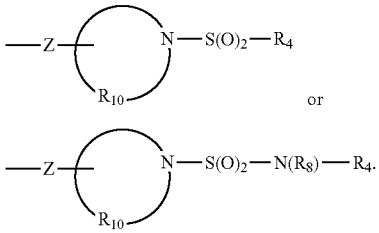

As another example, Z can be a bond when R$_{3-3}$ is

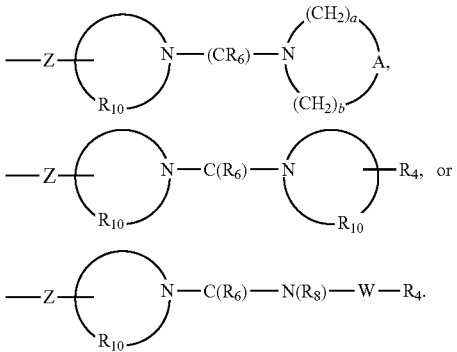

As another example, Z can be a bond when R$_{3-5}$ is

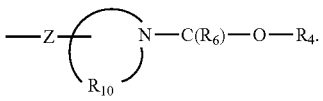

As another example, Z can be a bond when R$_{3-6}$ is

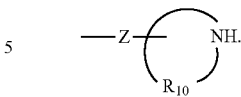

As another example, Z can be a bond when R$_3$ is —Z—S(O)$_2$—CH$_3$ or —Z—C(O)—NH—CH(CH$_3$)$_2$.

In certain embodiments, Z$_a$ is selected from the group consisting of a bond, alkylene, alkenylene, and alkynylene, wherein alkylene, alkenylene, and alkynylene can be optionally interrupted with one or more —O— groups. In certain embodiments, Z$_a$ is a bond or alkylene. In certain of these embodiments, Z$_a$ is C$_{1-4}$ alkylene. In certain embodiments, Z$_a$ is methylene.

In certain embodiments, Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, mercapto, cyano, aryloxy, arylalkyleneoxy, heteroaryloxy, heteroarylalkyleneoxy, heterocyclyl, hydroxyalkyleneoxyalkylenyl, amino, alkylamino, dialkylamino, (dialkylamino)alkyleneoxy, and oxo. In certain embodiments, Het is substituted by one or more substituents selected from the group consisting of alkyl, hydroxy, hydroxyalkyl, hydroxyalkyleneoxylalkylenyl, diakylamino, and heterocyclyl. In certain embodiments, Het is selected from the group consisting of tetrahydropyranyl and tetrahydrofuranyl.

In certain embodiments, Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, mercapto, cyano, aryloxy, arylalkyleneoxy, heteroaryloxy, heteroarylalkyleneoxy, amino, alkylamino, dialkylamino, (dialkylamino)alkyleneoxy, and oxo.

In certain embodiments, Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, mercapto, cyano, aryloxy, arylalkyleneoxy, heteroaryloxy, heteroarylalkyleneoxy, amino, alkylamino, dialkylamino, (dialkylamino)alkyleneoxy, and oxo.

In certain embodiments, Het or Het' is selected from the group consisting of tetrahydropyranyl, tetrahydrofuranyl, 1,3-dioxolanyl, pyrrolidinyl, piperidinyl, morpholinyl, thiomorpholinyl, thiazolidinyl, aziridinyl, azepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and piperazinyl.

In certain embodiments, Het is substituted by one or more substituents selected from the group consisting of alkyl, hydroxy, hydroxyalkyl, hydroxyalkyleneoxylalkylenyl, diakylamino, and heterocyclyl; Y is selected from the group consisting of —C(O)—, —C(O)—O—, —C(O)—N(H)—, and —N(H)—C(O)—; and R$_4$ is selected from the group consisting of hydrogen and alkyl.

In some embodiments of Formulas I-IX, R$_3$—O—, R$_{3-1}$—O—, R$_{3-2}$—O—, R$_{3-3}$—O—, R$_{3-4}$—O—, R$_{3-5}$—O—, or R$_{3-6}$—O— is at the 7- or 8-position. In some embodiments of Formulas I-IX, R$_3$—O—, R$_{3-1}$—O—, R$_{3-2}$—O—, R$_{3-3}$—O—, R$_{3-4}$—O—, R$_{3-5}$—O—, or R$_{3-6}$—O— at the 7-position. In some embodiments of Formulas I-IX, R$_3$—O—, R$_{3-1}$—O—, R$_{3-2}$—O—, R$_{3-3}$—O—, R$_{3-4}$—O—, R$_{3-5}$—O—, or R$_{3-6}$—O— is at the 8-position.

In certain embodiments, a and b are independently integers from 1 to 6 with the proviso that a+b is ≤7. In certain embodiments, a and b are each independently 1 to 3. In certain embodiments, a is 1 or 2, and b is 2. In certain embodiments, a and b are each 2.

In certain embodiments, n is 0 or 1. In some embodiments (e.g., of Formulas I-IX), n is 0.

Preparation of the Compounds

Compounds of the invention can be prepared according to Reaction Scheme I where R, $R_1$, $R_2$, $R_3$, and n are as defined above. In step (1) of Reaction Scheme I, a benzyloxyaniline of Formula XV is treated with the condensation product generated from 2,2-dimethyl-1,3-dioxane-4,6-dione (Meldrum's acid) and triethyl orthoformate to provide an imine of Formula XVI. The reaction is conveniently carried out by adding a solution of a benzyloxyaniline of Formula XV to a heated mixture of Meldrum's acid and triethyl orthoformate and heating the reaction at an elevated temperature such as 45° C. The product can be isolated using conventional methods.

In step (2) of Reaction Scheme I, an imine of Formula XVI undergoes thermolysis and cyclization to provide a benzyloxyquinolin-4-ol of Formula XVII. The reaction is conveniently carried out in medium such as DOWTHERM A heat transfer fluid at a temperature between 200 and 250° C. The product can be isolated using conventional methods.

In step (3) of Reaction Scheme I, the benzyloxyquinolin-4-ol of Formula XVII is nitrated under conventional nitration conditions to provide a benzyloxy-3-nitroquinolin-4-ol of Formula XVIII. The reaction is conveniently carried out by adding nitric acid to the benzyloxyquinolin-4-ol of Formula XVII in a suitable solvent such as propionic acid and heating the mixture at an elevated temperature such as 125° C. The product can be isolated using conventional methods.

In step (4) of Reaction Scheme I, a benzyloxy-3-nitroquinolin-4-ol of Formula XVIII is chlorinated using conventional chlorination chemistry to provide a benzyloxy-4-chloro-3-nitroquinoline of Formula XIX. The reaction is conveniently carried out by treating the benzyloxy-3-nitroquinolin-4-ol of Formula XVIII with phosphorous oxychloride in a suitable solvent such as N,N-dimethylformamide (DMF). The reaction can be carried out at an elevated temperature such as 100° C., and the product can be isolated using conventional methods.

In step (5) of Reaction Scheme I, a benzyloxy-4-chloro-3-nitroquinoline of Formula XIX is treated with an amine of Formula $R_1$—$NH_2$ to provide a benzyloxy-3-nitroquinolin-4-amine of Formula XX. The reaction is conveniently carried out by adding the amine of Formula $R_1$—$NH_2$ to a solution of the benzyloxy-4-chloro-3-nitroquinoline of Formula XIX in a suitable solvent such as dichloromethane or methanol in the presence of a tertiary amine such as triethylamine. The reaction can be carried out at ambient temperature or at an elevated temperature such as, for example, the reflux temperature of the solvent. The reaction product can be isolated using conventional methods. Several amines of Formula $R_1$—$NH_2$ are commercially available; others can be prepared by known synthetic methods. For example, methyl tetrahydro-2H-pyran-4-carboxylate treated with ammonium hydroxide to form tetrahydro-2H-pyran-4-carboxamide, which can then be reduced with lithium aluminum hydride to provide tetrahydro-2H-pyran-4-ylmethylamine.

In step (6) of Reaction Scheme I, a benzyloxy-3-nitroquinolin-4-amine of Formula XX is reduced to provide a benzyloxyquinoline-3,4-diamine of Formula XXI. The reaction can be carried out by hydrogenation using a heterogeneous hydrogenation catalyst such as platinum on carbon. The hydrogenation is conveniently carried out in a Parr apparatus in a suitable solvent such as toluene, methanol, or acetonitrile. The reaction can be carried out at ambient temperature, and the product can be isolated using conventional methods.

Alternatively, the reduction in step (6) can be carried out using nickel boride, prepared in situ from sodium borohydride and nickel(II) chloride. The reduction is conveniently carried out by adding a solution of the benzyloxy-3-nitroquinolin-4-amine of Formula XX in a suitable solvent or solvent mixture such as dichloromethane/methanol to a mixture of excess sodium borohydride and catalytic nickel (II) chloride in methanol. The reaction can be carried out at ambient temperature. The product can be isolated using conventional methods.

In step (7) of Reaction Scheme I, a benzyloxyquinoline-3,4-diamine of Formula XXI is treated with a carboxylic acid equivalent to provide a benzyloxy-1H-imidazo[4,5-c]quinoline of Formula XXII. Suitable carboxylic acid equivalents include orthoesters of Formula $R_2C(O\text{-alkyl})_3$, 1,1-dialkoxyalkyl alkanoates of Formula $R_2C(O\text{-alkyl})_2(O\text{—C}(O)\text{-alkyl})$, and acid chlorides of Formula $R_2C(O)Cl$. The selection of the carboxylic acid equivalent is determined by the desired substituent at $R_2$. For example, triethyl orthoformate will provide a compound where $R_2$ is hydrogen, and trimethyl orthovalerate will provide a compound where $R_2$ is a butyl group. The reaction is conveniently carried out by adding the carboxylic acid equivalent to a benzyloxyquinoline-3,4-diamine of Formula XXI in a suitable solvent such as toluene or xylenes. Optionally, catalytic pyridine hydrochloride can be added. The reaction is carried out at a temperature high enough to drive off alcohol or water formed during the reaction. Conveniently, a Dean-Stark trap can be used to collect the volatiles.

Alternatively, step (7) can be carried out in two steps when an acid chloride of Formula $R_2C(O)Cl$ is used as the carboxylic acid equivalent. Part (i) of step (7) is conveniently carried out by adding the acid chloride to a solution of a benzyloxyquinoline-3,4-diamine of Formula XXI in a suitable solvent such as dichloromethane or acetonitrile to afford an amide. Optionally, a tertiary amine such as triethylamine, pyridine, or 4-dimethylaminopyridine can be added. The reaction can be carried out at ambient temperature or at an elevated temperature. The amide product can be isolated and optionally purified using conventional techniques. Part (ii) of step (7) involves heating the amide prepared in part (i) to provide a benzyloxy-1H-imidazo[4,5-c]quinoline of Formula XXII. The reaction is conveniently carried out in a suitable solvent such as toluene at a temperature sufficient to drive off water formed during the reaction. The reaction can also be carried out in a solvent such as ethanol or methanol in the presence of a base such as triethylamine. The benzyloxy-1H-imidazo[4,5-c]quinoline of Formula XXII can be isolated using conventional methods.

In step (8) of Reaction Scheme I, the benzyl group of a benzyloxy-1H-imidazo[4,5-c]quinoline of Formula XXII is cleaved to provide a 1H-imidazo[4,5-c]quinolinol of Formula XXIII. The cleavage is conveniently carried out on a Parr apparatus under hydrogenolysis conditions using a suitable heterogeneous catalyst such as palladium on carbon in a solvent such as ethanol. Alternatively, the reaction can be carried out by transfer hydrogenation in the presence of a suitable hydrogenation catalyst. The transfer hydrogenation is conveniently carried out by adding ammonium formate to a solution of a benzyloxy-1H-imidazo[4,5-c]quinoline of Formula XXII in a suitable solvent such as ethanol in the presence of a catalyst such as palladium on carbon. The reaction is carried out at an elevated temperature, for example, the refluxing temperature of the solvent. The product or pharmaceutically acceptable salt thereof can be isolated using conventional methods.

In step (9) of Reaction Scheme I a 1H-imidazo[4,5-c]quinolinol of Formula XXIII is converted to an ether-substituted 1H-imidazo[4,5-c]quinoline of Formula IX using a Williamson-type ether synthesis. The reaction is effected by treating a 1H-imidazo[4,5-c]quinolinol of Formula XXIII with an alkyl halide of Formula Halide-Z—Y—R$_4$, Halide-Z—R$_5$, Halide-Z—Y—X—Y—R$_4$, or Halide-Z-Het, wherein Z, Y, X, R$_4$, R$_5$, and Het are as defined above, in the presence of a base. The reaction is conveniently carried out by combining the alkyl halide with a 1H-imidazo[4,5-c]quinolinol of Formula XXIII in a solvent such as DMF in the presence of a suitable base such as cesium carbonate. The reaction can be carried out at ambient temperature or at an elevated temperature, for example 65° C. or 85° C. Alternatively, the reaction can be carried out by treating a solution of a 1H-imidazo[4,5-c]quinolinol of Formula XXIII in a solvent such as DMF with sodium hydride and then adding a reagent of Formula Halide-Z—Y—R$_4$, Halide-Z—R$_5$, Halide-Z—Y—X—Y—R$_4$, or Halide-Z-Het. The product or pharmaceutically acceptable salt thereof can be isolated using conventional methods.

Numerous reagents of Formulas Halide-Z—Y—R$_4$ and Halide-Z-Het are commercially available, for example, bromo-substituted ketones, esters, and heterocycles. Other reagents of Formulas Halide-Z—Y—R$_4$, Halide-Z—R$_5$, Halide-Z—Y—X—Y—R$_4$, and Halide-Z-Het can be prepared using conventional synthetic methods; for example, a bromo-substituted acid halide of Formula ClC(O)—Z—Br or BrC(O)—Z—Br can be treated with a secondary amine in a suitable solvent such as dichloromethane to provide a variety of bromo-substituted amides of Formula Br—Z—C(O)—N(R$_8$)—R$_4$ or

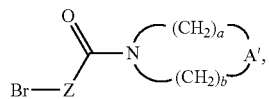

wherein R$_8$, a, b, and A' are as defined above. The reaction can be run at a sub-ambient temperature such as −25° C., and the product can be isolated using conventional methods.

Step (9) of Reaction Scheme I can alternatively be carried out by treating a 1H-imidazo[4,5-c]quinolinol of Formula XXIII with an alcohol of Formula HO—Z—Y—R$_4$, HO—Z—R$_5$, or HO—Z-Het under Mitsunobu reaction conditions. Numerous alcohols of these formulas are commercially available, and others can be prepared using conventional synthetic methods. The reaction is conveniently carried out by out by adding triphenylphosphine and an alcohol of Formula HO—Z—Y—R$_4$, HO—Z-Het, or HO—Z—R$_5$, for example, 1-(2-hydroxyethyl)pyrrolidin-2-one or 1-(3-hydroxypropyl)pyrrolidin-2-one, to a solution of a 1H-imidazo[4,5-c]quinolinol of Formula XXIII in a suitable solvent such as tetrahydrofuran and then slowly adding diisopropyl azodicarboxylate or diethyl azodicarboxylate. The reaction can be carried out at ambient temperature or at a sub-ambient temperature, such as 0° C. The product can be isolated using conventional methods.

In step (10) of Reaction Scheme I, an ether-substituted 1H-imidazo[4,5-c]quinoline of Formula IX is oxidized to provide a 1H-imidazo[4,5-c]quinoline-5N-oxide of Formula X using a conventional oxidizing agent capable of forming N-oxides. The reaction is conveniently carried out by adding 3-chloroperoxybenzoic acid to a solution of a compound of Formula IX in a solvent such as dichloromethane or chloroform. The reaction can be carried out at ambient temperature, and the product can be isolated using conventional methods.

In step (11) of Reaction Scheme I, a 1H-imidazo[4,5-c]quinoline-5N-oxide of Formula X is aminated to provide a 1H-imidazo[4,5-c]quinolin-4-amine of Formula II. Step (11) can be carried out by the activation of an N-oxide of Formula X by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula X in a suitable solvent such as dichloromethane or chloroform and then adding p-toluenesulfonyl chloride. The reaction can be carried out at ambient temperature. The product or pharmaceutically acceptable salt thereof can be isolated using conventional methods.

Alternatively step (11) can be carried out by the reaction of a 1H-imidazo[4,5-c]quinoline-5N-oxide of Formula X with trichloroacetyl isocyanate followed by base-promoted hydrolysis of the resulting intermediate to provide a 1H-imidazo[4,5-c]quinolin-4-amine of Formula II. The reaction is conveniently carried out in two steps by (i) adding trichloroacetyl isocyanate to a solution of the N-oxide of Formula X in a solvent such as dichloromethane and stirring at ambient temperature to provide an isolable amide intermediate. In step (ii), a solution of the intermediate in methanol is treated with a base such as sodium methoxide or ammonium hydroxide at ambient temperature. The product or pharmaceutically acceptable salt thereof can be isolated using conventional methods.

Steps (10) and (11) can alternatively be combined and carried out as a one-pot procedure by adding 3-chloroperoxybenzoic acid to a solution of a compound of Formula IX in a solvent such as dichloromethane or chloroform and then adding ammonium hydroxide and p-toluenesulfonyl chloride without isolating the N-oxide of Formula X. The product of Formula II or pharmaceutically acceptable salt thereof can be isolated using conventional methods.

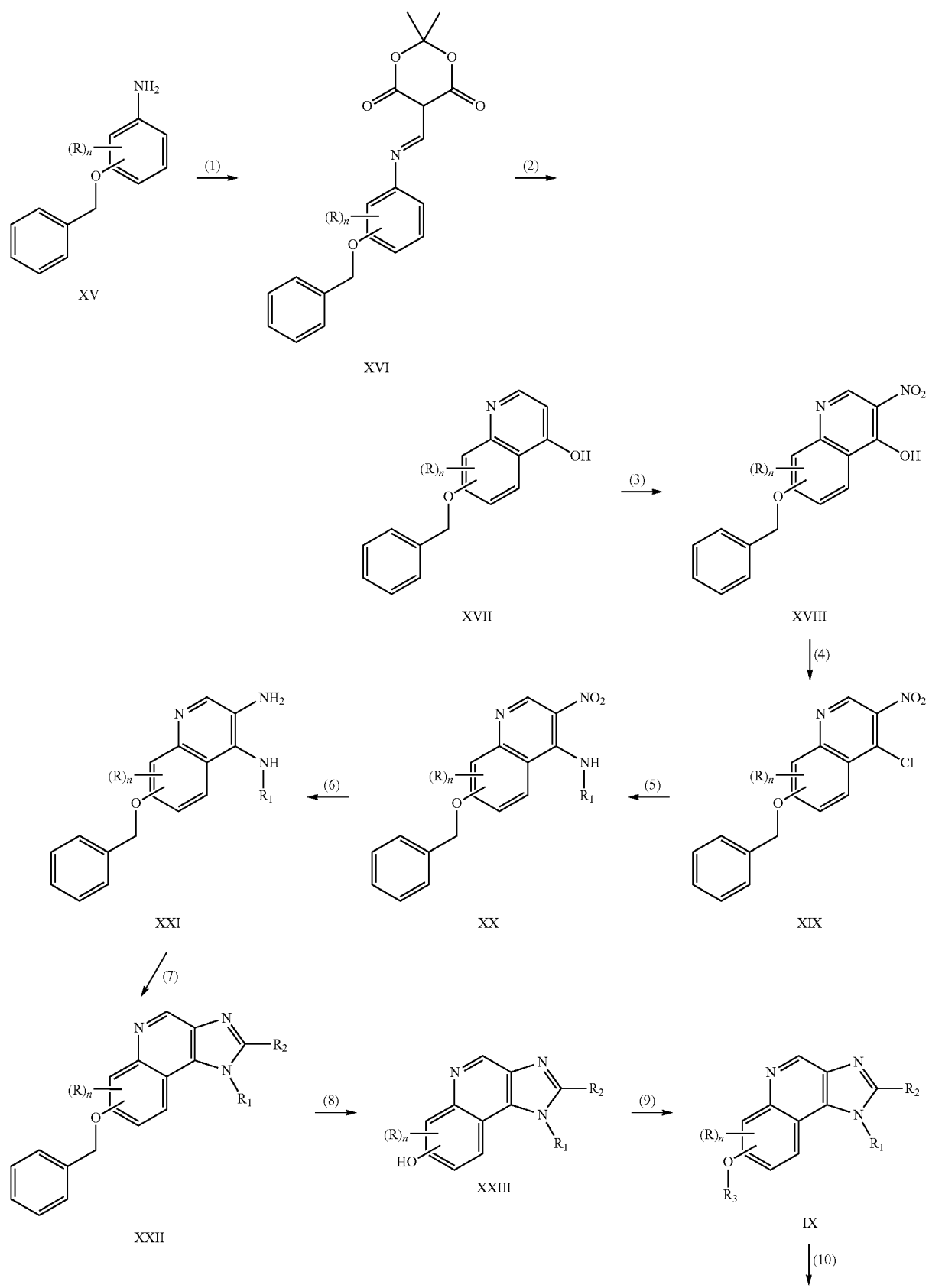
Reaction Scheme I

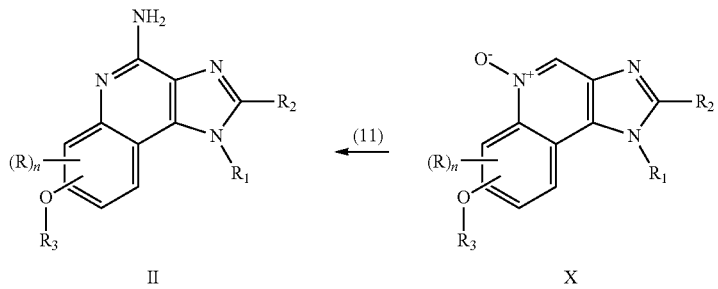

Compounds of the invention can also be prepared according to Reaction Scheme II, where R, $R_1$, $R_2$, $R_3$, and n are as defined above. In Reaction Scheme II, a benzyloxy-1H-imidazo[4,5-c]quinoline of Formula XXII is first oxidized to a benzyloxy-1H-imidazo[4,5-c]quinoline-5N-oxide of Formula XXIV, which is then aminated in step (2) to provide a benzyloxy-1H-imidazo[4,5-c]quinolin-4-amine of Formula XXV. In step (3) of Reaction Scheme II, the benzyl group of the benzyloxy-1H-imidazo[4,5-c]quinolin-4-amine of Formula XXV is cleaved to provide a 1H-imidazo[4,5-c]quinolinol of Formula XXVI, which is converted in step (4) to an ether-substituted 1H-imidazo[4,5-c]quinolin-4-amine of Formula II. Steps (1), (2), (3), and (4) of Reaction Scheme II can be carried out as described for steps (10), (11), (8), and (9), respectively, of Reaction Scheme I.

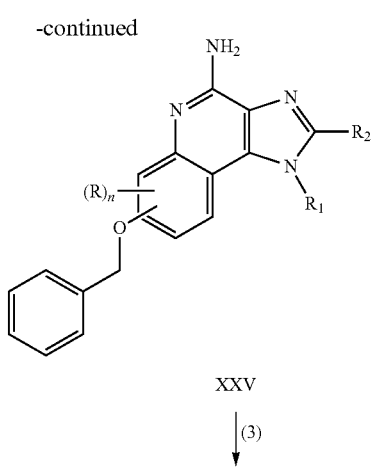

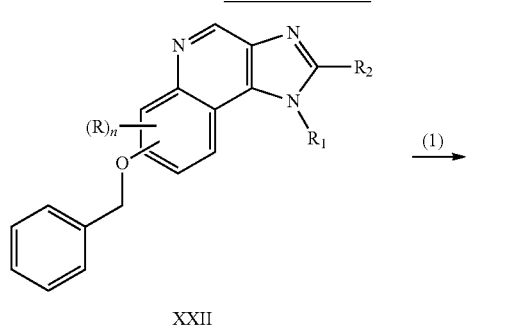

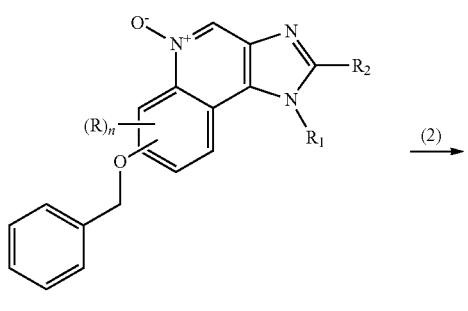

For some embodiments, compounds shown in Reaction Scheme I can be further elaborated using conventional synthetic methods. For example, an amine of Formula $R_1$—$NH_2$, used in step (5) of Reaction Scheme I, may be substituted by a hydroxy or second amino group, which can be further functionalized before step (6) of Reaction Scheme I. For example, a benzyloxy-3-nitroquinolin-4-amine of Formula XX, in which $R_1$ has an amino substituent, can react with an acid chloride of Formula $R_4C(O)Cl$, a sulfonyl chloride of Formula $R_4S(O)_2Cl$, a sulfonic anhydride of Formula $(R_4S(O)_2)_2O$, or an isocyanate of Formula $R_4N\!=\!C\!=\!O$ to provide a compound of Formula XX in which $R_1$ is —X—Y—$R_4$, where X and $R_4$ are as defined above, and Y is —N($R_8$)-Q-, where $R_8$ is as defined above and Q is —C(O)—, —$SO_2$—, or —C(O)—NH—. Numerous acid chlorides, sulfonyl chlorides, sulfonic anhydrides, and isocyanates are commercially available; others can be readily prepared using known synthetic methods. The reaction can be conveniently carried out by adding the sulfonic anhydride to a solution of a benzyloxy-3-nitroquinolin-4-amine of Formula XX, in which $R_1$ has an amino substituent, and a base such as triethylamine in a suitable solvent such as dichloromethane. The reaction can be carried out at ambient temperature. The product can then be treated according to steps (6) and (7) of Reaction Scheme I to provide a benzyloxy-1H-imidazo[4,5-c]quinoline of Formula XXII, which can be treated as described in steps (8)-(11) of Reaction Scheme I or steps (1)-(4) of Reaction Scheme II to provide a compound of Formula II.

Amines of Formula $R_1$—$NH_2$, used in step (5) of Reaction Scheme I, may contain a protected functional group, such as a tert-butoxycarbonyl-protected amino group or a isopropylidene ketal-protected diol. The protecting group installed in step (5) may be removed later in Reaction Scheme I or Reaction Scheme II to reveal, for example, an amino substituent or a diol on the $R_1$ group. An amino group introduced in this manner may be functionalized as described above, if desired.

Functional groups can also be installed at $R_1$ using a variety of other known methods. See, for example, U.S. Pat. No. 4,689,338 (Gerster), U.S. Pat. No. 4,929,624 (Gerster et al.), U.S. Pat. No. 5,268,376 (Gerster), U.S. Pat. No. 5,389,640 (Gerster et al.), U.S. Pat. No. 6,331,539 (Crooks et al.), U.S. Pat. No. 6,451,810 (Coleman et al.), U.S. Pat. No. 6,541,485 (Crooks et al.), U.S. Pat. No. 6,660,747 (Crooks et al.), U.S. Pat. No. 6,670,372 (Charles et al.), U.S. Pat. No. 6,683,088 (Crooks et al.), U.S. Pat. No. 6,656,938 (Crooks et al.), U.S. Pat. No. 6,664,264 (Dellaria et al.), U.S. Pat. No. 6,677,349 (Griesgraber), and U.S. Pat. No. 6,664,260 (Charles et al.).

Synthetic transformations can be made at $R_2$ if, for example, the acid chloride used in step (7) of Reaction Scheme I contains a protected hydroxy or amino group. Several acid chlorides of this type, for example acetoxyacetyl chloride, are commercially available. Others can be prepared by known synthetic methods. In addition, a methoxyalkylenyl group at $R_2$ is conveniently converted to a hydroxyalkylenyl group using conventional methods. The demethylation can be carried out by treating a compound of Formula II wherein $R_2$ is a methoxyalkylenyl group with boron tribromide in a suitable solvent such as dichloromethane at a sub-ambient temperature such as 0° C. For other examples of synthetic elaborations of an $R_2$ group, see U.S. Pat. No. 5,389,640 (Gerster et al.).

Functional group transformations in an $R_3$ group are also possible using known synthetic methods. For example, a 1H-imidazo[4,5-c]quinoline of Formula IX in which $R_3$ is —Z—C(O)OH and Z is as defined above, can be converted to an amide of Formula IX in which $R_3$ is —Z—C(O)—N($R_8$)—$R_4$,

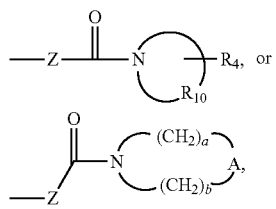

wherein Z, $R_{10}$, $R_8$, $R_4$, a, b, and A are as defined above, using a coupling reagent. The reaction is conveniently carried out by treating a solution of the 1H-imidazo[4,5-c]quinoline of Formula IX, in which $R_3$ is —Z—C(O)OH, with a secondary amine and 1-[3-(dimethylamino)propyl-3-ethylcarbodiimide hydrochloride. The reaction can be carried out at ambient temperature in a suitable solvent such as pyridine, and the product can be treated according to steps (10) and (11) of Reaction Scheme I to provide a compound of Formula II.

In another example, an $R_3$ group in a compound of Formula IX may contain a —S-functional group, which can be oxidized to —$S(O)_2$— in step (10) of Reaction Scheme I using an excess of the oxidizing agent. Step (11) of Reaction Scheme I may then be carried out to provide a compound of Formula II, wherein $R_3$ contains a —$S(O)_2$— functional group.

For some embodiments, compounds of the invention can be prepared according to Reaction Scheme III, where R, $R_1$, $R_2$, $R_8$, and n are defined as above; Z is selected from the group consisting of alkylene, alkenylene, and alkynylene wherein alkylene, alkenylene, and alkynylene can be optionally interrupted with one or more —O— groups; and $R_{3a}$ is —Z—N($R_8$)-Q-$R_4$ or —Z—$R_5$, wherein $R_5$ is

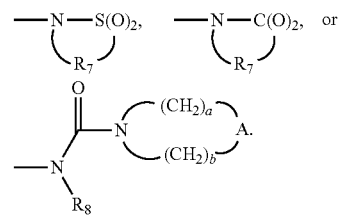

In step (1) of Reaction Scheme III, the amine of an amino alcohol of Formula XXVII is protected with a tert-butoxy carbonyl (Boc) group to provide a hydroxyalkylcarbamate of Formula XXVIII. Numerous amino alcohols of Formula XXVII are commercially available; others can be prepared using known synthetic methods. The reaction is conveniently carried out by treating the amino alcohol of Formula XXVII with di-tert-butyl dicarbonate in the presence of a base such as aqueous sodium hydroxide. The reaction can be run at ambient temperature in a suitable solvent such as tetrahydrofuran, and the product can be isolated using conventional methods.

In step (2) of Reaction Scheme III, a hydroxyalkylcarbamate of Formula XXVIII is converted to an iodoalkylcarbamate of Formula XXIX using conventional methods. The reaction is conveniently carried out by treating the hydroxyalkylcarbamate of Formula XXVIII with a solution of iodine, triphenylphosphine, and imidazole. The reaction can be run at ambient temperature in a suitable solvent such as dichloromethane, and the product can be isolated using conventional methods.

In step (3) of Reaction Scheme III, a 1H-imidazo[4,5-c]quinolinol of Formula XXIII is treated with an iodoalkylcarbamate of Formula XXIX to provide an ether-substituted 1H-imidazo[4,5-c]quinoline of Formula XXX. The reaction can be carried out according to the Williamson conditions described in step (9) of Reaction Scheme I, and the product can be isolated using conventional methods.

In steps (4) and (5) of Reaction Scheme III, a 1H-imidazo[4,5-c]quinoline of Formula XXX is oxidized to a 1H-imidazo[4,5-c]quinoline-5N-oxide of Formula XXXI, which is aminated to provide a 1H-imidazo[4,5-c]quinolin-4-amine of Formula XXXII, which is a subgenus Formula VII. Steps (4) and (5) of Reaction Scheme III can be carried out as described for steps (10) and (11), respectively, of Reaction Scheme I. In step (5), the preferred conditions for amination are the activation of an N-oxide of Formula XXXI by conversion to an ester and then reacting the ester with an aminating agent. Step (5) is conveniently carried out by adding ammonium hydroxide to a solution of the N-oxide of Formula XXXI in a suitable solvent such as dichloromethane and then adding p-toluenesulfonyl chloride and stirring at ambient temperature. The product or pharmaceutically acceptable salt thereof can be isolated using conventional methods.

In step (6) of Reaction Scheme III, the Boc protecting group of a 1H-imidazo[4,5-c]quinolin-4-amine of Formula XXXII is removed to provide an amino-substituted 1H-imidazo[4,5-c]quinolin-4-amine of Formula XXXIII, which is a subgenus of Formula VIII. The reaction is conveniently carried out by adding a solution of hydrochloric acid in ethanol to the 1H-imidazo[4,5-c]quinolin-4-amine of Formula XXXII. The reaction can be carried out at an elevated temperature, for example, the reflux temperature of the solvent. The product or pharmaceutically acceptable salt thereof can be isolated by conventional methods.

In step (7) of Reaction Scheme III, an amino-substituted 1H-imidazo[4,5-c]quinolin-4-amine of Formula XXXIII is converted to a 1H-imidazo[4,5-c]quinolin-1-yl compound of Formula IId, a subgenus of Formulas I and II, using conventional methods. For example, an amino-substituted 1H-imidazo[4,5-c]quinolin-4-amine of Formula XXXIII can react with an acid chloride of Formula $R_4C(O)Cl$ to provide a compound of Formula IId in which $R_{3a}$ is —Z—N($R_8$)—C(O)—$R_4$. In addition, a 1H-imidazo[4,5-c]quinolin-4-amine of Formula XXXIII can react with sulfonyl chloride of Formula $R_4S(O)_2Cl$ or a sulfonic anhydride of Formula $(R_4S(O)_2)_2O$ to provide a compound of Formula IId in which $R_{3a}$ is —Z—N($R_8$)—S(O)$_2$—$R_4$. Numerous acid chlorides of Formula $R_4C(O)Cl$, sulfonyl chlorides of Formula $R_4S(O)_2Cl$, and sulfonic anhydrides of Formula $(R_4S(O)_2)_2O$ are commercially available; others can be readily prepared using known synthetic methods. The reaction is conveniently carried out by adding the acid chloride of Formula $R_4C(O)Cl$, sulfonyl chloride of Formula $R_4S(O)_2Cl$, or sulfonic anhydride of Formula $(R_4S(O)_2)_2O$ to a solution of the amino-substituted 1H-imidazo[4,5-c]quinolin-4-amine of Formula XXXIII in a suitable solvent such as chloroform, dichloromethane, or 1-methyl-2-pyrrolidinone. Optionally a base such as triethylamine can be added. The reaction can be carried out at ambient temperature or a sub-ambient temperature such as 0° C. The product or pharmaceutically acceptable salt thereof can be isolated using conventional methods.

Amides of Formula IId can alternatively be prepared by treating an amino-substituted 1H-imidazo[4,5-c]quinolin-4-amine of Formula XXXIII with a carboxylic acid of Formula $R_4C(O)OH$ in the presence of a coupling reagent. The reaction is conveniently carried out by adding a solution of a carboxylic acid of Formula $R_4C(O)OH$ and a base such as triethylamine to a cooled solution of the amino-substituted 1H-imidazo[4,5-c]quinolin-4-amine of Formula XXXIII and benzotriazol-1-yloxytris(dimethylamino)phosphonium hexafluorophosphate. The reaction can be carried out in a suitable solvent such as dichloromethane at a sub-ambient temperature such as 0° C. The product or pharmaceutically acceptable salt thereof can be isolated using conventional methods.

Compounds of Formula IId where $R_{3a}$ is —Z—$R_5$ and $R_5$ is

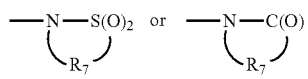

can be prepared by treating an amino-substituted 1H-imidazo[4,5-c]quinolin-4-amine of Formula XXXIII, wherein $R_8$ is hydrogen, with a chloroalkanesulfonyl chloride of Formula Cl—$R_7S(O)_2Cl$ or a chloroalkanoyl chloride of Formula Cl—$R_7C(O)Cl$. The reaction is conveniently carried out by adding the chloroalkanesulfonyl chloride or chloroalkanoyl chloride to a solution of the amino-substituted 1H-imidazo[4,5-c]quinolin-4-amine of Formula XXXIII in a suitable solvent such as chloroform at ambient temperature. The isolable intermediate chloroalkanesulfonamide or chloroalkanamide can then be treated with a base such as 1,8-diazabicyclo[5.4.0]undec-7-ene in a suitable solvent such as DMF to effect the cyclization. The product or pharmaceutically acceptable salt thereof can be isolated using conventional methods.

Ureas of Formula IId, where $R_{3a}$ is —Z—N($R_8$)-Q-$R_4$, Q is —C($R_6$)—N($R_8$)—W—, $R_6$ is =O, $R_8$ is as defined above, and W is a bond, can be prepared by reacting an amino-substituted 1H-imidazo[4,5-c]quinolin-4-amine of Formula XXXIII with isocyanates of Formula $R_4N$=C=O. Numerous isocyanates of Formula $R_4N$=C=O are commercially available; others can be readily prepared using known synthetic methods. The reaction can be conveniently carried out by adding the isocyanate of Formula $R_4N$=C=O to a solution of the amino-substituted 1H-imidazo[4,5-c]quinolin-4-amine of Formula XXXIII in a suitable solvent such as dichloromethane or chloroform. Optionally a base such as triethylamine can be added. The reaction can be carried out at ambient temperature or a sub-ambient temperature such as 0° C. Alternatively, a compound of Formula XXXIII can be treated with an isocyanate of Formula $R_4$(CO)N=C=O, a thioisocyanate of Formula $R_4N$=C=S, a sulfonyl isocyanate of Formula $R_4S(O)_2N$=C=O, or a carbamoyl chloride of Formula $R_4N$—($R_8$)—C(O)Cl or

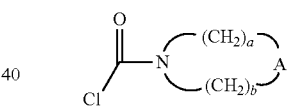

to provide a compound of Formula IId, where $R_{3a}$ is —Z—N($R_8$)-Q-$R_4$ or

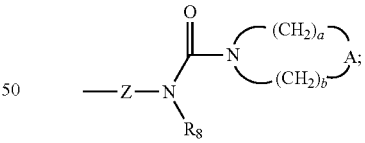

wherein $R_4$, A, Z, a, and b are defined as above and Q is —C($R_6$)—N($R_8$)—W—, where $R_6$, $R_8$, and W are defined as above. The product or pharmaceutically acceptable salt thereof can be isolated using conventional methods.

Sulfamides of Formula IId, where $R_{3a}$ is —Z—N($R_8$)-Q-$R_4$, Q is —S(O)$_2$—N($R_8$)—, and Z, $R_4$, and $R_8$ are as defined above, can be prepared by reacting a compound of Formula XXXIII with sulfuryl chloride to generate a sulfamoyl chloride in situ, and then reacting the sulfamoyl chloride with an amine of formula HN($R_8$)$R_4$. Alternatively, sulfamides of Formula IId can be prepared by reacting a compound of Formula XXXIII with a sulfamoyl chloride of formula $R_4(R_8)N$—S(O)$_2Cl$. The product or a pharmaceutically acceptable salt thereof can be isolated using conventional methods. Many amines of Formula $HN(R_8)R_4$ and some sulfamoyl chlorides of formula $R_4(R_8)N—S(O)_2Cl$ are commercially available; others can be prepared using known synthetic methods. The product or pharmaceutically acceptable salt thereof can be isolated using conventional methods.

Compounds of Formula IId, wherein $R_{3a}$ is —Z—N($R_8$)—$R_4$, and Z, $R_4$, and $R_8$ are as defined above, can be prepared by reductive alkylation of the amino-substituted 1H-imidazo[4,5-c]quinolin-4-amine of Formula XXXIII, wherein $R_8$ is hydrogen. The alkylation is conveniently carried out in two parts by (i) adding an aldehyde or ketone to a solution of a amino-substituted 1H-imidazo[4,5-c]quinolin-4-amine of Formula XXXIII or a salt thereof in a suitable solvent such as DMF in the presence of a base such as N,N-diisopropylethylamine. In part (ii) the reduction is carried out by adding a suitable reducing agent such as the borane-pyridine complex. Both part (i) and part (ii) can be carried out at ambient temperature, and the product or pharmaceutically acceptable salt thereof can be isolated using conventional methods. In compounds of Formula XXXIII, wherein $R_8$ is hydrogen, it is convenient to carry out the reductive alkylation followed by reaction with an acid chloride, sulfonyl chloride, sulfonic anhydride, isocyanate, or carbamoyl chloride as described above to provide a compound of Formula IId, wherein $R_{3a}$ is —Z—N($R_8$)-Q-$R_4$, wherein Z, $R_4$, $R_8$, and Q are as defined above.

Compounds of the invention can be prepared according to Reaction Scheme IV, where R, $R_1$, $R_2$, $R_{10}$, and n are as defined above; $Z_a$ is selected from the group consisting of a bond, alkylene, alkenylene, and alkynylene wherein alkylene, alkenylene, and alkynylene can be optionally interrupted with one or more —O— groups; $R_{3b}$ is

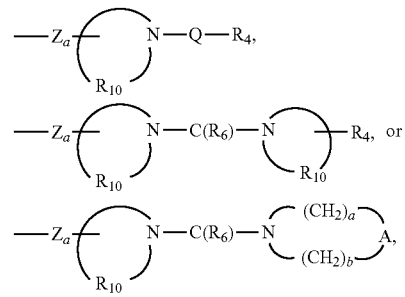

wherein $R_4$, $R_6$, A, Q, a, and b are as defined above. Steps (1) through (7) of Reaction Scheme IV can be run as described in steps (1) through (7) of Reaction Scheme III to provide compounds of Formula IIe, a subgenus of Formulas I and II.

Reaction Scheme III

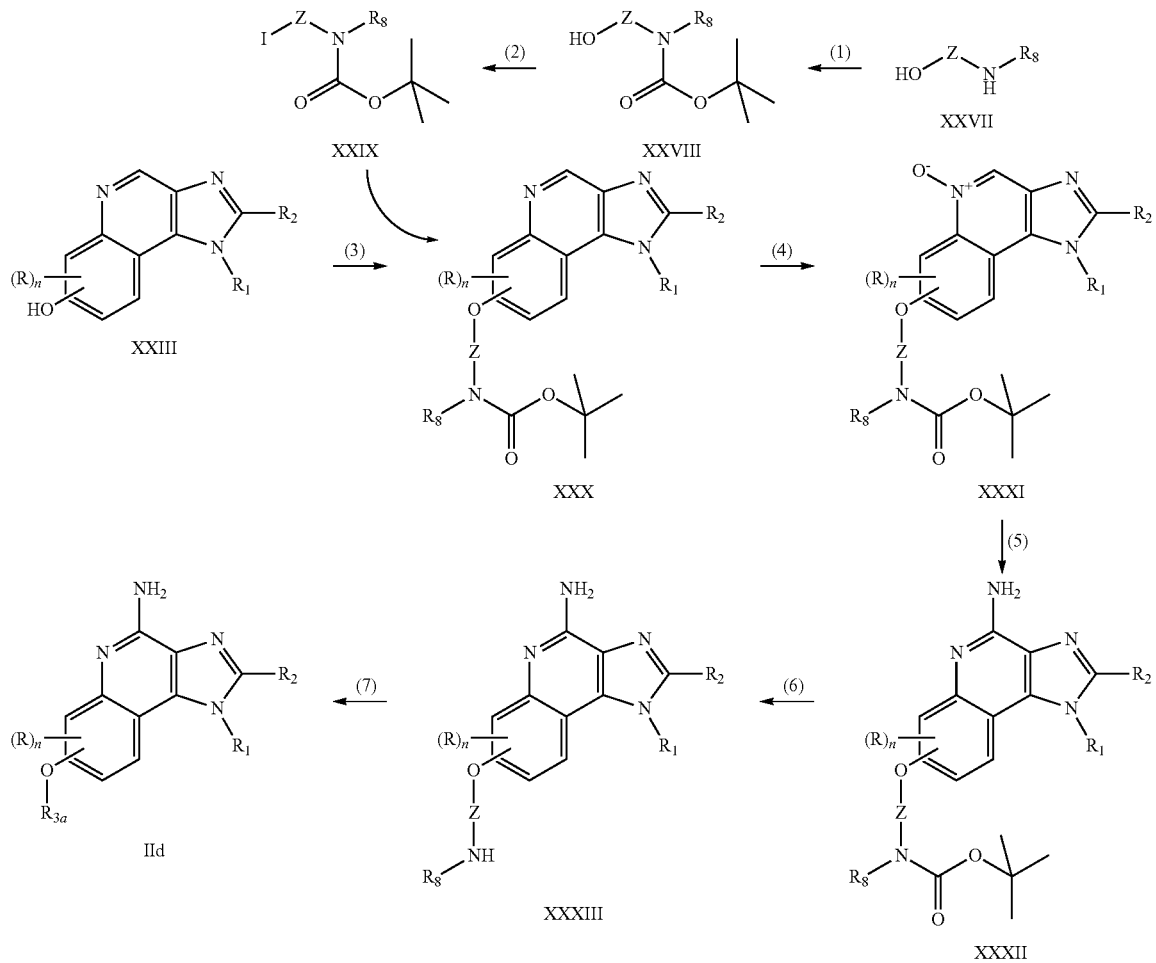

Alternatively, a compound of Formula XXXV can react with a 1H-imidazo[4,5-c]quinolinol of Formula XXIII under the Mitsunobu reaction conditions described in step (9) of Reaction Scheme I. For example, combining a 1H-imidazo[4,5-c]quinolinol of Formula XXIII, triphenylphosphine, and tert-butyl 4-hydroxy-1-piperdinecarboxylate in THF at 5° C. or ambient temperature and slowly adding diisopropyl azodicarboxylate provides a compound of Formula XXXVII wherein $Z_a$ is a bond and $R_{10}$ is pentylene.

The oxidation in step (4) of Reaction Scheme IV can be carried out according to the reaction conditions described in step (10) of Reaction Scheme I or by heating a solution of a compound of Formula XXXVII in a suitable solvent such as ethyl acetate with peracetic acid at a temperature such as 50° C. and then adding sodium metabisulfate. The product can be isolated using conventional methods. Steps (5) through (7) of Reaction Scheme IV can then be used to provide a compound of Formula IIe.

Compounds of the invention can also be prepared according to Reaction Scheme V, wherein R, $R_1$, $R_2$, and n are as defined above; Z is selected from the group consisting of alkylene, alkenylene, and alkynylene wherein alkylene, alkenylene, and alkynylene can be optionally interrupted with one or more —O— groups; and $R_{3c}$ is —Z-Het, —Z-Het'-$R_4$, or —Z-Het'-Y—$R_4$, wherein Het or Het' is attached to Z at a nitrogen atom.

In step (1) of Reaction Scheme V, a 1H-imidazo[4,5-c]quinolinol of Formula XXVI is treated with a dihalide of Formula I—Z—Cl or Br—Z—Cl using the Williamson conditions described in step (9) of Reaction Scheme I to provide a chloro-substituted compound of Formula XLI, a subgenus of Formulas I and II. The product or pharmaceutically acceptable salt thereof can be isolated using conventional methods.

In step (2) of Reaction Scheme V, a chloro-substituted compound of Formula XLI is treated with a cyclic secondary Reaction Scheme IV

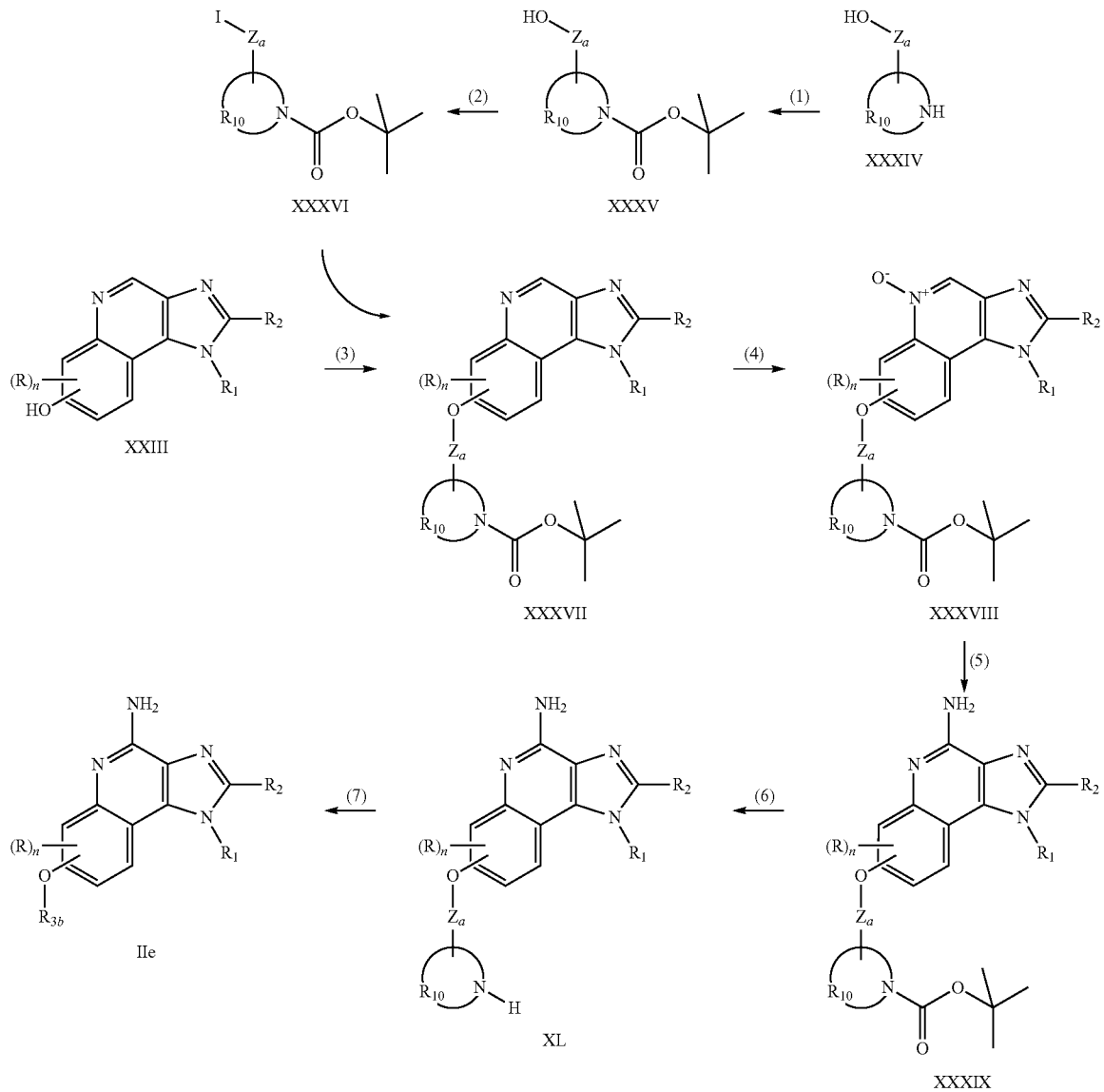

amine to provide a compound of Formula IIf, a subgenus of Formulas I and II. Many cyclic secondary amines are commercially available, such as unsubstituted or substituted aziridines, pyrrolidines, piperidines, morpholines, thiazolidines, thiomorpholines, piperazines, azepanes, diazepanes, dihydroisoquinolines, octahydroisoquinolines, dihydroquinolines, octahydroquinolines, and dihydroimidazoles; others can be prepared using conventional methods. The reaction is conveniently carried out by adding a cyclic secondary amine to a compound of Formula XLI in a suitable solvent such as DMF. The reaction is conveniently carried out in the presence of a base such as potassium carbonate at an elevated temperature such as 65° C. The product of Formula IIf or a pharmaceutically acceptable salt thereof can be isolated by conventional methods.

Compounds of Formula IIf are also prepared from 1H-imidazo[4,5-c]quinolinols of Formula XXIII, shown in Reaction Scheme I. A 1H-imidazo[4,5-c]quinolinol of Formula XXIII is first treated with a dihalide of Formula I—Z—Cl or Br—Z—Cl according to step (1) of Reaction Scheme V. The product is then oxidized and aminated according to the methods described in steps (10) and (11) of Reaction Scheme I to provide a compound of Formula XLI, which is then treated with a cyclic secondary amine as described in step (2) of Reaction Scheme V to provide a compound of Formula IIf. The product or pharmaceutically acceptable salt thereof can be isolated by conventional methods.

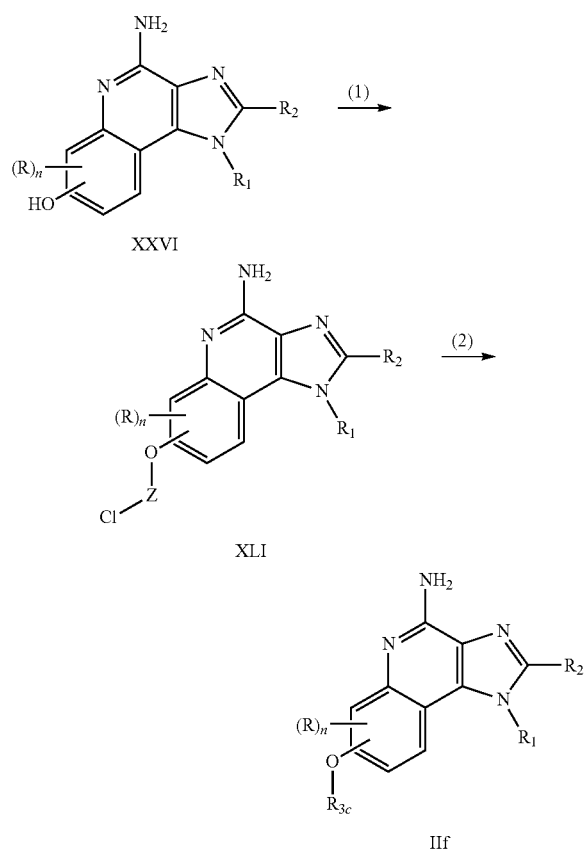

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce or inhibit the production of certain cytokines in experiments performed according to the tests set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5, and IL-13 may be inhibited upon administration of the compounds or salts.

Other cytokines whose production may be inhibited by the administration of compounds or salts of the invention include tumor necrosis factor-α (TNF-α). Among other effects, inhibition of TNF-α production can provide prophylaxis or therapeutic treatment of TNF-α mediated diseases in animals, making the compounds or salt useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which IRMs identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such *chlamydia*, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, an IRM compound or salt of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Certain IRM compounds or salts of the present invention may be particularly helpful in individuals having compromised immune function. For example, certain compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

Objects and advantages of this invention are further illustrated by the following examples, but the particular materials and amounts thereof recited in these examples, as well as other conditions and details, should not be construed to unduly limit this invention.

EXAMPLES

Example 1

2-(4-Amino-1-(2-methylpropyl)-2-propyl-1H-imidazo[4,5-c]quinolin-7-yloxy)-1-phenylethanone

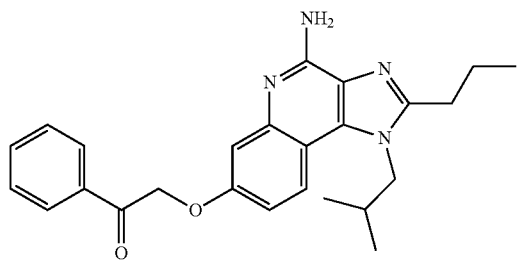 [SMILES: CCCc1nc2c(N)nc3cc(OCC(=O)c4ccccc4)ccc3c2n1CC(C)C]

Part A

A mixture of triethyl orthoformate (92 mL, 0.55 mol) and 2,2-dimethyl-[1,3]-dioxane-4,6-dione (75.3 g, 0.522 mol) (Meldrum's acid) was heated at 55° C. for 90 minutes and then cooled to 45° C. A solution of 3-benzyloxyaniline (100.2 g, 0.5029 mol) in methanol (200 mL) was slowly added to the reaction over a period 45 minutes while maintaining the reaction temperature below 50° C. The reaction was then heated at 45° C. for one hour, allowed to cool to room temperature, and stirred overnight. The reaction mixture was cooled to 1° C., and the product was isolated by filtration and washed with cold ethanol (~400 mL) until the filtrate was colorless. 5-{[(3-Benzyloxy)phenylimino]methyl}-2,2-dimethyl-[1,3]-dioxane-4,6-dione (170.65 g) was isolated as a tan, powdery solid.

$^1$H NMR (300 MHz, DMSO-d$_6$) δ 11.21 (d, J=14.2 Hz, 1H), 8.61 (d, J=14.2 Hz, 1H), 7.49-7.30 (m, 7H), 7.12 (dd, J=8.1, 1.96 Hz, 1H), 6.91 (dd, J=8.4, 2.1 Hz, 1H), 5.16 (s, 2H), 1.68 (s, 6H).

Part B

A mixture of 5-{[(3-benzyloxy)phenylimino]methyl}-2,2-dimethyl-[1,3]-dioxane-4,6-dione (170.65 g, 0.483 mol) and DOWTHERM A heat transfer fluid (800 mL) was heated to 100° C. and then slowly added to a flask containing DOWTHERM A heat transfer fluid (1.3 L, heated at 210° C.) over a period of 40 minutes. During the addition, the reaction temperature was not allowed to fall below 207° C. Following the addition, the reaction was stirred at 210° C. for one hour, and then allowed to cool to ambient temperature. A precipitate formed, which was isolated by filtration, washed with diethyl ether (1.7 L) and acetone (0.5 L), and dried in an oven to provide 76.5 g of 7-benzyloxyquinolin-4-ol as a tan powder.

$^1$H NMR (300 MHz, DMSO-d$_6$) δ 11.53 (s, 1H), 7.99 (dd, J=7.4, 2.4 Hz, 1H), 7.79 (d, J=7.4 Hz, 1H), 7.50-7.32 (m, 5H), 7.00 (s, 1H), 6.98 (dd, J=7.4, 2.5 Hz, 1H), 5.93 (d, J=7.5 Hz, 1H), 5.20 (s, 2H).

Part C

A mixture of 7-benzyloxyquinolin-4-ol (71.47 g, 0.2844 mol) and propionic acid (700 mL) was heated to 125° C. with vigorous stirring. Nitric acid (23.11 mL of 16 M) was slowly added over a period of 30 minutes while maintaining the reaction temperature between 121° C. and 125° C. After the addition, the reaction was stirred at 125° C. for 1 hour then allowed to cool to ambient temperature. The resulting solid was isolated by filtration, washed with water, and dried in an oven for 1.5 days to provide 69.13 g of 7-benzyloxy-3-nitroquinolin-4-ol as a grayish powder.

$^1$H NMR (300 MHz, DMSO-d$_6$) δ 12.77 (s, 1H), 9.12 (s, 1H), 8.17 (dd, J=6.3, 3.3 Hz, 1H), 7.51-7.33 (m, 5H), 7.21-7.17 (m, 2H), 5.25 (s, 2H).

Part D

N,N-Dimethylformamide (100 mL) (DMF) was cooled to 0° C., and phosphorous oxychloride (27.5 mL, 0.295 mol) was added dropwise. The resulting solution was stirred for 25 minutes and then added dropwise to a mixture of 7-benzyloxy-3-nitroquinolin-4-ol (72.87 g, 0.2459 mol) in DMF (400 mL). Following the addition, the reaction was heated at 100° C. for 5 minutes, cooled to ambient temperature, and poured into ice water with stirring. A tan precipitate formed, which was isolated by filtration and dissolved in dichloromethane. The resulting solution was dried over magnesium sulfate, filtered, and concentrated under reduced pressure to yield 72.9 g of 7-benzyloxy-4-chloro-3-nitroquinoline as a light brown solid.

$^1$H NMR (300 MHz, DMSO-d$_6$) δ 9.34 (s, 1H), 8.36 (d, J=8.7 Hz, 1H), 7.71 (d, J=2.4 Hz, 1H), 7.66 (dd, J=9.3, 2.4 Hz, 1H), 7.56-7.51 (m, 2H), 7.46-7.34 (m, 3H), 5.40 (s, 2H).

Part E

Triethylamine (38.6 mL, 0.277 mol) was added to a solution of 7-benzyloxy-4-chloro-3-nitroquinoline (72.9 g, 0.232 mol) in dichloromethane (1200 mL). Isobutylamine (25.24 mL, 0.2540 mol) was then added, and the reaction mixture was stirred for 18 hours at ambient temperature. The reaction mixture was diluted with dichloromethane, washed sequentially with water (2x) and brine, dried over anhydrous sodium sulfate, filtered, and concentrated under reduced pressure to yield 67.4 g of (7-benzyloxy-3-nitroquinolin-4-yl)(2-methylpropyl)amine as a brown solid.

$^1$H NMR (300 MHz, DMSO-d$_6$) δ 9.29 (t, J=4.8 Hz, 1H), 9.07 (s, 1H), 8.42 (d, J=9.4 Hz, 1H), 7.53-7.49 (m, 2H), 7.45-7.32 (m, 4H), 7.27 (dd, J=9.3, 2.6 Hz, 1H), 5.32 (s, 2H), 3.60 (t, J=6.0 Hz, 2H), 2.00 (septet, J=6.7 Hz, 1H), 0.96 (d, J=6.3 Hz, 6H).

Part F

Sodium borohydride (29.0 g, 0.767 mol) was added in small portions to a solution of nickel(II)chloride (22.8 g, 0.096 mol) in methanol (1.25 L). A solution of (7-benzyloxy-3-nitroquinolin-4-yl)(2-methylpropyl)amine (67.4 g, 0.192 mol) in methanol (300 mL) and dichloromethane (300 mL) was added to the resulting mixture. A precipitate was present and was dissolved by the addition of dichloromethane (500 mL). Additional sodium borohydride (~10 g) was added in small portions until the (7-benzyloxy-3-nitroquinolin-4-yl)(2-methylpropyl)amine was consumed. The reaction mixture was filtered through a layer of CELITE filter aid, and the filter cake was washed with 50:50 dichloromethane:methanol. The filtrate was concentrated under reduced pressure, and the black, oily residue was treated with water and dichloromethane. The organic solution was washed with water and brine, dried over magnesium sulfate, and filtered. The filtrate was treated with activated charcoal, filtered, and concentrated under reduced pressure to yield 55.4 g of 7-benzyloxy-$N^4$-(2-methylpropyl)quinoline-3,4-diamine a brown semi-solid.

$^1$H NMR (300 MHz, DMSO-$d_6$) δ 8.26 (s, 1H), 7.94 (d, J=9.4 Hz, 1H), 7.51-7.48 (m, 2H), 7.43-7.30 (m, 3H), 7.21 (d, J=3.2 Hz, 1H), 7.10 (dd, J=9.5, 2.4 Hz, 1H), 5.18 (s, 2H), 4.92 (t, J=7.0 Hz, 1H), 4.70 (s, 2H), 3.04 (t, J=6.9 Hz, 2H), 1.75 (septet, J=6.8 Hz, 1H), 0.89 (d, J=6.3 Hz, 6H).

Part G

Trimethyl orthobutyrate (29.75 mL, 0.1859 mol) was added in three portions to a solution of 7-benzyloxy-$N^4$-(2-methylpropyl)quinoline-3,4-diamine (54.6 g, 0.170 mol) in toluene (795 mL). Pyridine hydrochloride (1.96 g) was then added, and the reaction was heated at 105° C. and stirred for four hours. Additional trimethyl orthobutyrate (7 mL, 40 mmol) was then added, and the reaction was stirred for three hours. The reaction was allowed to cool to ambient temperature, and the solvent was removed under reduced pressure. The oily residue was treated with chloroform, which was removed under reduced pressure to remove residual toluene, and then again diluted with chloroform (1.2 L). The resulting solution was washed sequentially with 5% aqueous sodium bicarbonate, water, and brine; dried over magnesium sulfate; filtered; and concentrated under reduced pressure to yield 60.3 g of 7-benzyloxy-1-(2-methylpropyl)-2-propyl-1H-imidazo[4,5-c]quinoline as an oily brown solid, containing a small amount of toluene (0.93 equivalents).

$^1$H NMR (300 MHz, DMSO-$d_6$) δ 9.15 (s, 1H), 8.25 (d, J=8.8 Hz, 1H), 7.68 (d, J=2.6 Hz, 1H), 7.53-7.12 (m, 6H), 5.31 (s, 2H), 4.42 (d, J=7.5 Hz, 2H), 2.94 (t, J=7.5 Hz, 2H), 2.25-2.09 (m, 1H), 1.90 (sextet, J=7.4 Hz, 2H), 1.04 (t, J=7.5 Hz, 3H), 0.89 (d, J=6.3 Hz, 6H).

Part H

3-Chloroperoxybenzoic acid (60% pure, 22.9 g, 79.6 mmol) (mCPBA) was added in portions to a solution of 7-benzyloxy-1-(2-methylpropyl)-2-propyl-1H-imidazo[4,5-c]quinoline (27.0 g, 72.3 mmol) in dichloromethane (1 L), and the reaction was stirred for 30 minutes. Water (1 L) was added, and the resulting mixture was stirred for 30 minutes. The organic layer was washed with 1% aqueous sodium carbonate (2×200 mL), dried over magnesium sulfate, filtered, and concentrated under reduced pressure.

Part I

The material from Part H was dissolved in dichloromethane (800 mL), and concentrated ammonium hydroxide (300 mL) was added. p-Toluenesulfonyl chloride (16.6 g, 86.8 mmol) was added in small portions to the resulting mixture, and the reaction was stirred for 30 minutes and then diluted with water. The organic layer was dried over magnesium sulfate, filtered, and concentrated under reduced pressure. The crude product was recrystallized from acetonitrile to provide 21.4 g of 7-benzyloxy-1-(2-methylpropyl)-2-propyl-1H-imidazo[4,5-c]quinolin-4-amine as feathery, off-white crystals, mp 206.2-208.2° C.

$^1$H NMR (300 MHz, DMSO-$d_6$) δ 7.87 (d, J=9.1 Hz, 1H), 7.52-7.28 (m, 5H), 7.12 (d, J=2.4 Hz, 1H), 6.97 (dd, J=8.9, 2.8 Hz, 1H), 6.38 (s, 2H), 5.20 (s, 2H), 4.28 (d, J=6.8 Hz, 2H), 2.86 (t, J=7.5 Hz, 2H), 2.21-2.08 (m, 1H), 1.83 (sextet, J=7.3 Hz, 2H), 1.01 (t, J=7.5 Hz, 3H), 0.91 (d, J=7.0 Hz, 6H).

Part J

7-Benzyloxy-1-(2-methylpropyl)-2-propyl-1H-imidazo [4,5-c]quinolin-4-amine (21.4 g, 55.1 mmol) was dissolved in refluxing ethanol (2 L), and 10% palladium on carbon (5.4 g, 5.1 mmol) was added to the warm solution. The reaction was placed under hydrogen pressure (50 psi, 3.4×10$^5$ Pa) overnight. The catalyst was removed by filtration and washed with hot ethanol (500 mL) and methanol (400 mL). The filtrate was concentrated under reduced pressure to yield 14.5 g of an off-white solid. A small portion of the solid was recrystallized from 2-propanol to provide 4-amino-1-(2-methylpropyl)-2-propyl-1H-imidazo[4,5-c]quinolin-7-ol as white crystals, mp>265° C.

$^1$H NMR (300 MHz, DMSO-$d_6$) δ 9.44 (br s, 1H), 7.78 (d, J=8.9 Hz, 1H), 6.95 (d, J=2.5 Hz, 1H), 6.79 (dd, J=8.9, 2.6 Hz, 1H), 6.29 (br s, 2H), 4.26 (d, J=7.4 Hz, 2H), 2.84 (t, J=7.4 Hz, 2H), 2.14 (septet, J=6.7 Hz, 1H), 1.88-1.77 (m, 2H), 1.01 (t, J=7.3 Hz, 3H), 0.91 (d, J=6.6 Hz, 6H);

$^{13}$C NMR (75 MHz, DMSO-$d_6$) δ □□156.1, 152.3, 151.9, 146.9, 133.1, 126.5, 121.2, 111.9, 109.9, 108.4, 51.3, 28.8, 28.7, 21.0, 19.3, 13.9;

MS (APCI) m/z 299 (M+H)$^+$;

Anal. Calcd. for $C_{17}H_{22}N_4O$: % C, 68.43; % H, 7.43; % N, 18.78. Found: % C, 68.38; % H, 7.27; % N, 18.74.

Part K

A warm solution of 4-amino-1-(2-methylpropyl)-2-propyl-1H-imidazo[4,5-c]quinolin-7-ol (266 mg, 0.891 mmol) in DMF (20 mL) was cooled to approximately 0° C. Solid cesium carbonate (580 mg, 1.78 mmol) was added. After ten minutes, 2-bromoacetophenone (186 mg, 0.935 mmol) was added in one portion, and the reaction was allowed to warm to room temperature and was stirred overnight. An analysis by high-performance liquid chromatography (HPLC) indicated the presence of starting material. Additional 2-bromoacetophenone was added, and the reaction was stirred for six hours. The reaction was poured into deionized water (200-300 mL) and stirred for 15 hours. The resulting precipitate was isolated by filtration and purified by column chromatography on silica gel (eluting with chloroform:methanol ranging in ratios from 99.5:0.5 to 98:2). The product was then recrystallized from acetonitrile, isolated by filtration, and dried overnight under high vacuum to provide 222 mg of 2-(4-amino-1-(2-methylpropyl)-2-propyl-1H-imidazo[4,5-c]quinolin-7-yloxy)-1-phenylethanone as white crystals, mp 178.0-180.0° C.

$^1$H NMR (300 MHz, DMSO-$d_6$) δ 8.04-8.00 (m, 2H), 7.81 (d, J=9.1 Hz, 1H), 7.65-7.59 (m, 1H), 7.54-7.48 (m, 2H), 7.23 (d, J=2.7 Hz, 1H), 7.12 (dd, J=9.0, 2.7 Hz, 1H), 5.42 (s, 2H), 5.36 (br s, 2H), 4.20 (d, J=7.5 Hz, 2H), 2.86 (t, J=7.9 Hz, 2H), 2.34 (septet, J=6.8 Hz, 1H), 1.97-1.87 (m, 2H), 1.08 (t, J=7.4 Hz, 3H), 1.00 (d, J=6.7 Hz, 6H);

$^{13}$C NMR (75 MHz, DMSO-$d_6$) δ 193.7, 156.9, 153.1, 151.4, 146.3, 134.5, 133.8, 133.7, 128.8, 127.9, 125.7, 121.0, 113.4, 110.4, 108.5, 70.4, 52.4, 29.6, 29.0, 21.4, 19.7, 14.0;

MS (APCI) m/z 417 (M+H)$^+$;

Anal. Calcd. for $C_{25}H_{28}N_4O_2$: % C, 72.09; % H, 6.78; % N, 13.45. Found: % C, 71.89; % H, 6.58; % N, 13.24.

Example 2

8-(2-Aminoethoxy)-2-ethoxymethyl-1-propyl-1H-imidazo[4,5-c]quinolin-4-amine

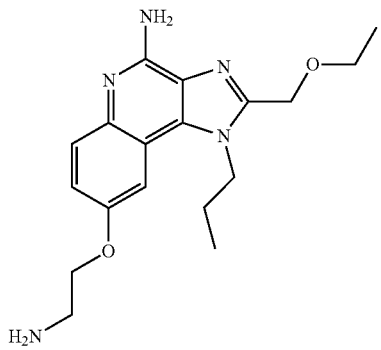 [SMILES: CCCn1c(COCC)nc2c(N)nc3ccc(OCCN)cc3c21]

Part A

The general procedure described in Part A of Example 1 was used with the following modification. A solution of 4-benzyloxyaniline (100 g, 0.5 mol) in methanol (150 mL) was used in lieu of a solution of 3-benzyloxyaniline. The addition of this solution was carried out over a period of one hour while maintaining the temperature between 57-60° C. The reaction product, 5-{[(4-benzyloxy)phenylimino)]methyl}-2,2-dimethyl-[1,3]-dioxane-4,6-dione (136.7 g) was isolated as a yellow powder.

$^1$H NMR (300 MHz, DMSO-$d_6$) δ 11.23 (d, J=15.2 Hz, 1H), 8.46 (d, J=14.3 Hz, 1H), 7.53-7.30 (m, 7H), 7.10-7.04 (m, 2H), 5.13 (s, 2H), 1.66 (s, 6H).

Part B

A solution of 5-{[(4-benzyloxy)phenylimino)]methyl}-2,2-dimethyl-[1,3]-dioxane-4,6-dione (127.2 g, 0.360 mol) and DOWTHERM A heat transfer fluid (500 mL) was heated to 100° C. and then slowly added to a flask containing DOWTHERM A heat transfer fluid (1 L, heated at 250° C.) over a period of 90 minutes. During the addition, the reaction temperature was not allowed to fall below 245° C. Following the addition, the reaction was stirred at 250° C. for 30 minutes, and then allowed to cool to ambient temperature. A precipitate formed, which was isolated by filtration, washed with diethyl ether (1 L) and acetone (250 mL), and dried for two hours under vacuum in to provide 65.7 g of 6-benzyloxyquinolin-4-ol as a yellow powder.

$^1$H NMR (300 MHz, DMSO-$d_6$) δ 11.72 (s, 1H), 7.84 (d, J=7.3 Hz, 1H), 7.59 (m, 8H), 5.98 (d, J=7.0 Hz, 1H), 5.18 (s, 2H).

Part C

The general method described in Part C of Example 1 was followed using 6-benzyloxyquinolin-4-ol (65.7 g, 0.261 mol) in lieu of 7-benzyloxyquinolin-4-ol. The reaction precipitate was isolated by filtration; washed with propionic acid (600 mL), isopropanol (500 mL) and diethyl ether (500 mL); and dried for two days under vacuum to provide 46.01 g of 6-benzyloxy-3-nitroquinolin-4-ol as a tan powder, containing 5% 6-benzyloxyquinolin-4-ol.

$^1$H NMR (300 MHz, DMSO-$d_6$) δ 12.98 (s, 1H), 9.12 (s, 1H), 7.75 (d, J=3.3 Hz, 1H), 7.70 (d, J=8.6 Hz, 1H), 7.53-7.30 (m, 6H), 5.25 (s, 2H).

Part D

The general method described in Part D of Example 1 was used to convert 6-benzyloxy-3-nitroquinolin-4-ol (46.93 g, 158.4 mmol) to 6-benzyloxy-4-chloro-3-nitroquinoline, which was isolated as a tan solid containing some DMF.

$^1$H NMR (500 MHz, DMSO-$d_6$) δ 9.23 (s, 1H), 8.16 (d, J=9.1 Hz, 1H), 7.80 (dd, J=9.1, 2.8 Hz, 1H), 7.76 (d, J=2.7 Hz, 1H), 7.57-7.53 (m, 2H), 7.45-7.34 (m, 3H), 5.39 (s, 2H).

Part E

Triethylamine (44 mL, 0.32 mol) was added to a solution of the material from Part D in dichloromethane (790 mL). n-Propylamine (19.48 mL, 237.0 mmol) was then added over a period of 25 minutes, and the reaction was stirred for 18 hours. The reaction mixture was diluted with dichloromethane (500 mL), washed sequentially with water and brine, dried over magnesium sulfate, filtered and concentrated under reduced pressure. The crude product was recrystallized from 2-propanol to provide 39.1 g of (6-benzyloxy-3-nitroquinolin-4-yl)propylamine as fine, yellowish-brown needles.

$^1$H NMR (300 MHz, DMSO-$d_6$) δ 8.89 (s, 1H), 8.57 (s, 1H), 7.93 (d, J=3.1 Hz, 1H), 7.85 (d, J=9.5 Hz, 1H), 7.58-7.33 (m, 6H), 5.30 (s, 2H), 3.41-3.35 (m, 2H), 1.67 (sextet, J=7.3 Hz, 2H), 0.87 (t, J=7.5 Hz, 3H).

Part F (6-Benzyloxy-3-nitroquinolin-4-yl)propylamine (18.00 g, 53.35 mmol), 5% platinum on carbon (5.3 g), toluene (200 mL) and 2-propanol (20 mL) were added to a Parr vessel. The vessel was purged with nitrogen and then placed under hydrogen pressure (30 psi, 2.1×10$^5$ Pa) and shaken for 20 minutes. The reaction mixture was filtered through a layer of CELITE filter aid, and the filter cake was washed with toluene (1 L) and 2-propanol (1 L). The orange filtrate was concentrated under reduced pressure. Heptane was added to the residue and subsequently removed under reduced pressure. The residue was dried under vacuum (0.1 torr, 13.3 Pa) for 30 minutes to provide 17.0 g of 6-benzyloxy-N$^4$-propylquinoline-3,4-diamine as a viscous, brown oil containing some toluene.

$^1$H NMR (300 MHz, DMSO-$d_6$) δ 8.23 (s, 1H), 7.64 (d, J=9.4 Hz, 1H), 7.52 (d, J=1.9 Hz, 1H), 7.43-7.11 (m, 5H), 7.05 (dd, J=9.4, 2.5 Hz, 1H), 5.22 (s, 2H), 4.99 (s, 2H), 4.62 (t, J=6.7 Hz, 1H), 2.99 (q, J=7.1 Hz, 2H), 1.47 (sextet, J=7.3 Hz, 2H), 0.85 (t, J=7.2 Hz, 3H).

Part G

A solution of ethoxyacetyl chloride (6.53 g, 53.3 mmol) in dichloromethane (65 mL) was added dropwise to a solution of the material from Part F in dichloromethane (200 mL), and the reaction was stirred for 16 hours. A precipitate formed and was isolated by filtration and washed with cold hexanes. The solid was dried for 30 minutes under reduced pressure to provide 16.1 g of N-(6-benzyloxy-4-propylaminoquinolin-3-yl)-2-ethoxyacetamide hydrochloride as a tan powder.

$^1$H NMR (300 MHz, DMSO-d$_6$) δ 14.14 (s, 1H), 9.74 (s, 1H), 8.56 (s, 1H), 8.43 (s, 1H), 8.06 (d, J=2.4 Hz, 1H), 7.89 (d, J=9.2 Hz, 1H), 7.68 (dd, J=9.4, 2.6 Hz, 1H), 7.56-7.35 (m, 5H), 5.30 (s, 2H), 4.11 (s, 2H), 3.64 (q, J=7.1 Hz, 2H), 3.68-3.60 (m, 2H), 1.61 (sextet, J=7.4 Hz, 2H), 1.23 (t, J=7.2 Hz, 3H), 0.89 (t, J=7.2 Hz, 3H).

Part H

Triethylamine (22.16 mL, 159.0 mmol) was added to a solution of N-(6-benzyloxy-4-propylaminoquinolin-3-yl)-2-ethoxyacetamide hydrochloride (16.1 g) in ethanol (265 mL), and the reaction mixture was heated at reflux and stirred for 3 hours. The reaction mixture was allowed to cool to ambient temperature. The ethanol was removed under reduced pressure and the residue dissolved in chloroform. The resulting solution was washed sequentially with water and brine, dried over magnesium sulfate, filtered and concentrated under reduced pressure. The resulting oil was dissolved in acetonitrile and concentrated under reduced pressure to yield 14.32 g of 8-benzyloxy-2-ethoxymethyl-1-propyl-1H-imidazo[4,5-c]quinoline as a brown, crystalline solid.

$^1$H NMR (300 MHz, DMSO-d$_6$) δ 9.03 (s, 1H), 8.09 (d, J=8.7 Hz, 1H), 7.64 (d, J=2.6 Hz, 1H), 7.54-7.33 (m, 6H), 5.38 (s, 2H), 4.83 (s, 2H), 4.59 (at, J=7.8 Hz, 2H), 3.57 (q, J=7.0 Hz, 2H), 1.84 (sextet, J=7.5 Hz, 2H), 1.16 (t, J=7.3 Hz, 3H), 0.96 (t, J=7.1 Hz, 3H).

Part I

8-Benzyloxy-2-ethoxymethyl-1-propyl-1H-imidazo[4,5-c]quinoline (15.00 g, 39.84 mmol) and ethanol (300 mL) were added to a Parr vessel. A mixture of palladium hydroxide (2.0 g, 20% on carbon) in ethanol (100 mL) was then added. The vessel was purged with nitrogen, placed under hydrogen pressure (25 psi, 1.7×10$^5$), and shaken for three hours. The vessel was then refilled with hydrogen (25 psi, 1.7×10$^5$) and shaken for 18 hours. The reaction mixture was filtered through a layer of CELITE filter aid, and the filter cake was washed with methanol (2 L). The filtrate was concentrated under reduced pressure, and the resulting orange oil was dissolved in toluene and concentrated under reduced pressure to provide 10.7 g of 2-ethoxymethyl-1-propyl-1H-imidazo[4,5-c]quinolin-8-ol as a granular, orange solid.

$^1$H NMR (300 MHz, DMSO-d$_6$) δ 10.11 (s, 1H), 8.94 (s, 1H), 7.99 (d, J=8.7 Hz, 1H), 7.54 (d, J=2.5 Hz, 1H), 7.24 (dd, J=8.8, 2.5 Hz, 1H), 4.82 (s, 2H), 4.51 (at, J=7.7 Hz, 2H), 3.57 (q, J=7.0 Hz, 2H), 1.91 (sextet, J=7.7 Hz, 2H), 1.16 (t, J=6.7 Hz, 3H), 1.06 (t, J=7.2 Hz, 3H).

Part J

A solution of di-tert-butyl dicarbonate (36.0 g, 0.165 mol) in tetrahydrofuran (THF) (80 mL) was added dropwise to a solution of 2-aminoethanol (10.0 g, 0.164 mol) in THF (50 mL) and 10% aqueous sodium hydroxide (66 mL), and the reaction was stirred for 16 hours. A precipitate formed. The THF was removed under reduced pressure, and 15% aqueous potassium hydrogen sulfate was slowly added to adjust the resulting mixture to pH 3. The mixture was then extracted with ethyl acetate (3×), and the combined extracts were washed sequentially with water and brine, dried over magnesium sulfate, filtered, and concentrated under reduced pressure to afford 23.6 g of tert-butyl 2-hydroxyethylcarbamate as a colorless oil containing some ethyl acetate.

Part K

Iodine (30.46 g, 0.120 mol) was added in three portions to a solution of triphenylphosphine (28.85 g, 0.110 mol) and imidazole (7.49 g, 0.110 mol) in dichloromethane (654 mL), and the reaction was stirred until the iodine dissolved. A solution of tert-butyl 2-hydroxyethylcarbamate (17.7 g, 0.110 mol) in dichloromethane (150 mL) was added over a period of 45 minutes, and the reaction was stirred for 16 hours at ambient temperature. The reaction mixture was poured into saturated aqueous sodium thiosulfate and stirred until the solution became colorless. The organic layer was washed sequentially with saturated aqueous sodium thiosulfate, water, and brine; dried over magnesium sulfate; filtered; and concentrated under reduced pressure. The resulting pale yellow oil was purified by column chromatography on silica gel (eluting with 80:20 hexanes:ethyl acetate) to provide a pale yellow oil which slowly crystallized to afford 24.6 g of tert-butyl 2-iodoethylcarbamate as a yellow solid.

Part L

Solid cesium carbonate (18.33 g, 56.22 mmol) was added to a solution of 2-ethoxymethyl-1-propyl-1H-imidazo[4,5-c]quinolin-8-ol (10.7 g, 37.5 mmol), prepared in Parts A-I, in DMF (185 mL). tert-Butyl 2-iodoethylcarbamate (11.17 g, 41.2 mmol), prepared in Parts J and K, was added, and the reaction mixture was heated at 65° C. for 18 hours. The solvent was removed under reduced pressure, and the residue was partitioned between dichloromethane and water. The organic fraction was washed with water (4×100 mL) and brine, dried over magnesium sulfate, filtered and concentrated under reduced pressure to provide a black oil. The oil was purified by column chromatography on silica gel (eluting with 98:2 dichloromethane:methanol) to yield 14.6 g of tert-butyl [2-(2-ethoxymethyl-1-propyl-1H-imidazo[4,5-c]quinolin-8-yloxy)ethyl]carbamate as a tan, waxy solid.

$^1$H NMR (300 MHz, DMSO-d$_6$) δ 9.02 (s, 1H), 8.07 (d, J=9.2 Hz, 1H), 7.57 (d, J=2.5 Hz, 1H), 7.36 (dd, J=8.9, 2.8 Hz, 1H), 7.10 (t, J=5.6 Hz, 1H), 4.84 (s, 2H), 4.64 (at, J=8.1 Hz, 2H), 4.21 (t, J=6.0 Hz, 2H), 3.57 (q, J=7.0 Hz, 2H), 3.41 (q, J=5.8 Hz, 2H), 1.93 (sextet, J=7.8 Hz, 2H), 1.39 (s, 9H), 1.16 (t, J=6.8 Hz, 3H), 1.04 (t, J=7.1 Hz, 3H).

Part M mCPBA (60% pure, 12.76 g, 44.36 mmol) was added in one portion to a solution of tert-butyl [2-(2-ethoxymethyl-1-propyl-1H-imidazo[4,5-c]quinolin-8-yloxy)ethyl]carbamate (14.4 g, 33.6 mmol) and chloroform (150 mL); the reaction mixture was stirred for 30 minutes. The reaction mixture was then poured into saturated aqueous sodium carbonate (100 mL) and stirred for 30 minutes. Chloroform (250 mL) was added, and the organic fraction was washed sequentially with 5% aqueous sodium carbonate, water, and brine; dried over magnesium sulfate; filtered; and concentrated under reduced pressure. The resulting red oil was triturated with ethyl acetate to provide 9.7 g of tert-butyl 2-[(2-ethoxymethyl-5-oxido-1-propyl-1H-imidazo[4,5-c]quinolin-8-yl)oxy]ethylcarbamate as a peach-colored powder.

$^1$H NMR (300 MHz, DMSO-d$_6$) δ 8.87 (s, 1H), 8.71 (d, J=9.3 Hz, 1H), 7.56 (d, J=2.7 Hz, 1H), 7.43 (dd, J=9.5, 2.3 Hz, 1H), 7.11 (t, J=5.6 Hz, 1H), 4.81 (s, 2H), 4.62 (at, J=7.8 Hz, 2H), 4.24 (t, J=5.6 Hz, 2H), 3.58 (q, J=6.9 Hz, 2H), 3.41 (q, J=5.8 Hz, 2H), 1.92 (sextet, J=7.6 Hz, 2H), 1.39 (s, 9H), 1.17 (t, J=6.8 Hz, 3H), 1.03 (t, J=7.6 Hz, 3H).

Part N

Ammonium hydroxide (50 mL) was added to a solution of tert-butyl 2-[(2-ethoxymethyl-5-oxido-1-propyl-1H-imidazo[4,5-c]quinolin-8-yl)oxy]ethylcarbamate (9.7 g, 22 mmol) in dichloromethane (120 mL), and the mixture was cooled to 10° C. p-Toluenesulfonyl chloride (4.16 g, 21.8 mmol) was added in small portions, while maintaining the reaction temperature below 15° C. The reaction was stirred for 16 hours; a tan precipitate formed. Dichloromethane (500 mL) was added, and the precipitate was isolated by filtration and washed with diethyl ether to provide 3.98 g of tert-butyl [2-(4-amino-2-ethoxymethyl-1-propyl-1H-imidazo[4,5-c]quinolin-8-yloxy)ethyl]carbamate as a fine powder. The organic layer was washed sequentially with ammonium hydroxide, water, and brine, dried over magnesium sulfate, filtered, and concentrated under reduced pressure. The resulting solid was recrystallized from acetonitrile to provide 4.4 g of tert-butyl 2-[(4-amino-2-ethoxymethyl-1-propyl-1H-imidazo[4,5-c]quinolin-8-yl)oxy]ethylcarbamate as a peach-colored powder.

$^1$H NMR (300 MHz, DMSO-d$_6$) δ 7.55 (d, J=8.8 Hz, 1H), 7.38 (d, J=2.6 Hz, 1H), 7.12 (dd, J=9.4, 2.5 Hz, 1H), 7.04 (t, J=5.3 Hz, 1H), 6.34 (s, 2H), 4.78 (s, 2H), 4.54 (at, J=7.9 Hz, 2H), 4.09 (t, J=5.9 Hz, 2H), 3.56 (q, J=7.1 Hz, 2H), 3.35 (q, J=5.8 Hz, 2H), 1.90 (sextet, J=7.7 Hz, 2H), 1.39 (s, 9H), 1.16 (t, J=6.9 Hz, 3H), 1.02 (t, J=7.3 Hz, 3H).

Part O

A solution of hydrogen chloride (55 mL of 1.2 M) in ethanol was added to tert-butyl 2-[(4-amino-2-ethoxymethyl-1-propyl-1H-imidazo[4,5-c]quinolin-8-yl)oxy]ethylcarbamate (3.98 g, 8.97 mmol), and the reaction was heated at reflux for one hour. The reaction mixture was allowed to cool to ambient temperature, and the solvent was removed under reduced pressure. The resulting yellow solid was dissolved in a small volume of water, and 10% aqueous sodium hydroxide was added to adjust to pH 13. The mixture was then extracted with dichloromethane (3×100 mL), and the combined extracts were washed sequentially with water and brine, dried over magnesium sulfate, and concentrated under reduced pressure. The resulting solid was recrystallized from acetonitrile to provide 2.63 g of 8-(2-aminoethoxy)-2-ethoxymethyl-1-propyl-1H-imidazo[4,5-c]quinolin-4-amine as fine, peach-colored needles, mp 157-159° C.

$^1$H NMR (300 MHz, DMSO-d$_6$) δ 7.55 (d, J=8.7 Hz, 1H), 7.39 (d, J=2.4 Hz, 1H), 7.14 (dd, J=9.2, 2.8 Hz, 1H), 6.32 (s, 2H), 4.77 (s, 2H), 4.55-4.50 (m, 2H), 4.04 (t, J=5.6 Hz, 2H), 3.56 (q, J=7.1 Hz, 2H), 2.94 (t, J=6.0 Hz, 2H), 1.91 (sextet, J=7.5 Hz, 2H), 1.59 (s, 2H), 1.16 (t, J=6.9 Hz, 3H), 1.04 (t, J=7.6 Hz, 3H);

$^{13}$C NMR (75 MHz, DMSO-d$_6$) δ 153.3, 150.5, 148.9, 140.0, 132.7, 127.6, 126.6, 117.1, 114.6, 102.3, 70.6, 65.3, 64.2, 46.8, 41.1, 23.3, 14.9, 10.8;

MS (APCI) m/z 344.2081 (344.2087 calcd for C$_{18}$H$_{25}$N$_5$O$_2$, M+H).

Anal. Calcd. for C$_{18}$H$_{25}$N$_5$O$_2$: % C, 62.95; % H, 7.34; % N, 20.39. Found: % C, 62.68; % H, 7.22; % N, 20.26.

Example 3

N-[2-(4-Amino-2-ethoxymethyl-1-propyl-1H-imidazo[4,5-c]quinolin-8-yloxy)ethyl]methanesulfonamide

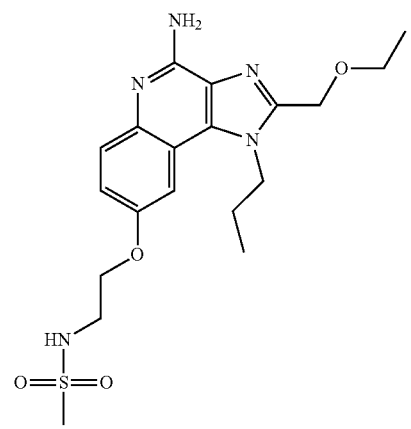 [SMILES: CCCn1c(COCC)nc2c(N)nc3ccc(OCCNS(C)(=O)=O)cc3c21]

Methanesulfonic anhydride (0.265 g, 1.52 mmol) was added in one portion to a solution of 8-(2-aminoethoxy)-2-ethoxymethyl-1-propyl-1H-imidazo[4,5-c]quinolin-4-amine (0.500 g, 1.46 mmol) in dichloromethane (10 mL), and the reaction was stirred for 30 minutes. A precipitate formed. Aqueous sodium hydroxide (25 mL of 10%) was added, and the mixture was stirred for 20 minutes. The aqueous layer was separated and extracted with dichloromethane. The combined organic fractions were washed sequentially with water and brine, dried over magnesium sulfate, filtered, and concentrated under reduced pressure. The resulting white solid was purified by column chromatography on silica gel (eluting with a dichloromethane:methanol ranging in ratios from 97:3 to 94:6) and then recrystallized from acetonitrile to yield 0.302 g of N-[2-(4-amino-2-ethoxymethyl-1-propyl-1H-imidazo[4,5-c]quinolin-8-yloxy)ethyl]methanesulfonamide as white, granular crystals, mp 178-179.5° C.

$^1$H NMR (300 MHz, DMSO-d$_6$) δ 7.57 (d, J=8.8 Hz, 1H), 7.39 (d, J=3.2 Hz, 1H), 7.33 (t, J=5.8 Hz, 1H), 7.15 (dd, J=9.2, 2.8 Hz, 1H), 6.36 (s, 2H), 4.77 (s, 2H), 4.56-4.51 (m, 2H), 4.17 (t, J=5.6 Hz, 2H), 3.56 (q, J=6.9 Hz, 2H), 3.40 (q, J=5.6 Hz, 2H), 2.98 (s, 3H), 1.91 (m, 2H), 1.16 (t, J=6.9 Hz, 3H), 1.03 (t, J=7.3 Hz, 3H);

$^{13}$C NMR (75 MHz, DMSO-d$_6$) δ 152.7, 150.6, 148.9, 140.1, 132.7, 127.6, 126.7, 117.0, 114.6, 102.6, 67.3, 65.3, 64.2, 46.7, 41.9, 23.3, 14.9, 10.8;

MS (APCI) m/z 422.1850 (422.1862 calcd for C$_{19}$H$_{27}$N$_5$O$_4$S, M+H).

Anal. Calcd. for C$_{19}$H$_{27}$N$_5$O$_4$S: % C, 54.14; % H, 6.46; % N, 16.61; % S, 7.61. Found: % C, 54.19; % H, 6.65; % N, 16.26; % S, 7.81.

Example 4

N-(2-{[4-Amino-2-(ethoxymethyl)-1-propyl-1H-imidazo[4,5-c]quinolin-8-yl]oxy}ethyl)morpholine-4-carboxamide

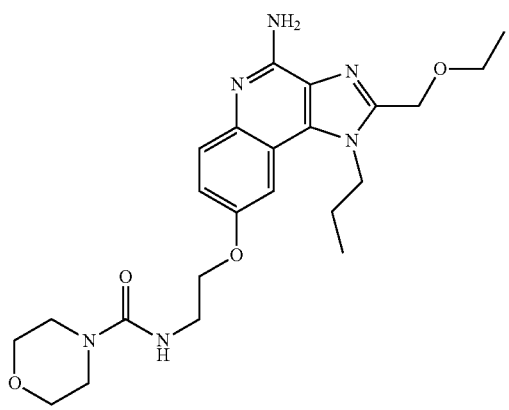 [SMILES: CCCn1c(COCC)nc2c(N)nc3ccc(OCCNC(=O)N4CCOCC4)cc3c21]

4-Morpholinecarbonyl chloride (0.177 mL, 1.52 mmol) was added dropwise to a solution of 8-(2-aminoethoxy)-2-ethoxymethyl-1-propyl-1H-imidazo[4,5-c]quinolin-4-amine (0.500 g, 1.46 mmol) in dichloromethane, and the reaction was stirred for ten minutes. Triethylamine (0.418 mL, 3.00 mmol) was then added, and the reaction was stirred for 16 hours. Aqueous sodium hydroxide (50%) was added, and the mixture was stirred for 30 minutes and then diluted with dichloromethane (100 mL). The organic layer was separated, washed sequentially with water and brine, dried over magnesium sulfate, filtered, and concentrated under reduced pressure. The residue was then treated with concentrated hydrochloric acid and water. A precipitate formed and was isolated by filtration, washed with water and diethyl ether, and dried in a vacuum oven at 60° C. to provide 0.180 g of N-(2-{[4-amino-2-(ethoxymethyl)-1-propyl-1H-imidazo[4,5-c]quinolin-8-yl]oxy}ethyl)morpholine-4-carboxamide hydrochloride as a white solid, mp 200-202° C. $^1$H NMR (300 MHz, DMSO-$d_6$) δ 13.47 (s, 1H), 8.71 (bs, 2H), 7.79 (d, J=9.4 Hz, 1H), 7.54 (d, J=2.5 Hz, 1H), 7.40 (dd, J=9.3, 2.5 Hz, 1H), 6.84 (t, J=5.4 Hz, 1H), 4.84 (s, 2H), 4.65 (t, J=7.8 Hz, 2H), 4.19 (t, J=6.1 Hz, 2H), 3.59 (q, J=7.0 Hz, 2H), 3.52 (t, J=4.7 Hz, 4H), 3.50-3.40 (m, 2H), 3.26 (t, J=4.9 Hz, 4H), 1.90 (sextet, J=7.4 Hz, 2H), 1.17 (t, J=7.2 Hz, 3H), 1.03 (t, J=7.3 Hz, 3H);

MS (APCI) m/z 457.2557 (457.2563 calcd for $C_{23}H_{32}N_6O_4$, M+H).

Anal. Calcd. for $C_{23}H_{32}N_6O_4 \cdot 1.0HCl \cdot 1.0H_2O$: % C, 54.06; % H, 6.90; % N, 16.45; % Cl, 6.94. Found: % C, 54.36; % H, 6.74; % N, 16.57; % Cl, 6.99.

The acidic filtrate was cooled to 0° C. and adjusted to pH 13 with the addition of 50% aqueous sodium hydroxide; the resulting opaque solution was extracted with dichloromethane. The combined extracts were washed with water and brine, dried over magnesium sulfate, and concentrated under reduced pressure. The resulting white solid was triturated with hot acetonitrile and isolated by filtration to yield 0.114 g of N-(2-{[4-amino-2-(ethoxymethyl)-1-propyl-1H-imidazo[4,5-c]quinolin-8-yl]oxy}ethyl)morpholine-4-carboxamide as a white powder, mp 203-208° C.

$^1$H NMR (300 MHz, DMSO-$d_6$) δ 7.55 (d, J=9.2 Hz, 1H), 7.41 (d, J=2.3 Hz, 1H), 7.14 (dd, J=9.2, 2.9 Hz, 1H), 6.79 (t, J=5.2 Hz, 1H), 6.33 (s, 2H), 4.77 (s, 2H), 4.57-4.52 (m, 2H), 4.12 (t, J=6.0 Hz, 2H), 3.59-3.42 (m, 7H), 3.28-3.24 (m, 5H), 1.97-1.81 (m, 2H), 1.16 (t, J=7.1 Hz, 3H), 1.02 (t, J=7.5 Hz, 3H).

Anal. Calcd. for $C_{23}H_{32}N_6O_4 \cdot 0.25H_2O$: % C, 59.92; % H, 7.11; % N, 18.23. Found: % C, 59.99; % H, 7.10; % N, 18.15.

Example 5

N-(2-{[4-Amino-2-(ethoxymethyl)-1-propyl-1H-imidazo[4,5-c]quinolin-8-yl]oxy}ethyl)-2-methylpropanamide hydrochloride

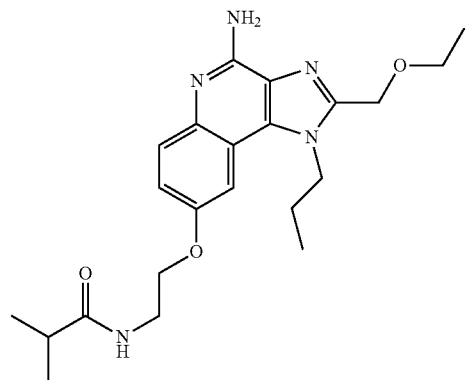 [SMILES: CCCn1c(COCC)nc2c(N)nc3ccc(OCCNC(=O)C(C)C)cc3c21]

Isobutyryl chloride (0.160 mL, 1.53 mmol) was added dropwise to a solution of 8-(2-aminoethoxy)-2-ethoxymethyl-1-propyl-1H-imidazo[4,5-c]quinolin-4-amine (0.500 g, 1.46 mmol) in dichloromethane (10 mL), and the reaction was stirred for 16 hours. A precipitate formed, and dichloromethane (10 mL) was added. The precipitate was isolated by filtration, washed with dichloromethane (20 mL) and diethyl ether (75 mL), and dried for one hour under reduced pressure to provide 0.511 g of N-(2-{[4-amino-2-(ethoxymethyl)-1-propyl-1H-imidazo[4,5-c]quinolin-8-yl]oxy}ethyl)-2-methylpropanamide hydrochloride as an off-white solid, mp 240-242° C.

$^1$H NMR (300 MHz, DMSO-$d_6$) δ 13.89 (s, 1H), 8.73 (bs, 2H), 8.06 (t, J=5.4 Hz, 1H), 7.79 (d, J=9.0 Hz, 1H), 7.51 (d, J=2.4 Hz, 1H), 7.40 (dd, J=8.9, 2.1 Hz, 1H), 4.84 (s, 2H), 4.67-4.61 (m, 2H), 4.18 (t, J=5.9 Hz, 2H), 3.59 (q, J=6.8 Hz, 2H), 3.48 (q, J=5.6 Hz, 2H), 2.41 (septet, J=6.9 Hz, 1H), 1.91 (sextet, J=7.3 Hz, 2H), 1.18 (t, J=6.8 Hz, 3H), 1.04 (t, J=7.4 Hz, 3H), 1.00 (d, J=6.9 Hz, 6H);

$^{13}$C NMR (75 MHz, DMSO-$d_6$) δ 176.5, 155.3, 152.1, 148.1, 134.9, 128.4, 124.7, 120.2, 119.3, 113.2, 104.2, 66.8, 65.6, 63.8, 47.1, 37.8, 33.9, 23.1, 19.5, 14.9, 10.6;

MS (APCI) m/z 414.2499 (414.2505 calcd for $C_{22}H_{31}N_5O_3$, M+H).

Anal. Calcd. for $C_{22}H_{31}N_5O_3 \cdot 1.0HCl$: % C, 58.72; % H, 7.17; % N, 15.56; % Cl, 7.88.

Found: % C, 58.51; % H, 7.40; % N, 15.56; % Cl, 7.88.

Example 6

N-(2-{[4-Amino-2-(ethoxymethyl)-1-propyl-1H-imidazo[4,5-c]quinolin-8-yl]oxy}ethyl)tetrahydro-furan-2-carboxamide

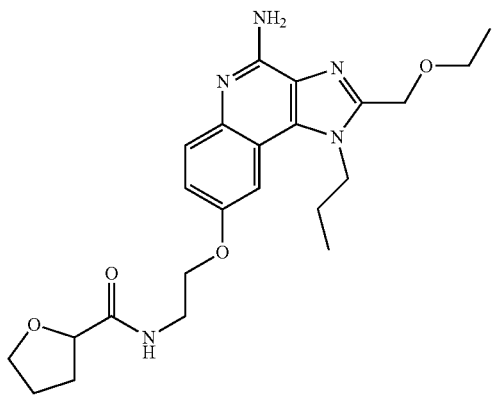 [SMILES: CCCn1c(COCC)nc2c(N)nc3ccc(OCCNC(=O)C4CCCO4)cc3c21]

A solution of 8-(2-aminoethoxy)-2-ethoxymethyl-1-propyl-1H-imidazo[4,5-c]quinolin-4-amine (0.500 g, 1.46 mmol) and benzotriazol-1-yloxytris(dimethylamino)phosphonium hexafluorophosphate (1.282 g, 2.90 mmol) in dichloromethane (15 mL) was cooled to 0° C. A solution of tetrahydro-2-furoic acid (0.168 g, 1.45 mmol) in dichloromethane (5 mL) and triethylamine (0.811 mL, 5.82 mmol) were sequentially added. The reaction was stirred at 0° C. for 30 minutes, allowed to warm to ambient temperature, stirred for two hours, and poured into water. The aqueous layer was extracted with dichloromethane. The combined organic fractions were washed sequentially with water (2×) and brine, dried over magnesium sulfate, filtered, and concentrated under reduced pressure. The residue was purified by column chromatography on silica gel (eluting with dichloromethane: methanol ranging in ratios from 99:1 to 96:4) to provide the desired product and a bis amide by-product. The bis amide by-product was treated with 1N aqueous hydrochloric acid, heated at reflux for 1.5 hours, and cooled to 0° C. The mixture was adjusted to pH 13 with the addition of 10% aqueous sodium hydroxide and extracted with dichloromethane. The combined extracts were washed with water and brine, dried over magnesium sulfate, filtered, and concentrated under reduced pressure to provide a yellow oil. The oil and the previously recovered amide were combined and recrystallized from acetonitrile to provide 0.220 g of N-(2-{[4-amino-2-(ethoxymethyl)-1-propyl-1H-imidazo[4,5-c]quinolin-8-yl]oxy}ethyl)tetrahydrofuran-2-carboxamide as a tan, crystalline solid, mp 202.5-204.5° C.

$^1$H NMR (300 MHz, DMSO-$d_6$) δ 7.96 (t, J=5.5 Hz, 1H), 7.55 (d, J=8.5 Hz, 1H), 7.39 (d, J=2.7 Hz, 1H), 7.13 (dd, J=9.3, 2.5 Hz, 1H), 6.34 (s, 2H), 4.77 (s, 2H), 4.56-4.51 (m, 2H), 4.25-4.21 (m, 1H), 4.14 (t, J=6.0 Hz, 2H), 3.91-3.84 (m, 1H), 3.79-3.72 (m, 1H), 3.56 (q, J=6.9 Hz, 2H), 3.54-3.48 (m, 2H), 2.17-2.05 (m, 1H), 1.96-1.69 (m, 5H), 1.16 (t, J=6.8 Hz, 3H), 1.02 (t, J=7.5 Hz, 3H);

$^{13}$C NMR (75 MHz, DMSO-$d_6$) δ 172.8, 152.9, 150.6, 148.9, 140.1, 132.7, 127.6, 126.7, 117.1, 114.6, 102.5, 77.7, 68.5, 66.2, 65.3, 64.2, 46.7, 37.7, 29.9, 24.8, 23.3, 14.9, 10.7;

MS (APCI) m/z 442.2459 (442.2454 calcd for $C_{23}H_{31}N_5O_4$, M+H).

Anal. Calcd. for $C_{23}H_{31}N_5O_4$: % C, 62.57; % H, 7.08; % N, 15.86. Found: % C, 62.47; % H, 7.14; % N, 15.91.

Example 7 tert-Butyl 3-{[4-amino-1-(2-methylpropyl)-2-propyl-1H-imidazo[4,5-c]quinolin-7-yl]oxy}propylcarbamate

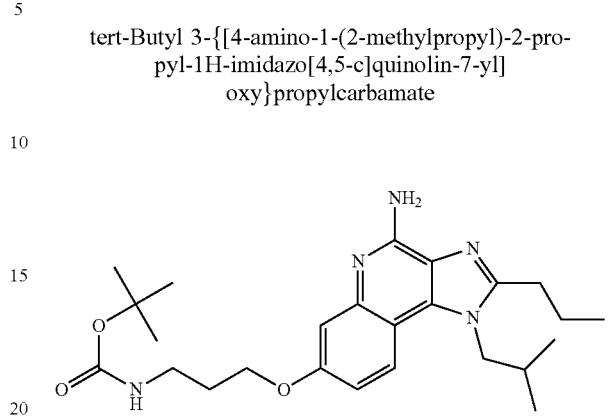

Part A

7-Benzyloxy-1-(2-methylpropyl)-2-propyl-1H-imidazo[4,5-c]quinoline (60.3 g, 0.188 mol), prepared as described in Parts A-G of Example 1, and 10% palladium on carbon (10 g) were mixed with ethanol (500 mL). Ammonium formate (101.53 g, 1.61 mol) and ethanol (500 mL) were then added, and the reaction mixture was heated at reflux for two hours. The mixture was allowed to cool to ambient temperature slowly and stirred overnight. The reaction mixture was filtered through a layer of CELITE filter aid, and the filter cake was washed with ethanol (1 L), methanol (2 L) and dichloromethane (2 L). The combined filtrates were concentrated under reduced pressure to provide a tan solid, which was triturated with cold ethanol and isolated by filtration to yield 30 g of 1-(2-methylpropyl)-2-propyl-1H-imidazo[4,5-c]quinolin-7-ol as a tan, granular solid.

$^1$H NMR (300 MHz, DMSO-$d_6$) δ 9.89 (s, 1H), 9.00 (s, 1H), 8.12 (d, J=9.3 Hz, 1H), 7.41 (d, J=2.5 Hz, 1H), 7.23 (dd, J=9.3, 2.5 Hz, 1H), 4.36 (d, J=7.4 Hz, 2H), 2.91 (t, J=7.5 Hz, 2H), 2.25-2.10 (m, 1H), 1.88 (sextet, J=7.4 Hz, 2H), 1.03 (t, J=7.5 Hz, 3H), 0.92 (d, J=7.1 Hz, 6H).

Part B

The general methods described in Parts J and K of Example 2 were used to prepare 16.2 g of tert-butyl 3-iodopropylcarbamate from 3-amino-1-propanol (6.55 g, 8.72 mmol); the product was isolated as a yellow solid.

Part C

A modification of the general method described in Part L of Example 2 was used to treat 1-(2-methylpropyl)-2-propyl-1H-imidazo[4,5-c]quinolin-7-ol with tert-butyl 3-iodopropylcarbamate. The reaction mixture was diluted with water; a precipitate formed. The precipitate was isolated by filtration, washed with water and then with diethyl ether until the filtrate was clear, and dried overnight in a vacuum oven at 60° C. to yield tert-butyl 3-{[1-(2-methylpropyl)-2-propyl-1H-imidazo[4,5-c]quinolin-7-yl]oxy}propylcarbamate as a tan powder.

$^1$H NMR (300 MHz, DMSO-$d_6$) δ 9.06 (s, 1H), 8.19 (d, J=9.3 Hz, 1H), 7.54 (d, J=2.6 Hz, 1H), 7.33 (dd, J=8.9, 2.9 Hz, 1H), 6.99-6.86 (m, 1H), 4.40 (d, J=8.0 Hz, 2H), 4.15 (t,

J=6.3 Hz, 2H), 3.14 (q, J=6.4 Hz, 2H), 2.92 (t, J=7.6 Hz, 2H), 2.27-2.09 (m, 1H), 1.98-1.80 (m, 4H), 1.38 (s, 9H), 1.04 (t, J=7.2 Hz, 3H), 0.92 (d, J=6.1 Hz, 6H).

Part D

The general methods described in Parts M and N of Example 2 were used to convert tert-butyl 3-{[1-(2-methylpropyl)-2-propyl-1H-imidazo[4,5-c]quinolin-7-yl]oxy}propylcarbamate to tert-butyl 3-{[4-amino-1-(2-methylpropyl)-2-propyl-1H-imidazo[4,5-c]quinolin-7-yl]oxy}propylcarbamate, which was isolated as off-white crystals, mp 162.5-164° C.

$^1$H NMR (300 MHz, DMSO-$d_6$) δ 7.86 (d, J=8.9 Hz, 1H), 7.04 (d, J=2.6 Hz, 1H), 6.94-6.88 (m, 1H), 6.89 (dd, J=9.2, 2.8, Hz, 1H), 6.36 (s, 2H), 4.28 (d, J=7.5 Hz, 2H), 4.04 (t, J=6.2 Hz, 2H), 3.11 (q, J=6.5 Hz, 2H), 2.86 (t, J=7.5 Hz, 2H), 2.2-2.09 (m, 1H), 1.91-1.77 (m, 4H), 1.38 (s, 9H), 1.01 (t, J=7.2 Hz, 3H), 0.91 (d, J=6.2 Hz, 6H);

MS (APCI) m/z 456.2960 (456.2975 calcd for $C_{25}H_{37}N_5O_3$, M+H).

Anal. Calcd. for $C_{25}H_{37}N_5O_3$: % C, 65.91; % H, 8.19; % N, 15.37. Found: % C, 65.65; % H, 8.18; % N, 15.19.

Example 8

7-(3-Aminopropoxy)-1-(2-methylpropyl)-2-propyl-1H-imidazo[4,5-c]quinolin-4-amine

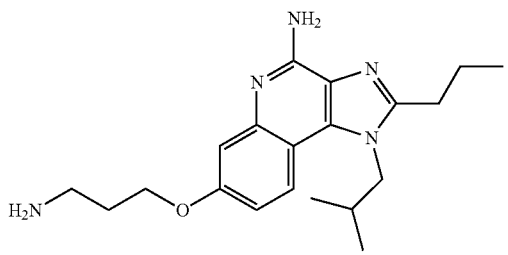 [SMILES: CCCc1nc2c(N)nc3cc(OCCCN)ccc3c2n1CC(C)C]

A modification of the general method described in Part O of Example 2 was used to deprotect tert-butyl 3-{[4-amino-1-(2-methylpropyl)-2-propyl-1H-imidazo[4, 5-c]quinolin-7-yl]oxy}propylcarbamate. A precipitate formed in the aqueous mixture at pH 13 and was isolated by filtration to provide 7-(3-aminopropoxy)-1-(2-methylpropyl)-2-propyl-1H-imidazo[4,5-c]quinolin-4-amine as a white solid, mp 173-174° C.

$^1$H NMR (300 MHz, DMSO-$d_6$) δ 7.85 (d, J=9.4 Hz, 1H), 7.06 (d, J=3.2 Hz, 1H), 6.89 (dd, J=8.8, 2.5 Hz, 1H), 6.35 (s, 2H), 4.28 (d, J=7.5 Hz, 2H), 4.10 (t, J=6.7 Hz, 2H), 2.86 (t, J=7.5 Hz, 2H), 2.72 (t, J=6.8 Hz, 2H), 2.2-2.08 (m, 1H), 1.90-1.77 (m, 4H), 1.6 (b s, 2H), 1.02 (t, J=7.6 Hz, 3H), 0.91 (d, J=6.8 Hz, 6H);

MS (APCI) m/z 356.2464 (356.2450 calcd for $C_{20}H_{29}N_5O$, M+H).

Anal. Calcd. for $C_{20}H_{29}N_5O$: % C, 67.58; % H, 8.22; % N, 19.70. Found: % C, 67.25; % H, 7.94; % N, 19.75.

Example 9 tert-Butyl 2-{[4-amino-2-methyl-1-(2-methylpropyl)-1H-imidazo[4,5-c]quinolin-7-yl]oxy}ethylcarbamate

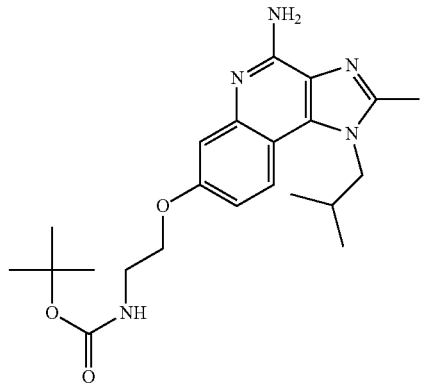 [SMILES: Cc1nc2c(N)nc3cc(OCCNC(=O)OC(C)(C)C)ccc3c2n1CC(C)C]

Part A

The preparation of 7-benzyloxy-$N^4$-(2-methylpropyl)quinoline-3,4-diamine is described in Parts A-F of Example 1. Under a nitrogen atmosphere, triethyl orthoacetate (4.59 mL, 25.0 mmol) was added to a solution of 7-benzyloxy-$N^4$-(2-methylpropyl)quinoline-3,4-diamine (8.05 g, 25.0 mmol) in xylenes (130 mL), and the resulting solution was heated at reflux (160° C.) overnight. The solvent volume was reduced to 70 mL using a Dean-Stark trap. Over a period of a few days, a precipitate formed. Diethyl ether was added, and the precipitate was isolated by filtration and washed with diethyl ether to provide 6.81 g of 7-benzyloxy-2-methyl-1-(2-methylpropyl)-1H-imidazo[4,5-c]quinoline as a light-brown powder.

Part B

The method described in Part J of Example 1 was used to convert 7-benzyloxy-2-methyl-1-(2-methylpropyl)-1H-imidazo[4,5-c]quinoline to 2-methyl-1-(2-methylpropyl)-1H-imidazo[4,5-c]quinolin-7-ol, which was obtained as a solid, mp>250° C.

$^1$H NMR (300 MHz, DMSO-$d_6$) δ 9.95 (s, 1H), 8.97 (s, 1H), 8.12 (d, J=9.2 Hz, 1H), 7.42 (d, J=2.6 Hz, 1H), 7.25 (dd, J=8.9, 2.8 Hz, 1H), 4.35 (d, J=7.6 Hz, 2H), 2.61 (s, 3H), 2.19 (septet, J=6.9 Hz, 1H), 0.94 (d, J=6.7 Hz, 6H);

MS (APCI) m/z 256.2 (256.3 calcd for $C_{15}H_{17}N_3O$, M+H).

Anal. Calcd. for $C_{15}H_{17}N_3O$: % C, 70.56; % H, 6.71; % N, 16.46. Found: % C, 70.33; % H, 6.66; % N, 16.35.

Part C tert-Butyl 2-iodoethylcarbamate (2.55 g, 9.41 mmol), prepared as described in Parts J and K of Example 2, was added to a mixture of 2-methyl-1-(2-methylpropyl)-1H-imidazo[4,5-c]quinolin-7-ol (2.00 g, 7.83 mmol) and cesium carbonate (3.83 g, 11.7 mmol) in DMF (30 mL), and the reaction was heated at 60° C. for four hours. The solvent was removed under reduced pressure, and the resulting solid was triturated with water and isolated by filtration to yield 2.57 g of tert-butyl 2-{[2-methyl-1-(2-methylpropyl)-1H-imidazo[4,5-c]quinolin-7-yl]oxy}ethylcarbamate as a light-brown solid.

$^1$H NMR (300 MHz, DMSO-$d_6$) δ 9.04 (s, 1H), 8.21 (d, J=9.2 Hz, 1H), 7.55 (d, J=2.9 Hz, 1H), 7.34 (dd, J=9.1, 2.8 Hz, 1H), 7.07-7.02 (m, 1H), 4.39 (d, J=8.0 Hz, 2H), 4.14 (t, J=5.5 Hz, 2H), 3.38 (q, J=5.9 Hz, 2H), 2.63 (s, 3H), 2.28-2.11 (m, 1H), 1.39 (s, 9H), 0.94 (d, J=6.4 Hz, 6H).

Part D

The general methods described in Parts M and N of Example 2 were followed using tert-butyl 2-{[2-methyl-1-(2-methylpropyl)-1H-imidazo[4,5-c]quinolin-7-yl]oxy}ethylcarbamate as the starting material. The crude product was recrystallized from ethanol to yield 1.29 g of tert-butyl 2-{[4-amino-2-methyl-1-(2-methylpropyl)-1H-imidazo[4,5-c]quinolin-7-yl]oxy}ethylcarbamate as a yellow-orange solid, mp 226.9-228.2° C.

$^1$H NMR (300 MHz, DMSO-$d_6$) δ 7.87 (d, J=8.8 Hz, 1H), 7.04 (d, J=2.5 Hz, 1H), 7.01 (t, J=5.9 Hz, 1H), 6.90 (dd, J=8.7, 2.5 Hz, 1H), 6.41 (s, 2H), 4.27 (d, J=7.6 Hz, 2H), 4.03 (t, J=5.9 Hz, 2H), 3.36-3.28 (m, 2H), 2.56 (s, 3H), 2.16 (m, 1H), 1.39 (s, 9H), 0.93 (d, J=6.9 Hz, 6H);

$^{13}$C NMR (75 MHz, DMSO-$d_6$) δ 157.0, 155.7, 151.9, 149.2, 146.5, 132.8, 125.0, 121.1, 111.4, 109.1, 108.2, 77.7, 66.1, 51.6, 28.8, 28.2, 19.2, 13.9;

MS (APCI) m/z 414.2507 (414.2505 calcd for $C_{21}H_{31}N_5O_3$, M+H).

Anal. Calcd. for $C_{21}H_{31}N_5O_3$: % C, 63.90; % H, 7.56; % N, 16.94. Found: % C, 63.74; % H, 7.41; % N, 16.80.

Example 10

7-(2-Aminoethoxy)-2-methyl-1-(2-methylpropyl)-1H-imidazo[4,5-c]quinolin-4-amine

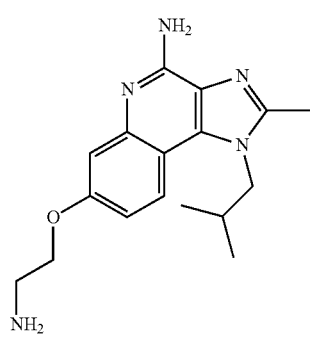 [SMILES: Cc1nc2c(N)nc3cc(OCCN)ccc3c2n1CC(C)C]

The general method described in Part O of Example 2 was used to convert tert-butyl 2-{[4-amino-2-methyl-1-(2-methylpropyl)-1H-imidazo[4,5-c]quinolin-7-yl]oxy}ethylcarbamate (1.29 g, 3.12 mmol) to 1.1 g of 7-(2-aminoethoxy)-2-methyl-1-(2-methylpropyl)-1H-imidazo[4,5-c]quinolin-4-amine, isolated as a white powder. The product was not recrystallized.

$^1$H NMR (300 MHz, DMSO-$d_6$) δ 7.86 (d, J=8.5 Hz, 1H), 7.05 (d, J=2.6 Hz, 1H), 6.91 (dd, J=9.4, 2.5 Hz, 1H), 6.40 (s, 2H), 4.27 (d, J=7.4 Hz, 2H), 4.00 (t, J=5.8 Hz, 2H), 2.92 (t, J=5.9 Hz, 2H), 2.56 (s, 3H), 2.23-2.09 (m, 1H), 1.94 (bs, 2H), 0.93 (d, J=7.1 Hz, 6H).

Example 11

N-{3-[4-Amino-1-(2-methylpropyl)-2-propyl-1H-imidazo[4,5-c]quinolin-7-yloxy]propyl}methanesulfonamide

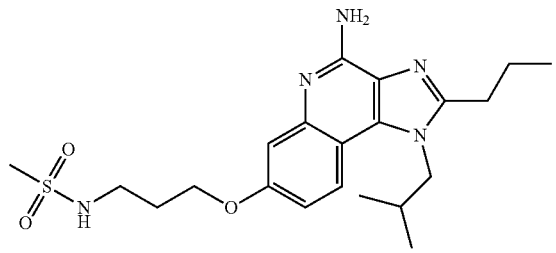 [SMILES: CCCc1nc2c(N)nc3cc(OCCCNS(C)(=O)=O)ccc3c2n1CC(C)C]

Methanesulfonic anhydride (0.245 g, 1.41 mmol) was added in one portion to a suspension of 7-(3-aminopropoxy)-1-(2-methylpropyl)-2-propyl-1H-imidazo[4,5-c]quinolin-4-amine (0.500 g, 1.41 mmol) in chloroform, and the reaction was stirred for 18 hours. Saturated aqueous sodium bicarbonate was added, and the reaction was stirred for 20 minutes. The aqueous layer was separated and extracted with chloroform. The combined organic fractions were washed with water and brine, dried over magnesium sulfate, filtered, and concentrated under reduced pressure. The resulting off-white solid was dissolved in concentrated hydrochloric acid; the solution was then cooled to 0° C. and adjusted to pH 13 with the addition of 50% aqueous sodium hydroxide. The opaque solution was extracted with dichloromethane. The extract was washed sequentially with water and brine, dried over magnesium sulfate, filtered and concentrated under reduced pressure. The resulting solid was recrystallized from acetonitrile to yield 0.160 g of N-{3-[4-amino-1-(2-methylpropyl)-2-propyl-1H-imidazo[4,5-c]quinolin-7-yloxy]propyl}methanesulfonamide as a flocculent, white solid, mp 166.5-168.5° C.

$^1$H NMR (300 MHz, DMSO-$d_6$) δ 7.86 (d, J=8.6 Hz, 1H), 7.085 (t, J=5.5 Hz, 1H), 7.06 (d, J=3.3 Hz, 1H), 6.91 (dd, J=8.7, 2.5 Hz, 1H), 6.37 (s, 2H), 4.29 (d, J=7.3 Hz, 2H), 4.11 (t, J=6.3 Hz, 2H), 3.14 (q, J=6.4 Hz, 2H), 2.90 (s, 3H), 2.86 (t, J=7.5 Hz, 2H), 2.14 (septet, J=7.0 Hz, 1H), 1.95 (quintet, J=6.6 Hz, 2H), 1.83 (sextet, J=7.3 Hz, 2H), 1.02 (t, J=7.6 Hz, 3H), 0.91 (d, J=7.1 Hz, 6H);

$^{13}$C NMR (125 MHz, DMSO-$d_6$) δ 157.1, 152.6, 151.8, 146.2, 132.8, 125.1, 121.2, 111.6, 109.0, 108.0, 64.7, 51.2, 39.4, 39.2, 29.3, 28.7, 28.5, 20.9, 19.1, 13.8;

MS (APCI) m/z 434.2235 (434.2226 calcd for $C_{21}H_{31}N_5O_3S$, M+H).

Anal. Calcd. for $C_{21}H_{31}N_5O_3S$: % C, 58.18; % H, 7.21; % N, 16.15; % S, 7.40. Found: % C, 57.87; % H, 7.56; % N, 16.02; % S, 7.72.

Example 12

N-{2-[4-Amino-2-methyl-1-(2-methylpropyl)-1H-imidazo[4,5-c]quinolin-7-yloxy]ethyl}methanesulfonamide

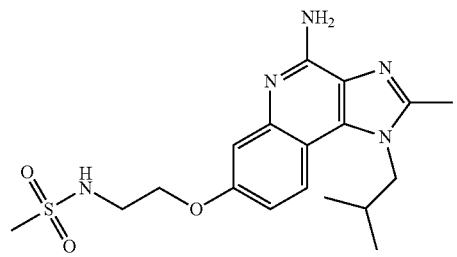

The general method described in Example 11 was used to convert 7-(3-aminopropoxy)-2-methyl-1-(2-methylpropyl)-1H-imidazo[4,5-c]quinolin-4-amine to 0.014 g of N-{2-[4-amino-2-methyl-1-(2-methylpropyl)-1H-imidazo[4,5-c]quinolin-7-yloxy]ethyl}methanesulfonamide, which was obtained as a white solid.

$^1$H NMR (300 MHz, DMSO-$d_6$) δ 7.93 (d, J=9.6 Hz, 1H), 7.32 (t, J=5.6 Hz, 1H), 7.12 (d, J=2.5 Hz, 1H), 6.99 (dd, J=9.3, 2.6 Hz, 1H), 6.92 (s, 2H), 4.30 (d, J=7.6 Hz, 2H), 4.13 (t, J=5.7 Hz, 2H), 3.39 (q, J=5.6 Hz, 2H), 2.97 (s, 3H), 2.58 (s, 3H), 2.24-2.08 (m, 1H), 0.93 (d, J=6.9 Hz, 6H);

MS (APCI) m/z 392.1758 (392.1756 calcd for $C_{18}H_{25}N_5O_3S$, M+H).

Example 13

7-[3-(1,1-Dioxidoisothiazolidin-2-yl)propoxy]-1-(2-methylpropyl)-2-propyl-1H-imidazo[4,5-c]quinolin-4-amine

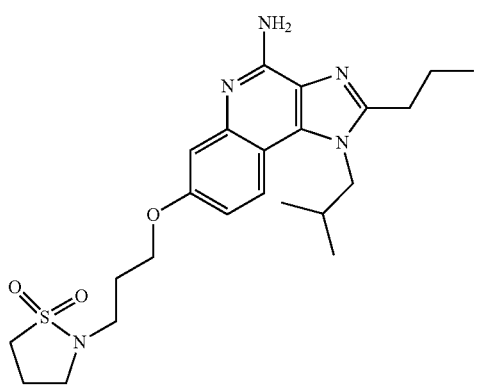 [SMILES: CCCc1nc2c(N)nc3cc(OCCCN4CCCS4(=O)=O)ccc3c2n1CC(C)C]

3-Chloropropanesulfonyl chloride (0.206 mL, 1.69 mmol) was added dropwise to a suspension of 7-(3-aminopropoxy)-1-(2-methylpropyl)-2-propyl-1H-imidazo[4,5-c]quinolin-4-amine (0.500 g, 1.41 mmol) in chloroform (17 mL), and the reaction was stirred for 30 minutes. The solvent was removed under reduced pressure, and the residue was dissolved in DMF (17 mL). 1,8-Diazabicyclo[5.4.0]undec-7-ene (0.316 mL, 2.11 mmol) was then added, and the reaction was stirred for 18 hours. The reaction was poured into water, and the mixture was extracted twice with dichloromethane. The combined organic fractions were washed sequentially with water and brine, dried over magnesium sulfate, and concentrated under reduced pressure. The residue was purified by column chromatography on silica gel (eluting with 97:3 dichloromethane:methanol) followed by recrystallization from acetonitrile to provide 0.237 g of 7-[3-(1,1-dioxidoisothiazolidin-2-yl)propoxy]-1-(2-methylpropyl)-2-propyl-1H-imidazo[4,5-c]quinolin-4-amine as needle-like, white crystals, mp 142-144° C.

$^1$H NMR (300 MHz, DMSO-$d_6$) δ 7.86 (d, J=9.1 Hz, 1H), 7.05 (d, J=2.6 Hz, 1H), 6.91 (dd, J=9.0, 2.6 Hz, 1H), 6.37 (s, 2H), 4.29 (d, J=7.4 Hz, 2H), 4.10 (t, J=6.2 Hz, 2H), 3.26-3.17 (m, 4H), 3.09 (t, J=7.0 Hz, 2H), 2.86 (at, J=7.5 Hz, 2H), 2.28-1.96 (m, 5H), 1.84 (sextet, J=7.5 Hz, 2H), 1.02 (t, J=7.3 Hz, 3H), 0.91 (d, J=6.6 Hz, 6H);

$^{13}$C NMR (75 MHz, DMSO-$d_6$) δ 157.0, 152.6, 151.9, 146.5, 132.8, 125.1, 121.2, 111.5, 109.0, 108.2, 64.8, 51.2, 46.8, 46.1, 41.3, 28.7, 28.6, 27.3, 20.9, 19.1, 18.3, 13.8;

MS (APCI) m/z 460.2391 (460.2382 calcd for $C_{23}H_{33}N_5O_3S$, M+H).

Anal. Calcd. for $C_{23}H_{33}N_5O_3S$: % C, 60.11; % H, 7.24; % N, 15.24; % S, 6.98. Found: % C, 59.52; % H, 7.23; % N, 15.16; % S, 6.80.

Example 14

N-(3-{[4-Amino-1-(2-methylpropyl)-2-propyl-1H-imidazo[4,5-c]quinolin-7-yl]oxy}propyl)-2-(1-naphthyl)ethanesulfonamide

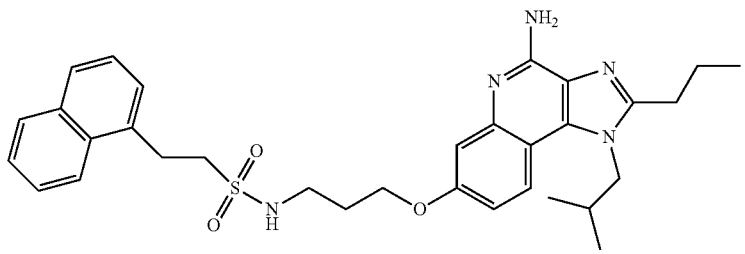 [SMILES: CCCc1nc2c(N)nc3cc(OCCCNS(=O)(=O)CCc4cccc5ccccc45)ccc3c2n1CC(C)C]

2-(1-Naphthyl)ethanesulfonyl chloride (0.358 g, 1.40 mmol) was added in one portion to a suspension of 7-(3-aminopropoxy)-1-(2-methylpropyl)-2-propyl-1H-imidazo[4,5-c]quinolin-4-amine (0.500 g, 1.41 mmol) in chloroform, and the reaction was stirred for 30 minutes. Triethylamine (0.250 mL, 1.79 mmol) was then added. The reaction mixture was poured into saturated aqueous sodium carbonate. The organic layer was separated, washed with water and brine, dried over magnesium sulfate, filtered, and concentrated under reduced pressure. The resulting pale yellow oil was purified by column chromatography on silica gel (eluting with dichloromethane:methanol ranging in ratios from 99:1 to 94:6) and subsequent recrystallization from acetonitrile to yield 0.341 g of N-(3-{[4-amino-1-(2- methylpropyl)-2-propyl-1H-imidazo[4,5-c]quinolin-7-yl]oxy}propyl)-2-(1-naphthyl)ethanesulfonamide as white crystals, mp 164-168° C.

$^1$H NMR (300 MHz, DMSO-$d_6$) δ 8.00 (ad, J=7.9 Hz, 1H), 7.96-7.92 (m, 1H), 7.85-7.75 (m, 2H), 7.61-7.49 (m, 2H), 7.43-7.33 (m, 3H), 7.08 (d, J=2.4 Hz, 1H), 6.89 (dd, J=9.2, 2.9 Hz, 1H), 6.38 (s, 2H), 4.28 (d, J=7.6 Hz, 2H), 4.14 (t, J=6.2 Hz, 2H), 3.47-3.31 (m, 4H), 3.22 (q, J=6.4 Hz, 2H), 2.86 (t, J=7.5 Hz, 2H), 2.21-2.06 (m, 1H), 1.99 (quintet, J=6.7 Hz, 2H), 1.84 (septet, J=7.3 Hz, 2H), 1.02 (t, J=7.4 Hz, 3H), 0.91 (d, J=6.5 Hz, 6H);

MS (APCI) m/z 574.2847 (574.2852 calcd for $C_{32}H_{39}N_5O_3S$, M+H).

Anal. Calcd. for $C_{32}H_{39}N_5O_3S$: % C, 66.99; % H, 6.85; % N, 12.21. Found: % C, 66.67; % H, 6.98; % N, 12.22.

Example 15

N-{3-[4-Amino-1-(2-methylpropyl)-2-propyl-1H-imidazo[4,5-c]quinolin-7-yloxy]propyl}-2-methylpropanamide

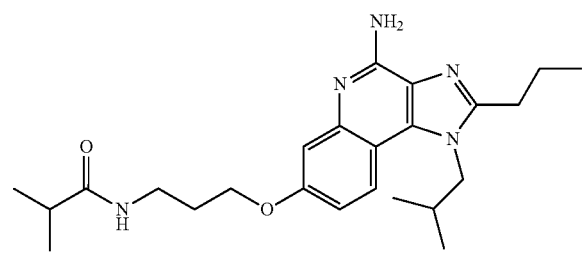 [SMILES: CCCc1nc2c(N)nc3cc(OCCCNC(=O)C(C)C)ccc3c2n1CC(C)C]

A solution of 7-(3-aminopropoxy)-1-(2-methylpropyl)-2-propyl-1H-imidazo[4,5-c]quinolin-4-amine (0.500 g, 1.41 mmol) in chloroform (15 mL) was cooled to 0° C. Isobutyryl chloride (0.147 mL, 1.40 mmol) was added dropwise, and the reaction was stirred for 30 minutes. The reaction was diluted with chloroform and poured into 3% aqueous sodium carbonate. The organic layer was separated, washed with water and brine, dried over magnesium sulfate, filtered, and concentrated under reduced pressure. The resulting white solid was recrystallized from acetonitrile to yield 0.450 g of N-{3-[4-amino-1-(2-methylpropyl)-2-propyl-1H-imidazo[4,5-c]quinolin-7-yloxy]propyl}-2-methylpropanamide as feathery, white crystals, mp 179-181° C.

$^1$H NMR (300 MHz, DMSO-$d_6$) δ 7.86 (d, J=9.1 Hz, 1H), 7.80 (t, J=5.3 Hz, 1H), 7.04 (d, J=2.4 Hz, 1H), 6.89 (dd, J=8.6, 2.5 Hz, 1H), 6.36 (s, 2H), 4.28 (d, J=7.6 Hz, 2H), 4.05 (t, J=6.5 Hz, 2H), 3.22 (q, J=6.4 Hz, 2H), 2.86 (t, J=7.5 Hz, 2H), 2.34 (quintet, J=6.9 Hz, 1H), 2.20-2.08 (m, 1H), 1.93-1.77 (m, 4H), 1.02 (t, J=7.6 Hz, 3H), 1.00 (d, J=6.9 Hz, 6H), 0.91 (d, J=6.6 Hz, 6H);

MS (APCI) m/z 426.2871 (426.2869 calcd for $C_{24}H_{35}N_5O_2$, M+H).

Anal. Calcd. for $C_{24}H_{35}N_5O_2$: % C, 67.74; % H, 8.29; % N, 16.46. Found: % C, 67.93; % H, 8.14; % N, 16.49.

Example 16

N-{3-[4-Amino-1-(2-methylpropyl)-2-propyl-1H-imidazo[4,5-c]quinolin-7-yloxy]propyl}nicotinamide

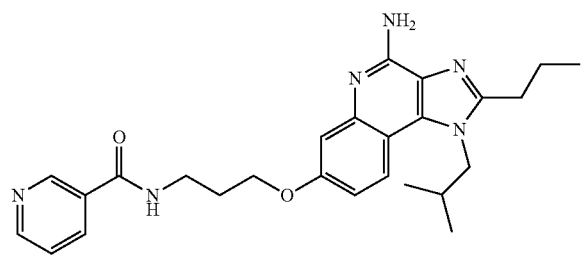 [SMILES: CCCc1nc2c(N)nc3cc(OCCCNC(=O)c4cccnc4)ccc3c2n1CC(C)C]

Nicotinoyl chloride hydrochloride (0.23 g, 1.29 mmol) was added in one portion to a solution of 7-(3-aminopropoxy)-1-(2-methylpropyl)-2-propyl-1H-imidazo[4,5-c]quinolin-4-amine (0.460 g, 1.29 mmol) and triethylamine (0.383 mL, 2.75 mmol) in chloroform (15 mL), and the reaction was stirred for 16 hours. The reaction mixture was poured into saturated aqueous sodium bicarbonate and stirred for 30 minutes. The aqueous layer was separated and extracted with chloroform. The combined organic fractions were washed sequentially with water and brine, dried over magnesium sulfate, filtered, and concentrated under reduced pressure. The resulting pale yellow oil was triturated with acetonitrile, which was removed under reduced pressure. The resulting solid was recrystallized from acetonitrile to yield 0.310 g of N-{3-[4-amino-1-(2-methylpropyl)-2-propyl-1H-imidazo[4,5-c]quinolin-7-yloxy]propyl}nicotinamide as off-white, granular crystals, mp 172-174° C.

$^1$H NMR (300 MHz, DMSO-$d_6$) δ 9.15 (d, J=2.5 Hz, 1H), 8.77 (t, J=5.7 Hz, 1H), 8.70 (dd, J=5.0, 1.3 Hz, 1H), 8.19 (dt, J=8.1, 1.7 Hz, 1H), 7.86 (d, J=8.9 Hz, 1H), 7.52-7.47 (m, 1H), 7.07 (d, J=2.6 Hz, 1H), 6.91 (dd, J=8.9, 2.8 Hz, 1H), 6.37 (s, 2H), 4.29 (d, J=7.6 Hz, 2H), 4.14 (t, J=5.9 Hz, 2H), 3.49 (q, J=6.1 Hz, 2H), 2.86 (t, J=7.8 Hz, 2H), 2.21-1.95 (m, 3H), 1.84 (sextet, J=7.4 Hz, 2H), 1.02 (t, J=7.6 Hz, 3H), 0.91 (d, J=6.1 Hz, 6H);

$^{13}$C NMR (75 MHz, DMSO-$d_6$) δ 164.8, 157.1, 152.5, 151.9, 151.7, 148.3, 146.5, 134.9, 132.8, 130.0, 125.1, 123.4, 121.2, 111.5, 109.0, 108.2, 65.2, 51.2, 36.4, 28.7, 28.5, 20.9, 19.1, 13.8;

MS (APCI) m/z 461.2655 (461.2665 calcd for $C_{26}H_{32}N_6O_2$, M+H).

Anal. Calcd. for $C_{26}H_{32}N_6O_2 \cdot 0.5H_2O$: % C, 66.50; % H, 7.08; % N, 17.90. Found: % C, 66.62; % H, 7.18; % N, 18.08.

Example 17

N-{2-[4-Amino-2-methyl-1-(2-methylpropyl)-1H-imidazo[4,5-c]quinolin-7-yloxy]ethyl}-2-methylpropanamide

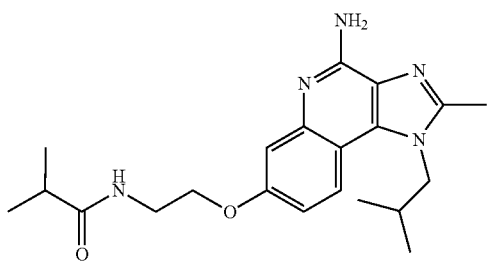 [SMILES: Cc1nc2c(N)nc3cc(OCCNC(=O)C(C)C)ccc3c2n1CC(C)C]

The method described in Example 15 was used to convert 7-(2-aminoethoxy)-2-methyl-1-(2-methylpropyl)-1H-imidazo[4,5-c]quinolin-4-amine to 0.170 g of N-{2-[4-amino-2-methyl-1-(2-methylpropyl)-1H-imidazo[4,5-c]quinolin-7-yloxy]ethyl}-2-methylpropanamide, which was isolated as flocculent, white crystals, mp 205-206° C.

$^1$H NMR (300 MHz, DMSO-$d_6$) δ 8.00 (t, J=5.2 Hz, 1H), 7.88 (d, J=9.1 Hz, 1H), 7.07 (d, J=3.0 Hz, 1H), 6.89 (dd, J=8.9, 2.8 Hz, 1H), 6.50 (s, 2H), 4.27 (d, J=7.5 Hz, 2H), 4.06 (t, J=5.7 Hz, 2H), 3.45 (q, J=5.6 Hz, 2H), 2.56 (s, 3H), 2.39 (m, 1H), 2.16 (septet, J=6.7 Hz, 1H), 1.00 (d, J=6.9 Hz, 6H), 0.93 (d, J=6.3 Hz, 6H);

MS (APCI) m/z 456.2960 (456.2975 calcd for $C_{21}H_{29}N_5O_2$, M+H).

Anal. Calcd. for $C_{21}H_{29}N_5O_2$: % C, 65.77; % H, 7.62; % N, 18.26. Found: % C, 65.42; % H, 7.88; % N, 17.96.

Example 18

1-{2-[4-Amino-1-(2-methylpropyl)-2-propyl-1H-imidazo[4,5-c]quinolin-7-yloxy]ethyl}pyrrolidin-2-one

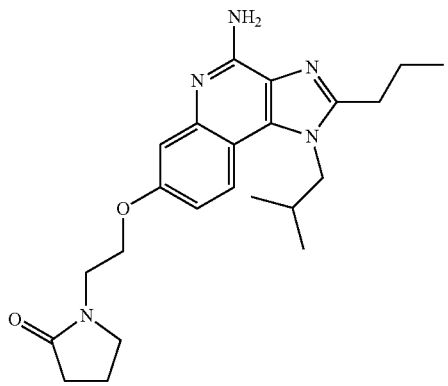 [SMILES: CCCc1nc2c(N)nc3cc(OCCN4CCCC4=O)ccc3c2n1CC(C)C]

Part A

A mixture of 1-(2-methylpropyl)-2-propyl-1H-imidazo[4,5-c]quinolin-7-ol (0.500 g, 1.76 mmol), triphenylphosphine (0.462 g, 1.76 mmol), and 1-(2-hydroxyethyl)pyrrolidin-2-one (0.200 mL, 1.77 mmol) in THF (17 mL) was cooled to 0° C. Diethyl azodicarboxylate (0.277 mL) was added dropwise, and the reaction mixture was allowed to warm to ambient temperature and stirred for 19 hours. Solid unreacted 1-(2-methylpropyl)-2-propyl-1H-imidazo[4,5-c]quinolin-7-ol (0.150 g, 0.42 mmol) was removed by filtration, and the filtrate was concentrated under reduced pressure. The residue was purified by column chromatography on silica gel (eluting with 98:2 dichloromethane:methanol) to provide 0.456 g of 1-{2-[1-(2-methylpropyl)-2-propyl-1H-imidazo[4,5-c]quinolin-7-yloxy]ethyl}pyrrolidin-2-one an off-white, waxy solid.

$^1$H NMR (300 MHz, DMSO-$d_6$) δ 9.08 (s, 1H), 8.20 (d, J=9.2 Hz, 1H), 7.58 (d, J=2.4 Hz, 1H), 7.35 (dd, J=9.2, 2.6 Hz, 1H), 4.40 (d, J=7.4 Hz, 2H), 4.27 (t, J=5.7 Hz, 2H), 3.63 (t, J=5.7 Hz, 2H), 3.50 (at, J=7.1 Hz, 2H), 2.92 (t, J=7.6 Hz, 2H), 2.30-2.10 (m, 3H), 1.98-1.83 (m, 4H), 1.04 (t, J=7.5 Hz, 3H), 0.92 (d, J=6.2 Hz, 6H).

Part B

The general methods described in Parts M and N of Example 2 were used to convert the material from Part A to 0.120 g of 1-{2-[4-amino-1-(2-methylpropyl)-2-propyl-1H-imidazo[4,5-c]quinolin-7-yloxy]ethyl}pyrrolidin-2-one, which was obtained as tan, granular crystals, mp 206-208° C.

$^1$H NMR (300 MHz, DMSO-$d_6$) δ 7.87 (d, J=8.6 Hz, 1H), 7.07 (d, J=2.3 Hz, 1H), 6.91 (dd, J=9.2, 2.9 Hz, 1H), 6.41 (s, 2H), 4.29 (d, J=7.5 Hz, 2H), 4.16 (t, J=5.5 Hz, 2H), 3.59 (t, J=5.7 Hz, 2H), 3.48 (t, J=7.2 Hz, 2H), 2.86 (t, J=7.5 Hz, 2H), 2.23 (t, J=8.0 Hz, 2H), 2.20-2.07 (m, 1H), 1.92 (quintet, J=7.2 Hz, 2H), 1.84 (sextet, J=7.1 Hz, 2H), 1.02 (t, J=7.0 Hz, 3H), 0.91 (d, J=6.8 Hz, 6H);

$^{13}$C NMR (75 MHz, DMSO-$d_6$) δ 174.1, 156.8, 152.6, 152.0, 146.4, 132.7, 125.1, 121.3, 111.5, 109.2, 108.2, 65.4, 51.2, 47.3, 41.4, 30.3, 28.7, 28.5, 20.9, 19.1, 17.6, 13.8;

MS (APCI) m/z 410.2541 (410.2556 calcd for $C_{23}H_{31}N_5O_2$, M+H).

Anal. Calcd. for $C_{23}H_{31}N_5O_2$: % C, 67.46; % H, 7.63; % N, 17.10. Found: % C, 67.28; % H, 7.53; % N, 17.16.

Example 19

N-(2-{[4-Amino-2-methyl-1-(2-methylpropyl)-1H-imidazo[4,5-c]quinolin-7-yl]oxy}ethyl)morpholine-4-carboxamide

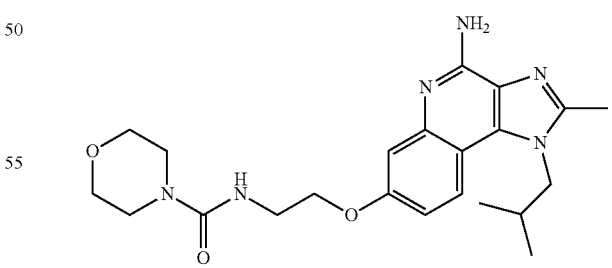

A suspension of 7-(2-aminoethoxy)-2-methyl-1-(2-methylpropyl)-1H-imidazo[4,5-c]quinolin-4-amine (0.300 g, 0.958 mmol) in chloroform (10 mL) was cooled to 0° C. 4-Morpholinecarbonyl chloride (0.110 mL, 0.942 mmol) was added dropwise, and the reaction was stirred for five minutes at 0° C. The reaction was then allowed to warm to ambient temperature over a period of 15 minutes, and the solvent was removed under reduced pressure. The resulting off-white solid was dissolved in dichloromethane. The solution was washed sequentially with 10% aqueous sodium hydroxide, water, and brine; dried over magnesium sulfate; filtered; and concentrated under reduced pressure. The residue was recrystallized from acetonitrile to provide 0.150 g of N-(2-{[4-amino-2-methyl-1-(2-methylpropyl)-1H-imidazo[4,5-c]quinolin-7-yl]oxy}ethyl)morpholine-4-carboxamide as a white powder, mp 215-219° C. (decomposition).

$^1$H NMR (300 MHz, DMSO-$d_6$) δ 7.86 (d, J=8.7 Hz, 1H), 7.06 (d, J=2.6 Hz, 1H), 6.91 (dd, J=9.1, 2.7 Hz, 1H), 6.77 (t, J=5.3 Hz, 1H), 6.42 (s, 2H), 4.27 (d, J=7.5 Hz, 2H), 4.07 (t, J=5.8 Hz, 2H), 3.53 (t, J=5.0 Hz, 4H), 3.44 (q, J=5.8 Hz, 2H), 3.27 (t, J=5.1 Hz, 4H), 2.56 (s, 3H), 2.16 (m, 1H), 0.93 (d, J=6.3 Hz, 6H);

MS (APCI) m/z 427.2475 (427.2458 calcd for $C_{22}H_{30}N_6O_3$, M+H).

Anal. Calcd. for $C_{22}H_{30}N_6O_3$: % C, 61.95; % H, 7.09; % N, 19.70. Found: % C, 61.96; % H, 7.18; % N, 19.37.

Example 20

N-(3-{[4-Amino-2-propyl-1-(2-methylpropyl)-1H-imidazo[4,5-c]quinolin-7-yl]oxy}propyl)morpholine-4-carboxamide

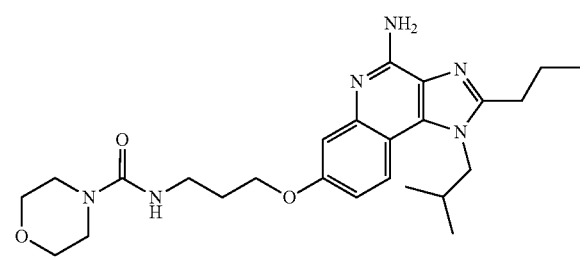 [SMILES: CCCc1nc2c(N)nc3cc(OCCCNC(=O)N4CCOCC4)ccc3c2n1CC(C)C]

The general method described in Example 19 was used to convert 7-(3-aminopropoxy)-1-(2-methylpropyl)-2-propyl-1H-imidazo[4,5-c]quinolin-4-amine to N-(3-{[4-amino-2-propyl-1-(2-methylpropyl)-1H-imidazo[4,5-c]quinolin-7-yl]oxy}propyl)morpholine-4-carboxamide, which was isolated as a white solid, mp 145° C.

$^1$H NMR (300 MHz, DMSO-$d_6$) δ 7.86 (d, J=9.5 Hz, 1H), 7.05 (d, J=2.7 Hz, 1H), 6.89 (dd, J=8.6, 2.4 Hz, 1H), 6.61 (t, J=5.2 Hz, 1H), 6.36 (s, 2H), 4.28 (d, J=7.7 Hz, 2H), 4.06 (t, J=6.2 Hz, 2H), 3.53 (t, J=4.8 Hz, 4H), 3.28-3.18 (m, 6H), 2.86 (t, J=7.5 Hz, 2H), 2.21-2.04 (m, 1H), 1.97-1.76 (m, 4H), 1.02 (t, J=7.0 Hz, 3H), 0.91 (d, J=6.8 Hz, 6H);

MS (APCI) m/z 469.2937 (469.2927 calcd for $C_{25}H_{36}N_6O_3$, M+H).

Anal. Calcd. for $C_{25}H_{36}N_6O_3 \cdot H_2O$: % C, 61.71; % H, 7.87; % N, 17.27. Found: % C, 61.36; % H, 7.96; % N, 17.55.

Example 21

N-{[(3-{[4-Amino-1-(2-methylpropyl)-2-propyl-1H-imidazo[4,5-c]quinolin-7-yl]oxy}propyl)amino]carbonyl}-4-fluorobenzenesulfonamide

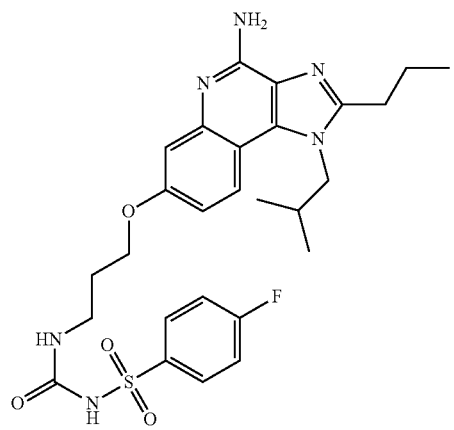 [SMILES: CCCc1nc2c(N)nc3cc(OCCCNC(=O)NS(=O)(=O)c4ccc(F)cc4)ccc3c2n1CC(C)C]

A solution of 7-(3-aminopropoxy)-1-(2-methylpropyl)-2-propyl-1H-imidazo[4,5-c]quinolin-4-amine (0.500 g, 1.41 mmol) in chloroform (15 mL) was cooled to 0° C.; 4-fluorobenzenesulfonyl isocyanate (0.548 g, 2.72 mmol) was added in three portions over a period of 30 minutes. A white precipitate was present and was isolated by filtration, washed with chloroform, and dried overnight in a vacuum oven at 60° C. to provide 0.671 g of N-{[(3-{[4-amino-1-(2-methylpropyl)-2-propyl-1H-imidazo[4,5-c]quinolin-7-yl]oxy}propyl)amino]carbonyl}-4-fluorobenzenesulfonamide as a white powder, mp 194-198° C.

$^1$H NMR (300 MHz, DMSO-$d_6$) δ 7.98-7.85 (m, 3H), 7.37 (t, J=8.7 Hz, 2H), 7.07 (d, J=2.5 Hz, 1H), 6.92 (dd, J=8.7, 2.5 Hz, 1H), 6.76 (s, 2H), 6.57 (s, 1H), 4.30 (d, J=7.6 Hz, 2H), 3.99 (t, J=6.3 Hz, 2H), 3.14 (aq, J=6.2 Hz, 2H), 2.87 (t, J=7.5 Hz, 2H), 2.22-2.05 (m, 1H), 1.91-1.77 (m, 4H), 1.02 (t, J=7.3 Hz, 3H), 0.92 (d, J=6.2 Hz, 6H);

MS (APCI) m/z 557.2365 (557.2346 calcd for $C_{27}H_{33}FN_6O_4S$, M+H).

Anal. Calcd. for $C_{27}H_{33}FN_6O_4S$: % C, 58.26; % H, 5.98; % N, 15.10; % S, 5.76; % F, 3.41. Found: % C, 57.96; % H, 5.96; % N, 15.04; % S, 5.47; % F, 3.59.

Example 22 tert-Butyl 4-(2-{[4-amino-1-(2-methylpropyl)-2-propyl-1H-imidazo[4,5-c]quinolin-7-yl]oxy}ethyl)piperidine-1-carboxylate

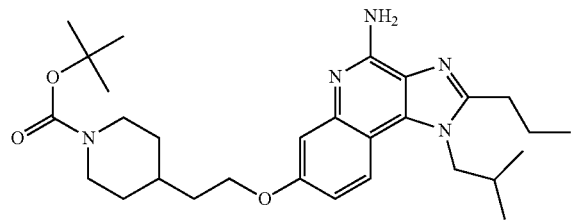 [SMILES: CCCc1nc2c(N)nc3cc(OCCC4CCN(C(=O)OC(C)(C)C)CC4)ccc3c2n1CC(C)C]

Part A

The general methods described in Parts J and K of Example 2 were used to prepare tert-butyl 4-(2-iodoethyl)piperidine-1-carboxylate, which was isolated as a yellow oil.

Part B

The general method described in Part L of Example 2 was used to treat 1-(2-methylpropyl)-2-propyl-1H-imidazo[4,5-c]quinolin-7-ol with tert-butyl 4-(2-iodoethyl)piperidine-1-carboxylate. After the work-up procedure, tert-butyl 4-(2-{[1-(2-methylpropyl)-2-propyl-1H-imidazo[4,5-c]quinolin-7-yl]oxy}ethyl)piperidine-1-carboxylate was isolated as a gray-brown solid and used without purification.

$^1$H NMR (300 MHz, DMSO-$d_6$) δ 9.06 (s, 1H), 8.18 (d, J=9.4 Hz, 1H), 7.56 (d, J=2.5 Hz, 1H), 7.33 (dd, J=9.0, 2.9 Hz, 1H), 4.39 (d, J=7.4 Hz, 2H), 4.19 (t, J=6.2 Hz, 2H), 3.99-3.86 (m, 3H), 2.92 (t, J=7.2 Hz, 2H), 2.81-2.62 (m, 2H), 2.25-2.06 (m, 1H), 1.89 (sextet, J=7.4 Hz, 2H), 1.80-1.64 (m, 4H), 1.39 (s, 9H), 1.20-1.00 (m, 2H), 1.04 (t, J=7.6 Hz, 3H), 0.92 (d, J=6.3 Hz, 6H).

Part C

The general methods described in Parts M and N of Example 2 were used to aminate tert-butyl 4-(2-{[1-(2-methylpropyl)-2-propyl-1H-imidazo[4,5-c]quinolin-7-yl]oxy}ethyl)piperidine-1-carboxylate. The crude product was triturated with hot acetonitrile and isolated by filtration to yield tert-butyl 4-(2-{[4-amino-1-(2-methylpropyl)-2-propyl-1H-imidazo[4,5-c]quinolin-7-yl]oxy}ethyl)piperidine-1-carboxylate as an orange solid, mp 196.4-199.6° C.

$^1$H NMR (300 MHz, DMSO-$d_6$) δ 7.84 (d, J=9.4 Hz, 1H), 7.05 (d, J=2.6 Hz, 1H), 6.89 (dd, J=8.9, 2.6 Hz, 1H), 6.38 (s, 2H), 4.28 (d, J=7.5 Hz, 2H), 4.09 (t, J=5.6 Hz, 2H), 3.98-3.88 (m, 2H), 2.86 (t, J=7.8 Hz, 2H), 2.80-2.63 (m, 2H), 2.18-2.08 (m, 1H), 1.83 (sextet, J=7.4 Hz, 2H), 1.76-1.63 (m, 5H), 1.39 (s, 9H), 1.15-1.01 (m, 2H), 1.01 (t, J=7.6 Hz, 3H), 0.91 (d, J=6.3 Hz, 6H);

MS (APCI) m/z 510.3424 (510.3444 calcd for $C_{29}H_{43}N_5O_3$, M+H).

Anal. Calcd. for $C_{29}H_{43}N_5O_3$: % C, 68.34; % H, 8.50; % N, 13.74. Found: % C, 68.05; % H, 8.67; % N, 13.54.

Example 23

1-(2-Methylpropyl)-7-(2-piperidin-4-ylethoxy)-2-propyl-1H-imidazo[4,5-c]quinolin-4-amine

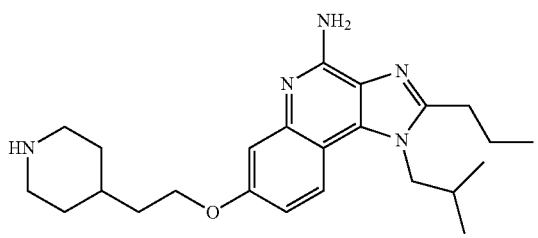 [SMILES: CCCc1nc2c(N)nc3cc(OCCC4CCNCC4)ccc3c2n1CC(C)C]

The general method described in Part O of Example 2 was used to convert tert-butyl 4-(2-{[4-amino-1-(2-methylpropyl)-2-propyl-1H-imidazo[4,5-c]quinolin-7-yl]oxy}ethyl)piperidine-1-carboxylate to 1-(2-methylpropyl)-7-(2-piperidin-4-ylethoxy)-2-propyl-1H-imidazo[4,5-c]quinolin-4-amine, which was isolated as a brown solid.

$^1$H NMR (300 MHz, DMSO-$d_6$) δ 7.85 (d, J=9.3 Hz, 1H), 7.04 (d, J=3.0 Hz, 1H), 6.89 (dd, J=9.1, 2.8 Hz, 1H), 6.35 (s, 2H), 4.28 (d, J=6.9 Hz, 2H), 4.08 (t, J=6.5 Hz, 2H), 2.97-2.88 (m, 2H), 2.86 (t, J=7.4 Hz, 2H), 2.50-2.37 (m, 2H), 2.21-2.07 (m, 1H), 1.83 (sextet, J=7.4 Hz, 2H), 1.70-1.50 (m, 6H), 1.18-0.97 (m, 2H), 1.02 (t, J=7.5 Hz, 3H), 0.91 (d, J=6.2 Hz, 6H);

MS (APCI) m/z 410.2918 (410.2920 calcd for $C_{24}H_{35}N_5O$, M+H).

Example 24

2-Methyl-1-(2-methylpropyl)-7-(2-piperidin-4-ylethoxy)-1H-imidazo[4,5-c]quinolin-4-amine

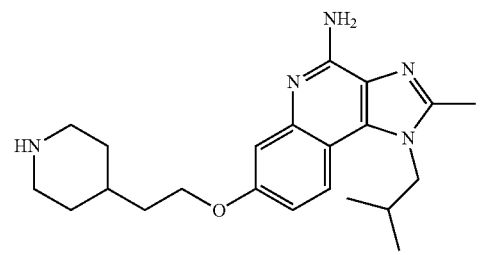 [SMILES: Cc1nc2c(N)nc3cc(OCCC4CCNCC4)ccc3c2n1CC(C)C]

Part A

The general method described in Part L of Example 2 was used to treat 2-methyl-1-(2-methylpropyl)-1H-imidazo[4,5-c]quinolin-7-ol with tert-butyl 4-(2-iodoethyl)piperidine-1-carboxylate. After chromatographic purification, tert-butyl 4-(2-{[2-methyl-1-(2-methylpropyl)-1H-imidazo[4,5-c]quinolin-7-yl]oxy}ethyl)piperidine-1-carboxylate was isolated as a viscous, orange oil.

$^1$H NMR (300 MHz, DMSO-$d_6$) δ 9.03 (s, 1H), 8.19 (d, J=9.0 Hz, 1H), 7.56 (d, J=2.1 Hz, 1H), 7.34 (dd, J=9.2, 2.6 Hz, 1H), 4.38 (d, J=7.5 Hz, 2H), 4.19 (t, J=6.3 Hz, 2H), 3.99-3.88 (m, 2H), 2.82-2.62 (m, 2H), 2.63 (s, 3H), 2.19 (septet, J=6.9 Hz, 1H), 1.81-1.61 (m, 5H), 1.39 (s, 9H), 1.18-0.99 (m, 2H), 0.93 (d, J=6.9 Hz, 6H).

Part B

The general methods described in Parts M and N of Example 2 were used to aminate tert-butyl 4-(2-{[2-methyl-1-(2-methylpropyl)-1H-imidazo[4,5-c]quinolin-7-yl]oxy}ethyl)piperidine-1-carboxylate (3.6 g, 9.8 mmol). The crude product was triturated with hot acetonitrile and isolated by filtration to yield 2.67 g of tert-butyl 4-(2-{[4-amino-2-methyl-1-(2-methylpropyl)-1H-imidazo[4,5-c]quinolin-7-yl]oxy}ethyl)piperidine-1-carboxylate as a white solid.

$^1$H NMR (300 MHz, DMSO-$d_6$) δ 7.85 (d, J=9.3 Hz, 1H), 7.05 (d, J=2.7 Hz, 1H), 6.89 (dd, J=8.6, 2.6 Hz, 1H), 6.39 (s, 2H), 4.27 (d, J=7.5 Hz, 2H), 4.09 (t, J=6.0 Hz, 2H), 3.99-3.87 (m, 2H), 2.81-2.63 (m, 2H), 2.56 (s, 3H), 2.24-2.08 (m, 1H), 1.80-1.60 (m, 5H), 1.39 (s, 9H), 1.18-0.98 (m, 2H), 0.93 (d, J=6.6 Hz, 6H).

Part C

The general method described in Part O of Example 2 was used to convert the material from Part B to 1.93 g of 2-methyl-1-(2-methylpropyl)-7-(2-piperidin-4-ylethoxy)-1H-imidazo[4,5-c]quinolin-4-amine, which was isolated as a tan solid.

$^1$H NMR (300 MHz, DMSO-$d_6$) δ 7.85 (d, J=8.7 Hz, 1H), 7.04 (d, J=1.8 Hz, 1H), 6.89 (d, J=8.7 Hz, 1H), 6.40 (s, 2H), 4.26 (d, J=6.9 Hz, 2H), 4.08 (t, J=5.4 Hz, 2H), 3.41-3.12 (m, 2H), 3.02-2.86 (m, 2H), 2.56 (s, 3H), 2.24-2.07 (m, 1H), 1.76-1.48 (m, 5H), 1.28-1.00 (m, 3H), 0.93 (d, J=6.3 Hz, 6H).

Example 25

7-{2-[1-(Methanesulfonyl)piperidin-4-yl]ethoxy}-2-methyl-1-(2-methylpropyl)-1H-imidazo[4,5-c]quinolin-4-amine

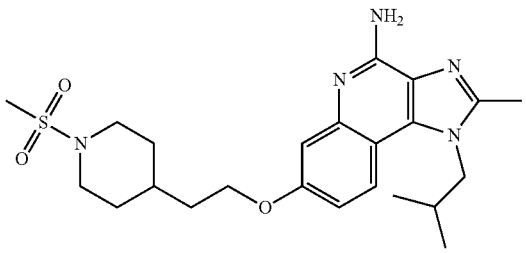

The general method described in Example 11 was used to convert 2-methyl-1-(2-methylpropyl)-7-(2-piperidin-4-ylethoxy)-1H-imidazo[4,5-c]quinolin-4-amine to 0.150 g of 7-{2-[1-(methanesulfonyl)piperidin-4-yl]ethoxy}-2-methyl-1-(2-methylpropyl)-1H-imidazo[4,5-c]quinolin-4-amine, which was isolated as an off-white powder.

$^1$H NMR (300 MHz, DMSO-$d_6$) δ 7.85 (d, J=9.3 Hz, 1H), 7.06 (d, J=2.5 Hz, 1H), 6.90 (dd, J=8.5, 2.5 Hz, 1H), 6.39 (s, 2H), 4.27 (d, J=6.8 Hz, 2H), 4.11 (t, J=6.3 Hz, 2H), 3.59-3.49 (m, 2H), 2.84 (s, 3H), 2.70 (ddd, J=11.9, 11.9, 1.4 Hz, 2H), 2.56 (s, 3H), 2.23-2.09 (m, 1H), 1.90-1.55 (m, 5H), 1.35-1.17 (m, 2H), 0.93 (d, J=7.2 Hz, 6H).

Example 26

1-(4-{2-[4-Amino-2-methyl-1-(2-methylpropyl)-1H-imidazo[4,5-c]quinolin-7-yloxy]ethyl}piperidin-1-yl)-2-methylpropan-1-one

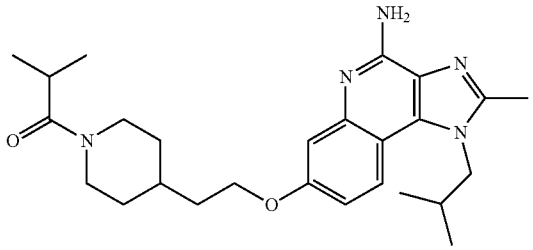 [SMILES: Cc1nc2c(N)nc3cc(OCCC4CCN(C(=O)C(C)C)CC4)ccc3c2n1CC(C)C]

The general method described in Example 15 was used to convert 2-methyl-1-(2-methylpropyl)-7-(2-piperidin-4-ylethoxy)-1H-imidazo[4,5-c]quinolin-4-amine to 0.158 g of 1-(4-{2-[4-amino-2-methyl-1-(2-methylpropyl)-1H-imidazo[4,5-c]quinolin-7-yloxy]ethyl}piperidin-1-yl)-2-methylpropan-1-one, which was isolated as an off-white solid, mp 205.1-207.1° C.

$^1$H NMR (300 MHz, DMSO-$d_6$) δ 7.85 (d, J=9.3 Hz, 1H), 7.05 (d, J=2.5 Hz, 1H), 6.90 (dd, J=8.6, 2.5 Hz, 1H), 6.40 (s, 2H), 4.39 (ad, J=11.7 Hz, 1H), 4.27 (d, J=7.5 Hz, 2H), 4.10 (t, J=6.3 Hz, 2H), 3.93 (ad, J=13.3 Hz, 1H), 3.00 (at, J=12.4 Hz, 1H), 2.85 (septet, J=6.7 Hz, 1H), 2.56 (s, 3H), 2.6-2.5 (m, 1H), 2.19 (m, 1H), 1.87-1.65 (m, 5H), 1.28-0.98 (m, 8H), 0.93 (d, J=7.0 Hz, 6H);

$^{13}$C NMR (75 MHz, DMSO-$d_6$) δ 173.9, 157.2, 151.9, 149.2, 146.5, 132.8, 124.9, 121.1, 111.5, 108.9, 108.1, 65.0, 51.6, 44.9, 41.2, 35.0, 32.7, 31.6, 28.9, 28.7, 19.5, 19.4, 19.2, 13.9;

MS (APCI) m/z 452.3037 (452.3026 calcd for $C_{26}H_{37}N_5O_2$, M+H).

Anal. Calcd. for $C_{26}H_{37}N_5O_2 \cdot 0.1H_2O$: % C, 68.87; % H, 8.27; % N, 15.45. Found: % C, 68.37; % H, 8.33; % N, 15.07.

Example 27

7-{2-[1-(Cyclopentylcarbonyl)piperidin-4-yl]ethoxy}-2-methyl-1-(2-methylpropyl)-1H-imidazo[4,5-c]quinolin-4-amine

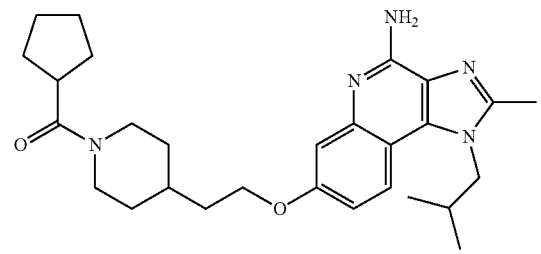 [SMILES: Cc1nc2c(N)nc3cc(OCCC4CCN(C(=O)C5CCCC5)CC4)ccc3c2n1CC(C)C]

The general method described in Example 15 was used to treat 2-methyl-1-(2-methylpropyl)-7-(2-piperidin-4-ylethoxy)-1H-imidazo[4,5-c]quinolin-4-amine with cyclopentanecarbonyl chloride to provide 0.158 g of 7-{2-[1-(cyclopentylcarbonyl)piperidin-4-yl]ethoxy}-2-methyl-1-(2-methylpropyl)-1H-imidazo[4,5-c]quinolin-4-amine, which was isolated as an off-white solid, mp 235.7-238.1° C.

$^1$H NMR (300 MHz, DMSO-$d_6$) δ 7.85 (d, J=9.1 Hz, 1H), 7.05 (d, J=1.7 Hz, 1H), 6.90 (dd, J=8.8, 2.5 Hz, 1H), 6.40 (s, 2H), 4.44-4.32 (m, 1H), 4.26 (d, J=6.6 Hz, 2H), 4.12-4.08 (m, 2H), 4.0-3.92 (m, 1H), 3.04-2.90 (m, 2H), 2.56 (s, 3H), 2.52-2.48 (m, 1H), 2.24-2.1 (m, 1H), 1.84-1.42 (m, 13H), 1.20-0.96 (m, 2H), 0.93 (d, J=7.2 Hz, 6H);

$^{13}$C NMR (75 MHz, DMSO-$d_6$) δ 173.0, 157.1, 151.9, 149.2, 146.5, 132.8, 124.9, 121.1, 111.5, 108.9, 108.1, 65.0, 51.6, 45.0, 41.4, 35.0, 32.7, 32.5, 31.6, 29.7, 28.7, 25.6, 19.2, 13.9;

MS (APCI) m/z 478.3189 (478.3182 calcd for $C_{28}H_{39}N_5O_2$, M+H).

Anal. Calcd. for $C_{28}H_{39}N_5O_2 \cdot 0.45H_2O$: % C, 69.23; % H, 8.28; % N, 14.42. Found: % C, 68.67; % H, 8.44; % N, 14.21.

Example 28

2-Methyl-1-(2-methylpropyl)-7-{2-[1-(morpholin-4-ylcarbonyl)piperidin-4-yl]ethoxy}-1H-imidazo[4,5-c]quinolin-4-amine

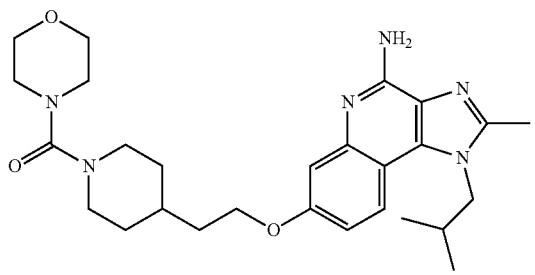 [SMILES: Cc1nc2c(N)nc3cc(OCCC4CCN(C(=O)N5CCOCC5)CC4)ccc3c2n1CC(C)C]

A modification of the method described in Example 19 was used to convert 2-methyl-1-(2-methylpropyl)-7-(2-piperidin-4-ylethoxy)-1H-imidazo[4,5-c]quinolin-4-amine to 0.195 g of 2-methyl-1-(2-methylpropyl)-7-{2-[1-(morpholin-4-ylcarbonyl)piperidin-4-yl]ethoxy}-1H-imidazo[4,5-c]quinolin-4-amine, which was isolated an off-white powder, mp 205-208° C. The product was not recrystallized.

$^1$H NMR (300 MHz, DMSO-$d_6$) δ 7.85 (d, J=9.2 Hz, 1H), 7.05 (d, J=3.1 Hz, 1H), 6.90 (dd, J=8.8, 2.5 Hz, 1H), 6.45 (s, 2H), 4.27 (d, J=7.4 Hz, 2H), 4.10 (t, J=5.5 Hz, 2H), 3.64-3.52 (m, 6H), 3.10 (at, J=4.6 Hz, 4H), 2.73 (at, J=11.9 Hz, 2H), 2.56 (s, 3H), 2.21-2.12 (m, 1H), 1.77-1.65 (m, 5H), 1.23-1.09 (m, 2H), 0.93 (d, J=6.6 Hz, 6H);

$^{13}$C NMR (75 MHz, DMSO-$d_6$) δ 163.2, 157.2, 151.8, 149.3, 146.3, 132.9, 124.9, 121.2, 111.6, 108.9, 107.9, 65.9, 65.0, 51.7, 47.1, 46.4, 35.2, 32.7, 31.3, 28.8, 19.3, 14.0;

MS (APCI) m/z 495.3080 (495.3084 calcd for $C_{27}H_{38}N_6O_3$, M+H).

Anal. Calcd. for $C_{27}H_{38}N_6O_3$: % C, 65.56; % H, 7.74; % N, 16.99. Found: % C, 65.21; % H, 7.40; % N, 16.68.

Example 29

4-(2-{[4-Amino-2-methyl-1-(2-methylpropyl)-1H-imidazo[4,5-c]quinolin-7-yl]oxy}ethyl)-N-cyclohexylpiperidine-1-carboxamide

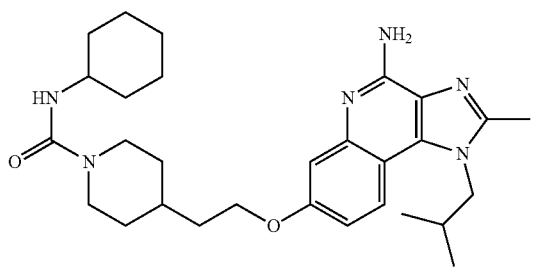 [SMILES: Cc1nc2c(N)nc3cc(OCCC4CCN(C(=O)NC5CCCCC5)CC4)ccc3c2n1CC(C)C]

A solution of 2-methyl-1-(2-methylpropyl)-7-(2-piperidin-4-ylethoxy)-1H-imidazo[4,5-c]quinolin-4-amine (0.300 g, 0.786 mmol) in chloroform was cooled to 0° C. Cyclohexyl isocyanate (0.100 mL, 0.783 mmol) was added dropwise, and the reaction was stirred for 30 minutes. The solvent was removed under reduced pressure, and the residue was purified by column chromatography on silica gel (eluting with dichloromethane:methanol ranging in ratios from 99:1 to 95:5). The resulting product was recrystallized from ethanol to provide 0.130 g of 4-(2-{[4-amino-2-methyl-1-(2-methylpropyl)-1H-imidazo[4,5-c]quinolin-7-yl]oxy}ethyl)-N-cyclohexylpiperidine-1-carboxamide as a white powder, mp 213.7-215.7° C.

$^1$H NMR (300 MHz, DMSO-$d_6$) δ 7.85 (d, J=9.5 Hz, 1H), 7.05 (d, J=3.0 Hz, 1H), 6.89 (dd, J=8.6, 2.5 Hz, 1H), 6.43 (s, 2H), 6.06 (d, J=7.6 Hz, 1H), 4.27 (d, J=7.5 Hz, 2H), 4.09 (t, J=6.0 Hz, 2H), 4.0-3.92 (m, 2H), 3.44-3.3 (m, 1H), 2.60 (t, J=11.5 Hz, 2H), 2.56 (s, 3H), 2.16 (m, 1H), 1.77-1.50 (m, 10H), 1.3-0.96 (m, 7H), 0.93 (d, J=6.3 Hz, 6H);

MS (APCI) m/z 507.3465 (507.3448 calcd for $C_{29}H_{42}N_6O_2$, M+H).

Anal. Calcd. for $C_{29}H_{42}N_6O_2 \cdot 0.5H_2O$: % C, 67.54; % H, 8.40; % N, 16.30. Found: % C, 67.78; % H, 8.43; % N, 16.46.

Example 30

2-Ethyl-1-(2-methylpropyl)-7-(2-morpholin-4-yl-2-oxoethoxy)-1H-imidazo[4,5-c]quinolin-4-amine

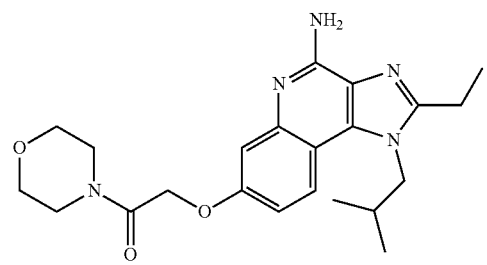 [SMILES: CCc1nc2c(N)nc3cc(OCC(=O)N4CCOCC4)ccc3c2n1CC(C)C]

Part A

The general method described in Part A of Example 9 was followed. Triethyl orthopropionate (7.66 mL, 58.1 mmol) was added in lieu of triethyl orthoacetate to a solution of 7-benzyloxy-$N^4$-(2-methylpropyl)quinoline-3,4-diamine (18.68 g, 58.11 mmol) in xylenes (200 mL). At the end of the reaction, the precipitate was collected in three crops to provide 7.16 g of 7-benzyloxy-2-ethyl-1-(2-methylpropyl)-1H-imidazo[4,5-c]quinoline as a light-brown solid, mp 127° C.

Anal. Calcd. for $C_{23}H_{25}N_3O$: % C, 76.85; % H, 7.01; % N, 11.69. Found: % C, 76.86; % H, 7.10; % N, 11.77.

Part B

The general method described in Part J of Example 1 was followed using 7-benzyloxy-2-ethyl-1-(2-methylpropyl)-1H-imidazo[4,5-c]quinoline (3.43 g, 9.54 mmol) in lieu of 7-benzyloxy-1-(2-methylpropyl)-2-propyl-1H-imidazo[4,5-c]quinolin-4-amine. The crude product was recrystallized from acetonitrile, isolated by filtration, and dried for two days in an oven at 60° C. to provide 0.92 g of 2-ethyl-1-(2-methylpropyl)-1H-imidazo[4,5-c]quinolin-7-ol as an off-white solid, mp>250° C.

Anal. Calcd. for $C_{16}H_{19}N_3O$: % C, 71.35; % H, 7.11; % N, 15.60. Found: % C, 71.36; % H, 7.02; % N, 15.60.

Part C

A solution of bromoacetyl bromide (3.0 mL, 0.034 mol) in dichloromethane (240 mL) was cooled to −25° C. A solution of morpholine (9.0 mL, 0.10 mol) in dichloromethane (20 mL) was slowly added over a period of one hour. After the addition was complete, the reaction was stirred at −25° C. for 15 minutes and allowed to warm to ambient temperature. Dichloromethane was added, and the resulting solution was washed with water, 1N aqueous hydrogen chloride, and brine; dried over magnesium sulfate; filtered; and concentrated under reduced pressure to provide 4-(2-bromoacetyl)morpholine as a colorless oil.

Part D

Under a nitrogen atmosphere, a mixture of 2-ethyl-1-(2-methylpropyl)-1H-imidazo[4,5-c]quinolin-7-ol (1.97 g, 7.31 mmol), solid cesium carbonate (4.77 g, 14.6 mmol), and DMF (105 mL) was heated at 85° C. for 30 minutes. The heat was removed, and a solution of 4-(2-bromoacetyl) morpholine (1.83 g, 8.77 mmol) in DMF (20 mL) was added over a period of 12 minutes. The reaction was heated at 85° C. for 3.5 hours, and methanol (1 mL) was then added. The reaction mixture was filtered to remove solids, and the filtrate was concentrated under reduced pressure to provide an orange oil. The oil was triturated with ethyl acetate and water to provide a fluffy, white solid that was isolated by filtration. The filtrate was concentrated under reduced pressure to provide a solid that was stirred with diethyl ether and water and isolated by filtration. The two solids were combined and dried in a vacuum oven at 60° C. to provide 2.75 g of 2-ethyl-1-(2-methylpropyl)-7-(2-morpholin-4-yl-2-oxoethoxy)-1H-imidazo[4,5-c]quinoline as a yellow semisolid.

Part E

Over a period of 30 minutes, mCPBA (1.85 g, 5.47 mmol, 50% pure) was added in four portions to a solution of 2-ethyl-1-(2-methylpropyl)-7-(2-morpholin-4-yl-2-oxoethoxy)-1H-imidazo[4,5-c]quinoline (2.13 g, 5.47 mmol) in chloroform (200 mL). The reaction was stirred overnight at ambient temperature, washed twice with 1% aqueous sodium carbonate, and concentrated under reduced pressure. The residue was purified by column chromatography on silica gel (eluting with 95:5 dichloromethane:methanol) to provide 0.53 g of 2-ethyl-1-(2-methylpropyl)-7-(2-morpholin-4-yl-2-oxoethoxy)-5-oxido-1H-imidazo[4,5-c]quinoline.

Part F

Ammonium hydroxide (0.5 mL) was added to a solution of 2-ethyl-1-(2-methylpropyl)-7-(2-morpholin-4-yl-2-oxoethoxy)-5-oxido-1H-imidazo[4,5-c]quinoline (0.53 g, 1.28 mmol) in dichloromethane (3 mL), and the mixture was cooled to 0° C. p-Toluenesulfonyl chloride (0.29 g, 1.5 mmol) was added in small portions over a period of 20 minutes. The reaction was stirred at ambient temperature overnight. The reaction mixture was partitioned between dichloromethane and 1% aqueous sodium carbonate. The organic fraction was washed with 1% aqueous sodium carbonate (2×30 mL), dried over magnesium sulfate, filtered, and concentrated under reduced pressure. The crude product was recrystallized from ethyl acetate, isolated by filtration, washed with cold hexanes, and dried under high vacuum at 55° C. to provide 0.391 g of 2-ethyl-1-(2-methylpropyl)-7-(2-morpholin-4-yl-2-oxoethoxy)-1H-imidazo[4,5-c]quinolin-4-amine as off-white needles, mp 219-220° C.

$^1$H NMR (300 MHz, DMSO-$d_6$) δ 7.87 (d, J=9.0 Hz, 1H), 7.05 (d, J=2.4 Hz, 1H), 6.94 (dd, J=9.0, 2.7 Hz, 1H), 6.4 (br s, 2H), 4.9 (s, 2H), 4.28 (d, J=7.2 Hz, 2H), 4.9-4.28 (m, 8H), 2.91 (q, J=7.5 Hz, 2H), 2.15 (septet, J=6.7 Hz, 1H), 1.36 (t, J=7.5 Hz, 3H), 0.91 (d, J=6.6 Hz, 6H);

$^{13}$C NMR (75 MHz, DMSO-$d_6$) δ 166.5, 156.9, 154.1, 152.3, 146.7, 133.2, 125.5, 121.5, 111.8, 109.7, 108.9, 66.4, 66.3, 51.5, 45.2, 42.0, 29.1, 20.5, 19.5, 12.4;

MS (ESI) m/z 412.2344 (412.2349 calcd. for $C_{22}H_{29}N_5O_3$, M+H).

Anal. Calcd. for $C_{22}H_{29}N_5O_3$: % C, 64.21; % H, 7.10; % N, 17.02. Found: % C, 64.07; % H, 7.21; % N, 16.99.

Example 31

2-Butyl-1-methyl-8-[(5-morpholin-4-yl-5-oxopentyl) oxy]-1H-imidazo[4,5-c]quinolin-4-amine trifluoroacetate

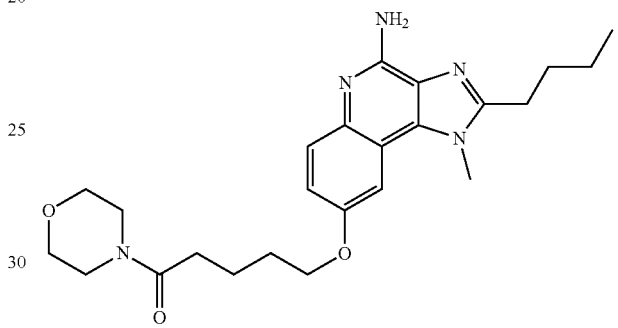

Part A

Methylamine (available as a 40% solution in water, 24 mL, 0.28 mol) was added to a solution of 6-benzyloxy-4-chloro-3-nitroquinoline (15.0 g, 48.5 mmol), prepared as described in Parts A-D of Example 2, in distilled water (300 mL), and the reaction was stirred at 100° C. for 1.5 hours. The reaction was allowed to cool to ambient temperature and stirred for four hours. A precipitate formed, which was isolated by filtration and washed with distilled water (3×60 mL). The solid was combined with material from another run and recrystallized from 2-propanol. The crystals were isolated by filtration, washed twice with cold hexanes, and dried for three days under high vacuum to provide 24.10 g of (6-benzyloxy-3-nitroquinolin-4-yl)methylamine as yellow crystals.

Part B

A warm solution (37° C.) of (6-benzyloxy-3-nitroquinolin-4-yl)methylamine (23.98 g, 77.6 mmol) in toluene (1.5 L) was added to a Parr vessel containing 5% platinum on carbon (11.78 g, 0.0604 mol) and a small volume of toluene. The vessel was placed under hydrogen pressure (35 psi, 2.4×10$^5$ Pa) for 2.5 hours. The catalyst was removed by filtration, and the filtrate was concentrated under reduced pressure at 55° C. to provide 15.57 g of 6-benzyloxy-N$^4$-methylquinoline-3,4-diamine as a brown oil.

Part C

Under a nitrogen atmosphere, trimethyl orthovalerate (18.51 mL, 0.107 mol) was added dropwise to a solution of 6-benzyloxy-$N^4$-methylquinoline-3,4-diamine (15.57 g, 0.0537 mol) in xylenes (150 mL), and the reaction was heated at reflux temperature overnight. The reaction was not complete as evidenced by thin layer chromatography (TLC), and additional trimethyl orthovalerate (9.25 mL, 0.0537 mol) was added. The reaction was heated at reflux overnight, and a Dean-Stark trap was used to collect the volatiles. The reaction was then heated at 170° C. for 4.5 hours, and about 100 mL of solvent were removed by distillation. The reaction mixture was allowed to cool to ambient temperature; a precipitate formed over a period of three days. The mixture was diluted with hexanes, and the precipitate was isolated by filtration and washed with hexanes to provide 15.64 g of 8-benzyloxy-2-butyl-1-methyl-1H-imidazo[4,5-c]quinoline.

Part D

A modification of the general method described in Part J of Example 1 was followed using 8-benzyloxy-2-butyl-1-methyl-1H-imidazo[4,5-c]quinoline (14.65 g, 42.4 mmol) in lieu of 7-benzyloxy-1-(2-methylpropyl)-2-propyl-1H-imidazo[4,5-c]quinolin-4-amine. The reaction was placed under hydrogen pressure for 3.5 hours. The catalyst was removed by filtration and washed with ethyl acetate. The filtrate was concentrated under reduced pressure to a small volume, and hexanes were added. A precipitate formed, and the mixture was stored overnight in a refrigerator. The solid was isolated by filtration, washed with hexanes (500 mL), and dried for three days under high vacuum to provide 9.40 g of 2-butyl-1-methyl-1H-imidazo[4,5-c]quinolin-8-ol as a white solid, mp 219-220.2° C.

$^1$H NMR (300 MHz, DMSO-$d_6$) δ 9.99 (s, 1H), 8.89 (s, 1H), 7.97 (d, J=9.0 Hz, 1H), 7.73 (d, J=2.5 Hz, 1H), 7.21 (dd, J=9.0, 2.7 Hz, 1H), 4.13 (s, 3H), 2.94 (t, J=7.6 Hz, 2H), 1.79 (quintet, J=7.6 Hz, 2H), 1.44 (sextet, J=7.4 Hz, 2H), 0.95 (t, J=7.3 Hz, 3H).

MS (APCI) m/e 256.2 (256.3 calcd for $C_{15}H_{17}N_3O$, M+H).

Anal. Calcd. for $C_{15}H_{17}N_3O$: % C, 70.56; % H, 6.71; % N, 16.46. Found: % C, 70.60; % H, 6.65; % N, 16.38.

Part E

Under a nitrogen atmosphere, 5-bromovaleryl chloride (4.0 mL, 30 mmol) was added dropwise to a solution of morpholine (3.13 mL, 36 mmol) and triethylamine (6.25 mL, 45 mmol) in anhydrous THF (200 mL), and the reaction was stirred for 3.5 hours. Water (100 mL) was added, and the resulting solution was extracted with ethyl acetate (250 mL+150 mL). The combined extracts were washed with aqueous hydrogen chloride (100 mL of 1 N), water (60 mL), and brine (100 mL); dried over magnesium sulfate; filtered; concentrated under reduced pressure; and further dried under high vacuum to provide 6.60 g of 4-(5-bromopentanoyl)morpholine as a yellow oil.

Part F

A modification of the general method described in Part D of Example 30 was followed using 2-butyl-1-methyl-1H-imidazo[4,5-c]quinolin-8-ol (1.2 g, 4.7 mmol) in lieu of 2-ethyl-1-(2-methylpropyl)-1H-imidazo[4,5-c]quinolin-7-ol and 4-(5-bromopentanoyl)morpholine (3.7 mmol) in lieu of 4-(2-bromoacetyl)morpholine. After the reaction was heated overnight, an analysis by TLC indicated the presence of starting material. Additional 4-(5-bromopentanoyl)morpholine (2.2 g) and cesium carbonate (0.5 g) were added, and the reaction was heated at 80° C. overnight. After the solution was concentrated, the residue was further dried under high vacuum overnight and then dissolved in ethyl acetate. The resulting solution was washed with water and concentrated under reduced pressure. The solid was purified by column chromatography on silica gel (eluting with 90:10 dichloromethane:methanol) to provide an oil, which was stirred with diethyl ether and allowed to stand over three days in a refrigerator. A precipitate formed, which was isolated by filtration to provide 0.770 g of 2-butyl-1-methyl-8-[(5-morpholin-4-yl-5-oxopentyl)oxy]-1H-imidazo[4,5-c]quinoline as pale yellow crystals.

Part G

The general method described in Part E of Example 30 was used to convert 2-butyl-1-methyl-8-[(5-morpholin-4-yl-5-oxopentyl)oxy]-1H-imidazo[4,5-c]quinoline (0.770 g, 1.81 mmol) to 2-butyl-1-methyl-8-[(5-morpholin-4-yl-5-oxopentyl)oxy]-5-oxido-1H-imidazo[4,5-c]quinoline, obtained as mixture with starting material.

Part H

Under a nitrogen atmosphere, trichloroacetyl isocyanate (0.357 mL, 2.99 mmol) was added dropwise to a solution of the material from Part G in anhydrous dichloromethane (25 mL), and the reaction was stirred for six hours at ambient temperature. The reaction was incomplete as evidenced by a TLC analysis. Additional trichloroacetyl isocyante (0.10 mL) was added, and the reaction was stirred for 1.5 hours. Ammonium hydroxide (four drops of 7% by weight in methanol) was added, and the volatiles were removed under reduced pressure. The resulting orange solid was purified by column chromatography on silica gel (eluting with 90:10 dichloromethane:methanol) and further purified by preparative high-performance liquid chromatography (prep HPLC) with fraction collection by UV triggering. The prep HPLC fractions were analyzed using a Micromass Platform LC/MS, and the appropriate fractions were centrifuge evaporated. The prep HPLC separation was done by reversed phase chromatography with a Phenomenex Luna C18(2) column (10×50 mm, 5 micron particle size) at a flow rate of 16 mL/min. The mobile phase was a gradient mixture of water and acetonitrile (0.05% trifluoroacetic acid in each) from 5 to 95% acetonitrile in 6.5 minutes. The resulting solid was dried under vacuum for several days to provide 2-butyl-1-methyl-8-[(5-morpholin-4-yl-5-oxopentyl)oxy]-1H-imidazo[4,5-c]quinoline trifluoroacetate as a beige powder, mp 155.5-156.2° C.

$^1$H NMR (300 MHz, DMSO-$d_6$) δ 8.67 (br s, 2H), 7.76 (d, J=9.3 Hz, 1H), 7.71 (d, J=2.7 Hz, 1H), 7.38 (dd, J=9.3, 2.4 Hz, 1H), 4.2-4.15 (m, 5H), 3.6-3.52 (m, 4H), 3.5-3.4 (m, 4H), 3.0 (t, J=7.8 Hz, 2H), 2.41 (t, J=7.2 Hz, 2H), 1.85-1.62 (m, 6H), 1.44 (sextet, J=7.2 Hz, 2H), 0.96 (t, J=7.5 Hz, 3H), $^{13}$C NMR (150 MHz, DMSO-$d_6$) δ 171.5, 157.3, 156.2, 148.7, 136.1, 128.8, 125.0, 120.4, 119.2, 114.6, 105.1, 68.7, 67.0, 46.2, 43.6, 42.2, 34.3, 32.5, 29.9, 29.1, 27.1, 22.6, 22.2, 14.5; MS (ESI) m/z 440.2676 (Calcd. for $C_{24}H_{33}N_5O_3$ 440.2662, M+H);

Anal. Calcd. for $C_{24}H_{33}N_5O_3 \cdot 1.5\ C_2HF_3O_2 \cdot 0.62\ H_2O$: % C, 52.11; % H, 5.80; % N, 11.25; % F, 13.74. Found: % C, 51.93; % H, 5.61; % N, 11.31; % F, 12.45.

Examples 32-36

Part A

The general methods described in Parts C-E of Example 30 were followed. According to the method of Part C the amine listed in the table below was used to prepare the bromo reagent listed in the table below. According to the method of Part D, 2-butyl-1-methyl-1H-imidazo[4,5-c]quinolin-8-ol was treated with the bromo reagent, and the product was oxidized according to the method of Part E. For Example 35, the crude product isolated after Part D was recrystallized from water. Chromatographic purification as described in Part E was carried out only for Example 36; the remaining N-oxides were used without purification.

Part B

Under a nitrogen atmosphere, trichloroacetyl isocyanate (1.5 equivalents) was added dropwise to a solution of the material from Part A in anhydrous dichloromethane, and the reaction was stirred for between two and five hours. The solvent was removed under reduced pressure. The residue was diluted with methanol, and a solution of sodium methoxide (5 equivalents, 25% in methanol) was slowly added. The reaction was stirred overnight, and a precipitate formed. The precipitate was isolated by filtration, washed with three times with cold hexanes. The purification and characterization of the final compounds are described for each example below the table.

Example 32

2-Butyl-1-methyl-8-(2-morpholin-4-yl-2-oxoethoxy)-1H-imidazo[4,5-c]quinolin-4-amine The crude product was recrystallized from methyl acetate to provide 2-butyl-1-methyl-8-(2-morpholin-4-yl-2-oxoethoxy)-1H-imidazo[4,5-c]quinolin-4-amine as a white solid, mp 256.8-257.2° C.

$^1$H NMR (500 MHz, DMSO-$d_6$) δ 7.61 (d, J=3.0 Hz, 1H), 7.54 (d, J=9.0 Hz, 1H), 7.12 (dd, J=9.0, 2.5 Hz, 1H), 6.24-6.19 (br s, 2H), 4.94 (s, 2H), 4.10 (s, 3H), 3.65-3.45 (m, 8H), 2.93 (t, J=7.5 Hz, 2H), 1.75 (pentet, J=7.5 Hz, 2H), 1.43 (sextet, J=7.5 Hz, 2H), 0.95 (t, J=7.5 Hz, 3H);

MS (APCI) m/z 398 (M+H)$^+$;

Anal. Calcd. for $C_{21}H_{27}N_5O_3$: % C, 63.46; % H, 6.85; % N, 17.62. Found: % C, 63.39; % H, 6.86; % N, 17.75.

Example 33

2-Butyl-1-methyl-8-(2-oxo-2-piperidin-1-ylethoxy)-1H-imidazo[4,5-c]quinolin-4-amine The crude product was recrystallized from methyl acetate and dried for four hours in a vacuum oven at 45° C. to provide 2-butyl-1-methyl-8-(2-oxo-2-piperidin-1-ylethoxy)-1H-imidazo[4,5-c]quinolin-4-amine as a white solid, mp 222.5-223.4° C.

$^1$H NMR (300 MHz, DMSO-$d_6$) δ 7.61 (d, J=2.7 Hz, 1H), 7.53 (d, J=9.0 Hz, 1H), 7.11 (dd, J=9.0, 2.7 Hz, 1H), 6.23 (br s, 2H), 4.89 (s, 2H), 4.1 (s, 3H), 3.46 (br s, 4H), 2.92 (t, J=8.1 Hz, 2H), 1.75 (pentet, J=7.5 Hz, 2H), 1.59-1.36 (m, 8H), 0.95 (t, J=7.2 Hz, 3H);

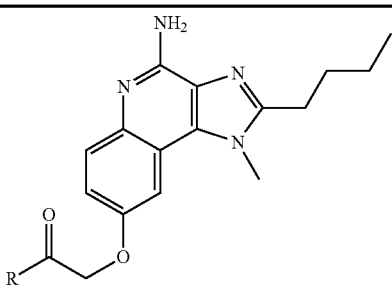

| Example | Amine | Bromo Reagent | R |
|---|---|---|---|
| 32 | Morpholine | 4-(2-Bromoacetyl)morpholine | —N(morpholine) |
| 33 | Piperidine | 2-Bromo-1-piperidin-1-ylethanone | —N(piperidine) |
| 34 | Benzylmethylamine | N-Benzyl-2-bromo-N-methylacetamide | —N(Bn)(Me) |
| 35 | Diethylamine | N,N-Diethyl-2-bromoacetamide | —N(Et)$_2$ |
| 36 | Bis(methoxyethylamine) | 2-Bromo-N,N-bis-(2-methoxyethyl)acetamide | —N(CH$_2$CH$_2$OCH$_3$)$_2$ |

MS (EI) m/z 395.2327 (Calcd. for $C_{22}H_{29}N_5O_2$ 395.2321).

Anal. Calcd. for $C_{26}H_{29}N_5O_2$: % C, 66.81; % H, 7.39; % N, 17.71. Found: % C, 66.81; % H, 7.18; % N, 17.63.

Example 34

2-[(4-Amino-2-butyl-1-methyl-1H-imidazo[4,5-c]quinolin-8-yl)oxy]-N-benzyl-N-methylacetamide The crude product was recrystallized from a mixture of DMF and water to provide 2-[(4-amino-2-butyl-1-methyl-1H-imidazo[4,5-c]quinolin-8-yl)oxy]-N-benzyl-N-methylacetamide as an off-white solid, mp 167.4-168.8° C.

$^1$H NMR (300 MHz, DMSO-$d_6$) δ 7.64 (d, J=2.7 Hz, 1H), 7.55 (d, J=9.0 Hz, 1H), 7.21 (br s, 5H), 7.10 (d, J=8.1 Hz, 1H), 5.89 (br s, 2H), 4.94 (s, 2H), 4.57 (br s, 2H), 4.03 (s, 3H), 3.01 (s, 3H), 2.91 (t, J=7.2 Hz, 2H), 1.78 (pentet, J=7.5 Hz, 2H), 1.45 (sextet, J=7.2 Hz, 2H), 0.95 (t, J=7.5 Hz, 3H);

MS (APCI) m/z 432 (M+H)$^+$,

Anal. Calcd. for $C_{25}H_{29}N_5O_2$: % C, 69.58; % H, 6.77; % N, 16.23. Found: % C, 69.35; % H, 6.47; % N, 16.13.

Example 35

2-[(4-Amino-2-butyl-1-methyl-1H-imidazo[4,5-c]quinolin-8-yl)oxy]-N,N-diethylacetamide The crude product was purified by column chromatography on silica gel (eluting with 95:5 dichloromethane:methanol). The pure fractions were concentrated under reduced pressure to a small volume, and hexanes were added. A precipitate formed and was washed with hexanes to provide 2-[(4-amino-2-butyl-1-methyl-1H-imidazo[4,5-c]quinolin-8-yl)oxy]-N,N-diethylacetamide as a white solid, mp 185.90-188.10° C.

$^1$H NMR (300 MHz, DMSO-$d_6$) δ 7.61 (d, J=2.6 Hz, 1H), 7.54 (d, J=9.1 Hz, 1H), 6.37 (dd, J=9.1, 2.7 Hz, 1H), 6.19 (s, 2H), 4.88 (s, 2H), 4.09 (s, 3H), 3.41 (m, 2H), 2.92 (t, J=7.6 Hz, 2H), 1.75 (m, 2H), 1.43 (m, 2H), 1.17 (t, J=7.0 Hz, 3H), 1.06 (t, J=7.0 Hz, 3H), 0.95 (t, J=7.3 Hz, 3H);

MS (EI) m/z 383.2326 (Calcd. for $C_{21}H_{29}N_5O_2$ 383.2321).

Anal. Calcd. for $C_{21}H_{29}N_5O_2 \cdot 0.15 H_2O$: % C, 65.31; % H, 7.65; % N, 18.13. Found: % C, 65.18; % H, 7.28; % N, 18.11.

Example 36

2-[(4-Amino-2-butyl-1-methyl-1H-imidazo[4,5-c]quinolin-8-yl)oxy]-N,N-bis(2-methoxyethyl)acetamide The product from the reaction with sodium methoxide did not precipitate from the reaction solution. The solvent was removed under reduced pressure, and the residue was recrystallized from 2-propanol, isolated by filtration, washed with hexanes, stirred with water for two hours, isolated by filtration, and washed with water. The solid was then recrystallized twice from methanol, purified by column chromatography on silica gel (eluting with 95:5 dichloromethane:methanol), and recrystallized from dimethyl sulfoxide to provide 2-[(4-amino-2-butyl-1-methyl-1H-imidazo[4,5-c]quinolin-8-yl)oxy]-N,N-bis(2-methoxyethyl)acetamide as a peach-colored, crystalline solid, mp 125-128° C.

$^1$H NMR (300 MHz, DMSO-$d_6$) δ 7.57 (d, J=3.0 Hz, 1H), 7.53 (d, J=9.3 Hz, 1H), 7.08 (dd, J=9.3, 3.0 Hz, 1H), 6.17 (s, 2H), 4.95 (s, 2H), 4.09 (s, 3H), 3.61 (t, J=4.8 Hz, 2H), 3.53 (t, J=4.8 Hz, 2H), 3.49 (t, J=5.1 Hz, 2H), 3.41 (t, J=4.8 Hz, 2H), 3.41 (s, 6H), 2.93 (t, J=7.2 Hz, 2H), 1.75 (pentet, J=7.8 Hz, 2H), 1.43 (sextet, J=7.8 Hz, 2H), 0.94 (t, J=7.8 Hz, 3H);

$^{13}$C NMR (75 MHz, DMSO-$d_6$) δ 167.6, 152.8, 152.0, 149.8, 139.2, 132.5, 126.7, 126.0, 115.7, 114.7, 102.5, 69.8, 69.2, 66.0, 57.9, 57.5, 46.5, 44.6, 32.4, 29.0, 25.8, 21.4, 13.3;

MS (EI) m/z 443.2529 (443.2533 calcd. for $C_{23}H_{33}N_5O_4$).

Example 37 tert-Butyl 4-[2-(4-amino-2-butyl-1-methyl-1H-imidazo[4,5-c]quinolin-8-yloxy)ethyl]piperidine-1-carboxylate

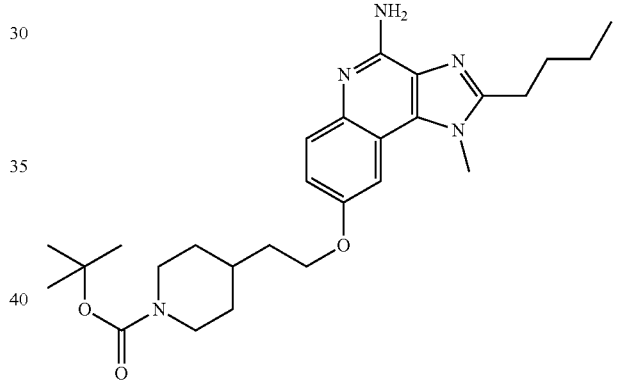

Part A

The method described in Part L of Example 2 was used to treat 2-butyl-1-methyl-1H-imidazo[4,5-c]quinolin-8-ol with tert-butyl 4-(2-iodoethyl)piperidine-1-carboxylate. Following chromatographic purification, tert-butyl 4-[2-(4-amino-2-butyl-1-methyl-1H-imidazo[4,5-c]quinolin-8-yloxy)ethyl]piperidine-1-carboxylate was isolated as a viscous, pale yellow oil containing some DMF.

$^1$H NMR (300 MHz, DMSO-$d_6$) δ 8.95 (s, 1H), 8.03 (d, J=9.6 Hz, 1H), 7.74 (d, J=3.0 Hz, 1H), 7.29 (dd, J=9.2, 2.6 Hz, 1H), 4.51-4.42 (m, 1H), 4.19 (s, 3H), 4.16 (t, J=7.2 Hz, 2H), 3.95-3.84 (m, 1H), 2.98 (t, J=5.4 Hz, 2H), 2.29-2.16 (m, 1H), 2.03-1.87 (m, 1H), 1.80 (quintet, J=7.7 Hz, 2H), 1.70-1.37 (m, 9H), 1.29 (s, 9H), 0.95 (t, J=7.7 Hz, 3H).

Part B

The methods described in Parts M and N of Example 2 were used to convert tert-butyl 4-[2-(4-amino-2-butyl-1-methyl-1H-imidazo[4,5-c]quinolin-8-yloxy)ethyl]piperidine-1-carboxylate to tert-butyl 4-[2-(4-amino-2-butyl-1- methyl-1H-imidazo[4,5-c]quinolin-8-yloxy)ethyl]piperidine-1-carboxylate, which was obtained as an off-white powder, mp 171.1-173.2° C.

$^1$H NMR (300 MHz, DMSO-$d_6$) δ 7.56 (d, J=3.1 Hz, 1H), 7.53 (d, J=8.6 Hz, 1H), 7.06 (dd, J=9.3, 2.9 Hz, 1H), 6.19 (s, 2H), 4.49-4.40 (m, 1H), 4.10 (s, 3H), 4.04 (t, J=6.0 Hz, 2H), 3.94-3.81 (m, 1H), 2.92 (t, J=7.9 Hz, 2H), 2.9-2.75 (m, 1H), 2.24-2.1 (m, 1H), 1.96-1.84 (m, 1H), 1.75 (quintet, J=7.7 Hz, 2H), 1.68-1.50 (m, 5H), 1.43 (sextet, J=7.5 Hz, 2H), 1.31 (s, 9H), 1.31-1.2 (m, 1H), 0.95 (t, J=7.2 Hz, 3H);

$^{13}$C NMR (75 MHz, DMSO-$d_6$) δ 154.0, 153.1, 152.9, 150.1, 139.5, 133.0, 127.3, 126.5, 116.2, 115.3, 102.2, 78.3, 65.2, 47.4, 32.9, 29.5, 29.1, 28.4, 28.0, 26.2, 25.3, 21.9, 18.6, 13.7; MS (APCI) m/z 482.3111 (482.3131 calcd for $C_{27}H_{39}N_5O_3$, M+H).

Anal. Calcd. for $C_{27}H_{39}N_5O_3$: % C, 67.33; % H, 8.16; % N, 14.54. Found: % C, 67.37; % H, 8.22; % N, 14.48.

Example 38

2-Butyl-1-methyl-8-(2-piperidin-4-ylethoxy)-1H-imidazo[4,5-c]quinolin-4-amine

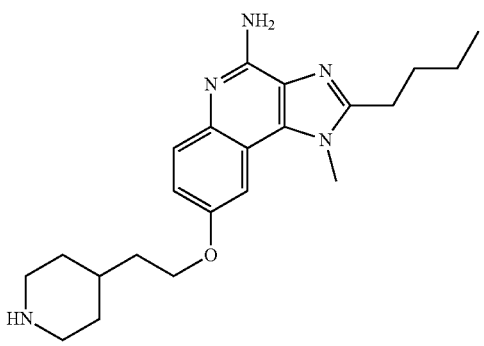 [SMILES: CCCCc1nc2c(N)nc3ccc(OCCC4CCNCC4)cc3c2n1C]

A modification of the method described in Part O of Example 2 was used to deprotect tert-butyl 4-[2-(4-amino-2-butyl-1-methyl-1H-imidazo[4,5-c]quinolin-8-yloxy)ethyl]piperidine-1-carboxylate. The crude product was triturated with diethyl ether and isolated by filtration to provide 2-butyl-1-methyl-8-(2-piperidin-4-ylethoxy)-1H-imidazo[4,5-c]quinolin-4-amine as a yellow powder, mp 210-212° C.

$^1$H NMR (300 MHz, DMSO-$d_6$) δ 7.58 (d, J=2.6 Hz, 1H), 7.52 (d, J=9.4 Hz, 1H), 7.08 (dd, J=9.2, 2.8 Hz, 1H), 6.16 (s, 2H), 4.16 (at, J=6.2 Hz, 2H), 4.12 (s, 3H), 2.96-2.87 (m, 1H), 2.92 (at, J=7.9 Hz, 2H), 2.68-2.56 (m, 1H), 2.56-2.43 (m, 1H), 2.12-1.96 (m, 1H), 1.75 (quintet, J=7.0 Hz, 2H), 1.69-1.60 (m, 4H), 1.51-1.24 (m, 5H), 1.03-0.97 (m, 1H), 0.95 (t, J=7.6 Hz, 3H);

MS (APCI) m/z 382.2621 (382.2607 calcd for $C_{22}H_{31}N_5O$, M+H).

Anal. Calcd. for $C_{22}H_{31}N_5O$: % C, 69.26; % H, 8.19; % N, 18.36. Found: % C, 68.87; % H, 8.13; % N, 18.12.

Example 39

1-{4-[2-(4-Amino-2-butyl-1-methyl-1H-imidazo[4,5-c]quinolin-8-yloxy)ethyl]piperidin-1-yl}-2-methylpropan-1-one

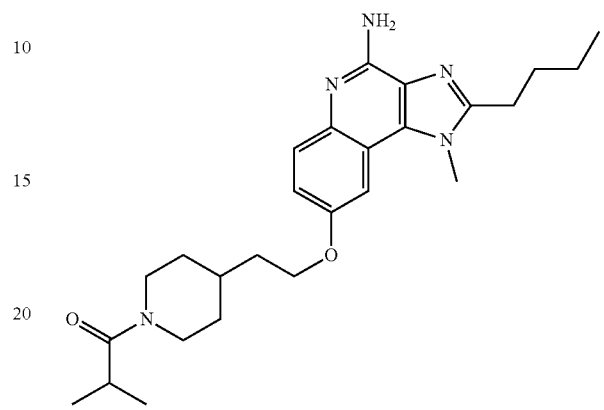

A modification of the method described in Example 15 was followed. The reaction solvent was 1-methylpyrrolidin-2-one, and 2-butyl-1-methyl-8-(2-piperidin-4-ylethoxy)-1H-imidazo[4,5-c]quinolin-4-amine was used as the starting material. Following recrystallization from acetonitrile, 1-{4-[2-(4-amino-2-butyl-1-methyl-1H-imidazo[4,5-c]quinolin-8-yloxy)ethyl]piperidin-1-yl}-2-methylpropan-1-one was isolated as yellow needles, mp 189.4-192.6° C.

MS (APCI) m/z 452.3031 (452.3026 calcd for $C_{26}H_{37}N_5O_2$, M+H).

Anal. Calcd. for $C_{26}H_{37}N_5O_2 \cdot 0.60H_2O$: % C, 67.53; % H, 8.33; % N, 15.14. Found: % C, 67.59; % H, 8.23; % N, 15.39.

Example 40

2-Butyl-8-{2-[1-(cyclopentylcarbonyl)piperidin-4-yl]ethoxy}-1-methyl-1H-imidazo[4,5-c]quinolin-4-amine

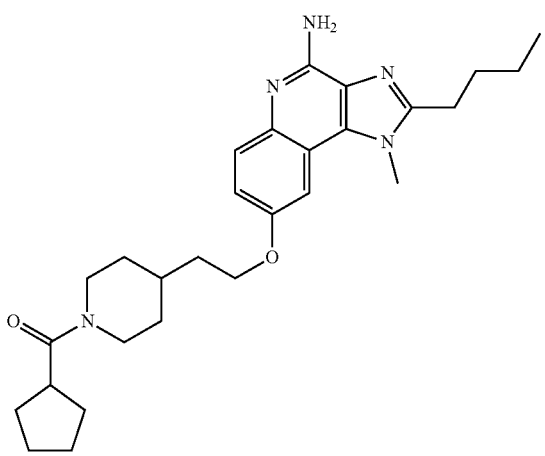 [SMILES: CCCCc1nc2c(N)nc3ccc(OCCC4CCN(C(=O)C5CCCC5)CC4)cc3c2n1C]

A modification of the method described in Example 15 was used to treat 2-butyl-1-methyl-8-(2-piperidin-4- ylethoxy)-1H-imidazo[4,5-c]quinolin-4-amine with cyclopentanecarbonyl chloride. The crude product was purified by column chromatography on silica gel to provide 2-butyl-8-{2-[1-(cyclopentylcarbonyl)piperidin-4-yl]ethoxy}-1-methyl-1H-imidazo[4,5-c]quinolin-4-amine as a white solid, mp 147.2-150.1° C.

MS (APCI) m/z 478.3173 (478.3182 calcd for $C_{24}H_{39}N_5O_2$, M+H).

Anal. Calcd. for $C_{24}H_{39}N_5O_2 \cdot 0.45H_2O$: % C, 69.23; % H, 8.28; % N, 14.42. Found: % C, 68.91; % H, 8.20; % N, 14.31.

Example 41

2-Butyl-8-{2-[1-(methanesulfonyl)piperidin-4-yl]ethoxy}-1-methyl-1H-imidazo[4,5-c]quinolin-4-amine

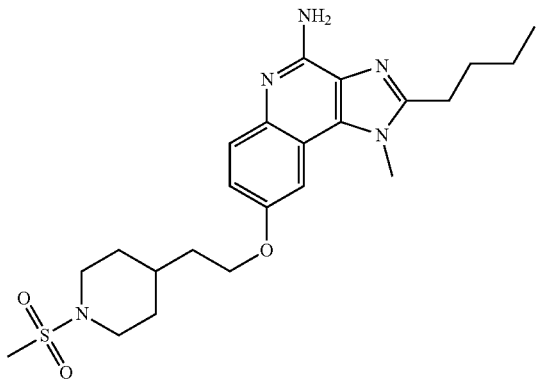 [SMILES: CCCCc1nc2c(N)nc3ccc(OCCC4CCN(S(C)(=O)=O)CC4)cc3c2n1C]

A suspension of 2-butyl-1-methyl-8-(2-piperidin-4-ylethoxy)-1H-imidazo[4,5-c]quinolin-4-amine (0.320 g, 0.839 mmol) and methanesulfonic anhydride (0.153, 0.878 mmol) in dichloromethane (20 mL) was stirred for five minutes. Triethylamine (0.122 mL, 0.875 mmol) was added dropwise, and the solution was stirred for 1.5 hours. The reaction was poured into water, and the organic layer was separated and stirred with 10% aqueous sodium hydroxide for 20 minutes. The organic layer was separated and washed with brine, dried over magnesium sulfate, filtered, and concentrated under reduced pressure. The resulting solid was recrystallized from acetonitrile to yield 0.174 g of 2-butyl-8-{2-[1-(methanesulfonyl)piperidin-4-yl]ethoxy}-1-methyl-1H-imidazo[4,5-c]quinolin-4-amine as a feathery, white solid, mp 198-199.5° C.

$^1$H NMR (300 MHz, DMSO-$d_6$) δ 7.60 (d, J=2.7 Hz, 1H), 7.53 (d, J=9.1 Hz, 1H), 7.09 (dd, J=9.1, 2.7 Hz, 1H), 6.16 (s, 2H), 4.20-4.16 (m, 3H), 4.10 (s, 3H), 3.65-3.56 (m, 1H), 3.11-3.01 (m, 1H), 2.98-2.90 (m, 2H), 2.93 (s, 3H), 2.28-2.16 (m, 1H), 1.98 (sextet, J=6.8 Hz, 1H), 1.80-1.36 (m, 10H), 0.95 (t, J=7.3 Hz, 3H);

$^{13}$C NMR (75 MHz, DMSO-$d_6$) δ 153.1, 152.8, 150.1, 139.5, 133.0, 127.3, 126.4, 116.4, 115.3, 102.7, 65.4, 49.3, 32.9, 29.5, 28.9, 27.8, 26.2, 24.7, 21.8, 18.2, 13.7;

MS (APCI) m/z 460.2396 (460.2382 calcd for $C_{23}H_{33}N_5O_3S$, M+H).

Anal. Calcd. for $C_{23}H_{33}N_5O_3S$: % C, 60.11; % H, 7.24; % N, 15.24; % S, 6.98. Found: % C, 59.95; % H, 7.21; % N, 15.30; % S, 6.92.

Example 42

2-Butyl-1-methyl-8-{2-[1-(morpholin-4-ylcarbonyl)piperidin-4-yl]ethoxy}-1H-imidazo[4,5-c]quinolin-4-amine

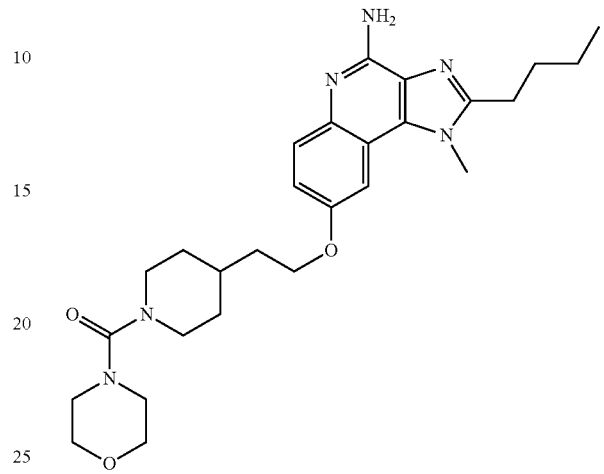

A modification of the method described in Example 19 was followed. The reaction solvent was 1-methylpyrrolidin-2-one, and 2-butyl-1-methyl-8-(2-piperidin-4-ylethoxy)-1H-imidazo[4,5-c]quinolin-4-amine was used as the starting material. The reaction mixture was poured into water, and a precipitate formed. The precipitate was isolated by filtration, washed with water, and dried for two days in a vacuum oven at 70° C. to provide 0.320 g of 2-butyl-1-methyl-8-{2-[1-(morpholin-4-ylcarbonyl)piperidin-4-yl]ethoxy}-1H-imidazo[4,5-c]quinolin-4-amine as a white solid, mp 152.8° C. (decomposition).

$^1$H NMR (300 MHz, DMSO-$d_6$) δ 7.56 (d, J=3.2 Hz, 1H), 7.53 (d, J=9.3 Hz, 1H), 7.06 (dd, J=9.2, 2.8 Hz, 1H), 6.17 (s, 2H), 4.19-3.96 (m, 3H), 4.11 (s, 3H), 3.54-3.34 (m, 5H), 3.14-2.90 (m, 7H), 2.26-2.09 (m, 1H), 2.04-1.89 (m, 1H), 1.75 (quintet, J=7.5 Hz, 2H), 1.68-1.51 (m, 5H), 1.43 (sextet, J=7.4 Hz, 2H), 1.46-1.28 (m, 1H), 0.95 (t, J=7.5 Hz, 3H);

MS (APCI) m/z 495.3080 (495.3084 calcd for $C_{27}H_{38}N_6O_3$, M+H).

Anal. Calcd. for $C_{27}H_{38}N_6O_3$: % C, 65.56; % H, 7.74; % N, 16.99. Found: % C, 65.33; % H, 7.88; % N, 16.95.

Example 43

N-[2-(4-Amino-2-butyl-1-methyl-1H-imidazo[4,5-c]quinolin-8-yloxy)ethyl]propanamide

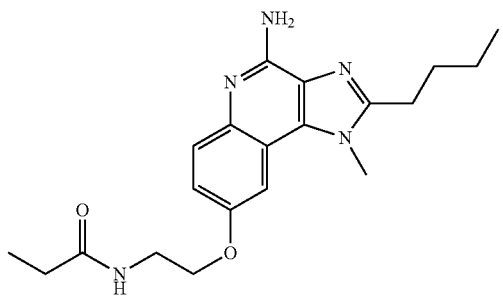 [SMILES: CCCCc1nc2c(N)nc3ccc(OCCNC(=O)CC)cc3c2n1C]

Part A

A mixture of 2-butyl-1-methyl-1H-imidazo[4,5-c]quinolin-8-ol (0.51 g, 2.0 mmol), prepared as described in Parts A-D of Example 31, and 2-ethyl-2-oxazoline (0.5 g, 5 mmol) were heated at 150° C. for four hours. Additional 2-ethyl-2-oxazoline (2 mL, 2 mmol) was added, and the heating was continued for a total of four days. The reaction was dissolved in dichloromethane, and the resulting solution was washed with aqueous potassium hydroxide (20 mL of 4 N), dried over magnesium sulfate, and concentrated under reduced pressure. The crude product was recrystallized from methyl acetate (20 mL) to provide 0.20 g of N-{2-[2-butyl-1-methyl-1H-imidazo[4,5-c]quinolin-8-yl)oxy]ethyl}propanamide.

Part B

The general method described in Part E of Example 30 was used to convert N-{2-[2-butyl-1-methyl-1H-imidazo[4,5-c]quinolin-8-yl)oxy]ethyl}propanamide (0.18 g, 0.51 mmol) to 0.14 g of N-{2-[2-butyl-1-methyl-5-oxido-1H-imidazo[4,5-c]quinolin-8-yl)oxy]ethyl}propanamide. The reaction was complete in two hours.

Part C

Ammonium hydroxide (5 mL) and p-toluenesulfonyl chloride (0.072 g, 0.38 mmol) were added with rapid stirring to a solution of N-{2-[2-butyl-1-methyl-5-oxido-1H-imidazo[4,5-c]quinolin-8-yl)oxy]ethyl}propanamide (0.14 g, 0.38 mmol) in dichloromethane (15 mL), and the mixture was stirred at ambient temperature for one hour. A precipitate formed and was isolated by filtration, washed with water, and dried under reduced pressure to provide N-[2-(4-amino-2-butyl-1-methyl-1H-imidazo[4,5-c]quinolin-8-yloxy)ethyl]propanamide as a solid, mp 250-255° C. (decomposition).

Example 44

2-[(4-Amino-1,2-dimethyl-1H-imidazo[4,5-c]quinolin-8-yl)oxy]acetic acid

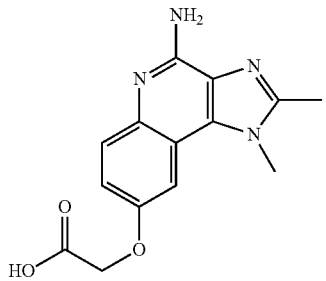 [SMILES: Cc1nc2c(N)nc3ccc(OCC(=O)O)cc3c2n1C]

Part A

7-Benzyloxy-1,2-dimethyl-1H-imidazo[4,5-c]quinoline was prepared according to the methods described in Parts A-C of Example 31. In Part C, triethyl orthoformate was used in lieu of trimethyl orthovalerate. A solution of 7-benzyloxy-1,2-dimethyl-1H-imidazo[4,5-c]quinoline in ethanol was added to a Parr vessel with 10% palladium on carbon. The reaction was placed under hydrogen pressure (35 psi, $2.4 \times 10^5$ Pa) for 20 hours. The reaction mixture was then filtered through a layer of CELITE filter aid, and the filtrate was concentrated under reduced pressure. The residue was dissolved in acetic acid with heating, and the hot solution was filtered and concentrated under reduced pressure. The resulting beige solid was dissolved in 1 N aqueous hydrochloric acid, and deactivated carbon was added. The solution was heated, filtered, and treated with 50% aqueous sodium hydroxide. A precipitate formed and was isolated by filtration to provide 1,2-dimethyl-1H-imidazo[4,5-c]quinolin-8-ol as a solid, mp>300° C.

Part B

Sodium hydride (0.61 g, 15 mmol, available as a 60% dispersion in mineral oil) was added to a solution of 1,2-dimethyl-1H-imidazo[4,5-c]quinolin-8-ol (2.5 g, 12 mmol) in DMF. The reaction mixture was stirred for 30 minutes, and ethyl bromoacetate (1.96 g, 11.7 mmol) was added. The stirring was continued for five hours, and a small volume of ethanol was added. The volatiles were removed under reduced pressure, and the residue was dissolved in dichloromethane. The resulting solution was washed three times with deionized water, dried over magnesium sulfate, filtered, and concentrated under reduced pressure. The resulting yellow solid was recrystallized from ethyl acetate to provide 1.65 g of ethyl 2-[(1,2-dimethyl-1H-imidazo[4,5-c]quinolin-8-yl)oxy]acetate as a white solid.

Part C

Ethyl 2-[(1,2-dimethyl-1H-imidazo[4,5-c]quinolin-8-yl)oxy]acetate (1.6 g, 5.35 mmol) was added to a solution of potassium hydroxide (0.90 g, 0.16 mol) in a 50:50 mixture of methanol:water (30 mL). The solution was stirred under a nitrogen atmosphere until it was complete as evidenced by HPLC analysis. The methanol was removed under reduced pressure, and 6 N aqueous hydrochloric acid was added until the solution exhibited a neutral pH. A precipitate formed and was isolated by filtration to provide 1.25 g of 2-[(1,2-dimethyl-1H-imidazo[4,5-c]quinolin-8-yl)oxy]acetic acid as a white solid, mp 290° C. (decomposition).

Part D

Morpholine (0.39 g, 4.4 mmol) and 1-[3-(dimethylamino)propyl]-3-ethylcarbodiimide hydrochloride (0.85 g, 4.4 mmol) were added to a solution of 2-[(1,2-dimethyl-1H-imidazo[4,5-c]quinolin-8-yl)oxy]acetic acid (1.20 g, 4.42 mmol) in pyridine, and the reaction was stirred for four days under a nitrogen atmosphere. The solvent was removed under reduced pressure, and the residue was stirred with heptane, which was then removed under reduced pressure. The resulting orange solid was purified by column chromatography on silica gel (eluting with 90:10 dichloromethane: methanol) to provide 2-[(1,2-dimethyl-1H-imidazo[4,5-c]quinolin-8-yl)oxy]-1-morpholin-1-ylethanone as a pale yellow solid.

Part E

The general method described in Part E of Example 30 was followed using 2-[(1,2-dimethyl-1H-imidazo[4,5-c]quinolin-8-yl)oxy]-1-morpholin-1-ylethanone (0.97 g, 2.85 mmol) as the starting material. The reaction was complete in two hours. The product was soluble in aqueous sodium carbonate; therefore, the aqueous washings were concentrated under reduced pressure. 2-Propanol was added to the residue with heating, and the mixture was filtered. The filtrate was concentrated under reduced pressure to provide 0.14 g of 2-[(1,2-dimethyl-5-oxido-1H-imidazo[4,5-c]quinolin-8-yl)oxy]-1-morpholin-1-ylethanone.

Part F

Ammonium hydroxide (30 mL) and p-toluenesulfonyl chloride (0.46 g, 2.4 mmol) were added with rapid stirring to a solution of 2-[(1,2-dimethyl-5-oxido-1H-imidazo[4,5-c]quinolin-8-yl)oxy]-1-morpholin-1-ylethanone (0.86 g, 2.4 mmol) in dichloromethane, and the mixture was stirred at ambient temperature for two days. The volatiles were removed under reduced pressure, and the residue was recrystallized from 2-propanol to provide 2-[(4-amino-1,2-dimethyl-1H-imidazo[4,5-c]quinolin-8-yl)oxy]-1-morpholin-1-ylethanone p-toluenesulfonate as a white solid.

Part G

Claisen Reagent, prepared from potassium hydroxide (35 g), water (25 mL), and methanol (100 mL), was added to the material from Part F, and the mixture was stirred for one hour. Hydrochloric acid (6 N) was added until the pH of the reaction mixture was neutral. A precipitate formed and was isolated by filtration to provide 0.01 g of 2-[(4-amino-1,2-dimethyl-1H-imidazo[4,5-c]quinolin-8-yl)oxy]acetic acid as an orange solid, mp 298° C. (decomposition).

Example 45

N-(2-{4-Amino-2-ethoxymethyl-7-[6-(methanesulfonylamino)hexyloxy]-1H-imidazo[4,5-c]quinolin-1-yl}-1,1-dimethylethyl)methanesulfonamide

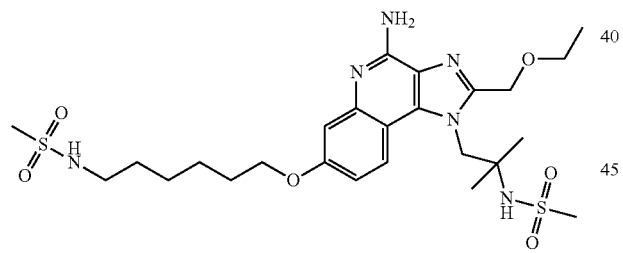

Part A

7-Benzyloxy-4-chloro-3-nitroquinoline (14.5 g, 46.0 mmol), prepared as described in Parts A-D of Example 1, was treated according to the general method described in Part E of Example 1. 1,2-Diamino-2-methylpropane (5.29 mL, 50.6 mmol) was used in lieu of isobutylamine. After the work-up, the crude product was passed through a layer of silica gel (eluting sequentially with chloroform and 96:4 chloroform:methanol) to provide 12.4 g of (2-amino-2-methylpropyl)(7-benzyloxy-3-nitroquinolin-4-yl)amine as a yellow solid.

Part B

Under a nitrogen atmosphere, a solution of (2-amino-2-methylpropyl)(7-benzyloxy-3-nitroquinolin-4-yl)amine (12.4 g, 33.9 mmol) in dichloromethane (400 mL) was cooled to 0° C. Triethylamine (9.43 mL, 67.8 mmol) and methanesulfonic anhydride (5.90 g, 33.9 mmol) were sequentially added, and the reaction was stirred at ambient temperature for two hours. An analysis by HPLC indicated that the reaction was incomplete, and additional methanesulfonic anhydride (1.4 g, 8.0 mmol) was added. The reaction was stirred for an additional 90 minutes, and additional methanesulfonic anhydride (0.7 g, 4 mmol) was added. The reaction was stirred for an additional three hours, and saturated aqueous sodium bicarbonate (200 mL) was added. A precipitate began to form in the organic layer, which was separated and concentrated under reduced pressure to provide a yellow solid. The solid was triturated with water (200 mL) with heating, isolated by filtration, washed with water (3×100 mL) and diethyl ether (3×50 mL), and dried overnight under vacuum to provide 14.8 g of N-[1,1-dimethyl-2-(3-nitro-7-benzyloxyquinolin-4-ylamino)ethyl]methanesulfonamide as a yellow powder.

Part C

N-[1,1-Dimethyl-2-(3-nitro-7-benzyloxyquinolin-4-ylamino)ethyl]methanesulfonamide (14.8 g, 33.3 mmol) was mixed with acetonitrile (300 mL) and added to a Parr flask; 5% platinum on carbon (2 g) was added. The reaction was flushed with nitrogen and placed under hydrogen pressure (40 psi, $2.8 \times 10^5$ Pa) for 5.5 hours with the hydrogen replaced after two hours. An analysis by TLC indicated the presence of starting material. Additional acetonitrile (200 mL) and 5% platinum on carbon (2 g) were added, and the reaction was placed under hydrogen pressure overnight. The reaction mixture was filtered through a layer of CELITE filter aid, and the filter cake was washed with acetonitrile. The filtrate was concentrated under reduced pressure. Toluene and dichloromethane were added and removed under reduced pressure twice to yield 12.6 g of N-[2-(3-amino-7-benzyloxyquinolin-4-ylamino)-1,1-dimethylethyl]methanesulfonamide as a solid.

Part D

Under a nitrogen atmosphere, a solution of N-[2-(3-amino-7-benzyloxyquinolin-4-ylamino)-1,1-dimethylethyl]methanesulfonamide (12.6 g, 30.4 mmol) in dichloromethane (300 mL) was cooled to ~0° C.; triethylamine (4.23 mL, 30.4 mmol) was added. Ethoxy acetyl chloride (3.33 mL, 30.4 mmol) was added dropwise, and the reaction was stirred at ambient temperature for 1.5 hours. The volatiles were removed under reduced pressure, and the residue was dissolved in ethanol (300 mL). Triethylamine (13 mL) was added, and the reaction was heated at reflux overnight and allowed to cool to ambient temperature. The volatiles were removed under reduced pressure. The residue was dissolved in dichloromethane (300 mL), and the resulting solution was washed with water (2×100 mL) and brine, dried over sodium sulfate, filtered, and concentrated under reduced pressure to provide a brown oil. The oil was purified by column chromatography on silica gel (eluting with 97.5:2.5 chloroform:methanol) to provide 12.4 g of N-[2-(7-benzyloxy-2-ethoxymethyl-1H-imidazo[4,5-c]quinolin-1-yl)-1,1-dimethylethyl]methanesulfonamide as a beige solid.

Part E

A solution of N-[2-(7-benzyloxy-2-ethoxymethyl-1H-imidazo[4,5-c]quinolin-1-yl)-1,1-dimethylethyl]methanesulfonamide (9.38 g, 19.5 mmol) in ethanol (150 mL) was added to a Parr vessel containing 10% palladium on carbon (0.83 g). The reaction was placed under hydrogen pressure (50 psi, 3.4×10[5] Pa) over two nights. Starting material remained as evidenced by a TLC analysis, and additional 10% palladium on carbon (1.02 g) was added. The reaction was continued for an additional eight hours. The reaction mixture was filtered through a layer of CELITE filter aid, and the filter cake was washed with ethanol and methanol. The filtrate was concentrated under reduced pressure, and the residue was several times dissolved in toluene and concentrated under reduced pressure to yield a yellow powder, which was dried under high vacuum to provide 7.37 g of N-[2-(2-ethoxymethyl-7-hydroxy-1H-imidazo[4,5-c]quinolin-1-yl)-1,1-dimethylethyl]methanesulfonamide as a yellow solid.

Part F

The methods described in Parts J and K of Example 2 were followed using 6-amino-1-hexanol (62 g, 0.53 mmol) in lieu of 2-aminoethanol to provide tert-butyl 6-iodohexylcarbamate as a light-yellow oil.

Part G

The general method described in Part L of Example 2 was followed. N-[2-(2-Ethoxymethyl-7-hydroxy-1H-imidazo[4,5-c]quinolin-1-yl)-1,1-dimethylethyl]methanesulfonamide (7.37 g, 18.8 mmol) was treated with tert-butyl 6-iodohexylcarbamate (6.75 g, 20.6 mmol). The crude product was purified by column chromatography on silica gel (eluting sequentially with 95:5 and 92.5:7.5 dichloromethane:methanol) to provide 8.5 g of tert-butyl {6-[2-ethoxymethyl-1-(2-methanesulfonylamino-2-methylpropyl)-1H-imidazo[4,5-c]quinolin-1-yloxy]hexyl}carbamate as a white solid.

Part H

A modification of the method described in Part M of Example 2 was used to convert tert-butyl {6-[2-ethoxymethyl-1-(2-methanesulfonylamino-2-methylpropyl)-1H-imidazo[4,5-c]quinolin-1-yloxy]hexyl}carbamate (8.5 g, 14.4 mmol) to tert-butyl {6-[2-ethoxymethyl-1-(2-methanesulfonylamino-2-methylpropyl)-5-oxido-1H-imidazo[4,5-c]quinolin-1-yloxy]hexyl}carbamate, which was obtained as a orange solid. The reaction was complete in two hours, and the product was used without purification.

Part I

Ammonium hydroxide (20 mL) and p-toluenesulfonyl chloride (2.74 g, 14.4 mmol) were added sequentially with rapid stirring to a mixture of the material from Part H in dichloromethane (150 mL), and the reaction was stirred for two hours. The organic layer was then washed with saturated aqueous sodium bicarbonate (2×) and brine, dried over sodium sulfate, filtered, and concentrated under reduced pressure to provide tert-butyl {6-[4-amino-2-ethoxymethyl-1-(2-methanesulfonylamino-2-methylpropyl)-1H-imidazo[4,5-c]quinolin-1-yloxy]hexyl}carbamate as a red solid.

Part J

A modification of the method described in Part O of Example 2 was used to deprotect tert-butyl {6-[4-amino-2-ethoxymethyl-1-(2-methanesulfonylamino-2-methylpropyl)-1H-imidazo[4,5-c]quinolin-1-yloxy]hexyl}carbamate with hydrochloric acid in ethanol (50 mL of 4.25 M). Following the treatment of the crude product with ammonium hydroxide and the remainder of the work-up procedure, 6.86 g of N-{2-[4-amino-7-(6-aminohexyloxy)-2-ethoxymethyl-1H-imidazo[4,5-c]quinolin-1-yl]-1,1-dimethylethyl}methanesulfonamide were obtained as a tan solid and used without further purification.

Part K

A suspension of N-{2-[4-amino-7-(6-aminohexyloxy)-2-ethoxymethyl-1H-imidazo[4,5-c]quinolin-1-yl]-1,1-dimethylethyl}methanesulfonamide (1.50 g, 2.96 mmol) in dichloromethane (50 mL) was cooled to 0° C.; triethylamine (825 µL, 5.92 mmol) and methanesulfonic anhydride (0.67 g, 3.85 mmol) were sequentially added. The reaction was stirred at 0° C. for 30 minutes, allowed to warm to room temperature, and stirred for four hours. The reaction solution was washed with saturated aqueous sodium bicarbonate (2×) and brine, dried over sodium sulfate, filtered, and concentrated under reduced pressure. The residue was purified by column chromatography on silica gel (eluting with 90:10 dichloromethane:methanol) and recrystallization from dichloroethane. The crystals were partitioned between dichloromethane and saturated aqueous sodium bicarbonate, and the aqueous layer was extracted with dichloromethane. The combined organic fractions were washed with brine, dried over sodium sulfate, filtered, concentrated under reduced pressure, and further dried for two days under high vacuum at 60° C. to provide 0.39 g of N-(2-{4-amino-2-ethoxymethyl-7-[6-(methanesulfonylamino)hexyloxy]-1H-imidazo[4,5-c]quinolin-1-yl}-1,1-dimethylethyl)methanesulfonamide as an off-white solid, mp 176-180° C.

$^1$H NMR (300 MHz, DMSO-$d_6$) δ 8.16 (d, J=9.4 Hz, 1H), 7.27 (s, 1H), 7.03 (d, J=2.5 Hz, 1H), 6.93 (m, 1H), 6.84 (dd, J=8.7, 2.5 Hz, 1H), 6.53 (s, 2H), 4.81 (s, 4H), 4.04 (t, J=6.2 Hz, 2H), 3.53 (m, 2H), 2.99 (s, 3H), 2.94 (m, 2H), 2.87 (s, 3H), 1.76 (m, 2H), 1.50-1.27 (m, 12H), 1.14 (m, 3H);

$^{13}$C NMR (75 MHz, DMSO-$d_6$) δ 157.9, 152.6, 150.0, 147.7, 134.9, 125.4, 122.6, 111.4, 109.5, 108.4, 67.5, 65.7, 65.1, 57.7, 54.6, 44.7, 42.8, 29.7, 29.0, 26.3, 25.8, 25.6, 15.3;

MS (APCI) m/z 585 (M+H)[+];

Anal. Calcd. for $C_{25}H_{40}N_6O_6S_2 \cdot 0.30\ H_2O$: % C, 50.88; % H, 6.94; % N, 14.24. Found: % C, 50.85; % H, 6.83; % N, 14.10.

Example 46

N-(6-{[4-Amino-2-ethoxymethyl-1-(2-methanesulfonylamino-2-methylpropyl)-1H-imidazo[4,5-c]quinolin-7-yl]oxy}hexyl)acetamide

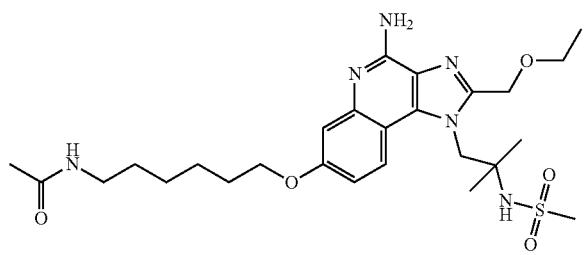 [SMILES: CCOCc1nc2c(N)nc3cc(OCCCCCCNC(C)=O)ccc3c2n1CC(C)(C)NS(C)(=O)=O]

A modification of the method described in Park K of Example 45 was followed using acetyl chloride (0.23 mL, 3.26 mmol) in lieu of methanesulfonic anhydride. A precipitate was present at the end of the reaction and was isolated by filtration, stirred with water for 30 minutes, and isolated by filtration. The remaining reaction solution was subjected to the aqueous work-up procedure. The two solids were combined and purified by column chromatography on silica gel (eluting sequentially with 90:10 and 85:15 dichloromethane:methanol) to provide 0.51 g of N-(6-{[4-amino-2-ethoxymethyl-1-(2-methanesulfonylamino-2-methylpropyl)-1H-imidazo[4,5-c]quinolin-7-yl]oxy}hexyl)acetamide as an off-white powder, mp 169-171° C.

$^1$H NMR (300 MHz, DMSO-d$_6$) δ 8.17 (d, J=9.4 Hz, 1H), 7.79 (m, 1H), 7.28 (s, 1H), 7.04 (d, J=2.5 Hz, 1H), 6.85 (dd, J=8.7, 2.5 Hz, 1H), 6.56 (s, 2H), 4.82 (s, 4H), 4.04 (m, 2H), 3.54 (q, J=6.9 Hz, 2H), 3.02 (m, 2H), 2.99 (s, 3H), 1.79 (s, 3H), 1.75 (m, 2H), 1.45-1.28 (m, 12H), 1.14 (m, 3H);

$^{13}$C NMR (75 MHz, DMSO-d$_6$) δ 169.2, 157.9, 152.6, 150.0, 147.6, 134.9, 125.4, 122.6, 111.4, 109.5, 108.4, 67.6, 65.7, 65.1, 57.7, 54.6, 44.7, 38.8, 29.5, 29.0, 26.6, 25.8, 25.7, 22.9, 15.3;

MS (APCI) m/z 549 (M+H)$^+$;

Anal. Calcd. for C$_{26}$H$_{40}$N$_6$O$_5$S: % C, 56.91; % H, 7.35; % N, 15.32. Found: % C, 56.70; % H, 7.49; % N, 15.26.

Example 47

N-(4-{4-Amino-7-[6-(methanesulfonylamino)hexyloxy]-2-propyl-1H-imidazo[4,5-c]quinolin-1-yl}butyl)methanesulfonamide

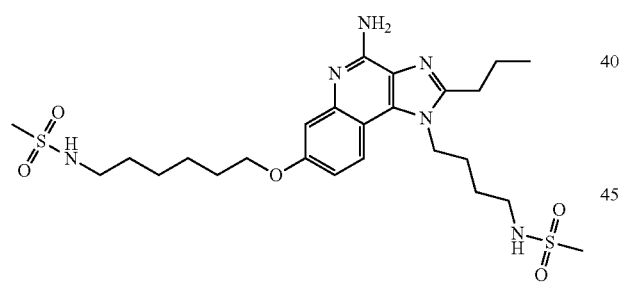

Part A

Under a nitrogen atmosphere, a solution of tert-butyl N-(4-aminobutyl)carbamate (13.8 g, 73.4 mmol) and triethylamine (15.3 mL, 110 mmol) was cooled to 0° C. Methanesulfonyl chloride (6.3 mL, 81 mmol) was added, and the reaction was allowed to warm to ambient temperature and stirred overnight. Aqueous acetic acid (200 mL of 10%) was added. The organic layer was then separated and washed with water (200 mL), saturated aqueous sodium bicarbonate (200 mL), water (200 mL), and brine; dried over sodium sulfate, filtered, and concentrated under reduced pressure to provide 18.9 g of tert-butyl [4-(methanesulfonylamino)butyl]carbamate as an off-white solid.

Part B

A solution of hydrochloric acid in ethanol was added to a solution of tert-butyl [4-(methanesulfonylamino)butyl]carbamate (18.9 g, 71.1 mmol) in ethanol (100 mL), and the reaction was heated at 100° C. for two hours. The solvent was removed under reduced pressure. A mixture of dichloromethane:hexanes was added to the resulting oil and removed under reduced pressure; this process was repeated several times. The residue was dried for three days under vacuum to provide 14.3 g of N-(4-aminobutyl)methanesulfonamide hydrochloride as a tan solid.

Part C

A modification of the method described in Part E of Example 1 was used to treat 7-benzyloxy-4-chloro-3-nitroquinoline (14.4 g, 45.8 mmol) with N-(4-aminobutyl)methanesulfonamide hydrochloride (10.2 g, 50.4 mmol) and triethylamine (19.2 mL, 137 mmol). The reaction mixture was concentrated under reduced pressure, and the residue was triturated with water while heating at reflux. The resulting solid was isolated by filtration, washed with water and diethyl ether (2×100 mL), and dried under high vacuum to provide 16.8 g of N-[4-(3-nitro-7-benzyloxyquinolin-4-ylamino)butyl]methanesulfonamide as a yellow powder.

Part D

The method described in Part C of Example 45 was used to convert N-[4-(3-nitro-7-benzyloxyquinolin-4-ylamino)butyl]methanesulfonamide (16.8 g, 37.8 mmol) to 15.1 g of N-[4-(3-amino-7-benzyloxyquinolin-4-ylamino)butyl]methanesulfonamide, which was obtained as a dark yellow solid.

Part E

The method described in Part D of Example 45 was used to treat N-[4-(3-amino-7-benzyloxyquinolin-4-ylamino)butyl]methanesulfonamide (15.1 g, 36.5 mmol) with butyryl chloride (4.77 mL, 46.2 mmol). The crude product was purified by column chromatography on silica gel (eluting with 96:4 chloroform:methanol containing ammonium hydroxide) to provide 11.8 g of N-[4-(7-benzyloxy-2-propyl-1H-imidazo[4,5-c]quinolin-1-yl)butyl]methanesulfonamide as a tan solid.

Part F

The method described in Part E of Example 45 was used to convert N-[4-(7-benzyloxy-2-propyl-1H-imidazo[4,5-c]quinolin-1-yl)butyl]methanesulfonamide (7.60 g, 16.3 mmol) to 5.75 g of N-[4-(7-hydroxy-2-propyl-1H-imidazo[4,5-c]quinolin-1-yl)butyl]methanesulfonamide, which was obtained as a light-yellow solid.

Part G

The general method described in Part L of Example 2 was followed. N-[4-(7-hydroxy-2-propyl-1H-imidazo[4,5-c]quinolin-1-yl)butyl]methanesulfonamide (5.75 g, 15.3 mmol) was treated with tert-butyl 6-iodohexylcarbamate (5.50 g, 16.8 mmol). The crude product was purified by column chromatography on silica gel (eluting sequentially with 95:5 and 92.5:7.5 dichloromethane:methanol) to provide 6.19 g of tert-butyl (6-{1-[4-(methanesulfonylamino)butyl]-2-propyl-1H-imidazo[4,5-c]quinolin-1-yloxy}hexyl)carbamate as a yellow solid.

Part H

A modification of the method described in Part M of Example 2 was used to convert tert-butyl (6-{1-[4-(methanesulfonylamino)butyl]-2-propyl-1H-imidazo[4,5-c]quinolin-1-yloxy}hexyl)carbamate (2.51 g, 4.36 mmol) to 2.54 g of tert-butyl (6-{1-[4-(methanesulfonylamino)butyl]-5-oxido-2-propyl-1H-imidazo[4,5-c]quinolin-1-yloxy}hexyl)carbamate, which was obtained as a yellow solid. The reaction was allowed to run overnight, and the product was used without purification.

Part I

The method described in Part I of Example 45 was used to convert tert-butyl (6-{1-[4-(methanesulfonylamino)butyl]-5-oxido-2-propyl-1H-imidazo[4,5-c]quinolin-1-yloxy}hexyl)carbamate (2.54 g, 4.29 mmol) to 2.51 g of tert-butyl (6-{4-amino-1-[4-(methanesulfonylamino)butyl]-2-propyl-1H-imidazo[4,5-c]quinolin-1-yloxy}hexyl)carbamate, obtained as a tan solid.

Part J

The method described in Part J of Example 45 was used to deprotect tert-butyl (6-{4-amino-1-[4-(methanesulfonylamino)butyl]-2-propyl-1H-imidazo[4,5-c]quinolin-1-yloxy}hexyl)carbamate (2.51 g, 4.25 mmol). The crude product was recrystallized from acetonitrile to provide 0.75 g of N-{4-[4-amino-7-(6-aminohexyloxy)-2-propyl-1H-imidazo[4,5-c]quinolin-1-yl]butyl}methanesulfonamide as a tan solid. The mother liquor was concentrated under reduced pressure, and the residue was recrystallized from dichloroethane to provide 0.48 g of N-{4-[4-amino-7-(6-aminohexyloxy)-2-propyl-1H-imidazo[4,5-c]quinolin-1-yl]butyl}methanesulfonamide as a brown powder.

Part K

A modification of the method described in Part K of Example 45 was followed using N-{4-[4-amino-7-(6-aminohexyloxy)-2-propyl-1H-imidazo[4,5-c]quinolin-1-yl]butyl}methanesulfonamide (0.86 g, 1.8 mmol) as the starting material. Methanesulfonic anhydride (470 mg, 2.7 mmol) was added over a period of 24 hours. The crude product was purified by column chromatography on silica gel (eluting sequentially with 90:10 and 85:15 dichloromethane:methanol), recrystallization from ethyl acetate, and a second recrystallization from 2-propanol to provide 0.38 g of N-(4-{4-amino-7-[6-(methanesulfonylamino)hexyloxy]-2-propyl-1H-imidazo[4,5-c]quinolin-1-yl}butyl)methanesulfonamide as a white powder, mp 138–140° C.

$^1$H NMR (300 MHz, DMSO-$d_6$) δ 7.92 (d, J=9.4 Hz, 1H), 7.05 (d, J=3.1 Hz, 1H), 6.98–6.88 (m, 3H), 6.38 (s, 2H), 4.46 (m, 2H), 4.04 (t, J=6.2 Hz, 2H), 2.99–2.92 (m, 6H), 2.87 (s, 3H), 2.86 (s, 3H), 1.82 (m, 6H), 1.61 (m, 2H), 1.44 (m, 6H), 1.03 (m, 3H);

$^{13}$C NMR (75 MHz, DMSO-$d_6$) δ 157.7, 152.4, 152.2, 146.7, 133.1, 125.3, 121.4, 112.1, 109.2, 108.3, 67.6, 44.6, 42.8, 42.4, 39.53, 39.49, 29.7, 29.0, 28.7, 27.4, 26.7, 26.3, 25.6, 21.3, 14.2;

MS (APCI) m/z 569 (M+H)$^+$;

Anal. Calcd. for $C_{25}H_{40}N_6O_5S_2$: % C, 52.80; % H, 7.09; % N, 14.78. Found: % C, 52.61; % H, 7.13; % N, 14.52.

Example 48

N-(6-{4-Amino-1-[4-(methanesulfonylamino)butyl]-2-propyl-1H-imidazo[4,5-c]quinolin-7-yloxy}hexyl)acetamide

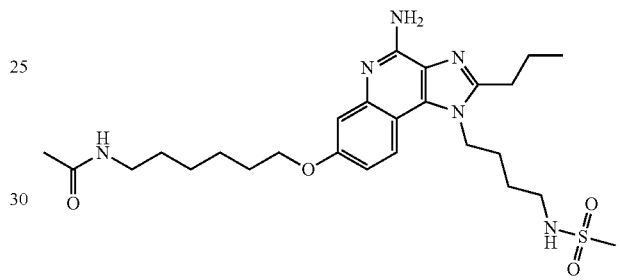

A modification of the method described in Park K of Example 45 was followed using acetyl chloride (135 μL, 1.91 mmol) in lieu of methanesulfonic anhydride and N-{4-[4-amino-7-(6-aminohexyloxy)-2-propyl-1H-imidazo[4,5-c]quinolin-1-yl]butyl}methanesulfonamide (0.85 g, 1.7 mmol) as the starting material. The crude product was purified by column chromatography on silica gel (eluting sequentially with 90:10 and 80:20 dichloromethane:methanol). The resulting white powder was stirred with water, isolated by filtration, and dissolved in 50:50 dichloromethane:methanol. The solution was dried over sodium sulfate, filtered, and concentrated under reduced pressure. The resulting solid was recrystallized from acetonitrile, and the crystals were dissolved in dichloromethane:methanol, concentrated under reduced pressure, and further dried overnight under high vacuum at 60° C. to provide 0.30 g of N-(6-{4-amino-1-[4-(methanesulfonylamino)butyl]-2-propyl-1H-imidazo[4,5-c]quinolin-7-yloxy}hexyl)acetamide as a white powder, mp 168–172° C.

$^1$H NMR (300 MHz, CDCl$_3$) δ 7.91 (d, J=9.4 Hz, 1H), 7.78 (m, 1H), 7.04 (d, J=2.5 Hz, 1H), 6.98 (m, 1H), 6.89 (dd, J=9.4, 2.5 Hz, 1H), 6.35 (s, 2H), 4.46 (m, 2H), 4.03 (t, J=6.2 Hz, 2H), 3.04–2.96 (m, 4H), 2.86 (m, 5H), 1.78 (m, 9H), 1.62 (m, 2H), 1.42 (m, 6H), 1.03 (t, J=7.5 Hz, 3H);

$^{13}$C NMR (75 MHz, DMSO-$d_6$) δ 169.2, 157.8, 152.4, 152.3, 146.9, 133.1, 125.3, 121.4, 112.1, 109.2, 108.4, 67.6, 44.6, 42.4, 39.5, 38.8, 29.5, 29.0, 28.7, 27.4, 26.6, 25.7, 23.0, 21.3, 14.2;

MS (APCI) m/z 533 (M+H)$^+$;

Anal. Calcd. for $C_{26}H_{40}N_6O_4S$·0.25 H$_2$O: % C, 58.13; % H, 7.60; % N, 15.64; % S, 5.97.

Found: % C, 57.90; % H, 7.69; % N, 15.54; % S, 6.23.

Example 49

N-(2-{4-Amino-2-ethoxymethyl-7-[6-(methanesulfonylamino)hexyloxy]-1H-imidazo[4,5-c]quinolin-1-yl}-1,1-dimethylethyl)acetamide

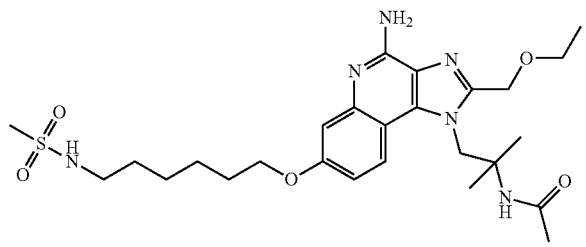 [SMILES: CCOCc1nc2c(N)nc3cc(OCCCCCCNS(C)(=O)=O)ccc3c2n1CC(C)(C)NC(C)=O]

Part A

Under a nitrogen atmosphere, a solution of (2-amino-2-methylpropyl)(7-benzyloxy-3-nitroquinolin-4-yl)amine (6.5 g, 17.5 mmol), prepared in Part A of Example 45, in dichloromethane (200 mL) was cooled to 0° C.; triethylamine (4.87 mL, 35.0 mmol) and acetyl chloride (1.37 mL, 19.2 mmol) were sequentially added. The reaction was stirred at 0° C. for 30 minutes, allowed to warm to ambient temperature, and stirred for three hours. The reaction was washed with saturated aqueous sodium bicarbonate (2×) and brine, dried over sodium sulfate, filtered, and concentrated under reduced pressure to provide N-[1,1-dimethyl-2-(3-nitro-7-benzyloxyquinolin-4-ylamino)ethyl]acetamide as a yellow powder.

Part B

The method described in Part C of Example 45 was used to convert the material from Part B to 6.16 g of N-[2-(3-amino-7-benzyloxyquinolin-4-ylamino)-1,1-dimethylethyl]acetamide, obtained as an orange solid.

Part C

A modification of the method described in Part D of Example 45 was followed using N-[2-(3-amino-7-benzyloxyquinolin-4-ylamino)-1,1-dimethylethyl]acetamide (6.16 g, 21.0 mmol) as the starting material. A solution of the intermediate in ethanol was heated at reflux for 24 hours. Sodium hydroxide (1.25 g) and water (25 mL) were added, and the reaction was heated at reflux for an additional 32 hours. The mixture was allowed to cool to ambient temperature, and the solvent was removed under reduced pressure. The residue was partitioned between dichloromethane and saturated aqueous sodium bicarbonate. The organic layer was separated and washed sequentially with saturated aqueous sodium bicarbonate and brine, dried over sodium sulfate, filtered, and concentrated under reduced pressure. The resulting orange solid was purified by column chromatography on silica gel (eluting with 95:5 dichloromethane:methanol) to provide 4.79 g of N-[2-(7-benzyloxy-2-ethoxymethyl-1H-imidazo[4,5-c]quinolin-1-yl)-1,1-dimethylethyl]acetamide as a yellow solid.

Part D

The method described in Part E of Example 45 was used to convert N-[2-(7-benzyloxy-2-ethoxymethyl-1H-imidazo[4,5-c]quinolin-1-yl)-1,1-dimethyl ethyl]acetamide (4.79 g, 10.7 mmol) to N-[2-(2-ethoxymethyl-7-hydroxy-1H-imidazo[4,5-c]quinolin-1-yl)-1,1-dimethylethyl]acetamide, obtained as a yellow solid.

Part E

The method described in Part L of Example 2 was followed. The material from Part D was treated with tert-butyl 6-iodohexylcarbamate (3.86 g, 11.8 mmol), and the reaction was complete in four hours. The crude product was purified by column chromatography on silica gel (eluting sequentially with 95:5 and 92.5:7.5 dichloromethane:methanol), and the resulting solid was dried overnight under high vacuum to provide 4.69 g of tert-butyl {6-[1-(2-acetylamino-2-methylpropyl)-2-ethoxymethyl-1H-imidazo[4,5-c]quinolin-7-yloxy]hexyl}carbamate as an off-white solid.

Part F

A modification of the method described in Part M of Example 2 was used to convert tert-butyl {6-[1-(2-acetylamino-2-methylpropyl)-2-ethoxymethyl-1H-imidazo[4,5-c]quinolin-7-yloxy]hexyl}carbamate (4.69 g, 8.44 mmol) to tert-butyl {6-[1-(2-acetylamino-2-methylpropyl)-2-ethoxymethyl-5-oxido-1H-imidazo[4,5-c]quinolin-7-yloxy]hexyl}carbamate, obtained as a orange solid. The reaction was complete in one hour, and the product was used without purification.

Part G

The method described in Part I of Example 45 was used to convert the material from Part F to 4.85 g of tert-butyl {6-[1-(2-acetylamino-2-methylpropyl)-4-amino-2-ethoxymethyl-1H-imidazo[4,5-c]quinolin-7-yloxy]hexyl}carbamate, obtained as an orange solid.

Part H

A modification of the method described in Part O of Example 2 was used to deprotect the material from Part G with hydrochloric acid in ethanol (100 mL of 3 M). Following the treatment of the crude product with ammonium hydroxide and the remainder of the work-up procedure, 3.64 g of N-{2-[4-amino-7-(6-aminohexyloxy)-2-ethoxymethyl-1H-imidazo[4,5-c]quinolin-1-yl]-1,1-dimethylethyl}acetamide were obtained as a tan solid and used without further purification.

Part I

A modification of the method described in Part K of Example 45 was followed using N-{2-[4-amino-7-(6-aminohexyloxy)-2-ethoxymethyl-1H-imidazo[4,5-c]quinolin-1-yl]-1,1-dimethylethyl}acetamide (1.2 g, 2.5 mmol) as the starting material. The reaction was run in 1-methyl-2-pyrrolidone (55 mL), and after completion, the reaction was poured into deionized water (400 mL) and stirred over three days. The mixture was extracted with dichloromethane (3×200 mL), and the combined extracts were washed with brine, dried over sodium sulfate, filtered, and concentrated under reduced pressure. The residue was dissolved in diethyl ether (100 mL) and treated with a solution of hydrochloric acid in ethanol. A solid formed, and the diethyl ether was decanted. The solid was partitioned between dichloromethane and dilute ammonium hydroxide. The aqueous layer was separated and extracted with dichloromethane (3×100 mL). The combined organic fractions were washed with brine, dried over sodium sulfate, filtered, and concentrated under reduced pressure. The resulting orange oil was triturated with diethyl ether overnight to form a solid, which was isolated by filtration and purified by column chromatography on silica gel (eluting with 92:8 dichloromethane:methanol). The resulting solid was dried overnight under high vacuum at 60° C. to provide 0.47 g of N-(2-{4-amino-2-ethoxymethyl-7-[6-(methanesulfonylamino)hexyloxy]-1H-imidazo[4,5-c]quinolin-1-yl}-1,1-dimethylethyl)acetamide as an off-white powder.

$^1$H NMR (300 MHz, DMSO-$d_6$) δ 8.20 (d, J=9.1 Hz, 1H), 7.70 (s, 1H), 7.01 (d, J=2.7 Hz, 1H), 6.92 (m, 1H), 6.84 (m, 1H), 6.50 (s, 2H), 4.93 (s, 2H), 4.69 (s, 2H), 4.03 (m, 2H), 3.50 (q, J=7.0 Hz, 2H), 2.92 (m, 2H), 2.86 (s, 3H), 1.80 (s, 3H), 1.74 (m, 2H), 1.48-1.38 (m, 6H), 1.18 (br s, 6H), 1.11 (t, J=7.0 Hz, 3H);

$^{13}$C NMR (75 MHz, DMSO-$d_6$) δ 170.3, 157.9, 152.6, 149.8, 147.6, 135.0, 125.3, 122.6, 111.4, 109.6, 108.4, 67.6, 65.7, 64.6, 55.0, 51.1, 42.8, 29.7, 29.0, 26.3, 25.9, 25.6, 24.0, 15.3; MS (APCI) m/z 549 (M+H)$^+$;

Anal. Calcd. for $C_{26}H_{40}N_6O_5S \cdot 0.70 H_2O$: % C, 55.64; % H, 7.44; % N, 14.97. Found: % C, 55.98; % H, 7.29; % N, 14.87.

Example 50

N-(2-{7-[6-(Acetylamino)hexyloxy]-4-amino-2-ethoxymethyl-1H-imidazo[4,5-c]quinolin-1-yl}-1,1-dimethylethyl)acetamide

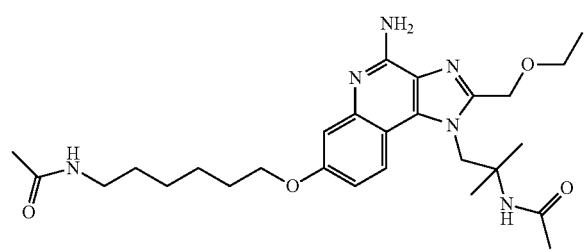 [SMILES: CCOCc1nc2c(N)nc3cc(OCCCCCCNC(C)=O)ccc3c2n1CC(C)(C)NC(C)=O]

A modification of the method described in Part K of Example 45 was followed using N-{2-[4-amino-7-(6-aminohexyloxy)-2-ethoxymethyl-1H-imidazo[4,5-c]quinolin-1-yl]-1,1-dimethylethyl}acetamide (1.2 g, 2.5 mmol) as the starting material and acetyl chloride (200 µL, 3 mmol) in lieu of methanesulfonic anhydride. Following chromatographic purification, the solid was recrystallized from acetonitrile, and the crystals were dissolved in dichloromethane:methanol, concentrated under reduced pressure, and further dried under high vacuum at 60° C. to provide 0.47 g of N-(2-{7-[6-(acetylamino)hexyloxy]-4-amino-2-ethoxymethyl-1H-imidazo[4,5-c]quinolin-1-yl}-1,1-dimethylethyl)acetamide as a white powder, mp 190-192° C.

$^1$H NMR (300 MHz, DMSO-$d_6$) δ 8.20 (d, J=9.0 Hz, 1H), 7.77 (m, 1H), 7.70 (s, 1H), 7.01 (d, J=2.6 Hz, 1H), 6.83 (dd, J=9.0, 2.6 Hz, 1H), 6.50 (s, 2H), 4.93 (s, 2H), 7.69 (s, 2H), 4.02 (t, J=6.4 Hz, 2H), 3.50 (m, 2H), 3.01 (m, 2H), 1.80 (s, 3H), 1.77 (s, 3H), 1.74 (m, 2H), 1.41 (m, 6H), 1.18 (br s, 6H), 1.11 (t, J=7.0 Hz, 3H);

$^{13}$C NMR (75 MHz, DMSO-$d_6$) δ 170.3, 169.2, 157.9, 152.6, 149.8, 147.6, 135.0, 125.4, 122.6, 111.4, 109.6, 108.4, 67.6, 65.7, 64.6, 55.0, 51.6, 38.8, 29.5, 29.0, 26.6, 25.9, 25.7, 24.0, 23.0, 15.3;

MS (APCI) m/z 513 (M+H)$^+$;

Anal. Calcd. for $C_{27}H_{40}N_6O_4 \cdot 0.8H_2O$: % C, 61.53; % H, 7.96; % N, 15.95. Found: % C, 61.65; % H, 8.05; % N, 15.88.

Example 51

N-[2-(4-Amino-2-ethoxymethyl-1-propyl-1H-imidazo[4,5-c]quinolin-7-yloxy)ethyl]methanesulfonamide

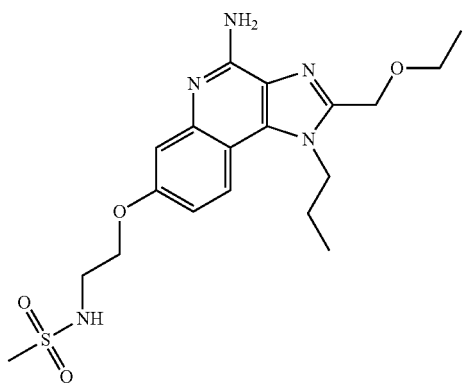 [SMILES: CCCn1c(COCC)nc2c(N)nc3cc(OCCNS(C)(=O)=O)ccc3c21]

Part A

The methods described in Parts A-H, M, and N of Example 2 were followed using 3-benzyloxyaniline in lieu of 4-benzyloxyaniline. The crude product was recrystallized from acetonitrile to provide 7-benzyloxy-2-ethoxymethyl-1-propyl-1H-imidazo[4,5-c]quinolin-4-amine as a flocculent, white solid, mp 188-189° C.

$^1$H NMR (300 MHz, DMSO-$d_6$): δ 7.91 (d, J=9.1 Hz, 1H), 7.52-7.30 (m, 5H), 7.13 (d, J=2.7 Hz, 1H), 7.00 (dd, J=8.9, 2.6 Hz, 1H), 6.53 (s, 2H), 5.21 (s, 2H), 4.74 (s, 2H), 4.49-4.44 (m, 2H), 3.54 (q, J=7.0 Hz, 2H), 1.92-1.78 (m, 2H), 1.15 (t, J=6.9 Hz, 3H), 1.00 (t, J=7.4 Hz, 3H).

$^{13}$C NMR (75 MHz, DMSO-$d_6$): δ 157.3, 152.3, 148.1, 146.9, 137.2, 133.4, 128.4, 127.7, 127.6, 124.9, 121.3, 111.9, 108.9, 108.7, 69.1, 65.3, 64.2, 46.6, 23.0, 14.9, 10.7.

MS (ESI) m/z 391.2134 (391.2117 calcd for $C_{23}H_{26}N_4O_2$, M+H$^+$).

Anal. Calcd. for $C_{23}H_{26}N_4O_2$: % C, 70.75; % H, 6.71; % N, 14.35. Found: % C, 70.49; % H, 6.57; % N, 14.22.

Part B

7-Benzyloxy-2-ethoxymethyl-1-propyl-1H-imidazo[4,5-c]quinolin-4-amine (3.9 g, 9.99 mmol) was mixed with ethanol and added to a Parr flask charged with 10% palladium on carbon (0.390 g) in ethanol. The flask was placed under hydrogen pressure and shaken for 18 hours. The reaction mixture was filtered through a layer of CELITE filter aid, and the filter cake was washed with warm DMF. The filtrate was concentrated under reduced pressure, and the residue was recrystallized from methanol to yield 2.4 g of 4-amino-2-ethoxymethyl-1-propyl-1H-imidazo[4,5-c]quinolin-7-ol as a white solid, mp>250° C.

$^1$H NMR (300 MHz, DMSO-$d_6$): δ 9.50 (s, 1H), 7.82 (d, J=8.9 Hz, 1H), 6.96 (d, J=2.5 Hz, 1H), 6.81 (dd, J=8.8, 2.6

Hz, 1H), 6.45 (s, 2H), 4.73 (s, 2H), 4.47-4.41 (m, 2H), 3.54 (q, J=7.0 Hz, 2H), 1.92-1.78 (m, 2H), 1.15 (t, J=6.9 Hz, 3H), 1.00 (t, J=7.4 Hz, 3H);

$^{13}$C NMR (75 MHz, DMSO-$d_6$): δ 156.4, 152.1, 147.7, 147.1, 133.6, 124.5, 121.2, 112.0, 109.8, 107.9, 65.2, 64.2, 46.6, 23.0, 14.9, 10.7;

Anal. Calcd. for $C_{16}H_{20}N_4O_2$: % C, 63.98; % H, 6.71; % N, 18.65. Found: % C, 63.71; % H, 6.48; % N, 18.53.

Part C

The method described in Part L of Example 2 was used to treat 4-amino-2-ethoxymethyl-1-propyl-1H-imidazo[4,5-c] quinolin-7-ol (1.89 g, 6.29 mmol) with cesium carbonate (4.10 g, 12.6 mmol) and tert-butyl 2-iodoethylcarbamate (1.79 g, 6.60 mmol). Following chromatographic purification, the product was recrystallized from acetonitrile to provide 1.26 g of tert-butyl [2-(4-amino-2-ethoxymethyl-1-propyl-1H-imidazo[4,5-c]quinolin-7-yloxy)ethyl]carbamate as a flocculent, white solid.

Part D

The method described in Part O of Example 2 was used to treat the material from Part C with 4 M hydrochloric acid in ethanol to provide 7-(2-aminoethoxy)-2-ethoxymethyl-1-propyl-1H-imidazo[4,5-c]quinolin-4-amine, which was used without purification.

Part E

A suspension of 7-(2-aminoethoxy)-2-ethoxymethyl-1-propyl-1H-imidazo[4,5-c]quinolin-4-amine (0.570 g, 1.66 mmol) in dichloromethane (11 mL) was cooled to 0° C. Methanesulfonic anhydride (0.303 g, 1.74 mmol) was added, and the mixture was stirred for 16 hours and allowed to warm to ambient temperature. Saturated aqueous sodium carbonate (25 mL) was added, and the mixture was stirred for 20 minutes. The aqueous layer was separated and extracted with chloroform (3×50 mL). The combined organic fractions were washed sequentially with water and brine, dried over magnesium sulfate, filtered, and concentrated under reduced pressure. The resulting white solid was purified by column chromatography on silica gel (eluting with chloroform:methanol:ammonium hydroxide ranging in ratios from 99.6:0.36:0.04 to 97:2.7:0.3) and subsequent recrystallization from acetonitrile to yield 0.500 g of N-[2-(4-amino-2-ethoxymethyl-1-propyl-1H-imidazo[4,5-c]quinolin-8-yloxy)ethyl]methanesulfonamide as white, granular powder mp 182-184.5° C.

$^1$H NMR (300 MHz, DMSO-$d_6$) δ 7.93 (d, J=9.1 Hz, 1H), 7.31 (t, J=6.2 Hz, 1H), 7.08 (d, J=3.2 Hz, 1H), 6.95 (dd, J=9.1, 2.6 Hz, 1H), 6.54 (s, 2H), 4.75 (s, 2H), 4.50-4.45 (m, 2H), 4.13 (t, J=5.6 Hz, 2H), 3.55 (q, J=7.0 Hz, 2H), 3.39 (q, J=5.8 Hz, 2H), 2.98 (s, 3H), 1.93-1.79 (m, 2H), 1.16 (t, J=7.0 Hz, 3H), 1.01 (t, J=7.3 Hz, 3H);

MS (APCI) m/z 422.1864 (422.1862 calcd for $C_{19}H_{27}N_5O_4S$, M+H).

Anal. Calcd. for $C_{19}H_{27}N_5O_4S$: % C, 54.14; % H, 6.46; % N, 16.61; % S, 7.61. Found: % C, 54.23; % H, 6.50; % N, 16.66; % S, 7.63.

Example 52

1-[4-Amino-2-ethyl-1-(2-phenoxyethyl)-1H-imidazo [4,5-c]quinolin-7-yloxy]-3,3-dimethylbutan-2-one

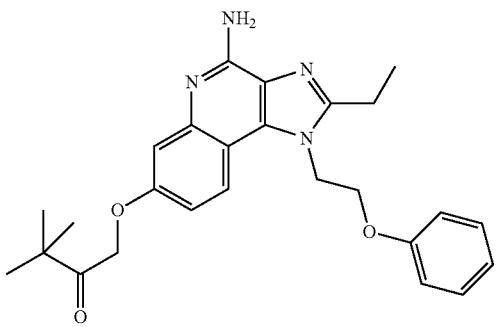 [SMILES: CCc1nc2c(N)nc3cc(OCC(=O)C(C)(C)C)ccc3c2n1CCOc1ccccc1]

Part A

The methods described in Parts E, F, and G of Example 1 were used to convert 7-benzyloxy-4-chloro-3-nitroquinoline, prepared in Parts A-D of Example 1, to 7-benzyloxy-2-ethyl-1-(2-phenoxyethyl)-1H-imidazo[4,5-c]quinoline. 2-Phenoxyethylamine was used in lieu of isobutylamine in Part E, and triethyl orthopropionate was used in lieu of trimethyl orthobutyrate in Part G.

Part B

The method described in Part J of Example 1 was used to convert 7-benzyloxy-2-ethyl-1-(2-phenoxyethyl)-1H-imidazo[4,5-c]quinoline to 2-ethyl-1-(2-phenoxyethyl)-1H-imidazo[4,5-c]quinolin-7-ol.

Part C

A suspension of 2-ethyl-1-(2-phenoxyethyl)-1H-imidazo [4,5-c]quinolin-7-ol (1.0 g, 3.0 mmol) and cesium carbonate (1.49 g, 4.57 mmol) in DMF was stirred for 15 minutes; 1-bromopinacolone (0.6 mL, 4.5 mmol) was added dropwise. The reaction was heated at 65° C. and stirred for 20 hours, and then the solvent was removed under reduced pressure. The residue was dissolved in dichloromethane, and the resulting solution was washed sequentially with water (3×) and brine, dried over magnesium sulfate, filtered, and concentrated under reduced pressure to provide 1.3 g of 1-[2-ethyl-1-(2-phenoxyethyl)-1H-imidazo[4,5-c]quinolin-7-yloxy]-3,3-dimethylbutan-2-one as an orange solid.

$^1$H NMR (300 MHz, DMSO-$d_6$) δ 9.06 (s, 1H), 8.44 (d, J=9.3 Hz, 1H), 7.45 (d, J=2.5 Hz, 1H), 7.34 (dd, J=9.1, 2.5 Hz, 1H), 7.23-7.18 (m, 2H), 6.91-6.86 (m, 1H), 6.78-6.75 (m, 2H), 5.32 (s, 2H), 5.05-4.98 (m, 2H), 4.44 (t, J=5.0 Hz, 2H), 3.08 (q, J=7.3 Hz, 2H), 1.43 (t, J=7.6 Hz, 3H), 1.23 (s, 9H).

Part D

The method described in Part M of Example 2 was used to oxidize 1-[2-ethyl-1-(2-phenoxyethyl)-1H-imidazo[4,5- c]quinolin-7-yloxy]-3,3-dimethylbutan-2-one (1.3 g, 3.0 mmol) to 1.4 g of 1-[2-ethyl-5-oxido-1-(2-phenoxyethyl)-1H-imidazo[4,5-c]quinolin-7-yloxy]-3,3-dimethylbutan-2-one, which was isolated as an orange solid and used without purification.

$^1$H NMR (300 MHz, DMSO-$d_6$) δ 8.96 (s, 1H), 8.55 (d, J=9.2 Hz, 1H), 8.12 (d, J=2.2 Hz, 1H), 7.48 (dd, J=9.3, 3.0 Hz, 1H), 7.23-7.17 (m, 2H), 6.91-6.86 (m, 1H), 6.76-6.73 (m, 2H), 5.38 (s, 2H), 5.04-4.99 (m, 2H), 4.44 (t, J=5.0 Hz, 2H), 3.07 (q, J=7.5 Hz, 2H), 1.41 (t, J=7.1 Hz, 3H), 1.24 (s, 9H).

Part E

Ammonium hydroxide (6 mL) was added to a solution of the material from Part D in dichloromethane (20 mL). p-Toluenesulfonyl chloride (0.629 g, 3.30 mmol) was added in two portions, and the mixture was stirred for 16 hours. The mixture was then diluted with dichloromethane and water. The aqueous layer was separated and extracted twice with chloroform. The combined organic fractions were washed sequentially with water and brine, dried over magnesium sulfate, filtered, and concentrated under reduced pressure. The resulting white solid was recrystallized from acetonitrile twice to yield 0.360 g of 1-[4-amino-2-ethyl-1-(2-phenoxyethyl)-1H-imidazo-[4,5-c]quinolin-7-yloxy]-3,3-dimethylbutan-2-one as feathery, white needles, mp 238-239° C. (decomposition).

$^1$H NMR (300 MHz, DMSO-$d_6$) δ 8.06 (d, J=9.2 Hz, 1H), 7.24-7.2 (m, 2H), 6.96 (d, J=2.5 Hz, 1H), 6.92-6.86 (m, 2H), 6.84-6.80 (m, 2H), 6.36 (s, 2H), 5.19 (s, 2H), 4.96-4.88 (m, 2H), 4.40 (t, J=5.0 Hz, 2H), 3.01 (q, J=7.5 Hz, 2H), 1.40 (t, J=7.2 Hz, 3H), 1.20 (s, 9H);

MS (APCI) m/z 447.2402 (447.2396 calcd for $C_{26}H_{30}N_4O_3$, M+H).

Anal. Calcd. for $C_{26}H_{30}N_4O_3 \cdot 1.0H_2O$: % C, 67.22; % H, 6.94; % N, 12.06. Found: % C, 67.29; % H, 6.81; % N, 12.03.

Example 53

2-Ethyl-7-(2-morpholin-4-yl-2-oxoethoxy)-1-(2-phenoxyethyl)-1H-imidazo[4,5-c]quinolin-4-amine

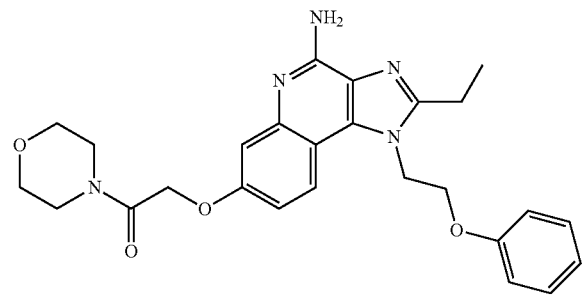 [SMILES: CCc1nc2c(N)nc3cc(OCC(=O)N4CCOCC4)ccc3c2n1CCOc1ccccc1]

Part A

The methods described in Parts A-D of Example 30 were used to convert 7-benzyloxy-N$^4$-(2-phenoxyethyl)quinoline-3,4-diamine to 2-ethyl-7-(2-morpholin-4-yl-2-oxoethoxy)-1-(2-phenoxyethyl)-1H-imidazo[4,5-c]quinoline. In Part D, after the reaction mixture was filtered, the filtrate was allowed to stand for three days. Crystals formed and were isolated by filtration and washed with diethyl ether. The filtrate was concentrated under reduced pressure, and the resulting oil with triturated with a mixture of ethyl acetate and water. The resulting solid was isolated by filtration, washed with diethyl ether, and combined with the crystals isolated from the reaction mixture. The combined solids were recrystallized from methanol, isolated by filtration, washed with cold hexanes, and dried overnight under high vacuum at 70° C. to provide 2-ethyl-7-(2-morpholin-4-yl-2-oxoethoxy)-1-(2-phenoxyethyl)-1H-imidazo[4,5-c]quinoline as a white solid, mp 190-191° C.

Anal. Calcd. for $C_{26}H_{28}N_4O_4$: % C, 67.81; % H, 6.13; % N, 12.17. Found: % C, 67.44; % H, 6.20; % N, 12.05.

Part B

The method described in Part E of Example 30 was used to convert 2-ethyl-7-(2-morpholin-4-yl-2-oxoethoxy)-1-(2-phenoxyethyl)-1H-imidazo[4,5-c]quinoline (0.855 g, 1.86 mmol) to 0.92 g of 2-ethyl-7-(2-morpholin-4-yl-2-oxoethoxy)-5-oxido-1-(2-phenoxyethyl)-1H-imidazo[4,5-c]quinoline.

Part C

Under a nitrogen atmosphere, trichloroacetyl isocyanate (0.35 mL, 2.9 mmol) was added dropwise to a solution of the material from Part B in anhydrous dichloromethane (335 mL), and the reaction was stirred for two hours. The solvent was removed under reduced pressure. The residue was diluted with methanol (23 mL), and a solution of sodium methoxide (0.17 mL, 2.9 mmol, 25% in methanol) was slowly added. The reaction was stirred overnight, and a precipitate formed. The precipitate was isolated by filtration, washed with three times with cold hexanes, and recrystallized from ethyl acetate to provide 0.495 g of 2-ethyl-7-(2-morpholin-4-yl-2-oxoethoxy)-1-(2-phenoxyethyl)-1H-imidazo[4,5-c]quinolin-4-amine as a white powder, mp 208-209° C.

$^1$H NMR (300 MHz, DMSO-$d_6$) δ 8.07 (d, J=9.3 Hz, 1H), 7.22 (m, 2H), 7.05 (d, J=2.7 Hz, 1H), 6.90 (t, J=2.7 Hz, 1H), 6.90 (d, J=9.0 Hz, 1H), 6.82 (d, J=0.9 Hz, 1H), 6.79 (d, J=0.9 Hz, 1H), 6.39 (s, 2H), 4.91 (s, 4H), 4.39 (t, J=4.8 Hz, 2H), 3.54 (m, 8H), 3.01 (q, J=7.5 Hz, 2H), 1.40 (t, J=7.5 Hz, 3H);

$^{13}$C NMR (75 MHz, DMSO-$d_6$) δ 166.5, 158.2, 157.0, 154.4, 152.3, 146.8, 133.4, 129.8, 125.3, 121.7, 121.4, 114.6, 111.8, 109.6, 108.8, 66.7, 66.4, 66.3, 45.2, 44.6, 42.0, 20.3, 12.2;

MS (EI) m/z 476.2282 (476.2298 calcd for $C_{26}H_{29}N_5O_4$).

Anal. Calcd for $C_{26}H_{29}N_5O_4$: % C, 65.67; % H, 6.15; % N, 14.73. Found: % C, 65.48; % H, 6.01; % N, 14.59.

Example 54

1-(2-Methylpropyl)-2-propyl-7-(tetrahydropyran-2-ylmethoxy)-1H-imidazo[4,5-c]quinolin-4-amine

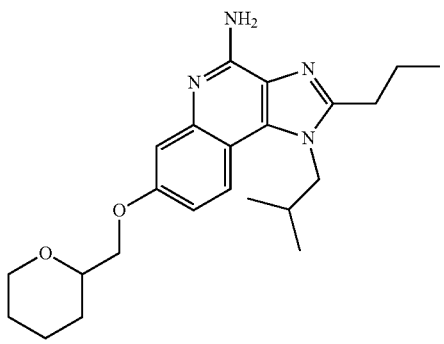 [SMILES: CCCc1nc2c(N)nc3cc(OCC4CCCCO4)ccc3c2n1CC(C)C]

The methods described in Parts L-N of Example 2 were used to treat 1-(2-methylpropyl)-2-propyl-1H-imidazo[4,5-c]quinolin-7-ol. In Part L, 2-(bromomethyl)tetrahydro-2H-pyran was used as the alkylating agent. The crude product was recrystallized from acetonitrile to yield 1-(2-methylpropyl)-2-propyl-7-(tetrahydropyran-2-ylmethoxy)-1H-imidazo[4,5-c]quinolin-4-amine as tan crystals, mp 126° C. (decomposition).

$^1$H NMR (300 MHz, DMSO-$d_6$) δ 7.85 (d, J=9.6 Hz, 1H), 7.03 (d, J=3.0 Hz, 1H), 6.90 (dd, J=9.2, 2.9 Hz, 1H), 6.37 (s, 2H), 4.28 (d, J=7.6 Hz, 2H), 4.02-3.86 (m, 3H), 3.71-3.61 (m, 1H), 3.46-3.34 (m, 1H), 2.86 (t, J=7.8 Hz, 2H), 2.21-2.05 (m, 1H), 1.90-1.77 (m, 3H), 1.72-1.63 (m, 1H), 1.58-1.27 (m, 4H), 1.02 (t, J=7.4 Hz, 3H), 0.91 (d, J=6.7 Hz, 6H);

MS (APCI) m/z 397.2600 (397.2604 calcd for $C_{23}H_{32}N_4O_2$, M+H).

Anal. Calcd. for $C_{23}H_{32}N_4O_2 \cdot 0.75H_2O$: % C, 67.37; % H, 8.23; % N, 13.66. Found: % C, 67.06; % H, 8.06; % N, 13.52.

Example 55

1-(2-Methylpropyl)-2-propyl-7-(tetrahydrofuran-3-yloxy)-1H-imidazo[4,5-c]quinolin-4-amine

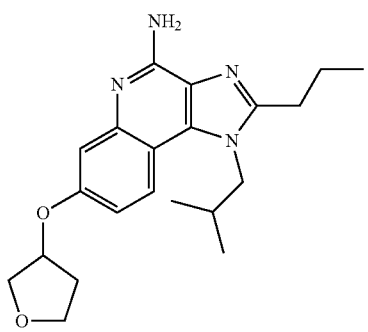 [SMILES: CCCc1nc2c(N)nc3cc(OC4CCOC4)ccc3c2n1CC(C)C]

Part A

3-Hydroxytetrahydrofuran (0.375 mL, 4.64 mmol) was added to a suspension of 1-(2-methylpropyl)-2-propyl-1H-imidazo[4,5-c]quinolin-7-ol (1.0 g, 3.5 mmol) and triphenylphosphine (1.5 g, 5.7 mmol) in THF. Diisopropyl azodicarboxylate (1.1 mL, 5.6 mmol) was added dropwise over a period of three minutes, and the reaction was stirred for 48 hours. The solvent was removed under reduced pressure, the residue was purified by column chromatography on silica gel (eluting with 98:2 dichloromethane:methanol) to provide 1.1 g of 1-(2-methylpropyl)-2-propyl-7-(tetrahydrofuran-3-yloxy)-1H-imidazo[4,5-c]quinoline as an off-white, crystalline solid.

Part B

The method described in Part M of Example 2 was used to treat 1-(2-methylpropyl)-2-propyl-7-(tetrahydrofuran-3-yloxy)-1H-imidazo[4,5-c]quinoline (1.1 g, 3.1 mmol) with mCPBA (1.07 g, 3.72 mmol). The crude product was purified by column chromatography on silica gel to afford 0.588 g of 1-(2-methylpropyl)-5-oxido-2-propyl-7-(tetrahydrofuran-3-yloxy)-1H-imidazo[4,5-c]quinoline as a yellow solid.

Part C

The method described in Part E of Example 52 was used to aminate the material from Part B. The crude product was recrystallized from acetonitrile to afford 0.242 g of 1-(2-methylpropyl)-2-propyl-7-(tetrahydrofuran-3-yloxy)-1H-imidazo[4,5-c]quinolin-4-amine as white needles, mp 178-182° C.

$^1$H NMR (300 MHz, DMSO-$d_6$) δ 7.87 (d, J=9.0 Hz, 1H), 7.02 (d, J=2.7 Hz, 1H), 6.89 (dd, J=8.9, 2.7 Hz, 1H), 6.40 (s, 2H), 5.13-5.09 (m, 1H), 4.29 (d, J=7.3 Hz, 2H), 3.96-3.73 (m, 4H), 2.86 (t, J=7.5 Hz, 2H), 2.33-1.97 (m, 3H), 1.84 (sextet, J=7.5 Hz, 2H), 1.02 (t, J=7.4 Hz, 3H), 0.91 (d, J=6.4 Hz, 6H);

$^{13}$C NMR (75 MHz, DMSO-$d_6$) δ 155.6, 152.6, 152.0, 146.4, 132.7, 125.2, 121.4, 112.0, 109.2, 109.0, 76.9, 72.3, 66.4, 51.2, 32.5, 28.7, 28.5, 20.9, 19.1, 13.8;

MS (APCI) m/z 369.2298 (369.2291 calcd for $C_{21}H_{28}N_4O_2$, M+H).

Anal. Calcd. for $C_{21}H_{28}N_4O_2$: % C, 68.45; % H, 7.66; % N, 15.20. Found: % C, 68.11; % H, 7.87; % N, 15.01.

Example 56

2-(2-Methoxyethyl)-1-propyl-7-(tetrahydrofuran-3-yloxy)-1H-imidazo[4,5-c]quinolin-4-amine

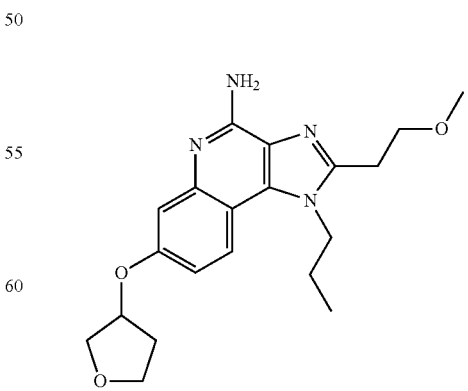

The methods described in Parts A and B of Example 51 were used to prepare 2-(2-methoxyethyl)-1-propyl-1H-imidazo[4,5-c]quinolin-7-ol, which was treated according to the methods described in Example 55. The crude product was purified by column chromatography on silica gel and subsequent recrystallization from 2-propanol to afford 2-(2-methoxyethyl)-1-propyl-7-(tetrahydrofuran-3-yloxy)-1H-imidazo[4,5-c]quinolin-4-amine as a tan powder, mp 192-194° C.

$^1$H NMR (300 MHz, DMSO-$d_6$) δ 7.90 (d, J=9.2 Hz, 1H), 7.02 (d, J=2.6 Hz, 1H), 6.89 (dd, J=9.0, 2.6 Hz, 1H), 6.41 (s, 2H), 5.14-5.10 (m, 1H), 4.46-4.41 (m, 2H), 3.97-3.74 (m, 6H), 3.30 (s, 3H), 3.16 (t, J=6.8 Hz, 2H), 2.33-2.21 (m, 1H), 2.08-1.98 (m, 1H), 1.87-1.74 (m, 2H), 0.98 (t, J=7.4 Hz, 3H);

MS (APCI) m/z 371.2074 (371.2083 calcd for $C_{20}H_{26}N_4O_3$, M+H).

Anal. Calcd. for $C_{20}H_{26}N_4O_3$: % C, 64.85; % H, 7.07; % N, 15.12. Found: % C, 64.88; % H, 7.03; % N, 15.20.

Examples 57-92

An acid chloride (1.1 equivalents) was added to a culture tube containing a solution of 7-(3-aminopropoxy)-1-(2-methylpropyl)-2-propyl-1H-imidazo[4,5-c]quinolin-4-amine (4.4 mg/mL) in chloroform (5 mL). The culture tubes were capped and placed on a shaker overnight (18 hours). The volatiles were removed by vacuum centrifugation. The compounds were purified by preparative high performance liquid chromatography (prep HPLC) using a Waters Fraction Lynx automated purification system. The prep HPLC fractions were analyzed using a Micromass LC-TOFMS, and the appropriate fractions were centrifuge evaporated to provide the trifluoroacetate salt of the desired compound. (Column: Phenomenex Luna C18(2), 21.2×50 mm, 10 micron particle size, 100 Å pore; flow rate: 25 mL/min.; non-linear gradient elution from 5-95% B in 9 min, then hold at 95% B for 2 min., where A is 0.05% trifluoroacetic acid/water and B is 0.05% trifluoroacetic acid/acetonitrile; fraction collection by mass-selective triggering.) The table below shows the structure made in each example and the observed accurate mass for the isolated trifluoroacetate salt.

Examples 57-92

| Example | R | Measured Mass (M + H) |
|---|---|---|
| 57 | cyclopropyl-C(=O)- | 424.2727 |
| 58 | (CH$_3$)$_2$CH-C(=O)- | 426.2879 |
| 59 | (CH$_3$)$_2$CH-CH$_2$-C(=O)- | 440.3047 |
| 60 | CH$_3$-C(=O)-O-CH$_2$-C(=O)- | 456.2622 |
| 61 | Ph-C(=O)- | 460.2736 |
| 62 | 2-thienyl-C(=O)- | 466.2288 |
| 63 | cyclohexyl-C(=O)- | 466.3162 |
| 64 | Ph-CH$_2$-C(=O)- | 474.2877 |
| 65 | 4-F-C$_6$H$_4$-C(=O)- | 478.2616 |
| 66 | 2-thienyl-CH$_2$-C(=O)- | 480.2419 |
| 67 | cyclopentyl-CH$_2$-CH$_2$-C(=O)- | 480.3356 |

| Example | R | Measured Mass (M + H) |
|---|---|---|
| 68 | 3-cyanophenyl ketone | 485.2668 |
| 69 | 4-cyanophenyl ketone | 485.2667 |
| 70 | cinnamyl ketone (PhCH=CH-C(O)CH3) | 486.2862 |
| 71 | phenylpropyl ketone (Ph-CH2CH2-C(O)CH3) | 488.3015 |
| 72 | 3-methoxyphenyl ketone | 490.2820 |
| 73 | 6-chloropyridin-3-yl ketone | 495.2273 |
| 74 | 2,5-difluorophenyl ketone | 496.2515 |
| 75 | methyl 6-oxoheptanoate | 498.3105 |
| 76 | trans-2-phenylcyclopropyl ketone | 500.3048 |
| 77 | 2-phenylbutan-1-one (H3C-CH(Et)(Ph)-C(O)CH3) | 502.3173 |
| 78 | benzo[d][1,3]dioxol-5-yl ketone | 504.2619 |
| 79 | benzyloxy acetone (PhCH2-O-CH2-C(O)CH3) | 504.2990 |
| 80 | phenylthio acetone (PhS-CH2-C(O)CH3) | 506.2589 |
| 81 | naphthalen-2-yl ketone | 510.2873 |
| 82 | methyl 4-acetylbenzoate | 518.2742 |

131

-continued

[Structure: imidazoquinoline core with NH2, N=, propyl, isobutyl, and R-NH-(CH2)3-O- substituent]

| Example | R | Measured Mass (M + H) |
|---------|---|------------------------|
| 83 | phenoxy-propyl-ketone group | 518.3122 |
| 84 | adamantyl methyl ketone | 518.3502 |
| 85 | 2,6-dimethoxyphenyl methyl ketone | 520.2934 |
| 86 | 3,5-dimethoxyphenyl methyl ketone | 520.2920 |
| 87 | (4-chlorophenoxy)methyl methyl ketone | 524.2440 |
| 88 | 1H-indol-3-yl glyoxal | 527.2756 |
| 89 | 3-(trifluoromethyl)phenyl methyl ketone | 528.2599 |

132

-continued

[Structure: imidazoquinoline core with NH2, N=, propyl, isobutyl, and R-NH-(CH2)3-O- substituent]

| Example | R | Measured Mass (M + H) |
|---------|---|------------------------|
| 90 | 4-(trifluoromethyl)phenyl methyl ketone | 528.2592 |
| 91 | 4-butoxyphenyl methyl ketone | 532.3278 |
| 92 | 4-(trifluoromethoxy)phenyl methyl ketone | 544.2535 |

Examples 93-129

The method described for Examples 57-92 was used to treat 1-(2-methylpropyl)-7-(2-piperidin-4-ylethoxy)-2-propyl-1H-imidazo[4,5-c]quinolin-4-amine with acid chlorides. The table below shows the structure made in each example and the observed accurate mass for the isolated trifluoroacetate salt.

Examples 93-129

[Structure: imidazoquinoline core with NH2, N=, propyl, isobutyl, and R-N(piperidine)-CH2CH2-O- substituent]

| Example | R | Measured Mass (M + H) |
|---------|---|------------------------|
| 93 | cyclopropyl methyl ketone | 478.3181 |

-continued

| Example | R | Measured Mass (M + H) |
|---|---|---|
| 94 | (CH3)2CHC(O)CH3 (isopropyl methyl ketone) | 480.3352 |
| 95 | (CH3)2CHCH2C(O)CH3 | 494.3478 |
| 96 | CH3C(O)OCH2C(O)CH3 | 510.3051 |
| 97 | PhC(O)CH3 | 514.3151 |
| 98 | 2-thienyl-C(O)CH3 | 520.2748 |
| 99 | cyclohexyl-C(O)CH3 | 520.3622 |
| 100 | PhCH2C(O)CH3 | 528.3341 |
| 101 | 4-F-C6H4-C(O)CH3 | 532.3076 |
| 102 | 2-thienyl-CH2C(O)CH3 | 534.2899 |
| 103 | cyclopentyl-CH2CH2C(O)CH3 | 534.3823 |
| 104 | 3-NC-C6H4-C(O)CH3 | 539.3121 |
| 105 | 4-NC-C6H4-C(O)CH3 | 539.3130 |
| 106 | PhCH=CH-C(O)CH3 | 540.3336 |
| 107 | PhCH2CH2C(O)CH3 | 542.3503 |
| 108 | 3-CH3O-C6H4-C(O)CH3 | 544.3304 |
| 109 | 4-CH3O-C6H4-C(O)CH3 | 544.3291 |
| 110 | 6-Cl-pyridin-3-yl-C(O)CH3 | 549.2761 |

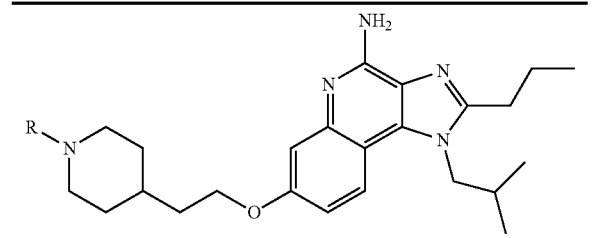

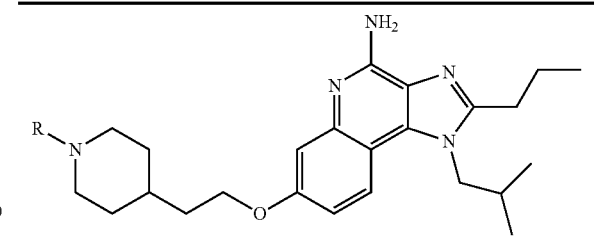

| Example | R | Measured Mass (M + H) |
|---|---|---|
| 111 | H₃C-O-C(=O)-(CH₂)₄-C(=O)-CH₃ | 552.3552 |
| 112 | trans-2-phenylcyclopropyl methyl ketone | 554.3510 |
| 113 | CH₃CH₂-CH(Ph)-C(=O)-CH₃ | 556.3687 |
| 114 | 3,4-methylenedioxyphenyl methyl ketone | 558.3102 |
| 115 | PhCH₂-O-CH₂-C(=O)-CH₃ | 558.3455 |
| 116 | PhS-CH₂-C(=O)-CH₃ | 560.3093 |
| 117 | 2-acetylnaphthalene | 564.3351 |
| 118 | methyl 4-acetylbenzoate | 572.3240 |
| 119 | PhO-(CH₂)₃-C(=O)-CH₃ | 572.3608 |
| 120 | 1-acetyladamantane | 572.3984 |
| 121 | 2,6-dimethoxyphenyl methyl ketone | 574.3419 |
| 122 | 3,5-dimethoxyphenyl methyl ketone | 574.3412 |
| 123 | 4-chlorophenoxy-CH₂-C(=O)-CH₃ | 578.2916 |
| 124 | 3-(trifluoromethyl)phenyl methyl ketone | 582.3076 |
| 125 | 4-(trifluoromethyl)phenyl methyl ketone | 582.3096 |

Examples 130-161
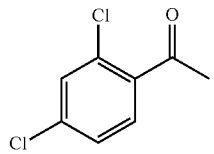
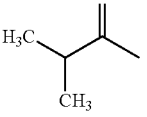
| Example | R | Measured Mass (M + H) |
|---|---|---|
| 126 | 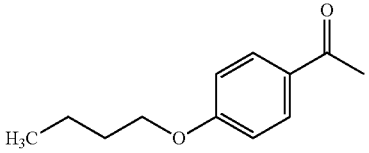 | 582.2361 |
| 127 | 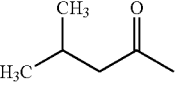 | 586.3799 |
| 128 | 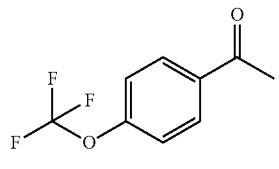 | 598.3027 |
| 129 | 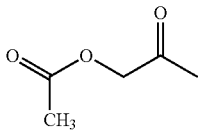 | 612.4310 |
Examples 130-161
The method described for Examples 57-92 was used to treat 8-(2-aminoethoxy)-2-ethoxymethyl-1-propyl-1H-imidazo[4,5-c]quinolin-4-amine with acid chlorides. The table below shows the structure made in each example and the observed accurate mass for the isolated trifluoroacetate salt.
| Example | R | Measured Mass (M + H) |
|---|---|---|
| 130 | 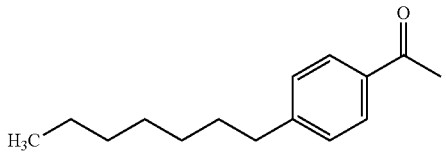 | 414.2480 |
| 131 | 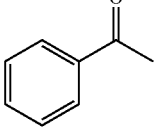 | 428.2674 |
| 132 | 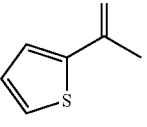 | 444.2262 |
| 133 | 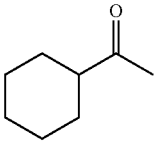 | 448.2362 |
| 134 | 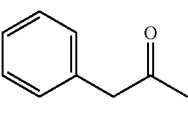 | 454.1902 |
| 135 | 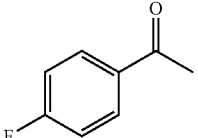 | 454.2825 |
| 136 | 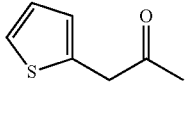 | 462.2513 |
| 137 | | 466.2257 |
| 138 | | 468.2071 |

-continued

[Structure: 4-amino-2-(ethoxymethyl)-1-propyl-imidazoquinoline with 8-O-CH2CH2-NHR substituent]

| Example | R | Measured Mass (M + H) |
|---|---|---|
| 139 | cyclopentyl-CH2CH2-C(=O)-CH3 | 468.2960 |
| 140 | 3-cyano-phenyl-C(=O)- | 473.2296 |
| 141 | (E)-cinnamoyl (Ph-CH=CH-C(=O)-) | 474.2487 |
| 142 | Ph-CH2CH2-C(=O)- | 476.2667 |
| 143 | 2-methoxy-phenyl-C(=O)- (H3C-O at position) | 478.2455 |
| 144 | 4-methoxy-phenyl-C(=O)- | 478.2453 |
| 145 | 6-chloro-pyridin-3-yl-C(=O)- | 483.1922 |

-continued

[Same core structure as 139]

| Example | R | Measured Mass (M + H) |
|---|---|---|
| 146 | 2,5-difluoro-phenyl-C(=O)- | 484.2175 |
| 147 | H3C-O-C(=O)-(CH2)4-C(=O)- | 486.2725 |
| 148 | trans-2-phenyl-cyclopropyl-C(=O)- | 488.2654 |
| 149 | CH3CH2-CH(Ph)-C(=O)- (actually: 2-phenyl-pentan-3-one derivative) | 490.2791 |
| 150 | benzo[d][1,3]dioxol-5-yl-C(=O)- | 492.2255 |
| 151 | Ph-CH2-O-CH2-C(=O)- | 492.2588 |
| 152 | Ph-S-CH2-C(=O)- | 494.2204 |

-continued

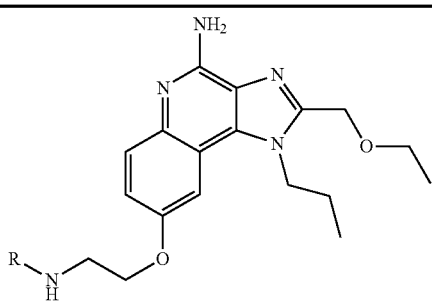

| Example | R | Measured Mass (M + H) |
|---|---|---|
| 153 | 2-acetylnaphthalene | 498.2528 |
| 154 | methyl 4-acetylbenzoate | 506.2372 |
| 155 | 5-phenoxy-2-pentanone moiety | 506.2751 |
| 156 | 2',6'-dimethoxyacetophenone | 508.2549 |
| 157 | 3',5'-dimethoxyacetophenone | 508.2546 |
| 158 | 3'-(trifluoromethyl)acetophenone | 516.2205 |
| 159 | 4'-(trifluoromethyl)acetophenone | 516.2219 |

-continued

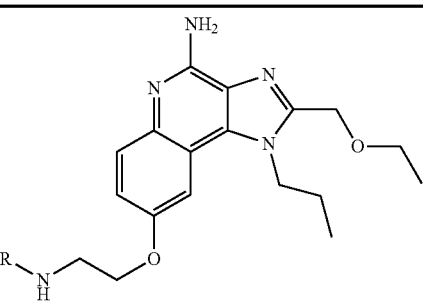

| Example | R | Measured Mass (M + H) |
|---|---|---|
| 160 | 2',4'-dichloroacetophenone | 516.1549 |
| 161 | 4'-butoxyacetophenone | 520.2924 |

Examples 162-189

The method described for Examples 57-92 was used to treat 7-(3-aminopropoxy)-1-(2-methylpropyl)-2-propyl-1H-imidazo[4,5-c]quinolin-4-amine with sulfonyl chlorides. The table below shows the structure made in each example and the observed accurate mass for the isolated trifluoroacetate salt.

Examples 162-189

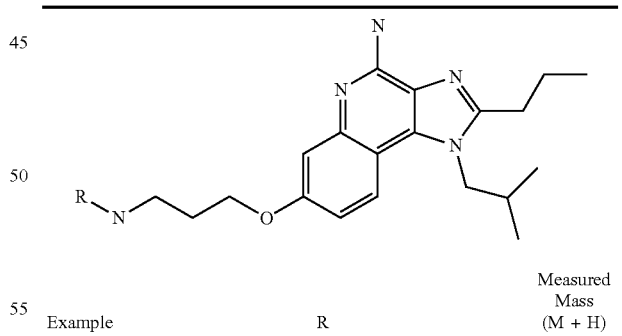

| Example | R | Measured Mass (M + H) |
|---|---|---|
| 162 | CH₃CH₂SO₂– | 448.2388 |
| 163 | CH₃CH(CH₃)SO₂– | 462.2542 |

-continued
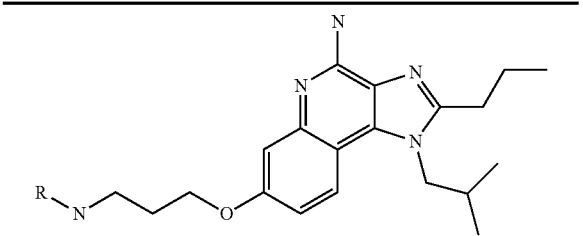
| Example | R | Measured Mass (M + H) |
|---|---|---|
| 164 | (CH3)2N-SO2-CH3 | 463.2517 |
| 165 | H3C-CH2-CH2-CH2-SO2-CH3 | 476.2714 |
| 166 | 3-F-C6H4-SO2-CH3 | 514.2286 |
| 167 | 2-CN-C6H4-SO2-CH3 | 521.2303 |
| 168 | 3-CN-C6H4-SO2-CH3 | 521.2302 |
| 169 | 4-CN-C6H4-SO2-CH3 | 521.2334 |
| 170 | PhCH=CH-SO2-CH3 | 522.2527 |
| 171 | 4-CH3O-C6H4-SO2-CH3 | 526.2491 |
-continued
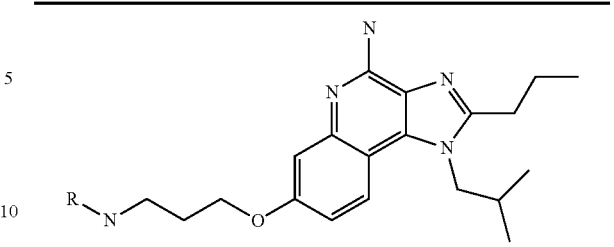
| Example | R | Measured Mass (M + H) |
|---|---|---|
| 172 | 2,4-F2-C6H3-SO2-CH3 | 532.2197 |
| 173 | 5-Cl-thiophen-2-yl-SO2-CH3 | 536.1563 |
| 174 | 4-iPr-C6H4-SO2-CH3 | 538.2829 |
| 175 | 4-HOOC-C6H4-SO2-CH3 | 540.2260 |
| 176 | naphth-1-yl-SO2-CH3 | 546.2551 |
| 177 | naphth-2-yl-SO2-CH3 | 546.2537 |

145
-continued

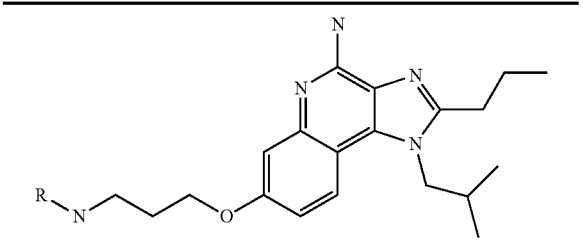

| Example | R | Measured Mass (M + H) |
|---|---|---|
| 178 | 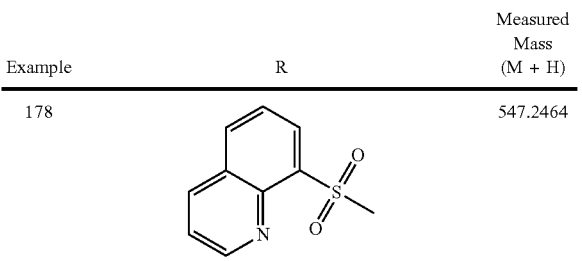 | 547.2464 |
| 179 | 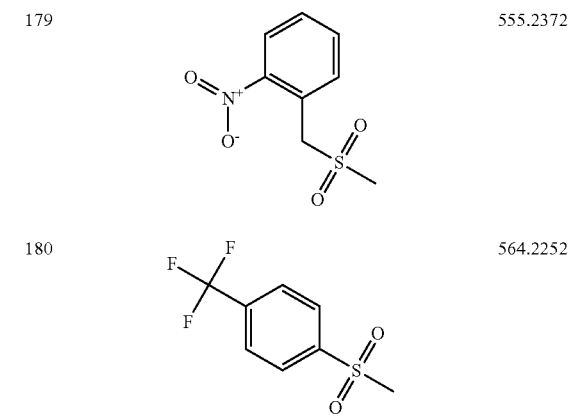 | 555.2372 |
| 180 | | 564.2252 |
| 181 | | 564.1624 |
| 182 | 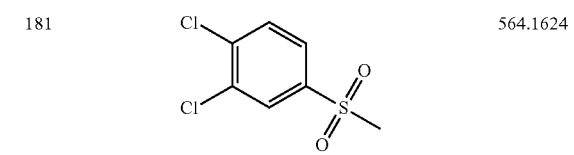 | 568.2946 |
| 183 | 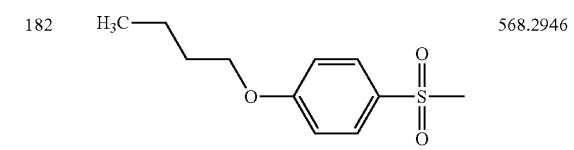 | 570.3129 |
| 184 | 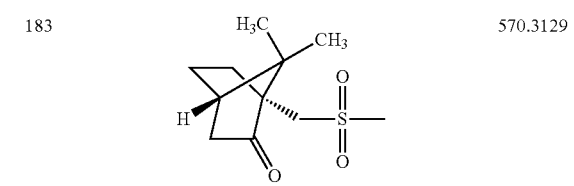 | 570.3125 |

146
-continued

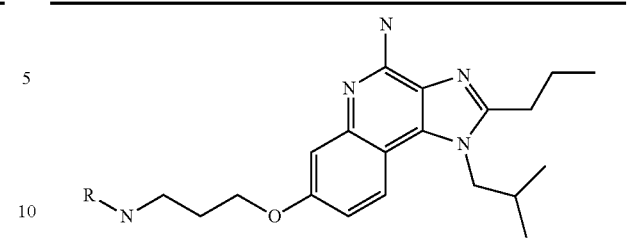

| Example | R | Measured Mass (M + H) |
|---|---|---|
| 185 | 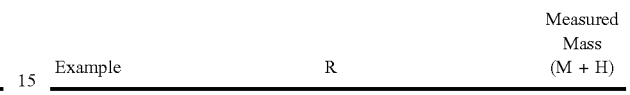 | 574.2169 |
| 186 | 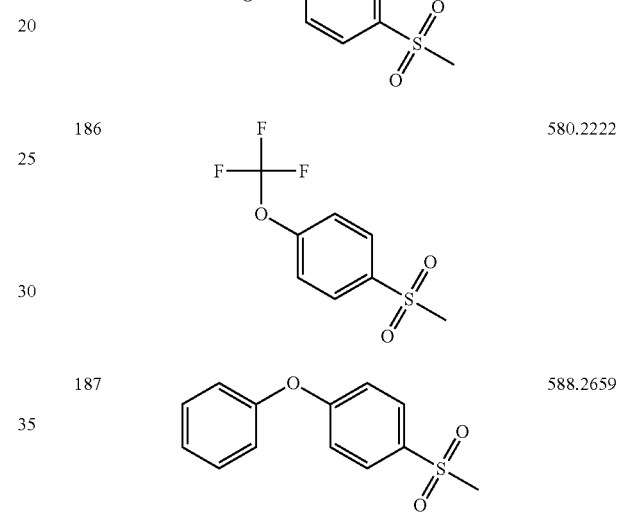 | 580.2222 |
| 187 | | 588.2659 |
| 188 | 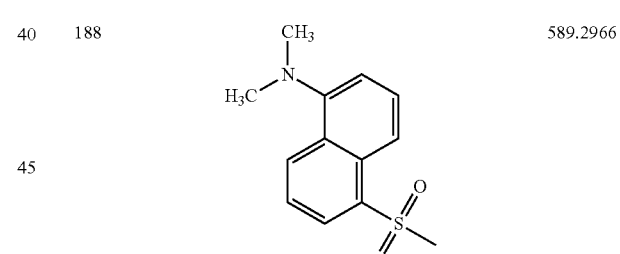 | 589.2966 |
| 189 | 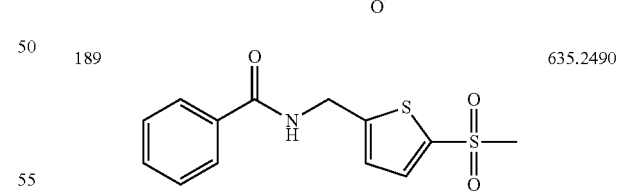 | 635.2490 |

Examples 190-217

The method described for Examples 57-92 was used to treat 1-(2-methylpropyl)-7-(2-piperidin-4-ylethoxy)-2-propyl-1H-imidazo[4,5-c]quinolin-4-amine with sulfonyl chlorides. The table below shows the structure made in each example and the observed accurate mass for the isolated trifluoroacetate salt.

Examples 190-217

| Example | R | Measured Mass (M + H) |
|---|---|---|
| 190 | ethylsulfonyl (CH₃CH₂SO₂–) | 502.2851 |
| 191 | isopropylsulfonyl | 516.2997 |
| 192 | (CH₃)₂N-SO₂- | 517.2976 |
| 193 | n-butylsulfonyl | 530.3141 |
| 194 | phenylsulfonyl | 550.2875 |
| 195 | thiophen-2-ylsulfonyl | 556.2460 |
| 196 | 3-fluorophenylsulfonyl | 568.2739 |
| 197 | 3,5-dimethylisoxazol-4-ylsulfonyl | 569.2917 |
| 198 | 2-cyanophenylsulfonyl | 575.2827 |
| 199 | 3-cyanophenylsulfonyl | 575.2785 |
| 200 | 4-methoxyphenylsulfonyl | 580.2991 |
| 201 | 5-chlorothiophen-2-ylsulfonyl | 590.2044 |
| 202 | 4-isopropylphenylsulfonyl | 592.3352 |
| 203 | 4-carboxyphenylsulfonyl | 594.2772 |
| 204 | naphthalen-2-ylsulfonyl | 600.3042 |

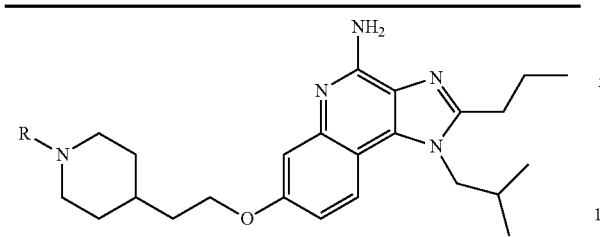
| Example | R | Measured Mass (M + H) |
|---|---|---|
| 205 | 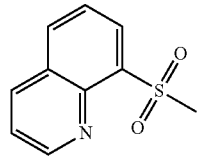 | 601.2969 |
| 206 | 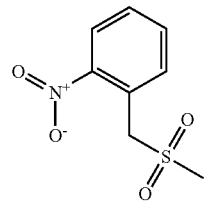 | 609.2883 |
| 207 | 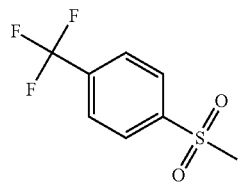 | 618.2733 |
| 208 | 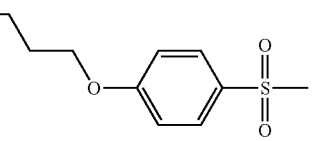 | 622.3428 |
| 209 | 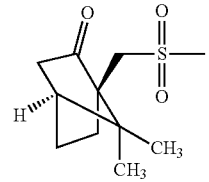 | 624.3610 |
| 210 | 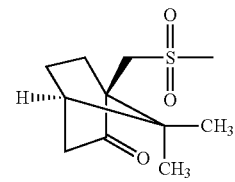 | 624.3606 |
| 211 | 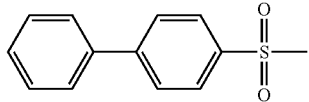 | 626.3162 |
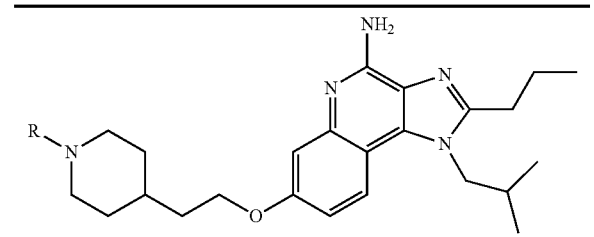
| Example | R | Measured Mass (M + H) |
|---|---|---|
| 212 | 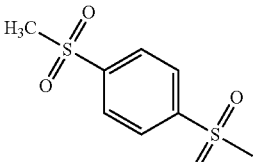 | 628.2621 |
| 213 | 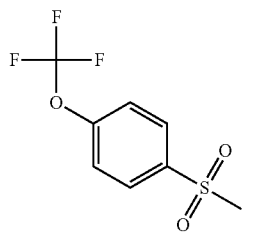 | 634.2709 |
| 214 | 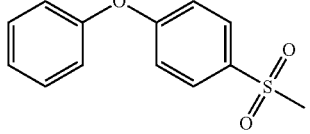 | 642.3131 |
| 215 | 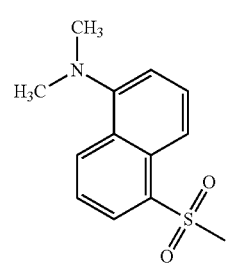 | 643.3466 |
| 216 | 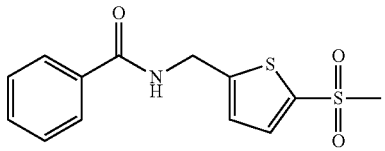 | 689.2985 |
| 217 | 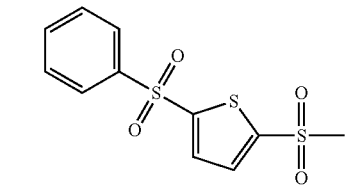 | 696.2326 |
Examples 218-242
The method described for Examples 57-92 was used to treat 8-(2-aminoethoxy)-2-ethoxymethyl-1-propyl-1H-imidazo[4,5-c]quinolin-4-amine with sulfonyl chlorides. The table below shows the structure made in each example and the observed accurate mass for the isolated trifluoroacetate salt.

Examples 218-242

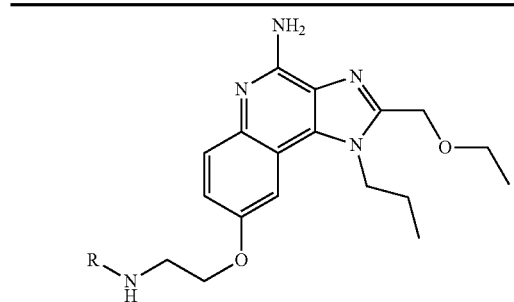

| Example | R | Measured Mass (M + H) |
|---|---|---|
| 218 | CH₃-CH₂-S(O)₂- | 436.2036 |
| 219 | (CH₃)₂CH-S(O)₂- | 450.2162 |
| 220 | (CH₃)₂N-S(O)₂- | 451.2139 |
| 221 | CH₃CH₂CH₂CH₂-S(O)₂- | 464.2341 |
| 222 | C₆H₅-S(O)₂- | 484.2017 |
| 223 | 3-F-C₆H₄-S(O)₂- | 502.1901 |
| 224 | 3,5-dimethylisoxazol-4-yl-S(O)₂- | 503.2099 |

-continued

| Example | R | Measured Mass (M + H) |
|---|---|---|
| 225 | 2-CN-C₆H₄-S(O)₂- | 509.1982 |
| 226 | 3-CN-C₆H₄-S(O)₂- | 509.1957 |
| 227 | 4-CN-C₆H₄-S(O)₂- | 509.1964 |
| 228 | (E)-PhCH=CH-S(O)₂- | 510.2191 |
| 229 | 4-CH₃O-C₆H₄-S(O)₂- | 514.2129 |
| 230 | 2,4-F₂-C₆H₃-S(O)₂- | 520.1815 |
| 231 | 5-Cl-thien-2-yl-S(O)₂- | 524.1172 |

-continued

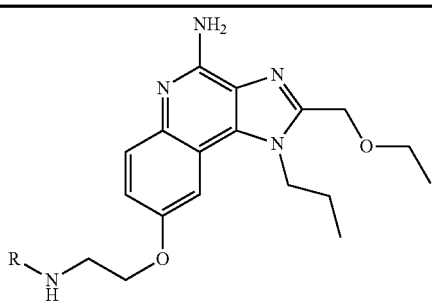

| Example | R | Measured Mass (M + H) |
|---|---|---|
| 232 | (4-isopropylphenyl)methylsulfonyl | 526.2491 |
| 233 | (quinolin-8-yl)sulfonyl | 535.2117 |
| 234 | (2-nitrobenzyl)methylsulfonyl | 543.2015 |
| 235 | (4-trifluoromethylphenyl)methylsulfonyl | 552.1878 |
| 236 | (1S)-camphorsulfonyl | 558.2752 |
| 237 | (1R)-camphorsulfonyl | 558.2780 |
| 238 | (biphenyl-4-yl)methylsulfonyl | 560.2318 |

-continued

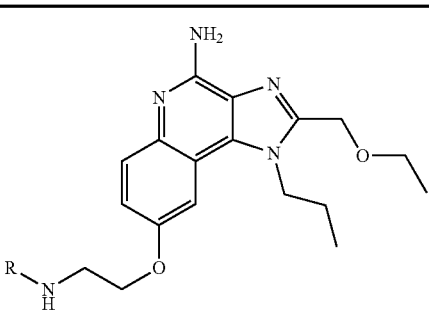

| Example | R | Measured Mass (M + H) |
|---|---|---|
| 239 | (4-methylsulfonylphenyl)methylsulfonyl | 562.1780 |
| 240 | (4-trifluoromethoxyphenyl)methylsulfonyl | 568.1868 |
| 241 | (5-dimethylaminonaphthalen-1-yl)methylsulfonyl | 577.2585 |
| 242 | N-((5-methylsulfonylthien-2-yl)methyl)benzamide | 623.2094 |

Examples 243-284

The method described for Examples 57-92 was used to treat 7-(3-aminopropoxy)-1-(2-methylpropyl)-2-propyl-1H-imidazo[4,5-c]quinolin-4-amine with isocyanates or carbamoyl chlorides. The table below shows the structure made in each example and the observed accurate mass for the isolated trifluoroacetate salt.

Examples 243-284
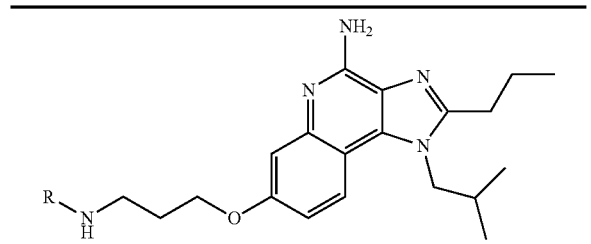
| Example | R | Measured Mass (M + H) |
|---|---|---|
| 243 | CH₃CH(CH₃)NHC(O)– | 441.3011 |
| 244 | CH₃CH₂CH₂CH₂NHC(O)– | 455.3159 |
| 245 | (CH₃)₂NC(O)– | 427.2842 |
| 246 | PhNHC(O)– | 475.2837 |
| 247 | cyclohexyl-NHC(O)– | 481.3302 |
| 248 | CH₃CH₂OC(O)CH₂NHC(O)– | 485.2899 |
| 249 | PhCH₂NHC(O)– | 489.2988 |
| 250 | pyrrolidin-1-yl-C(O)– | 453.2988 |
| 251 | PhNHC(S)– | 491.2608 |
| 252 | (CH₃CH₂)₂NC(O)– | 455.3156 |
| 253 | 3-cyanophenyl-NHC(O)– | 500.2784 |
| 254 | PhC(O)NHC(O)– | 503.2751 |
| 255 | (R)-PhCH(CH₃)NHC(O)– | 503.3134 |
| 256 | (S)-PhCH(CH₃)NHC(O)– | 503.3156 |
| 257 | PhCH₂CH₂NHC(O)– | 503.3123 |
| 258 | piperidin-1-yl-C(O)– | 467.3150 |
| 259 | 3-methoxyphenyl-NHC(O)– | 505.2916 |

157
-continued

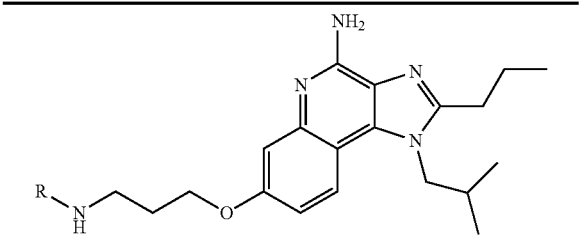

| Example | R | Measured Mass (M + H) |
|---|---|---|
| 260 | (4-acetylmorpholine) | 469.2950 |
| 261 | (furan-2-carbonyl thioamide) | 509.2340 |
| 262 | (N-heptylacetamide) | 511.3764 |
| 263 | (trans-2-phenylcyclopropyl acetamide) | 515.3130 |
| 264 | (3-acetylphenyl acetamide) | 517.2918 |
| 265 | (4-isopropylphenyl acetamide) | 517.3308 |
| 266 | (4-dimethylaminophenyl acetamide) | 518.3246 |
| 267 | (N,N-diisopropyl acetamide) | 483.3452 |

158
-continued

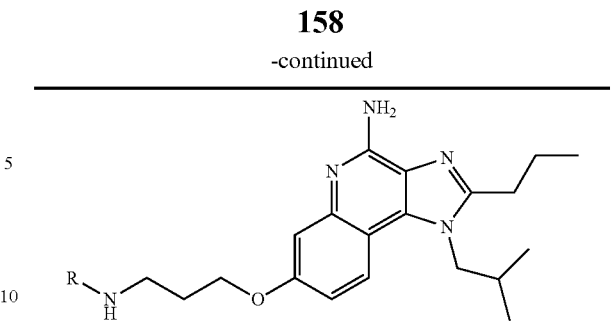

| Example | R | Measured Mass (M + H) |
|---|---|---|
| 268 | (3-methylthiophenyl acetamide) | 521.2693 |
| 269 | (4-methoxyphenyl thioacetamide) | 521.2685 |
| 270 | (naphthalen-1-yl acetamide) | 525.2961 |
| 271 | (N-methyl-N-phenyl acetamide) | 489.2985 |
| 272 | (N-(2-morpholinoethyl) thioacetamide) | 528.3100 |
| 273 | (adamantyl acetamide) | 533.3608 |
| 274 | (3-trifluoromethylphenyl acetamide) | 543.2682 |
| 275 | (4-trifluoromethylphenyl acetamide) | 543.2704 |

Examples 285-322

The method described for Examples 57-92 was used to treat 1-(2-methylpropyl)-7-(2-piperidin-4-ylethoxy)-2-propyl-1H-imidazo[4,5-c]quinolin-4-amine with isocyanates or carbamoyl chlorides. The table below shows the structure made in each example and the observed accurate mass for the isolated trifluoroacetate salt.

Examples 285-322

| Example | R | Measured Mass (M + H) |
|---|---|---|
| 276 | (2,4-dichlorophenyl)acetamide | 543.2021 |
| 277 | ethyl 3-acetamidobenzoate | 547.3023 |
| 278 | N-(adamantyl)thioacetamide | 549.3399 |
| 279 | N-(1-(naphthalen-1-yl)ethyl)acetamide | 553.3261 |
| 280 | N-(2,4-dichlorobenzyl)acetamide | 557.2203 |
| 281 | N-(2-phenoxyphenyl)acetamide | 567.3111 |
| 282 | N-(3-phenoxyphenyl)acetamide | 567.3104 |
| 283 | N-(4-phenoxyphenyl)acetamide | 567.3091 |
| 284 | N-(4-benzyloxyphenyl)acetamide | 581.3271 |
| 285 | N-isopropylacetamide | 495.3449 |
| 286 | N-butylacetamide | 509.3607 |
| 287 | N-tert-butylacetamide | 509.3616 |

| Example | R (161) | Measured Mass (M+H) |
|---|---|---|
| 288 | N,N-dimethylacetamide | 481.3298 |
| 289 | N-cyclohexylacetamide | 535.3751 |
| 290 | ethyl N-acetylglycinate | 539.3303 |
| 291 | N-benzylacetamide | 543.3445 |
| 292 | 1-acetylpyrrolidine | 507.3424 |
| 293 | N,N-diethylacetamide | 509.3565 |
| 294 | N-(3-cyanophenyl)acetamide | 554.3253 |
| 295 | (S)-N-(1-phenylethyl)acetamide | 557.3626 |

| Example | R (162) | Measured Mass (M+H) |
|---|---|---|
| 296 | (S)-N-(1-phenylethyl)acetamide | 557.3613 |
| 297 | N-phenethylacetamide | 557.3580 |
| 298 | 1-acetylpiperidine | 521.3593 |
| 299 | N-(3-methoxyphenyl)acetamide | 559.3403 |
| 300 | 4-acetylmorpholine | 523.3367 |
| 301 | N-(furan-2-carbonyl)thioacetamide | 563.2794 |
| 302 | N-octylacetamide | 565.4229 |
| 303 | N-(2-phenylcyclopropyl)acetamide | 569.3617 |

163
-continued
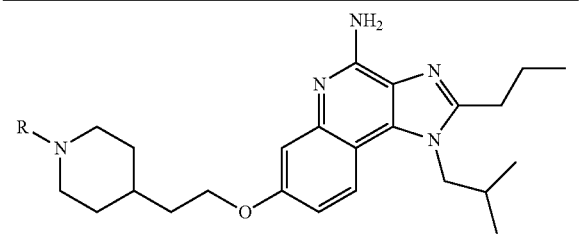
| Example | R | Measured Mass (M + H) |
|---|---|---|
| 304 | 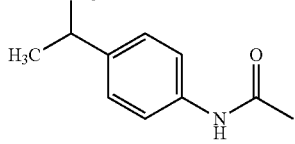 | 571.3754 |
| 305 | 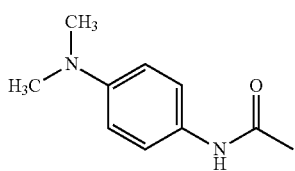 | 572.3731 |
| 306 | 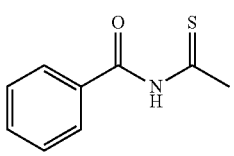 | 573.3036 |
| 307 | 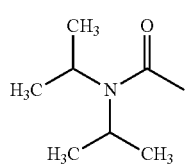 | 537.3932 |
| 308 | 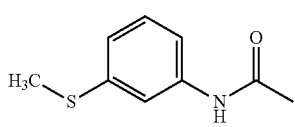 | 575.3166 |
| 309 | 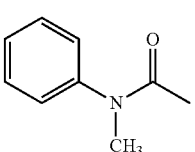 | 543.3455 |
| 310 | 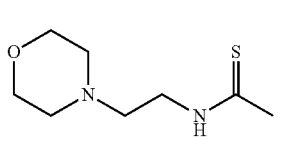 | 582.3604 |
| 311 | 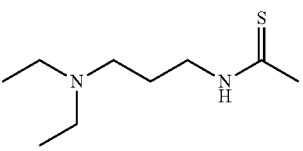 | 582.3961 |
164
-continued
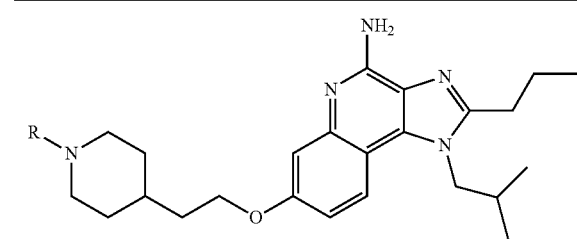
| Example | R | Measured Mass (M + H) |
|---|---|---|
| 312 | 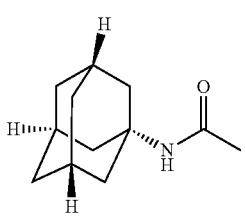 | 587.4092 |
| 313 | 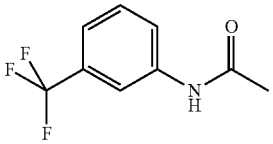 | 597.3188 |
| 314 | 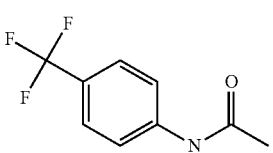 | 597.3159 |
| 315 | 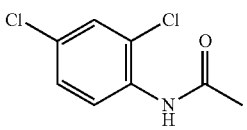 | 597.2525 |
| 316 | 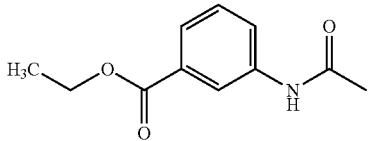 | 601.3510 |
| 317 | 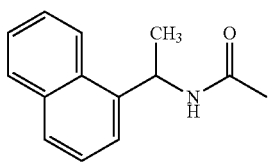 | 607.3763 |
| 318 | 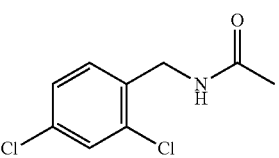 | 611.2715 |

Examples 323-365

| Example | R | Measured Mass (M + H) |
|---|---|---|
| 319 | 2-phenoxyphenyl-NHC(O)CH3 | 621.3568 |
| 320 | 3-phenoxyphenyl-NHC(O)CH3 | 621.3579 |
| 321 | 4-phenoxyphenyl-NHC(O)CH3 | 621.3558 |
| 322 | 4-benzyloxyphenyl-NHC(O)CH3 | 635.3752 |

Examples 323-365

The method described for Examples 57-92 was used to treat 8-(2-aminoethoxy)-2-ethoxymethyl-1-propyl-1H-imidazo[4,5-c]quinolin-4-amine with isocyanates or carbamoyl chlorides. The table below shows the structure made in each example and the observed accurate mass for the isolated trifluoroacetate salt.

| Example | R | Measured Mass (M + H) |
|---|---|---|
| 323 | (CH3)2CH-NHC(O)- | 429.2625 |
| 324 | CH3CH2CH2CH2-NHC(O)- | 443.2764 |
| 325 | (CH3)3C-NHC(O)- | 443.2767 |
| 326 | (CH3)2N-C(O)- | 415.2455 |
| 327 | phenyl-NHC(O)- | 463.2470 |
| 328 | cyclohexyl-NHC(O)- | 469.2912 |
| 329 | CH3CH2OC(O)CH2-NHC(O)- | 473.2515 |
| 330 | benzyl-NHC(O)- | 477.2578 |
| 331 | pyrrolidin-1-yl-C(O)- | 441.2581 |

| Example | R | Measured Mass (M + H) |
|---|---|---|
| 332 | N-phenyl thioacetamide derivative | 479.2237 |
| 333 | N,N-diethyl acetamide | 443.2777 |
| 334 | 3-cyanophenyl acetamide | 488.2429 |
| 335 | N-benzoyl acetamide | 491.2392 |
| 336 | (R)-1-phenylethyl acetamide | 491.2771 |
| 337 | (S)-1-phenylethyl acetamide | 491.2736 |
| 338 | 2-phenylethyl acetamide | 491.2767 |

| Example | R | Measured Mass (M + H) |
|---|---|---|
| 339 | 1-piperidinyl acetyl | 455.2770 |
| 340 | 3-methoxyphenyl acetamide | 493.2577 |
| 341 | 4-morpholinyl acetyl | 457.2596 |
| 342 | N-(furan-2-carbonyl) thioacetamide | 497.1951 |
| 343 | N-octyl acetamide | 499.3385 |
| 344 | trans-2-phenylcyclopropyl acetamide | 503.2771 |
| 345 | 4-isopropylphenyl acetamide | 505.2913 |
| 346 | 4-(dimethylamino)phenyl acetamide | 506.2881 |

| Example | R | Measured Mass (M + H) |
|---|---|---|
| 347 | benzoyl thioacetamide (PhC(O)NHC(S)CH₃) | 507.2170 |
| 348 | N,N-diisopropylacetamide | 471.3080 |
| 349 | 3-(methylthio)phenyl acetamide | 509.2324 |
| 350 | 4-methoxyphenyl thioacetamide | 509.2308 |
| 351 | naphthalen-1-yl acetamide | 513.2603 |
| 352 | N-methyl-N-phenyl acetamide | 477.2582 |
| 353 | morpholinoethyl thioacetamide | 516.2743 |
| 354 | 3-(diethylamino)propyl thioacetamide | 516.3096 |
| 355 | adamantan-1-yl acetamide | 521.3214 |
| 356 | phenylsulfonyl acetamide | 527.2079 |
| 357 | 3-(trifluoromethyl)phenyl acetamide | 531.2340 |
| 358 | 4-(trifluoromethyl)phenyl acetamide | 531.2343 |
| 359 | 2-acetamido-ethyl benzoate | 535.2642 |
| 360 | 1-(naphthalen-1-yl)ethyl acetamide | 541.2932 |
| 361 | 2,4-dichlorobenzyl acetamide | 545.1819 |

| Ex-ample | R | Measured Mass (M + H) |
|---|---|---|
| 362 | 2-phenoxyphenyl-NHC(O)CH3 | 555.2700 |
| 363 | 3-phenoxyphenyl-NHC(O)CH3 | 555.2697 |
| 364 | 4-phenoxyphenyl-NHC(O)CH3 | 555.2692 |
| 365 | 4-benzyloxyphenyl-NHC(O)CH3 | 569.2889 |

Example 366

4-Amino-2-(2-methoxyethyl)-1-propyl-1H-imidazo[4,5-c]quinolin-7-yl isopropylcarbamate

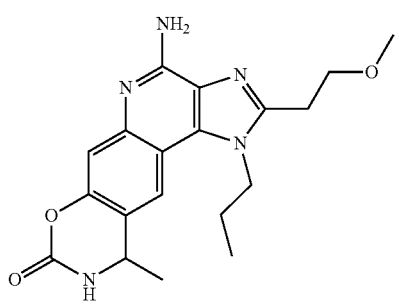 [SMILES: CCCn1c(CCOC)nc2c(N)nc3cc4c(cc3c21)C(C)NC(=O)O4]

Part A

The methods described in Parts A-I of Example 2 were followed using 3-benzyloxyaniline in lieu of 4-benzyloxyaniline and methoxypropionyl chloride in lieu of ethoxyacetyl chloride. 2-(2-Methoxyethyl)-1-propyl-1H-imidazo[4,5-c]quinolin-7-ol (2.0 g, 7.0 mmol), 4-(dimethylamino)pyridine (0.085 g, 0.70 mmol), and tetrahydrofuran (70 mL) were combined, and the mixture was cooled to 7° C. with an ice/water bath. Isopropyl isocyanate (0.689 mL, 7.01 mmol) was added dropwise to the mixture. After 20 minutes the cooling bath was removed and the reaction was stirred for an additional 24 hours. Analysis by HPLC indicated that no product had formed. Di-butyltin dilaurate (1 drop) was added, and the reaction was stirred at ambient temperature for 2.5 hours and then heated at reflux for 48 hours. The solvent was evaporated under reduced pressure, and the residue was dissolved in dichloromethane. The organic fraction was washed sequentially with water and brine, dried over magnesium sulfate, filtered, and concentrated under reduced pressure. Purification by column chromatography on silica gel (eluting with a chloroform:methanol:ammonium hydroxide gradient) provided 1.97 g of 2-(2-methoxyethyl)-1-propyl-1H-imidazo[4,5-c]quinolin-7-yl isopropylcarbamate as a white solid.

Part B 2-(2-Methoxyethyl)-1-propyl-1H-imidazo[4,5-c]quinolin-7-yl isopropylcarbamate (1.89 g, 5.10 mmol) was dissolved in chloroform (41 mL). 3-Chloroperoxybenzoic acid (60% pure, 1.60 g, 5.56 mmol) was added in one portion. After 30 minutes the golden solution was diluted with ammonium hydroxide (41 mL), and p-toluenesulfonyl chloride (0.927 g, 4.86 mmol) was added. The reaction was stirred for 1.5 hours. The layers were separated and the aqueous fraction was extracted with dichloromethane. The organic fractions were combined, washed sequentially with water and brine, dried over magnesium sulfate, filtered, and concentrated under reduced pressure. The solid residue was recrystallized from acetonitrile to provide 0.986 g of 4-amino-2-(2-methoxyethyl)-1-propyl-1H-imidazo[4,5-c]quinolin-7-yl isopropylcarbamate as a granular, peach-colored solid, mp 144.0-146.0° C.

$^1$H NMR (300 MHz, DMSO-$d_6$) δ 7.96 (d, J=9.0 Hz, 1H), 7.68 (d, J=7.62 Hz, 1H), 7.22 (d, J=2.43 Hz, 1H), 7.01 (dd, J=2.5, 8.9 Hz, 1H), 6.53 (s, 2H), 4.48-4.43 (m, 2H), 3.81 (t, J=6.7 Hz, 2H), 3.67 (sextet, J=6.8 Hz, 1H), 3.28 (s, 3H), 3.17 (t, J=6.7 Hz, 2H), 1.81 (sextet, J=7.4 Hz, 2H), 1.14 (d, J=6.6 Hz, 6H), 0.97 (t, J=7.3 Hz, 3H);

$^{13}$C NMR (75 MHz, DMSO-$d_6$) δ 153.5, 152.1, 150.5, 149.5, 145.7, 132.2, 126.0, 120.5, 117.4, 116.0, 111.9, 70.1, 58.1, 46.1, 42.6, 27.1, 23.0, 22.4, 10.6;

MS (ESI) m/z 386.2177 (386.2192 calcd for $C_{20}H_{27}N_5O_3$, M+H).

Anal. Calcd. for $C_{20}H_{27}N_5O_3$: % C, 62.32; % H, 7.06; % N, 18.17. Found: % C, 62.02; % H, 6.94; % N, 17.92.

Example 367

4-Amino-2-ethyl-1-(2-phenoxyethyl)-1H-imidazo[4,5-c]quinolin-7-yl methanesulfonate

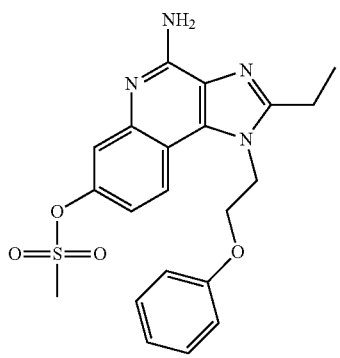 [SMILES: CCc1nc2c(N)nc3cc(OS(C)(=O)=O)ccc3c2n1CCOc1ccccc1]

Part A

2-Ethyl-1-(2-phenoxyethyl)-1H-imidazo[4,5-c]quinolin-7-ol (1.5 g, 4.5 mmol), chloroform (45 mL), and triethylamine (0.697 mL, 5.00 mmol) were combined. Methanesulfonyl chloride (0.348 mL, 4.50 mmol) was added dropwise to the mixture; a flocculent precipitate formed. The reaction was stirred for 72 hours and then quenched with methanol. The volatiles were removed under reduced pressure, and the residue was purified by column chromatography on silica gel (eluting with a dichloromethane:methanol gradient) to provide 0.628 g of 2-ethyl-1-(2-phenoxyethyl)-1H-imidazo[4,5-c]quinolin-7-yl methanesulfonate as a white solid.

Part B

2-Ethyl-1-(2-phenoxyethyl)-1H-imidazo[4,5-c]quinolin-7-yl methanesulfonate (0.625 g, 1.52 mmol) was dissolved in chloroform (15 mL). 3-Chloroperoxybenzoic acid (60% pure, 0.437 g, 1.52 mmol) was added in one portion, and the reaction was stirred for 25 minutes. Ammonium hydroxide (25 mL) was added. A precipitate formed, and the reaction was stirred until the precipitate dissolved. p-Toluenesulfonyl chloride (0.290 g, 1.52 mmol) was added in one portion, and the reaction mixture was stirred for an additional 16 hours. The layers were separated, and the aqueous fraction was extracted with dichloromethane followed by chloroform. The organics were combined, washed sequentially with water and brine, dried over sodium sulfate, filtered and concentrated under reduced pressure. Purification by column chromatography on silica gel (eluting with a chloroform:methanol:ammonium hydroxide gradient) followed by recrystallization from acetonitrile provided 0.150 g of 4-amino-2-ethyl-1-(2-phenoxyethyl)-1H-imidazo[4,5-c]quinolin-7-yl methanesulfonate as an orange solid, mp 213.0-214.5° C.

$^1$H NMR (300 MHz, DMSO-$d_6$) δ 8.26 (d, J=9.0 Hz, 1H), 7.50 (d, J=2.5 Hz, 1H), 7.23-7.17 (m, 3H), 6.88 (t, J=7.3 Hz, 1H), 6.80-6.76 (m, 2H), 6.67 (s, 2H), 4.98-4.94 (m, 2H), 4.42-4.39 (m, 2H), 3.39 (s, 3H), 3.04 (q, J=7.5 Hz, 2H), 1.40 (t, J=7.5 Hz, 3H);

$^{13}$C NMR (75 MHz, DMSO-$d_6$) δ 157.8, 155.3, 152.6, 147.4, 145.7, 132.4, 129.5, 126.4, 122.0, 121.0, 118.2, 115.0, 114.2, 113.8, 66.4, 44.4, 37.2, 20.0, 11.7;

MS (ESI) m/z 427.1444 (427.1440 calcd for $C_{21}H_{22}N_4O_4S$, M+H).

Anal. Calcd. for $C_{21}H_{22}N_4O_4S$: % C, 59.14; % H, 5.20; % N, 13.14; % S, 7.52. Found: % C, 58.90; % H, 4.95; % N, 13.13; % S, 7.55.

Example 368

N-(2-{4-Amino-2-(ethoxymethyl)-7-[(6-{[(isopropylamino)carbonothioyl]amino}hexyl)oxy]-1H-imidazo[4,5-c]quinolin-1-yl}-1,1-dimethylethyl)acetamide

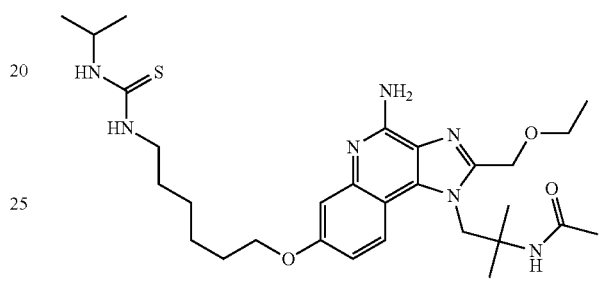

Isopropyl isothiocyanate (255 µL, 2.38 mmol) was added to a stirred suspension of N-{2-[4-amino-7-(6-aminohexyloxy)-2-ethoxymethyl-1H-imidazo[4,5-c]quinolin-1-yl]-1,1-dimethylethyl}acetamide (prepared as described in Part I of Example 49, 1.02 g, 2.17 mmol) in dichloromethane (100 mL) at 0° C. The mixture was stirred for 30 minutes at 0° C., then was allowed to warm to room temperature and was stirred over the weekend. The solution was concentrated under reduced pressure. The crude product was purified by flash chromatography (silica gel, gradient elution with 7.5-10% methanol in dichloromethane) followed by recrystallization from acetonitrile. The crystals were dissolved in 1:1 dichloromethane/methanol and the resulting solution was concentrated under reduced pressure to afford a white powder that was dried under vacuum at 60° C. to yield 0.43 g of N-(2-{4-amino-2-(ethoxymethyl)-7-[(6-{[(isopropylamino)carbonothioyl]amino}hexyl)oxy]-1H-imidazo[4,5-c]quinolin-1-yl}-1,1-dimethylethyl)acetamide as a white powder, mp 110-120° C.

$^1$H NMR (300 MHz, DMSO-$d_6$) δ 8.22 (d, J=9.0 Hz, 1H), 7.71 (s, 1H), 7.23 (br s, 1H), 7.11 (d, J=7.8 Hz, 1H), 7.03 (d, J=2.6 Hz, 1H), 6.85 (dd, J=9.0, 2.6 Hz, 1H), 6.51 (s, 2H), 4.94 (s, 2H), 4.70 (s, 2H), 4.22 (br s, 1H), 4.04 (t, J=6.3 Hz, 2H), 3.51 (q, J=7.0 Hz, 2H), 1.81 (s, 3H), 1.76 (m, 2H), 1.48 (m, 4H), 1.36 (m, 2H), 1.19 (s, 6H), 1.12-1.07 (m, 11H);

$^{13}$C NMR (75 MHz, DMSO-$d_6$) δ 181.3, 170.3, 157.9, 152.6, 149.8, 147.6, 135.0, 125.3, 122.6, 111.4, 109.6, 108.4, 67.6, 65.7, 64.6, 55.0, 51.1, 45.1, 43.6, 29.1, 29.0, 26.6, 25.9, 25.7, 24.0, 22.7, 15.3;

MS (APCI) m/z 572 (M+H)$^+$;

Anal. calcd for $C_{29}H_{45}N_7O_3S \cdot 0.40\ H_2O$: C, 60.16; H, 7.97; N, 16.93; S, 5.54. Found: C, 60.16; H, 8.08; N, 16.84; S, 5.54.

Example 369

N-(2-{4-Amino-2-(ethoxymethyl)-7-[(6-{[(isopropylamino)carbonyl]amino}hexyl)oxy]-1H-imidazo[4,5-c]quinolin-1-yl}-1,1-dimethylethyl)-N'-isopropylurea

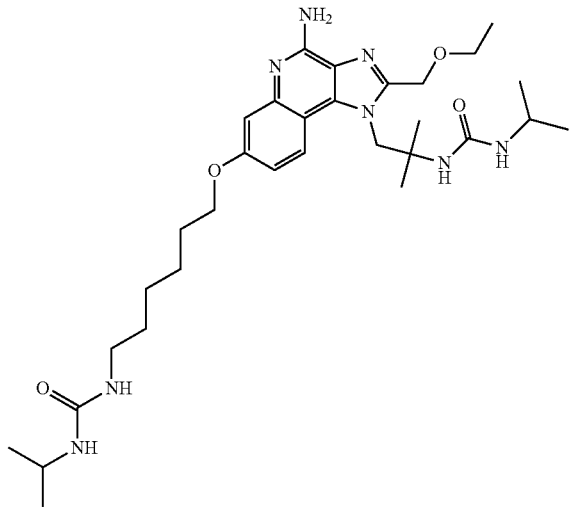 [SMILES: CCOCc1nc2c(N)nc3cc(OCCCCCCNC(=O)NC(C)C)ccc3c2n1CC(C)(C)NC(=O)NC(C)C]

Part A

Isopropyl isocyanate (2.05 mL, 20.9 mmol) was added to a stirred suspension of (2-amino-2-methylpropyl)(7-benzyloxy-3-nitroquinolin-4-yl)amine (prepared as described in Part A of Example 45, 6.95 g, 19.0 mmol) in dichloromethane (200 mL) at 0° C. After approximately 30 minutes, the reaction mixture was allowed to warm to room temperature and was stirred overnight. The solvent was removed under reduced pressure to afford 8.49 g of N-(2-{[7-(benzyloxy)-3-nitroquinolin-4-yl]amino}-1,1-dimethylethyl)-N'-isopropylurea.

Part B

A mixture of N-(2-{[7-(benzyloxy)-3-nitroquinolin-4-yl]amino}-1,1-dimethylethyl)-N'-isopropylurea (4.24 g, 9.39 mmol) and 5% platinum on carbon (1.0 g) in acetonitrile (700 mL) was hydrogenated at 30 psi ($2.1 \times 10^5$ Pa) overnight on a Parr apparatus. The mixture was filtered through CELITE filter agent, which was subsequently rinsed with acetonitrile and dichloromethane. The filtrate was concentrated under reduced pressure to yield 3.67 g of N-(2-{[3-amino-7-(benzyloxy)quinolin-4-yl]amino}-1,1-dimethylethyl)-N'-isopropylurea as a pale yellow foam that was used without purification.

Part C

The material from Part B was combined with N-(2-{[3-amino-7-(benzyloxy)quinolin-4-yl]amino}-1,1-dimethylethyl)-N'-isopropylurea from another experiment, suspended in toluene, and concentrated under reduced pressure. The N-(2-{[3-amino-7-(benzyloxy)quinolin-4-yl]amino}-1,1-dimethylethyl)-N'-isopropylurea (4.57 g, 10.8 mmol) was converted into N-{2-[7-(benzyloxy)-2-(ethoxymethyl)-1H-imidazo[4,5-c]quinolin-1-yl]-1,1-dimethylethyl}-N'-isopropylurea using the method described in Part D of Example 45. The crude product was purified using flash chromatography (silica gel, elution with 6% methanol in dichloromethane) to afford 3.81 g of N-{2-[7-(benzyloxy)-2-(ethoxymethyl)-1H-imidazo[4,5-c]quinolin-1-yl]-1,1-dimethylethyl}-N'-isopropylurea as an off white solid.

Part D

A mixture of N-{2-[7-(benzyloxy)-2-(ethoxymethyl)-1H-imidazo[4,5-c]quinolin-1-yl]-1,1-dimethylethyl}-N'-isopropylurea (3.82 g, 7.80 mmol) and 10% palladium on carbon (0.92 g) in ethanol (100 mL) was hydrogenated at 50 psi ($3.5 \times 10^5$ Pa) overnight on a Parr apparatus. The mixture was filtered through CELITE filter agent and the filtrate was concentrated under reduced pressure to yield 3.17 g of N-{2-[2-(ethoxymethyl)-7-hydroxy-1H-imidazo[4,5-c]quinolin-1-yl]-1,1-dimethylethyl}-N'-isopropylurea as a yellow solid.

Part E

Following the method described in Part L of Example 2, N-{2-[2-(ethoxymethyl)-7-hydroxy-1H-imidazo[4,5-c]quinolin-1-yl]-1,1-dimethylethyl}-N'-isopropylurea (3.12 g, 7.80 mmol) was treated with tert-butyl 6-iodohexylcarbamate (2.81 g, 8.58 mmol) to afford 4.31 g of tert-butyl 6-{[2-(ethoxymethyl)-1-(2-{[(isopropylamino)carbonyl]amino}-2-methylpropyl)-1H-imidazo[4,5-c]quinolin-7-yl]oxy}hexylcarbamate. The material was used without purification in the next step.

Part F

A modification of the method described in Part M of Example 2 was used to convert tert-butyl 6-{[2-(ethoxymethyl)-1-(2-{[(isopropylamino)carbonyl]amino}-2-methylpropyl)-1H-imidazo[4,5-c]quinolin-7-yl]oxy}hexylcarbamate (4.31 g, 7.20 mmol) into tert-butyl 6-{[2-(ethoxymethyl)-1-(2-{[(isopropylamino)carbonyl]amino}-2-methylpropyl)-5-oxido-1H-imidazo[4,5-c]quinolin-7-yl]oxy}hexylcarbamate, which was used without purification in the next step.

Part G

The material from Part F was converted into 4.20 g of tert-butyl 6-{[4-amino-2-(ethoxymethyl)-1-(2-{[(isopropylamino)carbonyl]amino}-2-methylpropyl)-1H-imidazo[4,5-c]quinolin-7-yl]oxy}hexylcarbamate using the method described in Part I of Example 45.

Part H

A solution of tert-butyl 6-{[4-amino-2-(ethoxymethyl)-1-(2-{[(isopropylamino)carbonyl]amino}-2-methylpropyl)-1H-imidazo[4,5-c]quinolin-7-yl]oxy}hexylcarbamate (4.20 g, 6.84 mmol) in 3 M HCl in ethanol (50 mL, 150 mmol) was heated at reflux for five minutes, then was allowed to cool to room temperature and was concentrated under reduced pressure. The resulting orange solid was dissolved water and the solution was washed with dichloromethane (2×). The aqueous layer was treated with ammonium hydroxide until a basic pH was reached, then was extracted with dichloromethane (3×). The combined organic layers were washed with brine, dried over sodium sulfate, filtered, and concentrated to yield 2.98 g of N-{2-[4-amino-7-[(6-aminohexyl)oxy]-2-(ethoxymethyl)-1H-imidazo[4,5-c]quinolin-1-yl]-1,1-dimethylethyl}-N'-isopropylurea as a dark orange solid.

Part I

Isopropyl isocyanate (190 μL, 1.93 mmol) was added to a stirred solution of N-{2-[4-amino-7-[(6-aminohexyl)oxy]-2-(ethoxymethyl)-1H-imidazo[4,5-c]quinolin-1-yl]-1,1-dimethylethyl}-N'-isopropylurea (0.90 g, 1.75 mmol) in dichloromethane (50 mL) at 0° C. After approximately 30 minutes, the solution was allowed to warm to room temperature. A precipitate formed and the mixture was stirred over the weekend. The solvent was removed under reduced pressure and the crude product was purified by flash chromatography (silica gel, gradient elution with 8-10% methanol in dichloromethane) to provide a solid that was dried under vacuum at 60° C. to yield 0.34 g of N-(2-{4-amino-2-(ethoxymethyl)-7-[(6-{[(isopropylamino)carbonyl]amino}hexyl)oxy]-1H-imidazo[4,5-c]quinolin-1-yl}-1,1-dimethylethyl)-N'-isopropylurea as a tan solid, mp 205-209° C.

$^1$H NMR (300 MHz, DMSO-$d_6$) δ 8.22 (d, J=9.1 Hz, 1H), 7.03 (d, J=2.5 Hz, 1H), 6.85 (dd, J=9.0, 2.5 Hz, 1H), 6.57 (s, 2H), 5.70-5.65 (m, 3H), 5.57 (d, J=7.7 Hz, 1H), 4.93 (s, 2H), 4.70 (br s, 2H), 4.04 (t, J=6.3 Hz, 2H), 3.73-3.63 (m, 2H), 3.51 (q, J=7.0 Hz, 2H), 2.97 (m, 2H), 175 (m, 2H), 1.44-1.35 (m, 8H), 1.12 (t, J=7.0 Hz, 3H), 1.07-0.99 (m, 16H);

$^{13}$C NMR (75 MHz, DMSO-$d_6$) δ 157.9, 157.8, 157.2, 152.5, 150.2, 147.3, 135.0, 125.3, 122.6, 111.5, 109.6, 108.2, 67.6, 65.6, 64.4, 54.2, 52.0, 41.1, 40.9, 39.4, 30.4, 29.1, 26.6, 26.4, 25.7, 23.6, 15.3;

MS (APCI) m/z 598 (M+H)$^+$;

Anal. calcd for $C_{31}H_{50}N_8O_4 \cdot 1.00 H_2O$: C, 60.37; H, 8.50; N, 18.17. Found: C, 60.65; H, 8.66; N, 18.20.

Example 370

N-(6-{[4-Amino-2-(ethoxymethyl)-1-(2-{[(isopropylamino)carbonyl]amino}-2-methylpropyl)-1H-imidazo[4,5-c]quinolin-7-yl]oxy}hexyl)acetamide

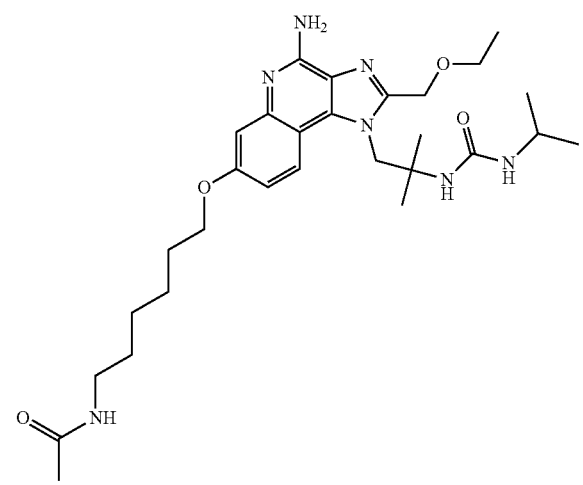 [SMILES: CCOCc1nc2c(N)nc3cc(OCCCCCCNC(C)=O)ccc3c2n1CC(C)(C)NC(=O)NC(C)C]

Acetyl chloride (180 μL, 2.53 mmol) was added to a stirred solution of N-{2-[4-amino-7-[(6-aminohexyl)oxy]-2-(ethoxymethyl)-1H-imidazo[4,5-c]quinolin-1-yl]-1,1-dimethylethyl}-N'-isopropylurea (prepared as described in Parts A-H of Example 369, 1.18 g, 2.30 mmol) and triethylamine (0.64 mL, 4.60 mmol) in dichloromethane (100 mL) at 0° C. After approximately 20 minutes, the solution was allowed to warm to room temperature and was stirred overnight. The solution was transferred to a separatory funnel and washed with water (2×). The organic layer was dried over sodium sulfate, filtered, and concentrated under reduced pressure. The crude product was purified by flash chromatography (silica gel, elution with 10% methanol in dichloromethane) to yield 0.34 g of N-(6-{[4-amino-2-(ethoxymethyl)-1-(2-{[(isopropylamino)carbonyl]amino}-2-methylpropyl)-1H-imidazo[4,5-c]quinolin-7-yl]oxy}hexyl)acetamide as a tan solid, mp 90-110° C.

$^1$H NMR (300 MHz, DMSO-$d_6$) δ 8.21 (d, J=9.1 Hz, 1H), 7.79 (m, 1H), 7.03 (d, J=2.6 Hz, 1H), 6.85 (dd, J=9.1, 2.6 Hz, 1H), 6.57 (s, 2H), 5.70-5.65 (m, 2H), 4.93 (s, 2H), 4.73 (br s, 2H), 4.04 (t, J=6.4 Hz, 2H), 3.72 (m, 1H), 3.51 (m, 2H), 3.03 (m, 2H), 1.78 (s, 3H), 1.76 (m, 2H), 1.42 (m, 10H), 1.12 (t, J=7.0 Hz, 3H), 1.07-1.04 (m, 8H);

$^{13}$C NMR (125 MHz, DMSO-$d_6$) δ 169.2, 158.0, 157.3, 152.5, 150.3, 147.4, 135.1, 125.4, 122.6, 111.6, 109.8, 108.7, 67.8, 65.7, 64.5, 54.3, 52.2, 41.0, 38.9, 29.5, 29.0, 26.6, 26.5, 25.7, 23.6, 23.0, 15.3;

MS (APCI) m/z 556 (M+H)$^+$;

Anal. calcd for $C_{29}H_{45}N_7O_4 \cdot 0.50 H_2O$: C, 61.68; H, 8.21; N, 17.36. Found: C, 61.81; H, 8.43; N, 17.22.

Example 371

N-(6-{[4-Amino-2-(ethoxymethyl)-1-(2-{[(isopropylamino)carbonyl]amino}-2-methylpropyl)-1H-imidazo[4,5-c]quinolin-7-yl]oxy}hexyl)methanesulfonamide

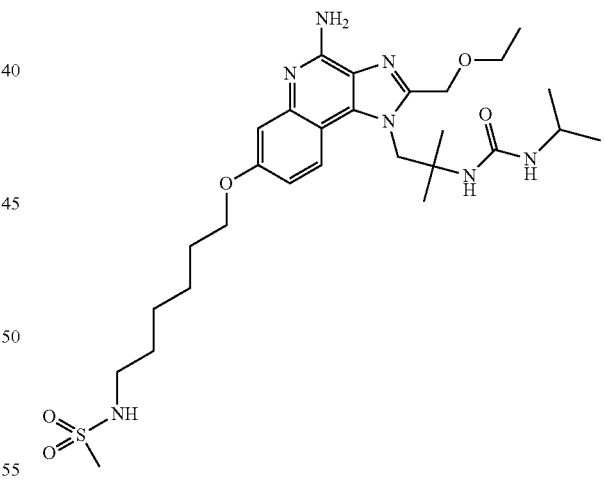

Methanesulfonic anhydride (0.34 g, 1.93 mmol) was added to a stirred solution of N-{2-[4-amino-7-[(6-aminohexyl)oxy]-2-(ethoxymethyl)-1H-imidazo[4,5-c]quinolin-1-yl]-1,1-dimethylethyl}-N'-isopropylurea (prepared as described in Parts A-H of Example 369, 10.9 g, 1.75 mmol) and triethylamine (0.35 mL, 3.5 mmol) in dichloromethane (50 mL) at 0° C. After approximately 30 minutes, the solution was allowed to warm to room temperature and was stirred overnight. The following morning, the solution was cooled to 0° C. and additional methanesulfonic anhydride (0.13 g) was added. After 30 minutes, the solution was allowed to warm to room temperature. After 2 hours, the solution was transferred to a separatory funnel and washed with water (2×) and brine. The organic layer was dried over sodium sulfate, filtered, and concentrated under reduced pressure. The crude product was purified by flash chromatography (silica gel, elution with 10% methanol in dichloromethane) followed purification by chromatography on a HORIZON HPFC system (an automated, modular high-performance flash purification product available from Biotage, Inc, Charlottesville, Va., USA) (silica gel, gradient elution with 0-40% CMA in chloroform where CMA is a solution of 80:18:2 chloroform/methanol/concentrated ammonium hydroxide) to yield 0.31 g of N-(6-{[4-amino-2-(ethoxymethyl)-1-(2-{[(isopropylamino)carbonyl]amino}-2-methylpropyl)-1H-imidazo[4,5-c]quinolin-7-yl]oxy}hexyl)methanesulfonamide as an off white solid, mp 190-194° C.

$^1$H NMR (300 MHz, DMSO-$d_6$) δ 8.21 (d, J=9.1 Hz, 1H), 7.02 (d, J=2.6 Hz, 1H), 6.94 (t, J=5.8 Hz, 1H), 6.85 (dd, J=9.1, 2.6 Hz, 1H), 6.52 (s, 2H), 5.70 (s, 1H), 5.66 (d, J=7.6 Hz, 1H), 4.93 (s, 2H), 4.72 (br s, 2H), 4.04 (t, J=6.3 Hz, 2H), 3.72 (m, 1H), 3.51 (q, J=7.0 Hz, 2H), 2.94 (m, 2H), 2.87 (s, 3H), 1.76 (m, 2H), 1.50-1.30 (m, 12H), 1.21 (t, J=7.0 Hz, 3H), 1.05 (d, J=6.5 Hz, 6H);

$^{13}$C NMR (75 MHz, DMSO-$d_6$) δ 157.8, 157.2, 152.6, 150.1, 147.6, 134.9, 125.3, 122.6, 111.4, 109.7, 108.4, 67.5, 65.6, 64.4, 54.2, 51.9, 42.8, 40.9, 29.7, 29.0, 26.4, 26.3, 25.6, 23.6, 15.3;

MS (APCI) m/z 592 (M+H)$^+$;

Anal. calcd for $C_{28}H_{45}N_7O_5S \cdot 0.12\ H_2O$: C, 56.57; H, 7.68; N, 16.49. Found: C, 56.25; H, 8.09; N, 16.37.

Example 372 tert-Butyl 2-{[4-amino-1-[(2,2-dimethyl-1,3-dioxolan-4-yl)methyl]-2-(ethoxymethyl)-1H-imidazo[4,5-c]quinolin-7-yl]oxy}ethylcarbamate

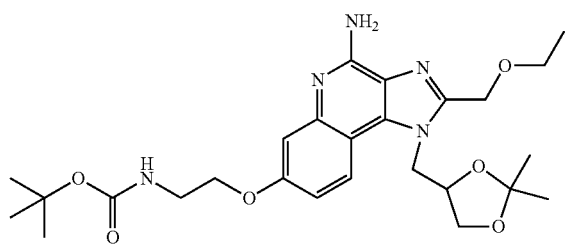 [SMILES: CCOCc1nc2c(N)nc3cc(OCCNC(=O)OC(C)(C)C)ccc3c2n1CC1COC(C)(C)O1]

Part A

Triethylamine (31.88 mL, 228.77 mmol) followed by 2,2-dimethyl-1,3-dioxolan-4-methanamine (20.0 g, 152.51 mmol) were added to a solution of 7-benzyloxy-4-chloro-3-nitroquinoline (48.00 g, 152.51 mmol) in dichloromethane (400 mL), which was then stirred at ambient temperature for 6 hours. The crude reaction mixture was concentrated under reduced pressure, and the resulting solid was treated with water. The mixture was stirred for 1 hour. The solid was collected by filtration, washed with water, dried, suspended in diethyl ether (400 mL), sonicated, and the resulting precipitate material was collected by filtration. The product was dried under vacuum at 40° C. for 12 hours to afford 60.1 g of (7-benzyloxy-3-nitro-quinolin4-yl)[(2,2-dimethyl[1,3]dioxolan-4-yl)methyl]amine as a yellow solid, mp 154-155° C.

$^1$H-NMR (300 MHz, CDCl$_3$) δ 9.74-9.62 (br m, 1H), 9.32 (s, 1H), 8.15 (d, J=9.4 Hz, 1H), 7.51-7.31 (m, 6H), 7.15 (dd, J=9.4, 2.7 Hz, 1H), 5.21 (s, 2H), 4.48-4.37 (m, 1H), 4.16-4.05 (m, 2H), 4.04-3.93 (m, 1H), 3.74 (dd, J=8.5, 5.9 Hz, 1H), 1.54 (s, 3H), 1.40 (s, 3H);

MS (APCI) m/z 410.1 (M+H)$^+$.

Part B

A solution of sodium dithionate (85% pure, 135.07 g, 659.42 mmol) and potassium carbonate (101.27 g, 732.73 mmol) in water (450 mL) was added dropwise to a mechanically stirred mixture of ethyl viologen dibromide (1.1 g, 2.93 mmol) and (7-benzyloxy-3-nitro-quinolin4-yl)[(2,2-dimethyl[1,3]dioxolan-4-yl)methyl]amine (60.0 g, 146.54 mmol) in dichloromethane (500 mL) and water (50 mL). The reaction mixture was stirred at ambient temperature overnight and then diluted with water (600 mL) and stirred for an additional 10 minutes. The organic phase was separated and the aqueous layer was reextracted with dichloromethane (400 mL). The combined organic layers were washed with water (800 mL) and brine (800 mL), dried over sodium sulfate, and concentrated under reduced pressure to afford 55.60 g of 7-benzyloxy-$N^4$-[(2,2-dimethyl[1,3]dioxolan-4-yl)methyl]quinoline-3,4-diamine as a brown foam.

$^1$H-NMR (300 MHz, CDCl$_3$) δ 8.38 (s, 1H), 7.83 (d, J=9.3 Hz, 1H), 7.51-7.28 (m, 6H), 7.18 (dd, J=9.2, 2.5 Hz, 1H), 5.16 (s, 2H), 4.35 (br s, 1H), 4.30-4.18 (m, 1H), 4.02 (dd, J=8.3, 6.5 Hz, 1H), 3.81 (br s, 2H), 3.68 (dd, J=8.3, 6.1 Hz, 1H), 3.60-3.46 (m, 1H), 3.40-3.25 (m, 1H), 1.52 (s, 3H), 1.37 (s, 3H);

MS (APCI) m/z 380.0 (M+H)$^+$.

Part C

Triethylamine (25.53 mL, 183.17 mmol) was added to a solution of 7-benzyloxy-$N^4$-[(2,2-dimethyl[1,3]dioxolan-4-yl)methyl]quinoline-3,4-diamine (55.60 g, 146.54 mmol) in dichloromethane (500 mL) at 0° C. Dropwise addition of ethoxyacetyl chloride (22.45 g, 183.17 mmol) to the reaction mixture followed, and the reaction mixture was allowed to stir for 4 hours at ambient temperature. The reaction mixture was concentrated under reduced pressure and the residue was added to a mixture of triethylamine (61.3 mL, 440 mmol) in ethanol (350 mL) and heated to reflux for 16 hours. The reaction mixture was concentrated under reduced pressure, extracted with dichloromethane (3×300 mL), washed with water (300 mL) and brine (300 mL) and dried over sodium sulfate. The crude material was purified by flash column chromatography (silica gel, eluted with 5% CMA in chloroform) and concentrated under reduced pressure to give 42.5 g of material as a brown solid. The material was recrystallized from diethyl ether to afford 37.5 g of 7-benzyloxy-1-[(2,2-dimethyl[1,3]dioxolan-4-yl)methyl]-2-ethoxymethyl-1H-imidazo[4,5-c]quinoline as a white crystalline solid, mp 110-111° C.

$^1$H-NMR (300 MHz, CDCl$_3$) δ 9.23 (s, 1H), 8.16 (d, J=9.2 Hz, 1H), 7.75 (d, J=2.7 Hz, 1H), 7.55-7.31 (m, 6H), 5.25 (s, 2H), 5.00 (d, J=12.7 Hz, 1H), 4.93-4.75 (m, 3H), 4.72-4.60 (m, 1H), 4.18 (dd, J=8.6, 6.2 Hz, 1H), 3.87 (dd, J=8.7, 6.2 Hz, 1H), 3.63 (q, J=7.0 Hz, 2H), 1.45 (s, 3H), 1.29 (s, 3H), 1.25 (t, J=7.0 Hz, 3H); $^{13}$C-NMR (75 MHz, CDCl$_3$) δ 157.8, 150.9, 146.9, 145.7, 136.5, 135.4, 134.9, 128.7, 128.2, 127.7, 121.2, 118.9, 112.4, 111.5, 110.3, 74.7, 70.2, 66.8, 66.4, 65.5, 48.4, 26.6, 25.1, 15.0;

MS (APCI) m/z 448.1 (M+H)+;

Anal. calcd for $C_{26}H_{29}N_3O_4$: C, 69.78; H, 6.53; N, 9.39. Found: C, 69.82; H, 6.74; N, 9.34.

Part D

Palladium hydroxide (Pearlman's catalyst) (20% wt. % palladium on carbon, 2.2 g) was added to a solution of 7-benzyloxy-1-[(2,2-dimethyl[1,3]dioxolan-4-yl)methyl]-2-ethoxymethyl-1H-imidazo[4,5-c]quinoline (22.2 g, 49.6 mmol) in acetonitrile (400 mL) and the reaction mixture was hydrogenated (30 psi, $2.1 \times 10^5$ Pa) for 24 hours on a Parr apparatus. The crude reaction mixture was diluted with 1:1 chloroform/methanol (1 L), then was filtered through a layer of CELITE filter agent. The filtrate was concentrated under reduced pressure and triturated with acetonitrile. The resulting crystalline material was collected by filtration, washed with acetonitrile, and dried to afford 16.55 g of 1-[(2,2-dimethyl-1,3-dioxolan-4-yl)methyl]-2-(ethoxymethyl)-1H-imidazo[4,5-c]quinolin-7-ol as a white powder, mp 239-240° C.

MS (APCI) m/z 358.1 (M+H)+;

Anal. calcd for $C_{19}H_{23}N_3O_4$: C, 63.85; H, 6.49; N, 11.76. Found: C, 63.88; H, 6.78; N, 11.75.

Part E

Using a modification on the procedure described in Part L of Example 2, 1-[(2,2-dimethyl-1,3-dioxolan-4-yl)methyl]-2-(ethoxymethyl)-1H-imidazo[4,5-c]quinolin-7-ol (8.50 g, 23.8 mmol) was treated with tert-butyl 2-iodoethylcarbamate (7.10 g, 26.2 mmol) and cesium carbonate (11.62 g, 35.67 mmol) in DMF (120 mL). During the workup, after the reaction mixture was concentrated under reduced pressure, the residue was treated with water (75 mL) and stirred for 30 minutes. A precipitate was isolated by filtration and washed with diethyl ether to yield 8.7 g of tert-butyl 2-{[1-[(2,2-dimethyl-1,3-dioxolan-4-yl)methyl]-2-(ethoxymethyl)-1H-imidazo[4,5-c]quinolin-7-yl]oxy}ethylcarbamate as an off-white solid, mp 152-153° C.

MS (ESI) m/z 501.3 (M+H)+;

Anal. calcd for $C_{26}H_{36}N_4O_6$: C, 62.38; H, 7.25; N, 11.19. Found: C, 62.33; H, 7.45; N, 11.08.

Part F mCPBA (75% pure, 7.6 g, 34 mmol) was added to a stirred solution of tert-butyl 2-{[1-[(2,2-dimethyl-1,3-dioxolan-4-yl)methyl]-2-(ethoxymethyl)-1H-imidazo[4,5-c]quinolin-7-yl]oxy}ethylcarbamate (8.5 g, 17 mmol) in dichloromethane (100 mL) at room temperature. The reaction mixture was stirred for 4 hours, then was diluted with dichloromethane (50 mL), washed with 4% aqueous sodium carbonate (2×75 mL), brine (100 mL), and concentrated under reduced pressure. The residue was dissolved in dichloromethane (100 mL) and concentrated ammonium hydroxide (50 mL) was added. The mixture was cooled to 0° C. and p-toluenesulfonyl chloride (4.04 g, 21.2 mmol) was added in portions. The reaction mixture was allowed to warm to room temperature and was stirred for 16 hours, then was diluted with dichloromethane (200 mL) and washed with 2 M aqueous sodium carbonate (2×150 mL). The aqueous layer was back-extracted with dichloromethane (100 mL). The combined organic layers were washed with brine, dried over sodium sulfate, filtered, and concentrated. The solid was triturated with diethyl ether and isolated by filtration to yield 3.55 g of tert-butyl 2-{[4-amino-1-[(2,2-dimethyl-1,3-dioxolan-4-yl)methyl]-2-(ethoxymethyl)-1H-imidazo[4,5-c]quinolin-7-yl]oxy}ethylcarbamate as a white powder, mp 82-84° C.

MS (APCI) m/z 516.3 (M+H)+;

Anal. calcd for $C_{26}H_{37}N_5O_6$: C, 60.57; H, 7.23; N, 13.58. Found: C, 60.28; H, 7.55; N, 13.45.

Example 373

3-[4-Amino-7-(2-aminoethoxy)-2-(ethoxymethyl)-1H-imidazo[4,5-c]quinolin-1-yl]propane-1,2-diol dihydrochloride

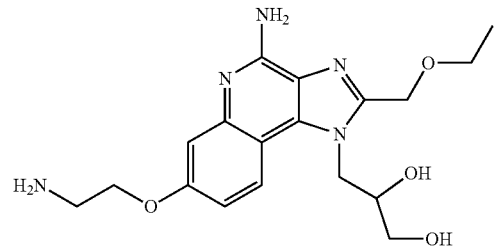 [SMILES: CCOCc1nc2c(N)nc3cc(OCCN)ccc3c2n1CC(O)CO]

A suspension of tert-butyl 2-{[4-amino-1-[(2,2-dimethyl-1,3-dioxolan-4-yl)methyl]-2-(ethoxymethyl)-1H-imidazo[4,5-c]quinolin-7-yl]oxy}ethylcarbamate (prepared in Example 372, 1.5 g, 2.9 mmol) in ethanol (20 mL) and 4.3 M HCl in ethanol (2.70 mL, 17.5 mmol) was heated at reflux overnight. The reaction mixture was allowed to cool to room temperature and a white solid was collected by filtration, washed with ethanol, and dried under vacuum at 60° C. to yield 0.85 g of 7-(2-aminoethoxy)-1-[(2,2-dimethyl-1,3-dioxolan-4-yl)methyl]-2-(ethoxymethyl)-1H-imidazo[4,5-c]quinolin-4-amine dihydrochloride as a white solid, mp 221-223° C.

MS (APCI) m/z 376.1 (M+H)+;

Anal. calcd for $C_{26}H_{37}N_5O_6 \cdot 2.2HCl \cdot 0.5H_2O$: C, 46.17; H, 6.09; N, 14.95. Found: C, 46.48; H, 6.13; N, 14.97.

Example 374 tert-Butyl 4-{[4-amino-1-[(2,2-dimethyl-1,3-dioxolan-4-yl)methyl]-2-(ethoxymethyl)-1H-imidazo[4,5-c]quinolin-7-yl]oxy}piperidine-1-carboxylate

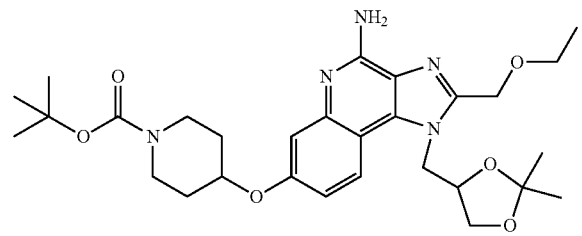 [SMILES: CCOCc1nc2c(N)nc3cc(OC4CCN(C(=O)OC(C)(C)C)CC4)ccc3c2n1CC1COC(C)(C)O1]

Part A

A solution of diisopropyldiazodicarboxylate (0.710 g, 3.50 mmol) in tetrahydrofuran (6 mL) was added dropwise to a mixture of 1-[(2,2-dimethyl-1,3-dioxolan-4-yl)methyl]-2-(ethoxymethyl)-1H-imidazo[4,5-c]quinolin-7-ol (prepared as described in Parts A-D of Example 372, 1.00 g, 2.80 mmol), tert-butyl 4-hydroxypiperidine-1-carboxylate (0.70 g, 3.50 mmol), and triphenylphosphine (0.920 g, 3.50 mmol) in tetrahydrofuran (35 mL) at 0° C. The resulting solution was allowed to warm to room temperature over 16 hours. The solution was concentrated under reduced pressure. The crude product was purified by chromatography (silica gel, gradient elution with 0-50% CMA in chloroform) to provide 1.16 g of tert-butyl 4-{[1-[(2,2-dimethyl-1,3-dioxolan-4-yl)methyl]-2-(ethoxymethyl)-1H-imidazo[4,5-c]quinolin-7-yl]oxy}piperidine-1-carboxylate as a white foam.

MS (ESI) m/z 541.4 (M+H)$^+$.

Part B

Using the method described in Part F of Example 372, tert-butyl 4-{[1-[(2,2-dimethyl-1,3-dioxolan-4-yl)methyl]-2-(ethoxymethyl)-1H-imidazo[4,5-c]quinolin-7-yl]oxy}piperidine-1-carboxylate (12.66 g, 23.42 mmol) was converted into 7.04 g of tert-butyl 4-{[4-amino-1-[(2,2-dimethyl-1,3-dioxolan-4-yl)methyl]-2-(ethoxymethyl)-1H-imidazo[4,5-c]quinolin-7-yl]oxy}piperidine-1-carboxylate, which was isolated as a white solid, mp 158-159° C.

MS (ESI) m/z 556.6 (M+H)$^+$;

Anal. calcd for $C_{29}H_{41}N_5O_6$: C, 62.68; H, 7.44; N, 12.60. Found: C, 62.29; H, 7.40; N, 12.37.

Example 375

3-[4-Amino-2-(ethoxymethyl)-7-(piperidin-4-yloxy)-1H-imidazo[4,5-c]quinolin-1-yl]propane-1,2-diol dihydrochloride Using the method described in Example 373, tert-butyl 4-{[4-amino-1-[(2,2-dimethyl-1,3-dioxolan-4-yl)methyl]-2-(ethoxymethyl)-1H-imidazo[4,5-c]quinolin-7-yl]oxy}piperidine-1-carboxylate (7.00 g, 12.6 mmol) was converted into 5.22 g of 3-[4-amino-2-(ethoxymethyl)-7-(piperidin-4-yloxy)-1H-imidazo[4,5-c]quinolin-1-yl]propane-1,2-diol dihydrochloride, which was isolated as a tan powder, mp 278-280° C.

MS (ESI) m/z 416.2 (M+H)$^+$;

Anal. calcd for $C_{21}H_{29}N_5O_4 \cdot 2HCl$: C, 51.64; H, 6.40; N, 14.34; Cl, 14.52. Found: C, 51.48; H, 6.38; N, 14.13; Cl, 14.49.

Examples 376-386

A reagent (0.10 mmol, 1.1 equivalents) from the table below was added to a test tube containing a solution of 3-[4-amino-7-(2-aminoethoxy)-2-(ethoxymethyl)-1H-imidazo[4,5-c]quinolin-1-yl]propane-1,2-diol dihydrochloride (43 mg, 0.09 mmol, prepared as described in Example 373) and N,N-diisopropylethylamine (0.051 mL, 0.29 mmol) in N,N-dimethylacetamide (1 mL). The test tubes were capped and shaken for 8 hours at room temperature and then two drops of water were added to each test tube. The solvent was removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent added to each test tube, the structure of the resulting compound, and the observed accurate mass for the isolated trifluoroacetate salt.

Examples 376-386

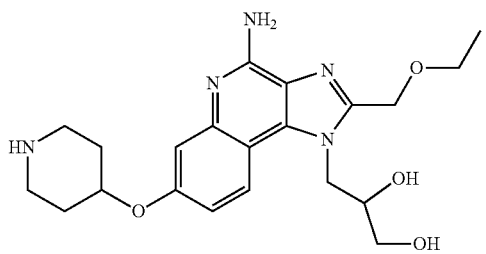 [SMILES: CCOCc1nc2c(N)nc3cc(OC4CCNCC4)ccc3c2n1CC(O)CO]

| Example | Reagent | R | Measured Mass (M + H) |
|---|---|---|---|
| 376 | Methyl isocyanate | (CH3)) | 433.2225 |
| 377 | Isopropyl isocyanate | CH(CH3)2) | 461.2533 |
| 378 | n-Butyl isocyanate | (CH2)3CH3) | 475.2686 |
| 379 | Cyclopentyl isocyanate | cyclopentyl) | 487.2704 |

185 -continued

| Example | Reagent | R | Measured Mass (M + H) |
|---|---|---|---|
| 380 | Phenyl isocyanate | phenyl-NH-C(=O)- | 495.2371 |
| 381 | Benzyl isocyanate | benzyl-NH-C(=O)- | 509.2525 |
| 382 | Benzoyl isocyanate | PhC(=O)-NH-C(=O)- | 523.2297 |
| 383 | 3-Methoxyphenyl isocyanate | 3-MeO-C6H4-NH-C(=O)- | 525.2471 |
| 384 | 3-Chlorophenyl isocyanate | 3-Cl-C6H4-NH-C(=O)- | 529.1983 |

186 -continued

| Example | Reagent | R | Measured Mass (M + H) |
|---|---|---|---|
| 385 | trans-2-Phenyl-cyclopropyl isocyanate | trans-2-phenylcyclopropyl-NH-C(=O)- | 535.2686 |
| 386 | 2-Morpholino-ethyl isothiocyanate | 2-morpholinoethyl-NH-C(=S)- | 548.2625 |

Example 387 tert-Butyl 4-{[4-amino-2-(2-methoxyethyl)-1-propyl-1H-imidazo[4,5-c]quinolin-7-yl]oxy}piperidine-1-carboxylate

Part A

A modification on the methods described in Parts A-H of Example 2 were used to prepare 2-(2-methoxyethyl)-1-propyl-1H-imidazo[4,5-c]quinolin-7-ol, with 3-benzyloxyaniline and 3-methoxypropanoyl chloride used in lieu of 4-benzyloxyaniline and ethoxyacetyl chloride, respectively. A solution of diisopropyl azodicarboxylate (6.28 mL, 31.9 mmol) in tetrahydrofuran (25.5 mL) was added dropwise to a mixture of 2-(2-methoxyethyl)-1-propyl-1H-imidazo[4,5-c]quinolin-7-ol (7.28 g, 25.5 mmol), triphenylphosphine (8.36 g, 31.9 mmol), and t-butyl 4-hydroxypiperidine-1-carboxylate (6.42 g, 31.9 mmol) in tetrahydrofuran (191 mL) at 5° C. The mixture was allowed to warm to room temperature. After 2 days, the solvent was removed under reduced pressure and the residue was purified by flash chromatography (silica gel, gradient elution with 1.5-4% methanol in dichloromethane) to yield 9.77 g of tert-butyl 4-{[2-(2-methoxyethyl)-1-propyl-1H-imidazo[4,5-c]quinolin-7-yl]oxy}piperidine-1-carboxylate as a gray amorphous solid.

Part B

A stirred solution of tert-butyl 4-{[2-(2-methoxyethyl)-1-propyl-1H-imidazo[4,5-c]quinolin-7-yl]oxy}piperidine-1-carboxylate (9.77 g, 20.8 mmol) in chloroform (175 mL) at room temperature was treated with mCPBA (55% pure, 6.54 g, 20.8 mmol). After 45 minutes, concentrated ammonium hydroxide (175 mL) was added, followed by p-toluenesulfonyl chloride (3.97 g, 20.8 mmol). The mixture was stirred for 62 hours, then the layers were separated and the aqueous layer was extracted with chloroform. The combined organic layers were washed with water and saturated aqueous sodium chloride, dried over anhydrous sodium sulfate, filtered and evaporated under reduced pressure. The crude product was purified by flash chromatography (silica gel, gradient elution with 1.5-12.5% CMA in chloroform) followed by recrystallization from acetonitrile to afford 6.3 g of tert-butyl 4-{[4-amino-2-(2-methoxyethyl)-1-propyl-1H-imidazo[4,5-c]quinolin-7-yl]oxy}piperidine-1-carboxylate as tan crystals, mp 173-175° C.

$^1$H NMR (300 MHz, DMSO-$d_6$) δ 7.89 (d, J=9.1 Hz, 1H), 7.10 (d, J=2.4 Hz, 1H), 6.93 (dd, J=9.0, 2.6 Hz, 1H), 6.39 (s, 2H), 4.70-4.61 (m, 1H), 4.46-4.41 (m, 2H), 3.81 (t, J=6.7 Hz, 2H), 3.75-3.67 (m, 2H), 3.29 (s, 3H), 3.26-3.12 (m, 4H), 2.02-1.91 (m, 2H), 1.87-1.75 (m, 2H), 1.64-1.51 (m, 2H), 1.41 (s, 9H), 0.97 (t, J=7.3 Hz, 3H);

MS (ESI) m/z 484.2923 (484.2924 calcd for $C_{26}H_{37}N_5O_4$, M+H$^+$).

Anal. calcd for $C_{26}H_{37}N_5O_4 \cdot 0.75H_2O$: C, 62.82; H, 7.81; N, 14.09. Found: C, 62.48; H, 8.16; N, 14.01.

Example 388

4-{[4-Amino-2-(2-methoxyethyl)-1-propyl-1H-imidazo[4,5-c]quinolin-7-yl]oxy}-N-isopropylpiperidine-1-carboxamide Part A tert-Butyl 4-{[4-amino-2-(2-methoxyethyl)-1-propyl-1H-imidazo[4,5-c]quinolin-7-yl]oxy}piperidine-1-carboxylate (prepared as described in Example 387, 2.11 g, 4.36 mmol) was treated with concentrated hydrochloric acid (3 mL). After vigorous bubbling, a solution formed. The solution was diluted with ethanol (50 mL) and evaporated (3×). The resulting oil was dissolved in brine (15 mL) and water (5 mL) and made basic with 50% aqueous sodium hydroxide (approximately 1.5 mL). The aqueous layer was extracted with dichloromethane (3×). The organic layers were combined, washed with water and brine, dried over anhydrous sodium sulfate, filtered, and concentrated under reduced pressure to provide 1.7 g of 2-(2-methoxyethyl)-7-(piperidin-4-yloxy)-1-propyl-1H-imidazo[4,5-c]quinolin-4-ylamine as a white solid.

Part B

Isopropyl isocyanate (0.256 mL, 2.61 mmol) was added dropwise to a stirred mixture of 2-(2-methoxyethyl)-7-(piperidin-4-yloxy)-1-propyl-1H-imidazo[4,5-c]quinolin-4-ylamine (1.00 g, 2.61 mmol) in chloroform at 0° C. The reaction mixture was allowed to warm to room temperature and was stirred for 16 hours. The solvent was evaporated under reduced pressure. The crude product was purified by flash chromatography (silica gel, gradient elution with 4-12% CMA in chloroform) followed by recrystallization from acetonitrile to afford 0.530 g of 4-{[4-amino-2-(2-methoxyethyl)-1-propyl-1H-imidazo[4,5-c]quinolin-7-yl]oxy}-N-isopropylpiperidine-1-carboxamide as white crystals, mp 176-179° C.

$^1$H NMR (300 MHz, DMSO-$d_6$) δ 7.88 (d, J=9.1 Hz, 1H), 7.08 (d, J=2.5 Hz, 1H), 6.91 (dd, J=9.0, 2.6 Hz, 1H), 6.36 (s, 2H), 6.17 (d, J=7.4 Hz, 1H), 4.66-4.56 (m, 1H), 4.47-4.37 (m, 2H), 3.80 (t, J=6.7 Hz, 2H), 3.77-3.66 (m, 3H), 3.28 (s, 3H), 3.17-3.04 (m, 4H), 2.00-1.87 (m, 2H), 1.86-1.72 (m, 2H), 1.58-1.44 (m, 2H), 1.05 (d, J=6.6 Hz, 6H), 0.96 (t, J=7.3 Hz, 3H);

MS (ESI) m/z 469.2912 (469.2927 calcd for $C_{25}H_{36}N_6O_3$, M+H$^+$).

Anal. calcd for $C_{25}H_{36}N_6O_3$: C, 64.08; H, 7.74; N, 17.93. Found: C, 63.73; H, 7.73; N, 17.76.

Example 389

7-[(1-Isobutyrylpiperidin-4-yl)oxy]-2-(2-methoxyethyl)-1-propyl-1H-imidazo[4,5-c]quinolin-4-amine

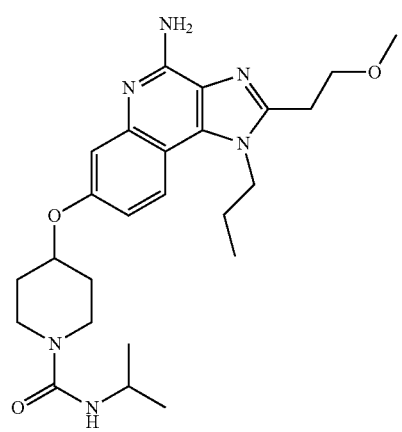 [SMILES: CCCn1c(CCOC)nc2c(N)nc3cc(OC4CCN(C(=O)NC(C)C)CC4)ccc3c21]

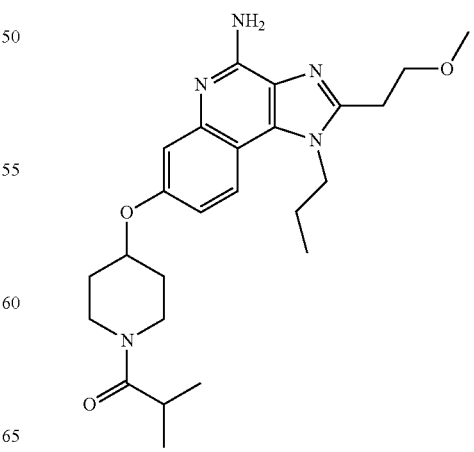

Isobutyryl chloride (0.273 mL, 2.61 mmol) was added dropwise to a stirred solution of 2-(2-methoxyethyl)-7-(piperidin-4-yloxy)-1-propyl-1H-imidazo[4,5-c]quinolin-4-ylamine (prepared as described in Part A of Example 388, 1.00 g, 2.61 mmol) in chloroform at 0° C. After 2 hours, the solution was allowed to warm to ambient temperature for 1 hour. Saturated aqueous sodium carbonate (15 mL) and water (10 mL) were added and the mixture was allowed to stir for 16 hours. The mixture was transferred to a separatory funnel, the layers were separated, and the aqueous layer was extracted with dichloromethane (2×30 mL). The organic layers were combined, washed with water and saturated aqueous sodium chloride, dried over anhydrous sodium sulfate, filtered, and concentrated under reduced pressure. Recrystallization from acetonitrile afforded 1.00 g of 7-[(1-isobutyrylpiperidin-4-yl)oxy]-2-(2-methoxyethyl)-1-propyl-1H-imidazo[4,5-c]quinolin-4-amine as a flocculent white solid, mp 165-166° C.

$^{1}$H NMR (300 MHz, DMSO-$d_6$) δ 7.88 (d, J=9.1 Hz, 1H), 7.11 (d, J=2.6 Hz, 1H), 6.92 (dd, J=9.0, 2.6 Hz, 1H), 6.37 (s, 2H), 4.75-4.65 (m, 1H), 4.47-4.37 (m, 2H), 3.98-3.85 (m, 1H), 3.85-3.77 (m, 1H), 3.80 (t, J=6.8 Hz, 2H), 3.47-3.34 (m, 1H), 3.28 (s, 3H), 3.30-3.19 (m, 1H), 3.15 (t, J=6.8 Hz, 2H), 2.94-2.84 (m, 1H), 2.06-1.89 (m, 2H), 1.86-1.72 (m, 2H), 1.69-1.46 (m, 2H), 1.00 (d, J=6.7 Hz, 6H), 0.96 (t, J=7.4 Hz, 3H);

MS (ESI) m/z 454.2810 (454.2818 calcd for $C_{25}H_{35}N_5O_3$, M+H$^+$).

Anal. calcd for $C_{25}H_{33}N_5O_3$: C, 66.20; H, 7.78; N, 15.44. Found: C, 65.95; H, 8.09; N, 15.43.

Example 390

2-(2-Methoxyethyl)-7-{[1-(methylsulfonyl)piperidin-4-yl]oxy}-1-propyl-1H-imidazo[4,5-c]quinolin-4-amine

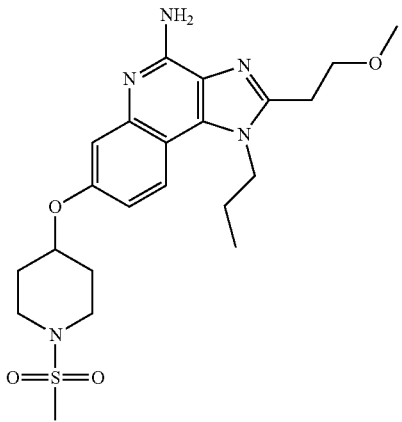

Using the method described in Example 389, 2-(2-methoxyethyl)-7-(piperidin-4-yloxy)-1-propyl-1H-imidazo[4,5-c]quinolin-4-ylamine (1.00 g, 2.61 mmol) was converted into 2-(2-methoxyethyl)-7-{[1-(methylsulfonyl)piperidin-4-yl]oxy}-1-propyl-1H-imidazo[4,5-c]quinolin-4-amine, using methanesulfonyl chloride (0.202 mL, 2.61 mmol) in lieu of isobutyryl chloride. The crude product was purified by flash chromatography (silica gel, eluting with a step gradient of CMA in chloroform (4-12% CMA increasing by 2% CMA every 500 mL) followed by trituration with acetonitrile to afford 1.1 g of 2-(2-methoxyethyl)-7-{[1-(methylsulfonyl)piperidin-4-yl]oxy}-1-propyl-1H-imidazo[4,5-c]quinolin-4-amine as a white solid, mp 224-225.5° C.

$^{1}$H NMR (300 MHz, DMSO-$d_6$) δ 7.90 (d, J=9.0 Hz, 1H), 7.12 (d, J=2.6 Hz, 1H), 6.95 (dd, J=9.0, 2.6 Hz, 1H), 6.39 (s, 2H), 4.70-4.62 (m, 1H), 4.46-4.41 (m, 2H), 3.81 (t, J=6.7 Hz, 2H), 3.44-3.34 (m, 2H), 3.29 (s, 3H), 3.19-3.12 (m, 4H), 2.92 (s, 3H), 2.12-2.00 (m, 2H), 1.87-1.73 (m, 4H), 0.97 (t, J=7.4 Hz, 3H);

MS (ESI) m/z 462.2184 (462.2175 calcd for $C_{22}H_{31}N_5O_4S$, M+H$^+$).

Anal. calcd for $C_{22}H_{31}N_5O_4S \cdot 0.10CH_2Cl_2$: C, 56.47; H, 6.69; N, 14.90; S, 6.82. Found: C, 56.36; H, 6.93; N, 14.80; S, 6.96.

Example 391

4-{[4-Amino-2-(2-methoxyethyl)-1-propyl-1H-imidazo[4,5-c]quinolin-7-yl]oxy}piperidine-1-carboxamide

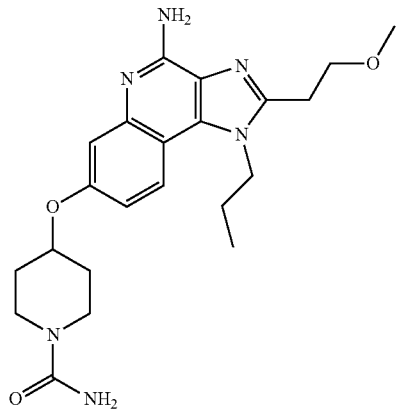 [SMILES: CCCn1c(CCOC)nc2c(N)nc3cc(OC4CCN(C(N)=O)CC4)ccc3c21]

Trimethylsilylisocyanate (0.225 mL, 1.67 mmol) was added dropwise to a slurry of 2-(2-methoxyethyl)-7-(piperidin-4-yloxy)-1-propyl-1H-imidazo[4,5-c]quinolin-4-ylamine (prepared as described in Part A of Example 388, 0.640 g, 1.67 mmol) in chloroform (16 mL) at 0° C. The reaction mixture was stirred for 40 minutes and water (10 mL) was added. The reaction mixture was stirred vigorously for 2 hours, diluted with 200 mL ethanol, and then concentrated under reduced pressure to approximately 100 mL. Another 100 mL ethanol was added and the solution was evaporated to afford a white solid that was recrystallized from ethanol to provide 0.625 g of 4-{[4-amino-2-(2-methoxyethyl)-1-propyl-1H-imidazo[4,5-c]quinolin-7-yl]oxy}piperidine-1-carboxamide as granular off-white crystals, mp 207-208.5° C.

$^{1}$H NMR (300 MHz, DMSO-$d_6$) δ 7.88 (d, J=9.0 Hz, 1H), 7.09 (d, J=2.5 Hz, 1H), 6.92 (dd, J=9.0, 2.5 Hz, 1H), 6.37 (s, 2H), 5.94 (s, 2H), 4.66-4.58 (m, 1H), 4.44-4.39 (m, 2H), 3.80 (t, J=6.7 Hz, 2H), 3.75-3.63 (m, 2H), 3.28 (s, 3H), 3.17-3.04 (m, 4H), 1.99-1.87 (m, 2H), 1.86-1.71 (m, 2H), 1.60-1.44 (m, 2H), 0.96 (t, J=7.3 Hz, 3H);

$^{13}$C NMR (75 MHz, DMSO-$d_6$) δ 158.0, 155.5, 151.9, 149.8, 146.5, 132.6, 125.1, 121.1, 112.5, 109.9, 109.0, 72.2, 70.2, 58.1, 46.1, 40.9, 30.6, 27.1, 23.0, 10.6;

MS (ESI) m/z 427.2443 (427.2458 calcd for $C_{22}H_{30}N_6O_3$, M+H$^+$).

Anal. calcd for $C_{22}H_{30}N_6O_3 \cdot 0.50H_2O$: C, 60.67; H, 7.17; N, 19.30. Found: C, 61.03; H, 7.60; N, 19.61.

Example 392

2-(2-Methoxyethyl)-7-[3-(methylsulfonyl)propoxy]-1-propyl-1H-imidazo[4,5-c]quinolin-4-amine

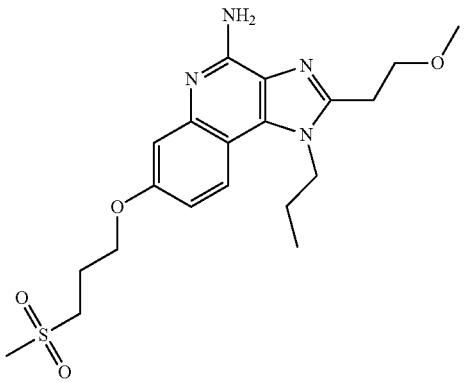

Part A

A modification on the methods described in Parts A-H of Example 2 were used to prepare 2-(2-methoxyethyl)-1-propyl-1H-imidazo[4,5-c]quinolin-7-ol, with 3-benzyloxyaniline and 3-methoxypropanoyl chloride used in lieu of 4-benzyloxyaniline and ethoxyacetyl chloride, respectively. Diisopropyl azodicarboxylate (2.07 mL, 10.5 mmol) was added dropwise to a slurry of 2-(2-methoxyethyl)-1-propyl-1H-imidazo[4,5-c]quinolin-7-ol (2.00 g, 7.01 mmol), triphenylphosphine (2.75 g, 10.5 mmol), and 3-(methylthio)propan-1-ol (1.08 mL, 10.5 mmol) in tetrahydrofuran (70 mL) at 0° C. The solution was stirred for 30 minutes at 0° C., then at room temperature for 16 hours. The solvent was removed under reduced pressure and the residue was dissolved in ethyl acetate, treated with 1 M hydrochloric acid (40 mL), and stirred for 30 minutes. The layers were separated and the aqueous layer was extracted with ethyl acetate (2×25 mL). The aqueous layer was adjusted to approximately pH 14 with 50% aqueous sodium hydroxide and then was extracted with dichloromethane (3×50 mL). The organic layers were combined, washed with water and saturated aqueous sodium chloride, dried over anhydrous sodium sulfate, filtered, and concentrated under reduced pressure. The crude product was purified by flash chromatography (silica gel, gradient elution with 1-4% methanol in dichloromethane) to provide 2.0 g of 2-(2-methoxyethyl)-7-[3-(methylthio)propoxy]-1-propyl-1H-imidazo[4,5-c]quinoline as an opaque solid.

Part B

3-Chloroperoxybenzoic acid (4.63 g, 16.1 mmol) was added to a solution of 2-(2-methoxyethyl)-7-[3-(methylthio)propoxy]-1-propyl-1H-imidazo[4,5-c]quinoline (2.0 g, 5.35 mmol) in chloroform (45 mL). After 1 hour, concentrated ammonium hydroxide (45 mL) was added and the mixture was stirred for 30 minutes. p-Toluenesulfonyl chloride (1.07 g, 5.62 mmol) was added in two portions. After the mixture was allowed to stir for 16 hours, the layers were separated and the aqueous layer was extracted with dichloromethane. The combined organic layers were washed with 14% aqueous ammonium hydroxide, water, and brine. The organic layer was dried over anhydrous sodium sulfate, filtered, and evaporated. The resulting oil was crystallized from hot acetonitrile to afford a tan solid that was isolated by filtration. The solid was subjected to flash column chromatography (silica gel, gradient elution with 2-14% CMA in chloroform) followed by recrystallization from acetonitrile to yield 0.510 g of 2-(2-methoxyethyl)-7-[3-(methylsulfonyl)propoxy]-1-propyl-1H-imidazo[4,5-c]quinolin-4-amine as red-violet crystals, mp 170-171° C.

$^1$H NMR (300 MHz, DMSO-$d_6$) δ 7.91 (d, J=9.0 Hz, 1H), 7.07 (d, J=2.6 Hz, 1H), 6.92 (dd, J=9.0, 2.6 Hz, 1H), 6.40 (s, 2H), 4.46-4.41 (m, 2H), 4.18 (t, J=6.2 Hz, 2H), 3.81 (t, J=6.7 Hz, 2H), 3.34-3.29 (m, 2H), 3.29 (s, 3H), 3.16 (t, J=6.8 Hz, 2H), 3.03 (s, 3H), 2.27-2.14 (m, 2H), 1.87-1.75 (m, 2H), 0.97 (t, J=7.4 Hz, 3H);

MS (ESI) m/z 421.1903 (421.1910 calcd for $C_{20}H_{28}N_4O_4S$, M+H$^+$).

Anal. calcd for $C_{20}H_{28}N_4O_4S$: C, 57.12; H, 6.71; N, 13.32; S, 7.62. Found: C, 57.16; H, 6.70; N, 13.46; S, 7.74.

Example 393 tert-Butyl 3-{[4-amino-2-(2-methoxyethyl)-1-propyl-1H-imidazo[4,5-c]quinolin-7-yl]oxy}propylcarbamate

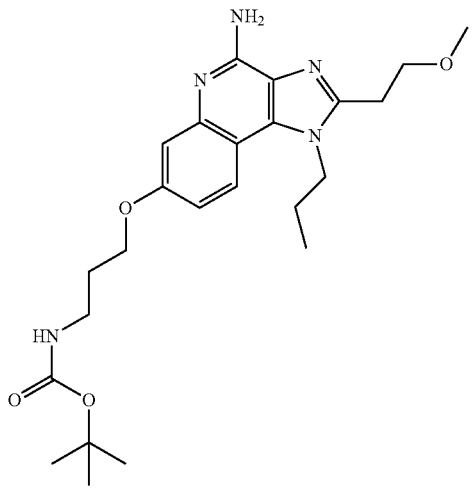 [SMILES: CCCn1c(CCOC)nc2c(N)nc3cc(OCCCNC(=O)OC(C)(C)C)ccc3c21]

Part A

A modification on the methods described in Parts A-H of Example 2 were used to prepare 2-(2-methoxyethyl)-1-propyl-1H-imidazo[4,5-c]quinolin-7-ol, with 3-benzyloxyaniline and 3-methoxypropanoyl chloride used in lieu of 4-benzyloxyaniline and ethoxyacetyl chloride, respectively. 2-(2-Methoxyethyl)-1-propyl-1H-imidazo[4,5-c]quinolin-7-ol (20.0 g, 70 mmol) was converted into tert-butyl {3-[2-(2-methoxyethyl)-1-propyl-1H-imidazo[4,5-c]quinolin-7-yloxy]propyl}carbamate using a modification of the method described in Part C of Example 7. The reaction was worked up by removing the solvent under reduced pressure. The residue was partitioned between ethyl acetate and water. The aqueous layer was extracted with ethyl acetate. The organic layers were combined, washed with water (2×500 mL) and brine, dried over anhydrous magnesium sulfate, filtered, and evaporated under reduced pressure to yield tert-butyl {3-[2-(2-methoxyethyl)-1-propyl-1H-imidazo[4,5-c]quinolin-7-yloxy]propyl}carbamate as a brown oil, which was used without further purification.

Part B

The material from Part A was dissolved in chloroform (700 mL) and treated with mCPBA (60% pure, 21.96 g, 75 mmol). After 1 hour, the reaction mixture was poured into 2% aqueous sodium carbonate. The layers were separated and the organic layer was washed with water and saturated aqueous sodium chloride. The organic layer was dried over anhydrous magnesium sulfate, filtered and evaporated. The crude product was purified by flash chromatography (silica gel, gradient elution with 2-7% methanol in dichloromethane) to afford 19.3 g of tert-butyl 3-{[2-(2-methoxyethyl)-5-oxido-1-propyl-1H-imidazo[4,5-c]quinolin-7-yl]oxy}propylcarbamate as a tan foam.

Part C p-Toluenesulfonyl chloride (8.0 g, 42 mmol) was added over ten minutes to a stirred mixture of tert-butyl 3-{[2-(2-methoxyethyl)-5-oxido-1-propyl-1H-imidazo[4,5-c]quinolin-7-yl]oxy}propylcarbamate (19.3 g, 42.0 mmol) in dichloromethane (300 mL) and concentrated ammonium hydroxide (300 mL) at 7° C. The mixture was allowed to stir for 20 minutes, then the cooling bath was removed and the mixture was allowed to stir at ambient temperature for 2 hours. The layers were separated and the aqueous layer was extracted with dichloromethane. The organic layers were combined, washed with water and saturated aqueous sodium chloride, dried over anhydrous magnesium sulfate, filtered, and evaporated under reduced pressure. Recrystallization from acetonitrile afforded 12.0 g of tert-butyl 3-{[4-amino-2-(2-methoxyethyl)-1-propyl-1H-imidazo[4,5-c]quinolin-7-yl]oxy}propylcarbamate as flocculent white crystals, mp 133.5-135° C.

$^1$H NMR (300 MHz, DMSO-$d_6$) δ 7.89 (d, J=9.0 Hz, 1H), 7.05 (d, J=2.7 Hz, 1H), 6.95-6.87 (m, 1H), 6.89 (dd, J=9.0, 2.7 Hz, 1H), 6.37 (s, 2H), 4.46-4.41 (m, 2H), 4.05 (t, J=6.2 Hz, 2H), 3.81 (t, J=6.8 Hz, 2H), 3.29 (s, 3H), 3.18-3.08 (m, 4H), 1.91-1.74 (m, 4H), 1.38 (s, 9H), 0.97 (t, J=7.3 Hz, 3H);

MS (ESI) m/z 458.2758 (458.2767 calcd for $C_{24}H_{35}N_5O_4$, M+H$^+$).

Anal. calcd for $C_{24}H_{35}N_5O_4 \cdot 0.73H_2O$: C, 61.24; H, 7.81; N, 14.88. Found: C, 61.23; H, 7.62; N, 14.78.

Example 394

7-(3-Aminopropoxy)-2-(2-methoxyethyl)-1-propyl-1H-imidazo[4,5-c]quinolin-4-amine

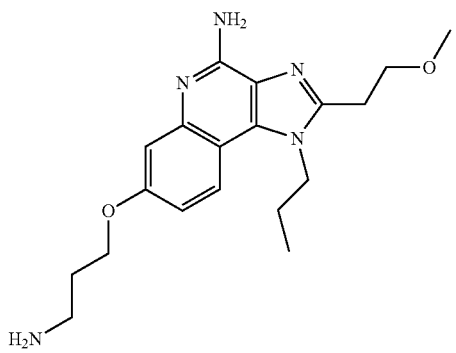 [SMILES: CCCn1c(CCOC)nc2c(N)nc3cc(OCCCN)ccc3c21]

Concentrated hydrochloric acid (8.5 mL) was added to a solution of tert-butyl 3-{[4-amino-2-(2-methoxyethyl)-1-propyl-1H-imidazo[4,5-c]quinolin-7-yl]oxy}propylcarbamate (prepared as described in Example 393, 12 g, 26 mmol) in ethanol (300 mL). The solution was heated at reflux for 4 hours. Upon cooling to ambient temperature a precipitate formed. The solid was isolated by filtration and the filtrate was evaporated to afford a white solid. The solids were combined and dissolved in water (40 mL). The solution was adjusted to approximately pH 12 with 50% aqueous sodium hydroxide and then was extracted with dichloromethane (4×250 mL). The organic layers were combined, washed with water and saturated aqueous sodium chloride, dried over anhydrous magnesium sulfate, filtered, and evaporated to yield a solid that was purified by trituration in hot acetonitrile to provide 6.5 g of 7-(3-aminopropoxy)-2-(2-methoxyethyl)-1-propyl-1H-imidazo[4,5-c]quinolin-4-amine as yellow crystals, mp 165-166.5° C.

$^1$H NMR (300 MHz, DMSO-$d_6$) δ 7.88 (d, J=9.0 Hz, 1H), 7.06 (d, J=2.6 Hz, 1H), 6.89 (dd, J=9.1, 2.6 Hz, 1H), 6.37 (s, 2H), 4.46-4.41 (m, 2H), 4.10 (t, J=6.4 Hz, 2H), 3.81 (t, J=6.7 Hz, 2H), 3.29 (s, 3H), 3.16 (t, J=6.7 Hz, 2H), 2.72 (t, J=6.7 Hz, 2H), 1.87-1.74 (m, 4H), 1.47 (br s, 2H), 0.97 (t, J=7.4 Hz, 3H);

MS (ESI) m/z 358.2231 (358.2243 calcd for $C_{19}H_{27}N_5O_2$, M+H$^+$).

Anal. calcd for $C_{19}H_{27}N_5O_2$: C, 63.84; H, 7.61; N, 19.59. Found: C, 63.50; H, 7.75; N, 19.46.

Example 395

N-(3-{[4-Amino-2-(2-hydroxyethyl)-1-propyl-1H-imidazo[4,5-c]quinolin-7-yl]oxy}propyl)-2-methylpropanamide

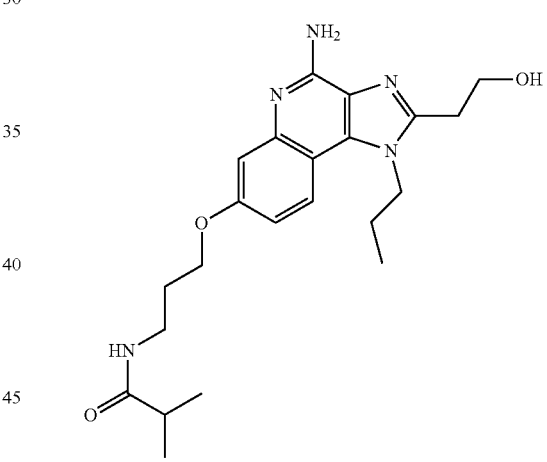

Part A

Isobutyryl chloride (0.375 mL, 3.58 mmol) was added dropwise to a slurry of 7-(3-aminopropoxy)-2-(2-methoxyethyl)-1-propyl-1H-imidazo[4,5-c]quinolin-4-amine (prepared as described in Example 394, 1.28 g, 3.58 mmol) in dichloromethane (22 mL) at 0° C. The reaction mixture was allowed to stir for 30 minutes at 0° C., then the reaction mixture was allowed to stir for 16 hours at ambient temperature. Saturated aqueous sodium carbonate was added and the reaction mixture was stirred for 1 hour, resulting in the formation of a flocculent solid. The solid was isolated by filtration and dissolved in dichloromethane. The dichloromethane was washed with water and saturated aqueous sodium chloride, dried over anhydrous sodium sulfate, filtered, and concentrated under reduced pressure. The resulting white solid was recrystallized from acetonitrile to afford 1.14 g of N-(3-{[4-amino-2-(2-methoxyethyl)-1-propyl-1H-imidazo[4,5-c]quinolin-7-yl]oxy}propyl)-2-methylpropanamide as an off-white solid.

Part B

A 1.0 M solution of boron tribromide in dichloromethane (2.55 mL, 2.55 mmol) was added over 1 minute to a slurry of N-(3-{[4-amino-2-(2-methoxyethyl)-1-propyl-1H-imidazo[4,5-c]quinolin-7-yl]oxy}propyl)-2-methylpropanamide (1.09 g, 2.55 mmol) at 0° C. The clumpy slurry was allowed to stir for 15 minutes at 0° C., then was allowed to stir for another hour at ambient temperature. Additional boron tribromide solution (0.6 mL, 0.6 mmol) was added. After 16 hours, the reaction was quenched with 6 M hydrochloric acid (10 mL), stirred until all the solids dissolved, and the dichloromethane was removed under reduced pressure. The aqueous layer was adjusted to approximately pH 13 with 50% aqueous sodium hydroxide and was extracted with ethyl acetate. The organic layer was washed with water and saturated aqueous sodium chloride, dried over anhydrous sodium sulfate, filtered, and evaporated. The material was purified by chromatography on a HORIZON HPFC system (silica gel, gradient elution with 2-22% CMA in chloroform) followed by trituration with acetonitrile to afford 0.325 g of N-(3-{[4-amino-2-(2-hydroxyethyl)-1-propyl-1H-imidazo[4,5-c]quinolin-7-yl]oxy}propyl)-2-methylpropanamide as a white solid, mp 190.5-192° C.

$^1$H NMR (300 MHz, DMSO-$d_6$) δ 7.89 (d, J=9.1 Hz, 1H), 7.81 (t, J=5.5 Hz, 1H), 7.05 (d, J=2.6 Hz, 1H), 6.90 (dd, J=9.0, 2.6 Hz, 1H), 6.43 (s, 2H), 4.88 (t, J=5.5 Hz, 1H), 4.47-4.42 (m, 2H), 4.06 (t, J=6.3 Hz, 2H), 3.90-3.84 (m, 2H), 3.26-3.20 (m, 2H), 3.06 (t, J=6.6 Hz, 2H), 2.42-2.28 (m, 1H), 1.93-1.75 (m, 4H), 1.00 (d, J=6.9 Hz, 6H), 0.98 (t, J=7.3 Hz, 3H);

$^{13}$C NMR (75 MHz, DMSO-$d_6$) δ 176.0, 157.2, 151.9, 150.5, 146.5, 132.6, 125.0, 120.9, 111.6, 108.9, 108.1, 65.1, 59.6, 46.0, 35.4, 34.0, 30.2, 28.9, 22.9, 19.5, 10.6;

MS (ESI) m/z 414.3 (M+H)$^+$;

Anal. calcd for $C_{22}H_{31}N_5O_3$: C, 63.90; H, 7.56; N, 16.94. Found: C, 63.76; H, 7.78; N, 16.92.

Example 396

N-(3-{[4-Amino-2-(2-hydroxyethyl)-1-propyl-1H-imidazo[4,5-c]quinolin-7-yl]oxy}propyl)nicotinamide

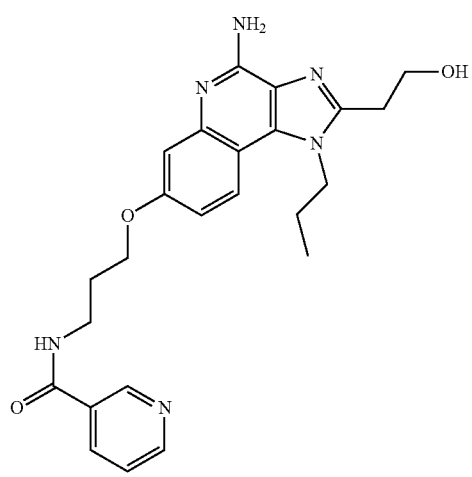 [SMILES: CCCn1c(CCO)nc2c(N)nc3cc(OCCCNC(=O)c4cccnc4)ccc3c21]

Using the procedures described in Parts A and B of Example 395, with nicotinoyl chloride hydrochloride (0.627 g, 3.52 mmol) used in lieu of isobutyryl chloride, 7-(3-aminopropoxy)-2-(2-methoxyethyl)-1-propyl-1H-imidazo[4,5-c]quinolin-4-amine (prepared as described in Example 394, 1.28 g, 3.58 mmol) was converted into 0.230 g of N-(3-{[4-amino-2-(2-hydroxyethyl)-1-propyl-1H-imidazo[4,5-c]quinolin-7-yl]oxy}propyl)nicotinamide after recrystallization from acetonitrile to yield pale yellow needles, mp 183.5-184.5° C.

$^1$H NMR (300 MHz, DMSO-$d_6$) δ 9.02 (dd, J=2.4, 0.7 Hz, 1H), 8.77 (t, J=5.4 Hz, 1H), 8.70 (dd, J=4.7, 1.7 Hz, 1H), 8.21-8.17 (m, 1H), 7.90 (d, J=9.1 Hz, 1H), 7.52-7.48 (m, 1H), 7.08 (d, J=2.6 Hz, 1H), 6.91 (dd, J=9.0, 2.6 Hz, 1H), 6.41 (s, 2H), 4.88 (t, J=5.6 Hz, 1H), 4.47-4.42 (m, 2H), 4.14 (t, J=6.2 Hz, 2H), 3.90-3.84 (m, 2H), 3.52-3.46 (m, 2H), 3.06 (t, J=6.6 Hz, 2H), 2.09-2.00 (m, 2H), 1.88-1.75 (m, 2H), 0.98 (t, J=7.3 Hz, 3H);

$^{13}$C NMR (75 MHz, DMSO-$d_6$) δ 157.2, 151.9, 151.7, 150.5, 148.3, 146.5, 134.8, 132.6, 130.0, 125.0, 123.3, 120.9, 111.6, 108.9, 108.2, 65.2, 59.6, 46.0, 36.4, 30.2, 28.8, 22.9, 10.6;

MS (ESI) m/z 449.3 (M+H)$^+$;

Anal. calcd for $C_{24}H_{28}N_6O_3$: C, 64.27; H, 6.29; N, 18.74. Found: C, 63.99; H, 6.53; N, 18.87.

Example 397 tert-Butyl 4-{4-amino-2-(ethoxymethyl)-7-[3-(2-oxopyrrolidin-1-yl)propoxy]-1H-imidazo[4,5-c]quinolin-1-yl}butylcarbamate

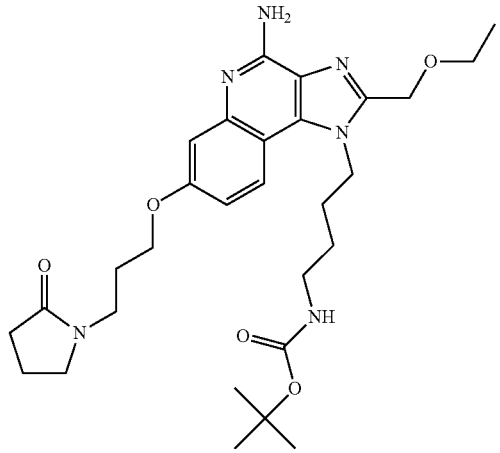 [SMILES: CCOCc1nc2c(N)nc3cc(OCCCN4CCCC4=O)ccc3c2n1CCCCNC(=O)OC(C)(C)C]

Part A

Using a modification on the procedure described in Part E of Example 2, tert-butyl 4-{[7-(benzyloxy)-3-nitroquinolin-4-yl]amino}butylcarbamate was synthesized using 7-benzyloxy-3-nitroquinolin-4-ol (prepared as described in Steps A-C of Example 1) and tert-butyl 4-aminobutylcarbamate in lieu of the 6-benzyloxy-3-nitroquinolin-4-ol and propylamine, respectively.

Part B

A mixture of tert-butyl 4-{[7-(benzyloxy)-3-nitroquinolin-4-yl]amino}butylcarbamate (30.0 g, 64.3 mmol) and 5% platinum on carbon (3.0 g) in toluene (675 mL) and 2-propanol (100 mL) was hydrogenated on a Parr apparatus for 12.5 hours at 24 psi (1.7×10⁵ Pa). The mixture was filtered through CELITE filter agent, which was rinsed afterwards with 1:1 toluene/2-propanol and 2-propanol. The combined filtrates were concentrated under reduced pressure to afford 28 g of tert-butyl 4-{[3-amino-7-(benzyloxy)quinolin-4-yl]amino}butylcarbamate as a viscous black oil that was used in the next step without purification.

Part C

Ethoxyacetyl chloride (7.87 mL, 64.3 mmol) was added dropwise to a stirred solution of the material from Part B in dichloromethane (319 mL). After 1 hour, the solution was concentrated under reduced pressure. The residue was dissolved in ethanol (319 mL) and triethylamine (35.84 mL, 257 mmol) and the solution was heated at reflux for 4 hours, then was allowed to cool to room temperature and was concentrated under reduced pressure. The residue was dissolved in dichloromethane and washed with water and saturated aqueous sodium chloride. The organic layer was dried over anhydrous sodium sulfate, filtered, and concentrated under reduced pressure. The resulting semi-solid was dissolved in hot acetonitrile and allowed to cool. Evaporation of the acetonitrile under reduced pressure afforded 30 g of tert-butyl 4-[7-(benzyloxy)-2-(ethoxymethyl)-1H-imidazo[4,5-c]quinolin-1-yl]butylcarbamate as a chunky brown solid.

Part D

A mixture of tert-butyl 4-[7-(benzyloxy)-2-(ethoxymethyl)-1H-imidazo[4,5-c]quinolin-1-yl]butylcarbamate (15 g, 29.7 mmol) and 10% palladium on carbon (4.5 g, wetted with ethanol) in 1:1 ethanol/methanol (400 mL) was hydrogenated using a Parr apparatus at 28 psi (1.9×10⁵ Pa) for 16 hours. The mixture was filtered through CELITE filter agent, which was subsequently washed with methanol. The filtrate was concentrated under reduced pressure to afforded 10.8 g of tert-butyl 4-[2-(ethoxymethyl)-7-hydroxy-1H-imidazo[4,5-c]quinolin-1-yl]butylcarbamate as a green-yellow solid.

Part E

Using the conditions described in Part A of Example 392, tert-butyl 4-[2-(ethoxymethyl)-7-hydroxy-1H-imidazo[4,5-c]quinolin-1-yl]butylcarbamate (3.50 g, 8.44 mmol) was converted into tert-butyl 4-{2-(ethoxymethyl)-7-[3-(2-oxopyrrolidin-1-yl)propoxy]-1H-imidazo[4,5-c]quinolin-1-yl}butylcarbamate using 1-(3-hydroxypropyl)pyrrolidin-2-one (1.64 mL, 12.7 mmol) in lieu of 3-(methylthio)propan-1-ol. The reaction was worked up by removing the solvent under reduced pressure. The residue was subjected to flash chromatography (silica gel, elution with ethyl acetate followed by gradient elution with 1-5% methanol in dichloromethane) to yield 3.79 g of tert-butyl 4-{2-(ethoxymethyl)-7-[3-(2-oxopyrrolidin-1-yl)propoxy]-1H-imidazo[4,5-c]quinolin-1-yl}butylcarbamate as a viscous yellow oil.

Part F

Using a modification on the procedure described in Part B of Example 392, tert-butyl 4-{2-(ethoxymethyl)-7-[3-(2-oxopyrrolidin-1-yl)propoxy]-1H-imidazo[4,5-c]quinolin-1-yl}butylcarbamate (3.79 g, 7.02 mmol) was converted into tert-butyl 4-{4-amino-2-(ethoxymethyl)-7-[3-(2-oxopyrrolidin-1-yl)propoxy]-1H-imidazo[4,5-c]quinolin-1-yl}butylcarbamate. After the p-toluenesulfonyl chloride was added, the mixture was allowed to stir for 72 hours. The layers were separated and the aqueous layer was extracted with dichloromethane. The organic layers were combined, washed with 5% aqueous sodium bicarbonate, water, and saturated aqueous sodium chloride, dried over anhydrous sodium sulfate, filtered, and evaporated. Recrystallization from acetonitrile afforded 3.1 g of tert-butyl 4-{4-amino-2-(ethoxymethyl)-7-[3-(2-oxopyrrolidin-1-yl)propoxy]-1H-imidazo[4,5-c]quinolin-1-yl}butylcarbamate as a white solid, mp 134.5-136° C.

¹H NMR (300 MHz, DMSO-d₆) δ 7.90 (d, J=9.0 Hz, 1H), 7.04 (d, J=2.5 Hz, 1H), 6.90 (dd, J=8.8, 2.3 Hz, 1H), 6.81 (t, J=5.0 Hz, 1H), 6.51 (s, 2H), 4.74 (s, 2H), 4.52-4.47 (m, 2H), 4.04 (t, J=6.2 Hz, 2H), 3.55 (q, J=7.0 Hz, 2H), 3.42-3.34 (m, 4H), 2.99-2.93 (m, 2H), 2.22 (t, J=8.0 Hz, 2H), 2.00-1.88 (m, 4H), 1.87-1.74 (m, 2H), 1.61-1.50 (m, 2H), 1.33 (s, 9H), 1.16 (t, J=7.0 Hz, 3H);

MS (ESI) m/z 555.3287 (555.3295 calcd for C₂₉H₄₂N₆O₅, M+H⁺).

Anal. calcd for C₂₉H₄₂N₆O₅·1.25H₂O: C, 60.35; H, 7.77; N, 14.56. Found: C, 60.35; H, 7.83; N, 14.12.

Example 398

1-(3-{[4-Amino-1-(4-aminobutyl)-2-(ethoxymethyl)-1H-imidazo[4,5-c]quinolin-7-yl]oxy}propyl)pyrrolidin-2-one dihydrochloride

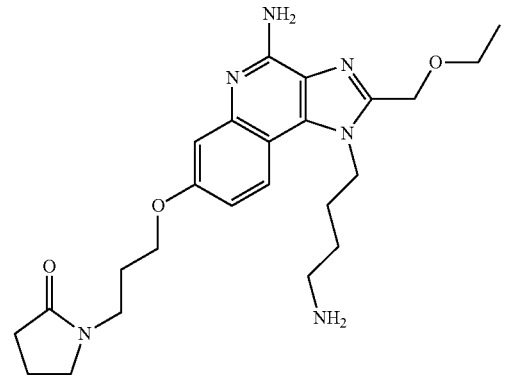 [SMILES: CCOCc1nc2c(N)nc3cc(OCCCN4CCCC4=O)ccc3c2n1CCCCN]

A solution of tert-butyl 4-{4-amino-2-(ethoxymethyl)-7-[3-(2-oxopyrrolidin-1-yl)propoxy]-1H-imidazo[4,5-c]quinolin-1-yl}butylcarbamate (prepared as described in Example 397, 2.90 g, 5.23 mmol) in 4 M ethanolic hydrogen chloride was heated at reflux for 2 hours. The solution was allowed to cool to room temperature and a precipitate formed that was isolated by filtration to afford 2.52 g of 1-(3-{[4-amino-1-(4-aminobutyl)-2-(ethoxymethyl)-1H-imidazo[4,5-c]quinolin-7-yl]oxy}propyl)pyrrolidin-2-one dihydrochloride as a white powder, mp>250° C. ¹H NMR (300 MHz, DMSO-d₆) δ 13.92 (s, 1H), 9.30-8.40 (br s, 2H), 8.15 (d, J=9.2 Hz, 1H), 8.13-8.00 (m, 3H), 7.30 (d, J=2.5 Hz, 1H), 7.20 (dd, J=9.1, 2.4 Hz, 1H), 4.83 (s, 2H), 4.65-4.60 (m, 2H), 4.10 (t, J=6.1 Hz, 2H), 3.60 (q, J=7.0 Hz, 2H), 3.41-3.37 (m, 4H), 2.87-2.76 (m, 2H), 2.22 (t, J=8.0 Hz, 2H), 2.04-1.85 (m, 6H), 1.81-1.70 (m, 2H), 1.19 (t, J=7.0 Hz, 3H);

MS (ESI) m/z 455.2784 (455.2771 calcd for C₂₄H₃₄N₆O₃, M+H⁺).

Anal. calcd for $C_{24}H_{34}N_6O_3 \cdot 1.60H_2O \cdot 2.15HCl$: C, 51.28; H, 7.06; N, 14.95; Cl, 13.59.

Found: C, 51.29; H, 7.36; N, 14.93; Cl, 13.48.

Example 399

N-(4-{4-Amino-2-(ethoxymethyl)-7-[3-(2-oxopyrrolidin-1-yl)propoxy]-1H-imidazo[4,5-c]quinolin-1-yl}butyl)-N'-isopropylurea

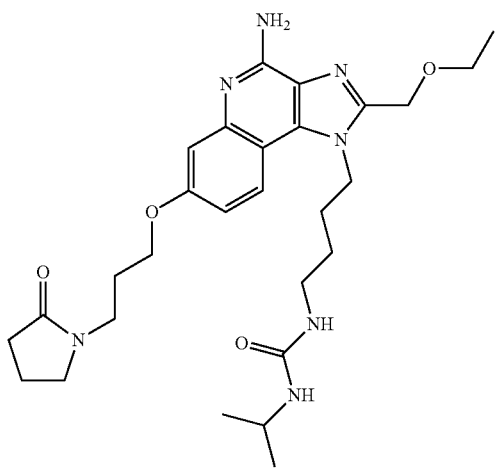 [SMILES: CCOCc1nc2c(N)nc3cc(OCCCN4CCCC4=O)ccc3c2n1CCCCNC(=O)NC(C)C]

Isopropyl isocyanate (0.187 mL, 1.90 mmol) was added dropwise to a stirred solution of 1-(3-{[4-amino-1-(4-aminobutyl)-2-(ethoxymethyl)-1H-imidazo[4,5-c]quinolin-7-yl]oxy}propyl)pyrrolidin-2-one dihydrochloride (prepared as described in Example 398, 1.0 g, 1.90 mmol) and triethylamine (0.530 mL, 3.80 mmol) in dichloromethane (20 mL) at room temperature. After 1.5 hours, the solvent was removed under reduced pressure and the residue was purified by flash chromatography (silica gel, gradient elution with 2-12% CMA in chloroform) followed by recrystallization from acetonitrile to yield 0.730 g of N-(4-{4-amino-2-(ethoxymethyl)-7-[3-(2-oxopyrrolidin-1-yl)propoxy]-1H-imidazo[4,5-c]quinolin-1-yl}butyl)-N'-isopropylurea as an opaque solid, mp 98-101° C.

$^1$H NMR (300 MHz, DMSO-$d_6$) δ 7.90 (d, J=9.0 Hz, 1H), 7.05 (d, J=2.6 Hz, 1H), 6.91 (dd, J=9.0, 2.6 Hz, 1H), 6.55 (s, 2H), 5.69 (t, J=5.7 Hz, 1H), 5.57 (d, J=7.7 Hz, 1H), 4.74 (s, 2H), 4.53-4.48 (m, 2H), 4.04 (t, J=6.3 Hz, 2H), 3.69-3.58 (m, 1H), 3.55 (q, J=7.0 Hz, 2H), 3.40-3.34 (m, 4H), 3.03 (q, J=6.3 Hz, 2H), 2.22 (t, J=8.0 Hz, 2H), 2.00-1.88 (m, 4H), 1.88-1.76 (m, 2H), 1.58-1.48 (m, 2H), 1.16 (t, J=7.0 Hz, 3H), 0.98 (d, J=6.5 Hz, 6H);

$^{13}$C NMR (75 MHz, DMSO-$d_6$) δ 173.9, 157.5, 157.4, 152.2, 148.0, 146.8, 133.4, 124.8, 121.4, 111.7, 108.7, 108.0, 65.3, 64.2, 46.5, 45.1, 40.8, 39.1, 30.4, 27.3, 26.7, 23.2, 17.5, 14.9;

MS (ESI) m/z 540.3315 (540.3298 calcd for $C_{28}H_{41}N_7O_4$, M+H$^+$).

Anal. calcd for $C_{28}H_{41}N_7O_4$: C, 62.32; H, 7.66; N, 18.17. Found: C, 61.95; H, 7.90; N, 18.46.

Example 400

N-(4-{4-Amino-2-(ethoxymethyl)-7-[3-(2-oxopyrrolidin-1-yl)propoxy]-1H-imidazo[4,5-c]quinolin-1-yl}butyl)methanesulfonamide

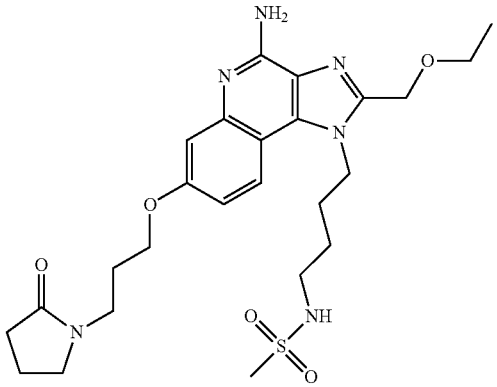 [SMILES: CCOCc1nc2c(N)nc3cc(OCCCN4CCCC4=O)ccc3c2n1CCCCNS(C)(=O)=O]

Using the procedure described in Example 399, 1-(3-{[4-amino-1-(4-aminobutyl)-2-(ethoxymethyl)-1H-imidazo[4,5-c]quinolin-7-yl]oxy}propyl)pyrrolidin-2-one dihydrochloride (prepared as described in Example 398, 1.0 g, 1.90 mmol) was converted into N-(4-{4-amino-2-(ethoxymethyl)-7-[3-(2-oxopyrrolidin-1-yl)propoxy]-1H-imidazo[4,5-c]quinolin-1-yl}butyl)methanesulfonamide using methanesulfonyl chloride (0.147 mL, 1.90 mmol) in lieu of isopropyl isocyanate. Recrystallization from acetonitrile afforded 0.246 g of N-(4-{4-amino-2-(ethoxymethyl)-7-[3-(2-oxopyrrolidin-1-yl)propoxy]-1H-imidazo[4,5-c]quinolin-1-yl}butyl)methanesulfonamide as white crystals, mp 157° C.

$^1$H NMR (300 MHz, DMSO-$d_6$) δ 7.96 (d, J=9.0 Hz, 1H), 7.06 (d, J=2.6 Hz, 1H), 6.99 (dd, J=9.0, 2.6 Hz, 1H), 6.93 (dd, J=9.0, 2.6 Hz, 1H), 6.65 (s, 2H), 4.75 (s, 2H), 4.55-4.50 (m, 2H), 4.04 (t, J=6.2 Hz, 2H), 3.56 (q, J=7.0 Hz, 2H), 3.40-3.34 (m, 4H), 2.99 (q, J=6.3 Hz, 2H), 2.87 (s, 3H), 2.22 (t, J=8.0 Hz, 2H), 2.00-1.83 (m, 6H), 1.69-1.59 (m, 2H), 1.17 (t, J=7.0 Hz, 3H);

MS (ESI) m/z 533.2565 (533.2546 calcd for $C_{25}H_{36}N_6O_5S$, M+H$^+$).

Anal. calcd for $C_{25}H_{36}N_6O_5S$: C, 56.37; H, 6.81; N, 15.78; S, 6.02. Found: C, 56.08; H, 6.74; N, 15.47; S, 6.31.

Example 401

1-[4-(1,1-Dioxidoisothiazolidin-2-yl)butyl]-2-(ethoxymethyl)-7-(tetrahydrofuran-3-yloxy)-1H-imidazo[4,5-c]quinolin-4-amine

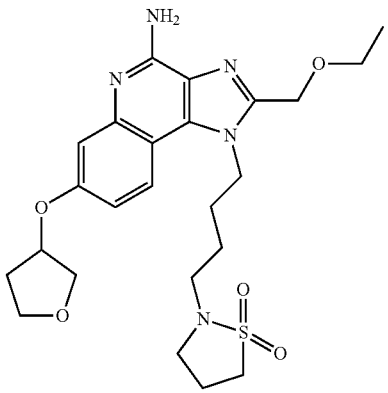 [SMILES: CCOCc1nc2c(N)nc3cc(OC4CCOC4)ccc3c2n1CCCCN1CCCS1(=O)=O]

Part A

A solution of tert-butyl 4-[7-(benzyloxy)-2-(ethoxymethyl)-1H-imidazo[4,5-c]quinolin-1-yl]butylcarbamate (prepared as described in Parts A-C of Example 397, 21.0 g, 41.6 mmol) and concentrated hydrochloric acid (13 mL) in ethanol (100 mL) was heated at reflux for 1 hour. The solution was allowed to cool to room temperature and a precipitate formed that was isolated by filtration to yield 12.10 g of 4-[7-(benzyloxy)-2-(ethoxymethyl)-1H-imidazo[4,5-c]quinolin-1-yl]butan-1-amine dihydrochloride as a light brown solid.

Part B

3-Chloropropanesulfonyl chloride (4.58 mL, 37.7 mmol) was added dropwise to a solution of 4-[7-(benzyloxy)-2-(ethoxymethyl)-1H-imidazo[4,5-c]quinolin-1-yl]butan-1-amine dihydrochloride (12.1 g, 25.3 mmol) and triethylamine (14.0 mL, 101 mmol) in dichloromethane (168 mL) at room temperature. The solution was stirred for 17 hours, then transferred to a separatory funnel and washed with 5% aqueous sodium carbonate, water, and saturated aqueous sodium chloride. The organic layer was dried over anhydrous sodium sulfate, filtered, and concentrated under reduced pressure. The residue was dissolved in DMF (168 mL) and treated with 1,8-diazabicyclo[5.4.0]undec-7-ene (5.70 mL, 38 mmol). The solution was stirred for 40 hours, then the DMF was removed under reduced pressure. The residue was dissolved in dichloromethane and washed repeatedly with water then saturated aqueous sodium carbonate. The organic layer was dried over anhydrous sodium sulfate, filtered, and evaporated to afford 7-(benzyloxy)-1-[4-(1,1-dioxidoisothiazolidin-2-yl)butyl]-2-(ethoxymethyl)-1H-imidazo[4,5-c]quinoline in almost quantitative yield with some residual 1,8-diazabicyclo[5.4.0]undec-7-ene as a brown oil, which was used without further purification.

Part C

A mixture of 7-(benzyloxy)-1-[4-(1,1-dioxidoisothiazolidin-2-yl)butyl]-2-(ethoxymethyl)-1H-imidazo[4,5-c]quinoline (4.6 g, 9.04 mmol) and palladium hydroxide (1.5 g) in acetonitrile (50 mL) and methanol (75 mL) was hydrogenated on a Parr apparatus at 50 psi (3.5×10$^5$ Pa) for 28 hours. The mixture was filtered through CELITE filter agent, which was rinsed afterwards with 40% methanol in acetonitrile (600 mL). The filtrates were combined and concentrated under reduced pressure to yield a yellow solid that was triturated with acetonitrile and isolated by filtration to afford 2.2 g of 1-[4-(1,1-dioxidoisothiazolidin-2-yl)butyl]-2-(ethoxymethyl)-1H-imidazo[4,5-c]quinolin-7-ol as a pale yellow powder.

Part D

Using a modification of the method described in Part A of Example 392, 1-[4-(1,1-dioxidoisothiazolidin-2-yl)butyl]-2-(ethoxymethyl)-1H-imidazo[4,5-c]quinolin-7-ol (1.1 g, 2.63 mmol) was converted into 1-[4-(1,1-dioxidoisothiazolidin-2-yl)butyl]-2-(ethoxymethyl)-7-(tetrahydrofuran-3-yloxy)-1H-imidazo[4,5-c]quinoline, using 3-hydroxytetrahydrofuran (0.320 mL, 3.94 mmol) in lieu of 3-(methylthio)propan-1-ol. The reaction mixture was allowed to stir at ambient temperature for 72 hours, then was treated with 3 M hydrochloric acid (30 mL) and extracted with ethyl acetate. The aqueous layer was adjusted to a basic pH with saturated aqueous sodium carbonate and was extracted with dichloromethane. The organic layer was washed with water and saturated sodium chloride, dried over anhydrous sodium sulfate, filtered, and concentrated under reduced pressure to afford 1.0 g of 1-[4-(1,1-dioxidoisothiazolidin-2-yl)butyl]-2-(ethoxymethyl)-7-(tetrahydrofuran-3-yloxy)-1H-imidazo[4,5-c]quinoline as a yellow waxy solid.

Part E

Using a modification of the method described in Part B of Example 392, 1-[4-(1,1-dioxidoisothiazolidin-2-yl)butyl]-2-(ethoxymethyl)-7-(tetrahydrofuran-3-yloxy)-1H-imidazo[4,5-c]quinoline (1.0 g, 2.05 mmol) was converted into 1-[4-(1,1-dioxidoisothiazolidin-2-yl)butyl]-2-(ethoxymethyl)-7-(tetrahydrofuran-3-yloxy)-1H-imidazo[4,5-c]quinolin-4-amine. In the workup, the layers were separated and the aqueous was extracted with chloroform. The combined organic layers were washed with water and saturated aqueous sodium chloride, dried over anhydrous sodium sulfate, filtered, and evaporated under reduced pressure. The crude product was recrystallized from acetonitrile to 0.511 g of 1-[4-(1,1-dioxidoisothiazolidin-2-yl)butyl]-2-(ethoxymethyl)-7-(tetrahydrofuran-3-yloxy)-1H-imidazo[4,5-c]quinolin-4-amine as red-tan crystals, mp 195.5-197° C.

$^1$H NMR (300 MHz, DMSO-d$_6$) δ 7.95 (d, J=9.0 Hz, 1H), 7.02 (d, J=2.6 Hz, 1H), 6.90 (dd, J=9.0, 2.6 Hz, 1H), 6.57 (s, 2H), 5.17-5.10 (m, 1H), 4.75 (s, 2H), 4.58-4.48 (m, 2H), 3.97-3.74 (m, 4H), 3.55 (q, J=7.0 Hz, 2H), 3.19-3.13 (m, 4H), 2.93 (t, J=6.6 Hz, 2H), 2.33-2.14 (m, 3H), 2.08-1.99 (m, 1H), 1.92-1.82 (m, 2H), 1.76-1.66 (m, 2H), 1.16 (t, J=7.0 Hz, 3H);

$^{13}$C NMR (75 MHz, DMSO-d$_6$) δ 156.1, 152.3, 148.1, 146.9, 133.3, 124.9, 121.7, 112.2, 109.0, 108.8, 77.0, 72.3, 66.5, 65.3, 64.2, 46.5, 46.1, 45.0, 43.7, 32.5, 27.1, 24.3, 18.3, 14.9;

MS (ESI) m/z 504.2276 (504.2281 calcd for C$_{24}$H$_{33}$N$_5$O$_5$S, M+H$^+$).

Anal. calcd for C$_{24}$H$_{33}$N$_5$O$_5$S: C, 57.24; H, 6.60; N, 13.91; S, 6.37. Found: C, 56.91; H, 6.47; N, 13.73; S, 6.50.

Example 402

1-(3-{[4-Amino-1-[4-(1,1-dioxidoisothiazolidin-2-yl)butyl]-2-(ethoxymethyl)-1H-imidazo[4,5-c]quinolin-7-yl]oxy}propyl)pyrrolidin-2-one

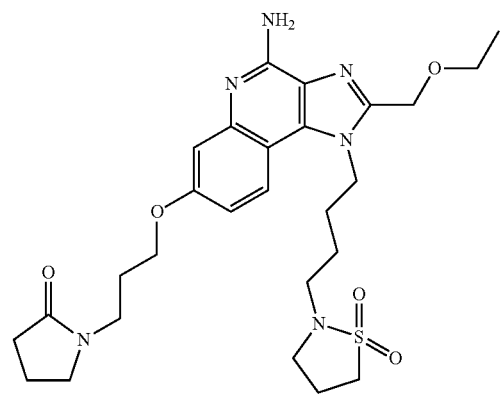 [SMILES: CCOCc1nc2c(N)nc3cc(OCCCN4CCCC4=O)ccc3c2n1CCCCN1CCCS1(=O)=O]

Using a modification of the procedures described in Parts D and E of Example 401, 1-[4-(1,1-dioxidoisothiazolidin- 2-yl)butyl]-2-(ethoxymethyl)-1H-imidazo[4,5-c]quinolin-7-ol (prepared as described in Steps A-C of Example 401, 1.1 g, 2.63 mmol) was converted into 1-(3-{[4-amino-1-[4-(1,1-dioxidoisothiazolidin-2-yl)butyl]-2-(ethoxymethyl)-1H-imidazo[4,5-c]quinolin-7-yl]oxy}propyl)pyrrolidin-2-one, using 1-(3-hydroxypropyl)pyrrolidin-2-one in lieu of 3-hydroxytetrahydrofuran in step D. Purification by chromatography on a HORIZON HPFC system (silica gel, gradient elution with 1-20% CMA in chloroform) followed by trituration with acetonitrile and isolation by filtration afforded 0.551 g of 1-(3-{[4-amino-1-[4-(1,1-dioxidoisothiazolidin-2-yl)butyl]-2-(ethoxymethyl)-1H-imidazo[4,5-c]quinolin-7-yl]oxy}propyl)pyrrolidin-2-one as a white solid, mp 142-144° C.

$^1$H NMR (300 MHz, DMSO-$d_6$) δ 7.94 (d, J=9.0 Hz, 1H), 7.05 (d, J=2.6 Hz, 1H), 6.91 (dd, J=8.9, 2.6 Hz, 1H), 6.52 (s, 2H), 4.75 (s, 2H), 4.55-4.50 (m, 2H), 4.04 (t, J=6.2 Hz, 2H), 3.55 (q, J=7.0 Hz, 2H), 3.40-3.34 (m, 4H), 3.18-3.13 (m, 4H), 2.94 (t, J=6.6 Hz, 2H), 2.24-2.14 (m, 4H), 2.00-1.82 (m, 6H), 1.76-1.66 (m, 2H), 1.16 (t, J=7.0 Hz, 3H);

$^{13}$C NMR (75 MHz, DMSO-$d_6$) δ 173.9, 157.5, 152.3, 148.0, 147.0, 133.3, 124.8, 121.4, 111.7, 108.7, 108.0, 65.3, 65.3, 64.1, 46.5, 46.1, 44.9, 43.7, 39.1, 30.4, 27.1, 26.7, 24.3, 18.3, 17.5, 14.9;

MS (ESI) m/z 559.2718 (559.2703 calcd for $C_{27}H_{38}N_6O_5S$, M+H$^+$).

Anal. calcd for $C_{27}H_{38}N_6O_5S$: C, 58.05; H, 6.86; N, 15.04. Found: C, 57.95; H, 7.22; N, 15.15.

Example 403

4-{2-[(4-Amino-1-isobutyl-2-methyl-1H-imidazo[4,5-c]quinolin-7-yl)oxy]ethyl}-N-cyclohexylpiperidine-1-carboxamide

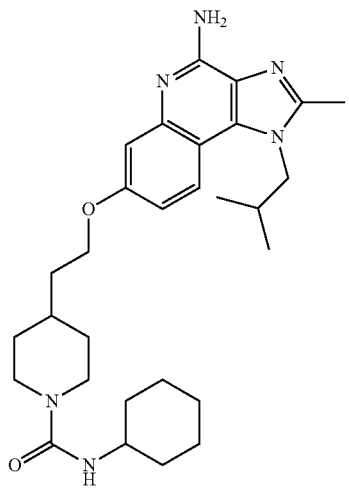 [SMILES: Cc1nc2c(N)nc3cc(OCCC4CCN(C(=O)NC5CCCCC5)CC4)ccc3c2n1CC(C)C]

The preparation of 2-methyl-1-(2-methylpropyl)-7-(2-piperidin-4-ylethoxy)-1H-imidazo[4,5-c]quinolin-4-amine is described in Example 24. Cyclohexyl isocyanate (0.100 mL, 0.786 mmol) was added dropwise to a stirred solution of 2-methyl-1-(2-methylpropyl)-7-(2-piperidin-4-ylethoxy)-1H-imidazo[4,5-c]quinolin-4-amine (0.300 g, 0.786 mmol) in dichloromethane (10 mL) at 0° C. After 30 minutes, the solution was concentrated under reduced pressure and the resulting residue was purified by flash chromatography (silica gel, sequential elution with 2% and 5% methanol in dichloromethane) followed by recrystallization from ethanol to afford 0.141 g of 4-{2-[(4-amino-1-isobutyl-2-methyl-1H-imidazo[4,5-c]quinolin-7-yl)oxy]ethyl}-N-cyclohexylpiperidine-1-carboxamide as a white powder, mp 213.7-215.7° C.

$^1$H NMR (300 MHz, DMSO-$d_6$) δ 7.85 (d, J=9.5 Hz, 1H), 7.05 (d, J=3.0 Hz, 1H), 6.89 (dd, J=8.6, 2.5 Hz, 1H), 6.43 (s, 2H), 6.06 (d, J=7.6 Hz, 1H), 4.27 (d, J=7.5 Hz, 2H), 4.09 (t, J=6.0 Hz, 2H), 4.0-3.92 (m, 2H), 3.44-3.30 (m, 1H), 2.64-2.56 (m, 2H), 2.56 (s, 3H), 2.23-2.09 (m, 1H), 1.77-1.50 (m, 10H), 1.3-0.96 (m, 7H), 0.93 (d, J=6.7 Hz, 6H);

MS (ESI) m/z 507.3465 (507.3448 calcd for $C_{29}H_{42}N_6O_2$, M+H$^+$).

Anal. calcd for $C_{29}H_{42}N_6O_2 \cdot 0.5H_2O$: C, 67.54; H, 8.41; N, 16.30. Found: C, 67.78; H, 8.43; N, 16.46.

Example 404 tert-Butyl 4-({[4-amino-2-(ethoxymethyl)-1-propyl-1H-imidazo[4,5-c]quinolin-8-yl]oxy}acetyl)piperazine-1-carboxylate

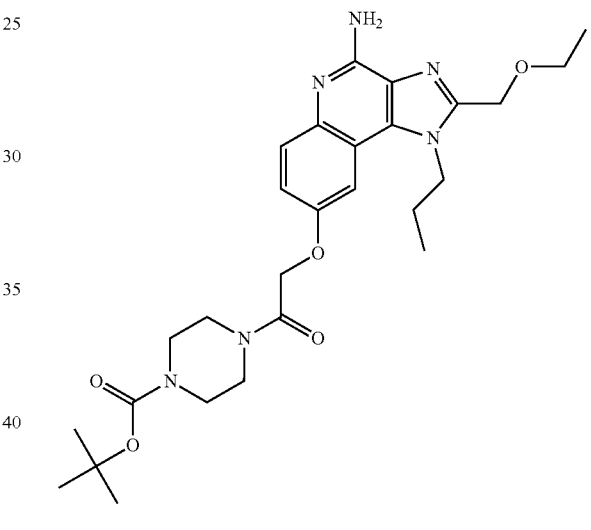

Part A

Di-tert-butyl dicarbonate (19.05 g, 0.087 mol) in dichloromethane (218 mL) was added dropwise over 2 hours to a solution of piperazine (15.0 g, 0.174 mol) in dichloromethane (436 mL). The reaction mixture was allowed to stir for 16 hours, then the solution was concentrated under reduced pressure to yield a solid that was treated with water (500 mL). The mixture was stirred vigorously and a white solid was isolated by filtration and washed with water. The solid was discarded. The filtrate was extracted with dichloromethane. The organic layer was dried over anhydrous sodium sulfate, filtered, and concentrated under reduced pressure to yield 12.7 g of tert-butyl piperazine-1-carboxylate as clear yellow crystals.

Part B

Bromoacetyl bromide (2.97 mL, 34.1 mmol) in dichloromethane (25 mL) was added dropwise to the solution of tert-butyl piperazine-1-carboxylate (6.35 g, 34.1 mmol) and diisopropylethylamine (5.8 mL, 33.3 mmol) in dichloromethane (38 mL) at 0° C. The solution was allowed to warm to ambient temperature and was stirred for 2 hours, then was poured into a separatory funnel. The solution was washed with water, dried over anhydrous sodium sulfate, filtered, and concentrated under reduced pressure. Purification by flash chromatography (silica gel, eluting sequentially with 20%, 33%, and finally 50% ethyl acetate in hexanes) afforded 4.05 g of tert-butyl 4-(2-bromoacetyl)piperazine-1-carbamate as a brown crystalline solid.

Part C

The synthesis of 2-(ethoxymethyl)-1-propyl-1H-imidazo[4,5-c]quinolin-8-ol is described in Parts A-I of Example 2. A mixture of 2-ethoxymethyl-1-propyl-1H-imidazo[4,5-c]quinolin-8-ol (4.5 g, 15.8 mmol), tert-butyl 4-(2-bromoacetyl)piperazine-1-carbamate (4.57 g, 14.9 mmol), and potassium carbonate (3.27 g, 23.7 mmol) in DMF (158 mL) was heated to 55° C. for 2.5 hours, then was allowed to cool to room temperature and was stirred for 16 hours. The solution was poured into water (500 mL), which was extracted with diethyl ether (300 mL), ethyl acetate (300 mL) and dichloromethane (300 mL). The combined organic layers were concentrated under reduced pressure. The crude product was purified by flash chromatography (silica gel, gradient elution with 0-5% methanol in dichloromethane to provide 7.9 g of tert-butyl 4-({[2-(ethoxymethyl)-1-propyl-1H-imidazo[4,5-c]quinolin-8-yl]oxy}acetyl)piperazine-1-carboxylate as a tan waxy solid that contained 15% of DMF by weight.

Part D

The material from Part C was dissolved in chloroform (150 mL) and treated with mCPBA (70% w/w, 3.80 g, 15.4 mmol). The solution was stirred for 30 minutes, and additional mCPBA (1.0 g) was added. After 1 hour, the reaction was diluted with chloroform (150 mL) and washed with 1:1 saturated aqueous sodium carbonate/water. The layers were separated and the aqueous layer was extracted with chloroform. The organic layers were combined, washed with water and saturated aqueous sodium chloride, dried over sodium sulfate, filtered, and concentrated under reduced pressure to afford 14.9 g of approximately 54% pure tert-butyl 4-({[2-(ethoxymethyl)-5-oxido-1-propyl-1H-imidazo[4,5-c]quinolin-8-yl]oxy}acetyl)piperazine-1-carboxylate was isolated as a red-orange oil, which was used in the next step without purification.

Part E

A modification of the procedure described in Part C of Example 393 was used to convert the material from Part D into tert-butyl 4-({[4-amino-2-(ethoxymethyl)-1-propyl-1H-imidazo[4,5-c]quinolin-8-yl]oxy}acetyl)piperazine-1-carboxylate. After the p-toluenesulfonyl chloride (2.93 g, 15.4 mmol) was added, the reaction mixture was allowed to stir for 1 hour, then the ice bath was replaced with a water bath and the reaction mixture was allowed to stir for 16 hours. The mixture was diluted with dichloromethane and the layers were separated. The reaction was worked up as described in Example 393 and the crude product was recrystallized from acetonitrile to yield 4.7 g of tert-butyl 4-({[4-amino-2-(ethoxymethyl)-1-propyl-1H-imidazo[4,5-c]quinolin-8-yl]oxy}acetyl)piperazine-1-carboxylate as tan crystals, mp 192-197° C. (decomposition).

$^1$H NMR (300 MHz, DMSO-$d_6$) δ 7.55 (d, J=9.1 Hz, 1H), 7.41 (d, J=2.7 Hz, 1H), 7.15 (dd, J=9.1, 2.6 Hz, 1H), 6.36 (s, 2H), 4.96 (s, 2H), 4.77 (s, 2H), 4.54-4.49 (m, 2H), 3.59-3.31 (m, 10H), 1.93-1.81 (m, 2H), 1.41 (s, 9H), 1.16 (t, J=7.0 Hz, 3H), 1.02 (t, J=7.3 Hz, 3H);
$^{13}$C NMR (75 MHz, DMSO-$d_6$) δ 166.4, 153.7, 152.5, 150.6, 149.0, 140.2, 132.7, 127.5, 126.6, 117.0, 114.4, 102.8, 79.2, 66.9, 65.3, 64.2, 46.7, 44.2, 41.1, 28.0, 23.3, 14.9, 10.8;
MS (ESI) m/z 527.2992 (527.2982 calcd for $C_{27}H_{38}N_6O_5$, M+H$^+$).
Anal. calcd for $C_{27}H_{38}N_6O_5$: C, 61.58; H, 7.27; N, 15.96. Found: C, 61.41; H, 7.49; N, 15.96.

Example 405

1-(3-{[4-Amino-2-(ethoxymethyl)-1-propyl-1H-imidazo[4,5-c]quinolin-8-yl]oxy}propyl)pyrrolidin-2-one

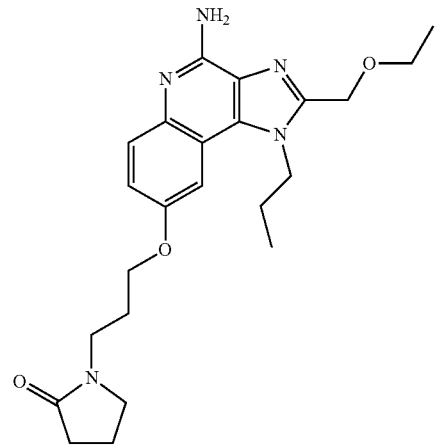 [SMILES: CCCn1c(COCC)nc2c(N)nc3ccc(OCCCN4CCCC4=O)cc3c21]

Part A

The synthesis of 2-(ethoxymethyl)-1-propyl-1H-imidazo[4,5-c]quinolin-8-ol is described in Parts A-I of Example 2. A modification of the method described in Part A of Example 392 was used to convert 2-ethoxymethyl-1-propyl-1H-imidazo[4,5-c]quinolin-8-ol (1.5 g, 5.26 mmol) into 1-[3-(2-ethoxymethyl-1-propyl-1H-imidazo[4,5-c]quinolin-8-yloxy)propyl]-pyrrolidin-2-one using 1-(3-hydroxypropyl)pyrrolidin-2-one (1.02 mL, 7.88 mL) in lieu of 3-(methylthio)propan-1-ol. After the reaction mixture was allowed to stir for 16 hours at ambient temperature, additional diisopropyl azodicarboxylate, triphenylphosphine, and 1-(3-hydroxypropyl)pyrrolidin-2-one (0.5 equivalent of each) were added and the reaction mixture was allowed to stir for 2 hours. The solvent was removed under reduced pressure and the resulting residue was purified by flash chromatography (silica gel, elution with ethyl acetate followed by gradient elution with 1-5% methanol in dichloromethane) to yield 2.9 g of 1-[3-(2-ethoxymethyl-1-propyl-1H-imidazo[4,5-c]quinolin-8-yloxy)propyl]-pyrrolidin-2-one a pale yellow solid.

Part B

3-Chloroperoxybenzoic acid (50% pure, 1.8 g, 5.26 mmol) was added to a solution of 1-[3-(2-ethoxymethyl-1- propyl-1H-imidazo[4,5-c]quinolin-8-yloxy)propyl]-pyrrolidin-2-one (2.9 g, 5.26 mmol) in chloroform (50 mL). After 30 minutes, saturated aqueous sodium carbonate (20 mL) was added to the solution and the resulting mixture was allowed to stir for 1 hour. The layers were separated and the aqueous layer was extracted with chloroform (3×50 mL). The organic layers were combined, washed with water and saturated aqueous sodium chloride, dried over anhydrous sodium sulfate, filtered, and concentrated under reduced pressure. The crude product was purified by flash chromatography (silica gel, gradient elution with 1-4% methanol in dichloromethane) to yield 1.56 g of 1-(3-{[2-(ethoxymethyl)-5-oxido-1-propyl-1H-imidazo[4,5-c]quinolin-8-yl]oxy}propyl)pyrrolidin-2-one as a tan foam.

Step C p-Toluenesulfonyl chloride (0.700 g, 3.66 mmol) was added to a stirred mixture of 1-(3-{[2-(ethoxymethyl)-5-oxido-1-propyl-1H-imidazo[4,5-c]quinolin-8-yl]oxy}propyl)pyrrolidin-2-one (1.56 g, 3.66 mmol), ammonium hydroxide (24 mL), and dichloromethane (36 mL) at room temperature. After 16 hours, the layers were separated and the aqueous layer was extracted with dichloromethane (3×50 mL). The organic layers were combined, washed with water and saturated aqueous sodium chloride, dried over anhydrous sodium sulfate, filtered, and concentrated under reduced pressure. Recrystallization from acetonitrile afforded 0.759 g of 1-(3-{[4-amino-2-(ethoxymethyl)-1-propyl-1H-imidazo[4,5-c]quinolin-8-yl]oxy}propyl)pyrrolidin-2-one as off-white needles, mp 188.5-190° C.

$^1$H NMR (300 MHz, DMSO-$d_6$) δ 7.54 (d, J=9.1 Hz, 1H), 7.36 (d, J=2.6 Hz, 1H), 7.11 (dd, J=9.1, 2.6 Hz, 1H), 6.33 (s, 2H), 4.76 (s, 2H), 4.53-4.48 (m, 2H), 4.07 (t, J=6.2 Hz, 2H), 3.54 (q, J=7.0 Hz, 2H), 3.37 (t, J=7.0 Hz, 4H), 2.22-2.17 (m, 2H), 2.00-1.83 (m, 6H), 1.15 (t, J=7.0 Hz, 3H), 1.02 (t, J=7.3 Hz, 3H);

$^{13}$C NMR (75 MHz, DMSO-$d_6$) δ 173.8, 153.0, 150.5, 148.9, 140.0, 132.7, 127.6, 126.6, 117.2, 114.6, 102.3, 65.8, 65.3, 64.2, 46.8, 46.4, 39.1, 30.4, 26.8, 23.3, 17.5, 14.9, 10.7;

MS (ESI) m/z 426.2518 (426.2505 calcd for $C_{23}H_{31}N_5O_3$, M+H$^+$.

Anal. calcd for $C_{23}H_{31}N_5O_3$: C, 64.92; H, 7.34; N, 16.46. Found: C, 64.80; H, 6.99; N, 16.37.

Example 406

2-(Ethoxymethyl)-1-propyl-8-(tetrahydrofuran-3-yloxy)-1H-imidazo[4,5-c]quinolin-4-amine

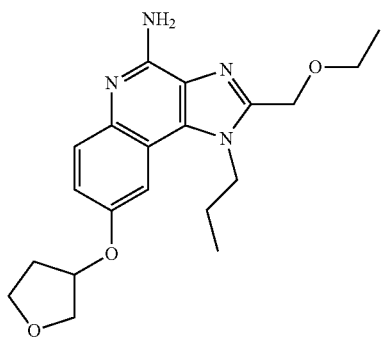 [SMILES: CCCn1c(COCC)nc2c(N)nc3ccc(OC4CCOC4)cc3c21]

The synthesis of 2-(ethoxymethyl)-1-propyl-1H-imidazo[4,5-c]quinolin-8-ol is described in Parts A-I of Example 2. A modification of the method described in Part A of Example 405 was used to convert 2-ethoxymethyl-1-propyl-1H-imidazo[4,5-c]quinolin-8-ol into 2-(ethoxymethyl)-1-propyl-8-(tetrahydrofuran-3-yloxy)-1H-imidazo[4,5-c]quinoline using 3-hydroxytetrahydrofuran in lieu of 1-(3-hydroxypropyl)pyrrolidin-2-one. Modifications of the methods described in Parts B and C of Example 405 were used to convert 2-(ethoxymethyl)-1-propyl-8-(tetrahydrofuran-3-yloxy)-1H-imidazo[4,5-c]quinoline into 2-(ethoxymethyl)-1-propyl-8-(tetrahydrofuran-3-yloxy)-1H-imidazo[4,5-c]quinolin-4-amine. Parts B and C were combined by omitting the aqueous work up of Part B, in other words, the ammonium hydroxide and p-toluenesulfonyl chloride reagents used in Part C were added to the reaction mixture in Part B. The reaction was worked up as described in Part C of Example 405. 2-(Ethoxymethyl)-1-propyl-8-(tetrahydrofuran-3-yloxy)-1H-imidazo[4,5-c]quinolin-4-amine was isolated as tan needles, mp 173-175° C.

$^1$H NMR (300 MHz, DMSO-$d_6$) δ 7.56 (d, J=9.1 Hz, 1H), 7.34 (d, J=2.7 Hz, 1H), 7.11 (dd, J=9.1, 2.6 Hz, 1H), 6.36 (s, 2H), 5.21-5.14 (m, 1H), 4.78 (s, 2H), 4.58-4.48 (m, 2H), 3.97-3.76 (m, 4H), 3.56 (q, J=7.0 Hz, 2H), 2.31-2.19 (m, 1H), 2.13-2.04 (m, 1H), 1.97-1.84 (m, 2H), 1.16 (t, J=7.0 Hz, 3H), 1.02 (t, J=7.4 Hz, 3H);

$^{13}$C NMR (75 MHz, DMSO-$d_6$) δ 151.5, 150.6, 148.9, 140.4, 132.6, 127.8, 126.7, 117.8, 114.6, 103.3, 77.4, 72.2, 66.4, 65.3, 64.2, 46.8, 32.3, 23.3, 14.9, 10.8;

MS (ESI) m/z 371.2084 (371.2083 calcd for $C_{20}H_{26}N_4O_3$, M-+H$^+$).

Anal. calcd for $C_{20}H_{26}N_4O_3$: C, 64.85; H, 7.07; N, 15.12. Found: C, 64.50; H, 7.09; N, 15.29.

Example 407

N-(6-{[4-Amino-2-(ethoxymethyl)-1-propyl-1H-imidazo[4,5-c]quinolin-8-yl]oxy}hexyl)-2-methylpropanamide

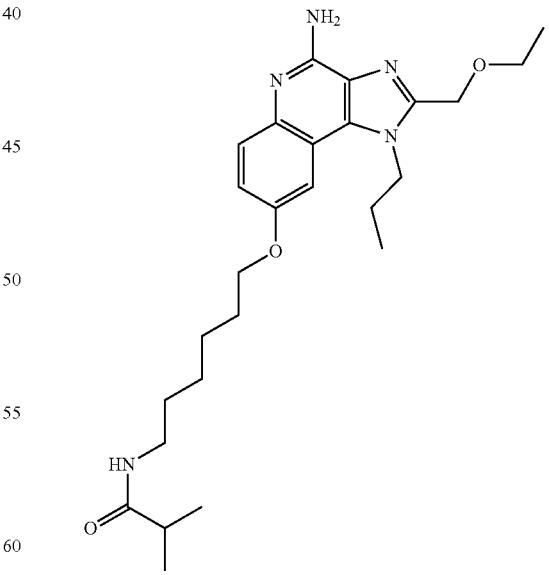

Part A

The synthesis of 2-(ethoxymethyl)-1-propyl-1H-imidazo[4,5-c]quinolin-8-ol is described in Parts A-I of Example 2.

The general method described in Part L of Example 2 was followed. 2-(Ethoxymethyl)-1-propyl-1H-imidazo[4,5-c]quinolin-8-ol (4.43 g, 15.5 mmol) was treated with tert-butyl 6-iodohexylcarbamate (prepared as described in Part F of Example 45, 6.1 g, 18.6 mmol). After the work up, the crude product was not purified to yield 9.9 g of tert-butyl 6-{[2-(ethoxymethyl)-1-propyl-1H-imidazo[4,5-c]quinolin-8-yl]oxy}hexylcarbamate as a tan waxy solid that contained DMF and dichloromethane.

Part B

A modification of the procedure described in Part B of Example 392 was used to convert the crude tert-butyl 6-{[2-(ethoxymethyl)-1-propyl-1H-imidazo[4,5-c]quinolin-8-yl]oxy}hexylcarbamate from Part A into tert-butyl 6-{[4-amino-2-(ethoxymethyl)-1-propyl-1H-imidazo[4,5-c]quinolin-8-yl]oxy}hexylcarbamate. The reaction mixture was transferred to a separatory funnel and the layers were separated. The aqueous layer was extracted with dichloromethane (2×100 mL). The organic layers were combined, washed with 5% aqueous sodium bicarbonate, water, and saturated aqueous sodium chloride. The organic layer was then dried over anhydrous sodium sulfate, filtered, and concentrated under reduced pressure. The crude product was purified by flash chromatography (silica gel, gradient elution 1-5% methanol in dichloromethane) to afford 4.60 g of tert-butyl 6-{[4-amino-2-(ethoxymethyl)-1-propyl-1H-imidazo[4,5-c]quinolin-8-yl]oxy}hexylcarbamate as a tan solid that contained some impurities but was used in the next step without further purification.

Part C

A solution of the material from Part B in 4.0 M ethanolic hydrogen chloride (22 mL) was heated at reflux for 1 hour. The solution was allowed to cool to room temperature and was concentrated under reduced pressure to yield an oily residue. Water (approximately 10 mL) and saturated aqueous sodium chloride (10 mL) were added to the oily residue, then the solution was adjusted to approximately pH 13 with 50% aqueous sodium hydroxide. The aqueous solution was extracted with 9:1 chloroform/methanol (2×100 mL). The organic layers were combined, dried over anhydrous magnesium sulfate, filtered, and concentrated under reduced pressure. The crude product was triturated with acetonitrile and a solid was isolated by filtration to afford 3.1 g of 8-(6-aminohexyloxy)-2-(ethoxymethyl)-1-propyl-1H-imidazo[4,5-c]quinolin-4-ylamine as a pale violet solid.

Part D

Isobutyryl chloride (0.236 mL, 2.25 mmol) was added dropwise, followed by triethylamine (0.2 mL, 1.4 mmol), to a stirred slurry of 8-(6-aminohexyloxy)-2-(ethoxymethyl)-1-propyl-1H-imidazo[4,5-c]quinolin-4-ylamine (0.900 g, 2.25 mmol) in dichloromethane (25 mL) at room temperature. After 30 minutes, water (15 mL) was added and the mixture was allowed to stir for 30 minutes. The layers were separated and the aqueous layer was extracted with dichlormethane. The organic layers were combined, washed with water and brine, dried over anhydrous sodium sulfate, filtered and concentrated under reduced pressure. Purification by flash chromatography (silica gel, gradient elution with 1-6% CMA in chloroform) followed by recrystallization from acetonitrile afforded 0.285 g of N-(6-{[4-amino-2-(ethoxymethyl)-1-propyl-1H-imidazo[4,5-c]quinolin-8-yl]oxy}hexyl)-2-methylpropanamide as a white crystalline solid, mp 136-138° C.

$^1$H NMR (300 MHz, DMSO-$d_6$) δ 7.64 (t, J=5.5 Hz, 1H), 7.53 (d, J=9.1 Hz, 1H), 7.35 (d, J=2.6 Hz, 1H), 7.10 (dd, J=9.1, 2.6 Hz, 1H), 6.31 (s, 2H), 4.76 (s, 2H), 4.53-4.48 (m, 2H), 4.07 (t, J=6.5 Hz, 2H), 3.54 (q, J=7.0 Hz, 2H), 3.02 (q, J=6.1 Hz, 2H), 2.37-2.23 (m, 1H), 1.96-1.83 (m, 2H), 1.80-1.71 (m, 2H), 1.50-1.26 (m, 6H), 1.15 (t, J=7.0 Hz, 3H), 1.02 (t, J=7.4 Hz, 3H), 0.96 (d, J=6.9 Hz, 6H);

$^{13}$C NMR (75 MHz, DMSO-$d_6$) δ 175.8, 153.2, 150.5, 148.8, 139.9, 132.7, 127.6, 126.6, 117.2, 114.6, 102.1, 67.6, 65.3, 64.2, 46.7, 38.2, 34.0, 29.1, 28.7, 26.1, 25.3, 23.3, 19.6, 14.9, 10.7;

MS (ESI) m/z 470.3118 (470.3131 calcd for $C_{26}H_{39}N_5O_3$, M+H$^+$).

Anal. calcd for $C_{26}H_{39}N_5O_3$: C, 66.50; H, 8.37; N, 14.91. Found: C, 66.24; H, 8.35; N, 14.77.

Example 408

N-(6-{[4-Amino-2-(ethoxymethyl)-1-propyl-1H-imidazo[4,5-c]quinolin-8-yl]oxy}hexyl)-N'-isopropylurea

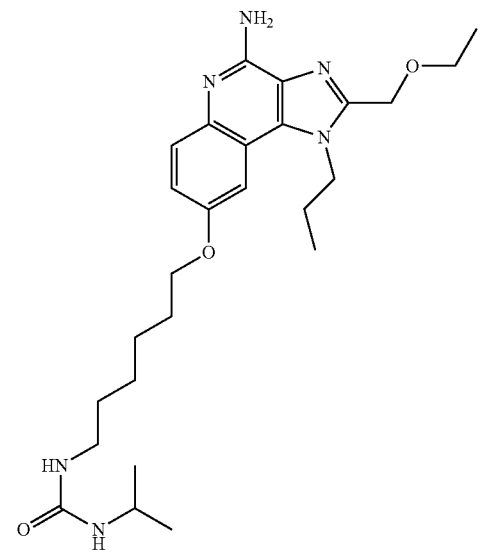 [SMILES: CCCn1c(COCC)nc2c(N)nc3ccc(OCCCCCCNC(=O)NC(C)C)cc3c21]

A modification of the procedure described in Part A of Example 369 was used to convert 8-(6-aminohexyloxy)-2-(ethoxymethyl)-1-propyl-1H-imidazo[4,5-c]quinolin-4-ylamine (prepared as described in Parts A-C of Example 407, 0.900 g, 2.25 mmol) into N-(6-{[4-amino-2-(ethoxymethyl)-1-propyl-1H-imidazo[4,5-c]quinolin-8-yl]oxy}hexyl)-N'-isopropylurea. The crude product was purified by flash chromatography followed by recrystallization from acetonitrile to provide 0.528 g of N-(6-{[4-amino-2-(ethoxymethyl)-1-propyl-1H-imidazo[4,5-c]quinolin-8-yl]oxy}hexyl)-N'-isopropylurea as flocculent white crystals, mp 167-169° C.

$^1$H NMR (300 MHz, DMSO-$d_6$) δ 7.53 (d, J=9.1 Hz, 1H), 7.35 (d, J=2.6 Hz, 1H), 7.10 (dd, J=9.1, 2.6 Hz, 1H), 6.31 (s, 2H), 5.63 (t, J=5.6 Hz, 1H), 5.54 (d, J=7.7 Hz, 1H), 4.76 (s, 2H), 4.53-4.48 (m, 2H), 4.07 (t, J=6.5 Hz, 2H), 3.70-3.57 (m, 1H), 3.54 (q, J=7.0 Hz, 2H), 2.96 (q, J=6.1 Hz, 2H), 1.96-1.83 (m, 2H), 1.80-1.71 (m, 2H), 1.49-1.26 (m, 6H), 1.15 (t, J=7.0 Hz, 3H), 1.02 (t, J=7.3 Hz, 3H), 0.98 (d, J=6.5 Hz, 6H);
$^{13}$C NMR (75 MHz, DMSO-$d_6$) δ 157.4, 153.2, 150.5, 148.8, 139.9, 132.7, 127.6, 126.6, 117.2, 114.6, 102.1, 67.7, 65.3, 64.2, 46.8, 40.7, 39.0, 30.0, 28.7, 26.2, 25.3, 23.3, 23.2, 14.9, 10.7;
MS (ESI) m/z 485.3237 (485.3240 calcd for $C_{26}H_{40}N_6O_3$, M+H$^+$).
Anal. calcd for $C_{26}H_{40}N_6O_3$: C, 64.44; H, 8.32; N, 17.34. Found: C, 64.15; H, 8.43; N, 17.21.

Example 409

N-(6-{[4-Amino-2-(ethoxymethyl)-1-propyl-1H-imidazo[4,5-c]quinolin-8-yl]oxy}hexyl)methanesulfonamide

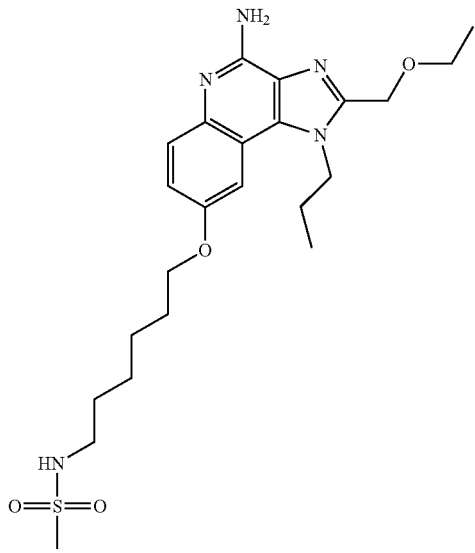 [SMILES: CCCn1c(COCC)nc2c(N)nc3ccc(OCCCCCCNS(C)(=O)=O)cc3c21]

A modification of the procedure described in Part D of Example 407 was used to convert 8-(6-aminohexyloxy)-2-(ethoxymethyl)-1-propyl-1H-imidazo[4,5-c]quinolin-4-ylamine (prepared as described in Parts A-C of Example 407, 0.900 g, 2.25 mmol) into N-(6-{[4-amino-2-(ethoxymethyl)-1-propyl-1H-imidazo[4,5-c]quinolin-8-yl]oxy}hexyl)methanesulfonamide. The reaction was run using methanesulfonyl chloride (0.174 mL, 2.25 mmol) in lieu of isobutyryl chloride and without triethylamine. The reaction was quenched with saturated aqueous sodium carbonate (10 mL) instead of water. The crude product was purified by flash chromatography followed by recrystallization from acetonitrile to afford 0.350 g of N-(6-{[4-amino-2-(ethoxymethyl)-1-propyl-1H-imidazo[4,5-c]quinolin-8-yl]oxy}hexyl)methanesulfonamide as flocculent white crystals, mp 164-167° C.
$^1$H NMR (300 MHz, DMSO-$d_6$) δ 7.53 (d, J=9.1 Hz, 1H), 7.36 (d, J=2.6 Hz, 1H), 7.10 (dd, J=9.1, 2.6 Hz, 1H), 6.91 (t, J=5.8 Hz, 1H), 6.31 (s, 2H), 4.76 (s, 2H), 4.54-4.48 (m, 2H), 4.08 (t, J=6.5 Hz, 2H), 3.54 (q, J=7.0 Hz, 2H), 2.92 (q, J=6.6 Hz, 2H), 2.86 (s, 3H), 1.96-1.84 (m, 2H), 1.81-1.72 (m, 2H), 1.53-1.31 (m, 6H), 1.15 (t, J=7.0 Hz, 3H), 1.02 (t, J=7.4 Hz, 3H);
$^{13}$C NMR (75 MHz, DMSO-$d_6$) δ 153.2, 150.5, 148.8, 139.9, 132.7, 127.6, 126.6, 117.2, 114.6, 102.1, 67.6, 65.3, 64.2, 46.8, 42.4, 39.1, 29.4, 28.6, 25.9, 25.2, 23.3, 14.9, 10.7;
MS (ESI) m/z 478.2485 (478.2488 calcd for $C_{23}H_{35}N_5O_4S$, M+H$^+$).
Anal. calcd for $C_{23}H_{35}N_5O_4S$: C, 57.84; H, 7.39; N, 14.66. Found: C, 57.97; H, 7.60; N, 14.67.

Example 410 tert-Butyl 4-{[4-amino-2-(ethoxymethyl)-1-propyl-1H-imidazo[4,5-c]quinolin-8-yl]oxy}piperidine-1-carboxylate

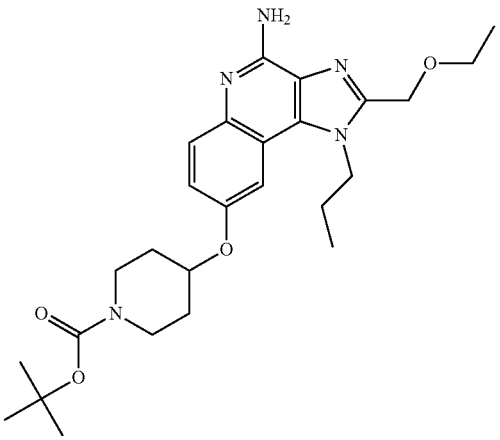 [SMILES: CCCn1c(COCC)nc2c(N)nc3ccc(OC4CCN(C(=O)OC(C)(C)C)CC4)cc3c21]

Part A

The synthesis of 2-(ethoxymethyl)-1-propyl-1H-imidazo[4,5-c]quinolin-8-ol is described in Parts A-I of Example 2. The general method described in Part A of Example 374 was followed starting with 2-(ethoxymethyl)-1-propyl-1H-imidazo[4,5-c]quinolin-8-ol (6.0 g, 21.0 mmol). The crude product was purified by flash chromatography (silica gel, gradient elution with 1-7% CMA in chloroform) to yield 9.76 g of tert-butyl 4-{[2-(ethoxymethyl)-1-propyl-1H-imidazo[4,5-c]quinolin-8-yl]oxy}piperidine-1-carboxylate as a slightly impure tan semi-solid that was used in the next step without further purification.

Part B

A solution of the material from Part A (9.7 g, 20.7 mmol) and 32% peracetic acid in acetic acid (7.36 mL, 31.0 mmol) in ethyl acetate (69 mL) was heated at 50° C. for 3.5 hours. A solution of sodium metabisulfite (4.92 g, 25.9 mmol) in water (10 mL) was added over 15 minutes. The reaction mixture was allowed to stir at 50° C. for 30 minutes. Heating was discontinued and the reaction was adjusted to pH 10 with 50% aqueous sodium hydroxide. The mixture was allowed to cool to ambient temperature and was transferred to a separatory funnel. The layers were separated and the aqueous layer was extracted with ethyl acetate. The organic layers were combined and washed with water and saturated aqueous sodium chloride. The aqueous layers were combined and were back-extracted with dichloromethane. All the organic layers were combined, dried over anhydrous sodium sulfate, filtered, and concentrated under reduced pressure. The crude product was purified by chromatography on a HORIZON HPFC system (silica gel, gradient elution with 10-22% CMA in chloroform) to yield 4.5 g of tert-butyl 4-{[2-(ethoxymethyl)-5-oxido-1-propyl-1H-imidazo[4,5-c]quinolin-8-yl]oxy}piperidine-1-carboxylate as a orange-white solid.

Part C

Trichloroacetyl isocyanate (1.22 mL, 10.2 mmol) was added dropwise a stirred solution of tert-butyl 4-{[2-(ethoxymethyl)-5-oxido-1-propyl-1H-imidazo[4,5-c]quinolin-8-yl]oxy}piperidine-1-carboxylate (4.5 g, 9.29 mmol) in dichloromethane (90 mL) at room temperature. After 1.5 hours, ammonium hydroxide (4.5 mL) was added and the mixture was allowed to stir for 1 hour. Saturated aqueous sodium carbonate (60 mL) and water (20 mL) were added to the mixture. After 30 minutes, the mixture was transferred to a separatory funnel and the layers were separated. The aqueous layer was extracted with chloroform (2×100 mL). The organic layers were combined, washed with water and saturated aqueous sodium chloride, dried over anhydrous sodium sulfate, filtered, and concentrated under reduced pressure. The crude product was purified by chromatography on a HORIZON HPFC system (silica gel, gradient elution with 1-25% CMA in chloroform) followed by recrystallization from acetonitrile to yield 2.3 g of tert-butyl 4-{[4-amino-2-(ethoxymethyl)-1-propyl-1H-imidazo[4,5-c]quinolin-8-yl]oxy}piperidine-1-carboxylate as a gray solid, mp 179.5-181° C.

$^1$H NMR (300 MHz, DMSO-d$_6$) δ 7.55 (d, J=9.0 Hz, 1H), 7.42 (d, J=2.5 Hz, 1H), 7.16 (dd, J=9.0, 2.6 Hz, 1H), 6.36 (s, 2H), 4.77 (s, 2H), 4.69-4.61 (m, 1H), 4.55-4.50 (m, 2H), 3.75-3.65 (m, 2H), 3.56 (q, J=7.0 Hz, 2H), 3.28-3.15 (m, 2H), 2.01-1.82 (m, 4H), 1.68-1.54 (m, 2H), 1.41 (s, 9H), 1.16 (t, J=7.0 Hz, 3H), 1.03 (t, J=7.4 Hz, 3H);

MS (ESI) m/z 484.5 (M+H)$^+$;

Anal. calcd for C$_{26}$H$_{37}$N$_5$O$_4$: C, 64.57; H, 7.71; N, 14.48. Found: C, 64.33; H, 7.91; N, 14.52.

Example 411

2-(Ethoxymethyl)-8-(piperidin-4-yloxy)-1-propyl-1H-imidazo[4,5-c]quinolin-4-amine

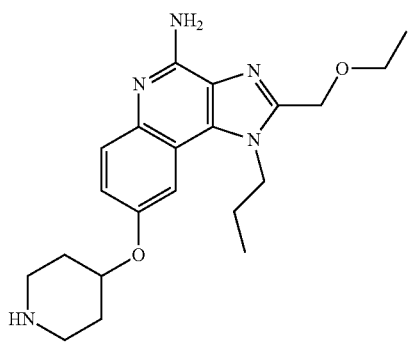 [SMILES: CCCn1c(COCC)nc2c(N)nc3ccc(OC4CCNCC4)cc3c21]

A solution of tert-butyl 4-{[4-amino-2-(ethoxymethyl)-1-propyl-1H-imidazo[4,5-c]quinolin-8-yl]oxy}piperidine-1-carboxylate (prepared as described in Example 410, 2.9 g, 6.0 mmol) and 4 M ethanolic hydrogen chloride (15 mL) in ethanol (20 mL) was heated at reflux for 2 hours. The solution was allowed to cool to ambient temperature and was concentrated under reduced pressure to approximately 17 mL, causing a solid to form. Water was added to dissolve the solid and the remainder of the ethanol was evaporated under reduced pressure. The aqueous solution was adjusted to approximately pH 13 with 50% aqueous sodium hydroxide, then was extracted with chloroform. The organic layers were combined, washed with water and saturated aqueous sodium chloride, dried over anhydrous sodium sulfate, filtered, and concentrated under reduced pressure. The product was recrystallization from acetonitrile to yield 1.25 g of 2-(ethoxymethyl)-8-(piperidin-4-yloxy)-1-propyl-1H-imidazo[4,5-c]quinolin-4-amine as off-white needles, mp 176-178° C.

$^1$H NMR (300 MHz, DMSO-d$_6$) δ 7.54 (d, J=9.0 Hz, 1H), 7.39 (d, J=2.6 Hz, 1H), 7.11 (dd, J=9.0, 2.6 Hz, 1H), 6.33 (s, 2H), 4.77 (s, 2H), 4.54-4.44 (m, 3H), 3.56 (q, J=7.0 Hz, 2H), 3.02-2.95 (m, 2H), 2.62-2.54 (m, 2H), 2.07-1.83 (m, 5H), 1.57-1.45 (m, 2H), 1.16 (t, J=7.0 Hz, 3H), 1.04 (t, J=7.4 Hz, 3H);

$^{13}$C NMR (75 MHz, DMSO-d$_6$) δ 151.4, 150.5, 148.8, 140.0, 132.6, 127.7, 126.6, 118.5, 114.6, 104.0, 74.1, 65.3, 64.2, 46.8, 43.8, 32.4, 23.3, 14.9, 10.7;

MS (ESI) m/z 384.2414 (384.2400 calcd for C$_{21}$H$_{29}$N$_5$O$_2$, M+H$^+$).

Anal. calcd for C$_{21}$H$_{29}$N$_5$O$_2$: C, 65.77; H, 7.62; N, 18.26. Found: C, 65.55; H, 7.60; N, 18.17.

Example 412

4-{[4-Amino-2-(ethoxymethyl)-1-propyl-1H-imidazo[4,5-c]quinolin-8-yl]oxy}-N-isopropylpiperidine-1-carboxamide

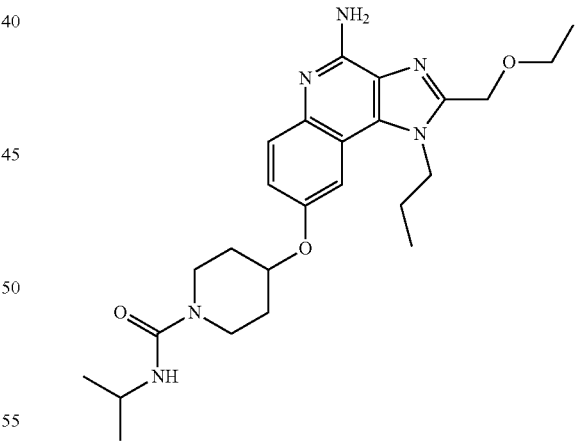

Isopropyl isocyanate (0.190 mL, 1.90 mmol) was added dropwise to a solution of 2-(ethoxymethyl)-8-(piperidin-4-yloxy)-1-propyl-1H-imidazo[4,5-c]quinolin-4-amine (prepared as described in Example 411, 0.730 g, 1.90 mmol) in dichloromethane (15 mL) at room temperature. The reaction was diluted with dichloromethane and stirred vigorously. A precipitate formed that was isolated by filtration to afford 0.743 g of 4-{[4-amino-2-(ethoxymethyl)-1-propyl-1H-imidazo[4,5-c]quinolin-8-yl]oxy}-N-isopropylpiperidine-1-carboxamide as a white solid, mp 236.5-239° C.

$^1$H NMR (300 MHz, DMSO-$d_6$) δ 7.55 (d, J=9.0 Hz, 1H), 7.42 (d, J=2.5 Hz, 1H), 7.15 (dd, J=9.0, 2.5 Hz, 1H), 6.35 (s, 2H), 6.20 (t, J=7.6 Hz, 1H), 4.78 (s, 2H), 4.67-4.59 (m, 1H), 4.55-4.50 (m, 2H), 3.82-3.69 (m, 3H), 3.56 (q, J=7.0 Hz, 2H), 3.16-3.07 (m, 2H), 2.01-1.82 (m, 4H), 1.65-1.49 (m, 2H), 1.16 (t, J=7.0 Hz, 3H), 1.06 (d, J=6.6 Hz, 6H), 1.03 (t, J=7.4 Hz, 3H);

$^{13}$C NMR (125 MHz, DMSO-$d_6$) δ 156.7, 151.3, 150.6, 148.9, 140.2, 132.6, 127.7, 126.6, 118.4, 114.7, 104.6, 73.0, 65.3, 64.2, 46.7, 41.7, 40.9, 30.5, 23.2, 22.9, 14.9, 10.8;

MS (ESI) m/z 469.2936 (469.2927 calcd for $C_{25}H_{36}N_6O_3$, M+H$^+$).

Anal. calcd for $C_{25}H_{36}N_6O_3$: C, 64.08; H, 7.74; N, 17.93. Found: C, 63.85; H, 7.67; N, 17.89.

Example 413

2-(Ethoxymethyl)-8-{[1-(methylsulfonyl)piperidin-4-yl]oxy}-1-propyl-1H-imidazo[4,5-c]quinolin-4-amine

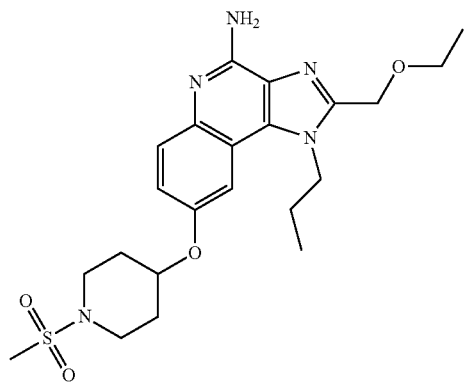 [SMILES: CCCn1c(COCC)nc2c(N)nc3ccc(OC4CCN(S(C)(=O)=O)CC4)cc3c21]

Methanesulfonic anhydride (0.295 g, 1.69 mmol) was added in one portion to a stirred solution of 2-(ethoxymethyl)-8-(piperidin-4-yloxy)-1-propyl-1H-imidazo[4,5-c]quinolin-4-amine (prepared as described in Example 411, 0.650 g, 1.69 mmol) in dichloromethane (15 mL) at room temperature, resulting in a white precipitate. After 16 hours, 2.0 M aqueous sodium carbonate was added and the reaction mixture was allowed to stir for 45 minutes. The precipitate dissolved and the mixture was transferred to a separatory funnel where the layers were separated. The aqueous layer was extracted with chloroform. The organic layers were combined, washed with water and brine, dried over anhydrous sodium sulfate, filtered, and concentrated under reduced pressure. The crude product was purified by trituration in boiling acetonitrile and isolated by filtration to yield 0.650 g of 2-(ethoxymethyl)-8-{[1-(methylsulfonyl)piperidin-4-yl]oxy}-1-propyl-1H-imidazo[4,5-c]quinolin-4-amine as an off-white crystalline solid, mp 240-243.5° C.

$^1$H NMR (300 MHz, DMSO-$d_6$) δ 7.57 (d, J=9.0 Hz, 1H), 7.43 (d, J=2.5 Hz, 1H), 7.18 (dd, J=9.0, 2.5 Hz, 1H), 6.38 (s, 2H), 4.78 (s, 2H), 4.70-4.61 (m, 1H), 4.55-4.50 (m, 2H), 3.56 (q, J=7.0 Hz, 2H), 3.44-3.36 (m, 2H), 3.20-3.12 (m, 2H), 2.92 (s, 3H), 2.10-2.00 (m, 2H), 1.95-1.79 (m, 4H), 1.16 (t, J=7.0 Hz, 3H), 1.03 (t, J=7.4 Hz, 3H);

$^{13}$C NMR (125 MHz, DMSO-$d_6$) δ 151.3, 150.7, 148.9, 140.3, 132.6, 127.7, 126.6, 118.4, 114.7, 105.0, 71.4, 65.3, 64.2, 46.7, 42.5, 34.4, 29.8, 23.2, 14.9, 10.8;

MS (ESI) m/z 462.2172 (462.2175 calcd for $C_{22}H_{31}N_5O_4S$, M+H$^+$).

Anal. calcd for $C_{22}H_{31}N_5O_4S \cdot 0.15CHCl_3$: C, 55.49; H, 6.55; N, 14.61; Cl, 3.33. Found: C, 55.51; H, 6.71; N, 14.66; Cl, 3.25.

Example 414

2-(Ethoxymethyl)-8-[(1-isobutyrylpiperidin-4-yl)oxy]-1-propyl-1H-imidazo[4,5-c]quinolin-4-amine

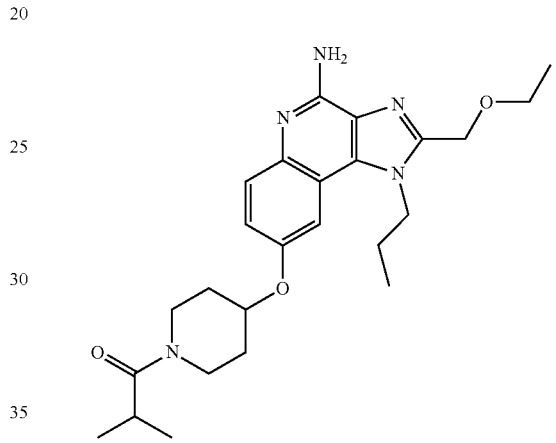

A modification of the procedure described in Example 413 was used. 2-(Ethoxymethyl)-8-(piperidin-4-yloxy)-1-propyl-1H-imidazo[4,5-c]quinolin-4-amine (prepared as described in Example 411, 0.650 g, 1.69 mmol) was treated with isobutyryl chloride instead of the methanesulfonic anhydride. After the work up, the crude product was purified by chromatography on a HORIZON HPFC system (silica gel, gradient elution with 2-25% CMA in chloroform) followed by recrystallization from acetonitrile to yield 0.500 g of 2-(ethoxymethyl)-8-[(1-isobutyrylpiperidin-4-yl)oxy]-1-propyl-1H-imidazo[4,5-c]quinolin-4-amine as a white solid, mp 177-179° C.

$^1$H NMR (300 MHz, DMSO-$d_6$) δ 7.56 (d, J=9.0 Hz, 1H), 7.44 (d, J=2.6 Hz, 1H), 7.17 (dd, J=9.1, 2.6 Hz, 1H), 6.36 (s, 2H), 4.78 (s, 2H), 4.78-4.68 (m, 1H), 4.55-4.50 (m, 2H), 3.96-3.74 (m, 2H), 3.56 (q, J=7.0 Hz, 2H), 3.46-3.36 (m, 1H), 2.98-2.83 (m, 1H), 2.09-1.80 (m, 4H), 1.76-1.53 (m, 2H), 1.16 (t, J=7.0 Hz, 3H), 1.03 (t, J=7.4 Hz, 3H), 1.01 (d, J=6.7 Hz, 6H);

$^{13}$C NMR (125 MHz, DMSO-$d_6$) δ 174.1, 151.2, 150.6, 148.9, 140.2, 132.6, 127.7, 126.6, 118.3, 114.6, 104.8, 72.6, 65.3, 64.2, 46.7, 41.9, 38.3, 31.3, 30.3, 28.9, 23.2, 19.4, 14.9, 10.7;

MS (ESI) m/z 454.2819 (454.2818 calcd for $C_{25}H_{35}N_5O_3$, M+H$^+$).

Anal. calcd for $C_{25}H_{35}N_5O_3$: C, 66.20; H, 7.78; N, 15.44. Found: C, 66.05; H, 7.72; N, 15.57.

Example 415 tert-Butyl 4-{[4-amino-2-(ethoxymethyl)-1-propyl-1H-imidazo[4,5-c]quinolin-7-yl]oxy}piperidine-1-carboxylate

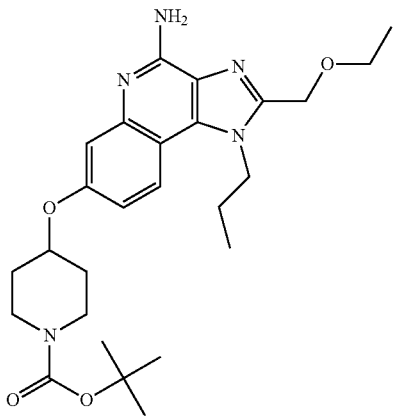 [SMILES: CCCn1c(COCC)nc2c(N)nc3cc(OC4CCN(C(=O)OC(C)(C)C)CC4)ccc3c21]

Part A 2-(Ethoxymethyl)-1-propyl-1H-imidazo[4,5-c]quinolin-7-ol (3.00 g, 10.5 mmol) and triphenylphosphine (3.43 g, 13.1 mmol) were slurried in THF (105 mL) and cooled with an ice/water bath. tert-Butyl 4-hydroxypiperidine-1-carboxylate (2.64 g, 13.1 mmol) was added followed by the dropwise addition of diisopropyl azodicarboxylate (2.58 mL, 13.1 mmol). The water bath was removed and the mixture was stirred for 72 hours under nitrogen. The solvent was removed under reduced pressure and the residue was purified by chromatography on a HORIZON HPFC system (silica gel, gradient elution with 1-15% CMA in chloroform) to afford 5.17 g of tert-butyl 4-{[2-(ethoxymethyl)-1-propyl-1H-imidazo[4,5-c]quinolin-7-yl]oxy}piperidine-1-carboxylate as an off-white crystalline solid.

Part B

To a stirring solution of tert-butyl 4-{[2-(ethoxymethyl)-1-propyl-1H-imidazo[4,5-c]quinolin-7-yl]oxy}piperidine-1-carboxylate (5.17 g, 10.5 mmol) in chloroform (100 mL) was added 3-chloroperoxybenzoic acid (3.62 g, 10.5 mmol, based on 50% purity). After 30 minutes, concentrated ammonium hydroxide (50 mL) was added and the mixture was stirred for 30 minutes. p-Toluenesulfonyl chloride (2.00 g, 10.5 mmol) was added in 3 portions and the mixture was stirred for 16 hours. The layers were separated and the organic fraction was sequentially washed with 5% aqueous sodium bicarbonate, water, and saturated aqueous sodium chloride. The organic fraction was dried over anhydrous sodium sulfate, filtered and evaporated under reduced pressure. Recrystallization from acetonitrile afforded 2.58 g of tert-butyl 4-{[4-amino-2-(ethoxymethyl)-1-propyl-1H-imidazo[4,5-c]quinolin-7-yl]oxy}piperidine-1-carboxylate as a reddish-tan crystalline solid, mp 194-195° C.

$^1$H NMR (300 MHz, DMSO-d$_6$) δ 7.90 (d, J=9.0 Hz, 1H), 7.11 (d, J=2.6 Hz, 1H), 6.95 (dd, J=9.0, 2.6 Hz, 1H), 6.51 (s, 2H), 4.75 (s, 2H), 4.71-4.60 (m, 1H), 4.53-4.41 (m, 2H), 3.77-3.65 (m, 2H), 3.56 (q, J=7.0 Hz, 2H), 3.27-3.12 (m, 2H), 2.03-1.91 (m, 2H), 1.91-1.78 (m, 2H), 1.64-1.49 (m, 2H), 1.41 (s, 9H), 1.16 (t, J=7.0 Hz, 3H), 1.00 (t, J=7.4 Hz, 3H);

MS (ESI) m/z 484.3 (M+H)$^+$;

Anal. calcd for C$_{26}$H$_{37}$N$_5$O$_4$: C, 64.57; H, 7.71; N, 14.48. Found: C, 64.36; H, 7.66; N, 14.65.

Example 416

2-(Ethoxymethyl)-7-(piperidin-4-yloxy)-1-propyl-1H-imidazo[4,5-c]quinolin-4-amine

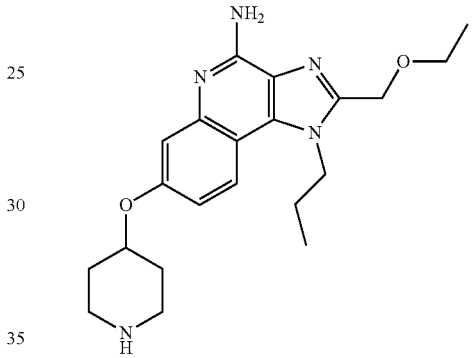

tert-Butyl 4-{[4-amino-2-(ethoxymethyl)-1-propyl-1H-imidazo[4,5-c]quinolin-7-yl]oxy}piperidine-1-carboxylate (2.45 g, 5.07 mmol) was taken up in 4.0M ethanolic hydrogen chloride (15 mL) and heated to 65° C. for 1 hour. The heat was removed and the reaction was allowed to cool to ambient temperature. The ethanol was removed under reduced pressure and the solid residue was dissolved in water (10 mL) and saturated aqueous sodium chloride (10 mL). The solution was brought to pH 13 with 50% aqueous sodium hydroxide and then extracted with chloroform. The organic fraction was sequentially washed with water and saturated aqueous sodium chloride, dried over anhydrous sodium sulfate, filtered and evaporated. Trituration with acetonitrile, followed by filtration afforded 1.70 g of 2-(ethoxymethyl)-7-(piperidin-4-yloxy)-1-propyl-1H-imidazo[4,5-c]quinolin-4-amine as a tan solid, mp 202-204° C.

$^1$H NMR (300 MHz, DMSO-d$_6$) δ 7.89 (d, J=9.0 Hz, 1H), 7.07 (d, J=2.5 Hz, 1H), 6.92 (dd, J=9.0, 2.5 Hz, 1H), 6.51 (s, 2H), 4.74 (s, 2H), 4.54-4.39 (m, 3H), 3.55 (q, J=7.0 Hz, 2H), 3.03-2.90 (m, 2H), 2.67-2.54 (m, 2H), 2.03-1.78 (m, 5H), 1.57-1.40 (m, 2H), 1.16 (t, J=7.0 Hz, 3H), 1.00 (t, J=7.3 Hz, 3H);

MS (ESI) m/z 384.2 (M+H)$^+$;

Anal. calcd for C$_{21}$H$_{29}$N$_5$O$_2$: C, 65.77; H, 7.62; N, 18.26. Found: C, 65.61; H, 7.62; N, 18.23.

Example 417

4-{[4-Amino-2-(ethoxymethyl)-1-propyl-1H-imidazo[4,5-c]quinolin-7-yl]oxy}-N-isopropylpiperidine-1-carboxamide

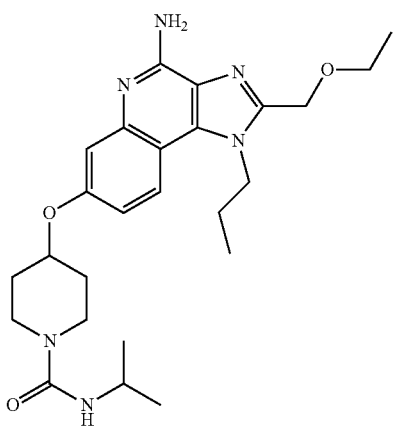

2-(Ethoxymethyl)-7-(piperidin-4-yloxy)-1-propyl-1H-imidazo[4,5-c]quinolin-4-amine (0.500 g, 1.3 mmol) was slurried in dichloromethane (13 mL). Isopropyl isocyanate was added dropwise to the slurry and the reaction was stirred for 16 hours. The reaction was purified by chromatography on a HORIZON HPFC system (silica gel, gradient elution with 2-22% CMA in chloroform) followed by recrystallization from acetonitrile yielded 0.430 g of 4-{[4-amino-2-(ethoxymethyl)-1-propyl-1H-imidazo[4,5-c]quinolin-7-yl]oxy}-N-isopropylpiperidine-1-carboxamide as a white solid, mp 163-164.5° C.

$^1$H NMR (300 MHz, DMSO-$d_6$) δ 7.90 (d, J=9.0 Hz, 1H), 7.11 (d, J=2.6 Hz, 1H), 6.94 (dd, J=9.0, 2.6 Hz, 1H), 6.52 (s, 2H), 6.19 (d, J=7.6 Hz, 1H), 4.75 (s, 2H), 4.58-4.52 (m, 1H), 4.52-4.41 (m, 2H), 3.84-3.66 (m, 3H), 3.55 (q, J=7.0 Hz, 2H), 3.18-3.04 (m, 2H), 2.02-1.77 (m, 4H), 1.62-1.44 (m, 2H), 1.16 (t, J=7.0 Hz, 3H), 1.06 (d, J=6.6 Hz, 6H), 1.00 (t, J=7.3 Hz, 3H);

$^{13}$C NMR (125 MHz, DMSO-$d_6$) δ 156.7, 155.9, 152.3, 148.1, 147.0, 133.4, 124.9, 121.4, 112.6, 109.8, 108.9, 72.3, 65.3, 64.2, 46.7, 41.7, 40.9, 30.5, 23.0, 22.9, 14.9, 10.7;

MS (APCI) m/z 469.3 (M+H)$^+$;

Anal. calcd for $C_{25}H_{36}N_6O_3 \cdot 0.4H_2O$: C, 63.11; H, 7.80; N, 17.66. Found: C, 63.20; H, 7.94; N, 17.92.

Examples 418-422

A solution of 1 M boron tribromide in heptane (400 µL) was added to a 0° C., stirred solution of a starting material from the table below (approximately 25 mg) in dichloromethane (1 mL). The reaction mixture was stirred at 0° C. for 30 minutes and then at room temperature overnight. Methanol (1 mL) and 6 M aqueous hydrochloric acid (250 µL) was added to each reaction vessel, which was vortexed shortly afterwards. The volatiles were removed by vacuum centrifugation. The compounds were purified using the method described in Examples 376-386. The table below shows the starting material added to each reaction vessel, the structure of the resulting compound, and the observed accurate mass for the isolated trifluoroacetate salt.

Examples 418-422

| Example | Starting Material | R | Measured Mass (M + H) |
|---|---|---|---|
| 418 | Example 56 | 3-methyltetrahydrofuran-yl | 357.1910 |
| 419 | Example 366 | CH$_3$CH(NHC(O)CH$_3$)– | 372.2025 |
| 420 | Example 394 | H$_2$N(CH$_2$)$_4$– | 344.2099 |
| 421 | Example 389 | CH$_3$CH(CH$_3$)C(O)-(4-methylpiperidin-1-yl) | 440.2666 |
| 422 | Example 388 | CH$_3$CH(CH$_3$)NHC(O)-(4-methylpiperidin-1-yl) | 455.2815 |

Examples 423-438

A reagent (0.11 mmol, 1.1 equivalents) from the table below was added to a test tube containing 3-[4-amino-7-(2-aminoethoxy)-2-(ethoxymethyl)-1H-imidazo[4,5-c]quinolin-1-yl]propane-1,2-diol dihydrochloride (45 mg, 0.1 mmol, prepared as described in Example 373) and N,N-diisopropylethylamine (0.071 mL, 0.40 mmol) in N,N-dimethylacetamide (1 mL). The test tubes were capped and shaken overnight at room temperature and then two drops of water were added to each test tube. The solvent was removed by vacuum centrifugation. The compounds were purified using the method described in Examples 376-386. The table below shows the reagent added to each test tube, the structure of the resulting compound, and the observed accurate mass for the isolated trifluoroacetate salt.

Examples 423-438

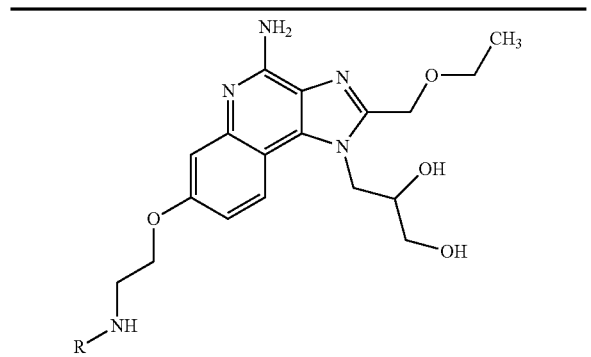

| Example | Reagent | R | Measured Mass (M + H) |
|---|---|---|---|
| 423 | None | H– | 376.2022 |
| 424 | Acetyl chloride | H₃C–C(=O)– | 418.2082 |
| 425 | Cyclopropanecarbonyl chloride | cyclopropyl-C(=O)– | 444.2210 |
| 426 | Butyryl chloride | CH₃CH₂CH₂–C(=O)– | 446.2388 |
| 427 | Isobutyryl chloride | (CH₃)₂CH–C(=O)– | 446.2406 |
| 428 | Benzoyl chloride | Ph–C(=O)– | 480.2225 |
| 429 | Isonicotinoyl chloride hydrochloride | 4-pyridyl–C(=O)– | 481.2214 |
| 430 | Nicotinoyl chloride hydrochloride | 3-pyridyl–C(=O)– | 481.2206 |

-continued

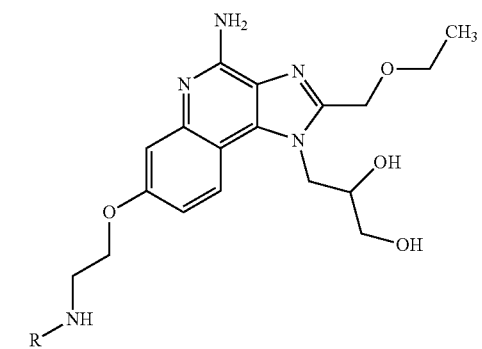

| Example | Reagent | R | Measured Mass (M + H) |
|---|---|---|---|
| 431 | Methanesulfonyl chloride | H₃C–S(=O)₂– | 454.1791 |
| 432 | Ethanesulfonyl chloride | CH₃CH₂–S(=O)₂– | 468.1954 |
| 433 | 1-Propanesulfonyl chloride | CH₃CH₂CH₂–S(=O)₂– | 482.2046 |
| 434 | Isopropylsulfonyl chloride | (CH₃)₂CH–S(=O)₂– | 482.2057 |
| 435 | Dimethylsulfamoyl chloride | (CH₃)₂N–S(=O)₂– | 483.2048 |
| 436 | 1-Butanesulfonyl chloride | CH₃CH₂CH₂CH₂–S(=O)₂– | 496.2247 |

223

-continued

| Example | Reagent | R | Measured Mass (M + H) |
|---|---|---|---|
| 437 | Benzenesulfonyl chloride | (phenylsulfonyl) | 516.1933 |
| 438 | 1-Methylimidazole-4-sulfonyl chloride | (1-methylimidazol-4-yl sulfonyl) | 520.1968 |

Examples 439-459

The free base of 3-[4-amino-2-(ethoxymethyl)-7-(piperidin-4-yloxy)-1H-imidazo[4,5-c]quinolin-1-yl]propane-1,2-diol dihydrochloride (prepared as described in Example 375) was prepared. A reagent (0.11 mmol, 1.1 equivalents) from the table below was added to a test tube containing 3-[4-amino-2-(ethoxymethyl)-7-(piperidin-4-yloxy)-1H-imidazo[4,5-c]quinolin-1-yl]propane-1,2-diol (42 mg, 0.10 mmol) and N,N-diisopropylethylamine (0.033 mL, 0.20 mmol) in N,N-dimethylacetamide (1 mL). The test tubes were capped and shaken overnight at room temperature and then two drops of water were added to each test tube. The solvent was removed by vacuum centrifugation. The compounds were purified using the method described in Examples 376-386. The table below shows the reagent added to each test tube, the structure of the resulting compound, and the observed accurate mass for the isolated trifluoroacetate salt.

224

Examples 439-459

| Example | Reagent | R | Measured Mass (M + H) |
|---|---|---|---|
| 439 | None | H | 416.2302 |
| 440 | Methyl chloroformate | (methoxycarbonyl) | 474.2354 |
| 441 | Cyclopropanecarbonyl chloride | (cyclopropanecarbonyl) | 484.2601 |
| 442 | Isobutyryl chloride | (isobutyryl) | 486.2735 |
| 443 | Cyclopentanecarbonyl chloride | (cyclopentanecarbonyl) | 512.2896 |
| 444 | Cyclohexanecarbonyl chloride | (cyclohexanecarbonyl) | 526.3023 |
| 445 | Isonicotinoyl chloride hydrochloride | (isonicotinoyl) | 521.2510 |
| 446 | Nicotinoyl chloride hydrochloride | (nicotinoyl) | 521.2501 |

-continued

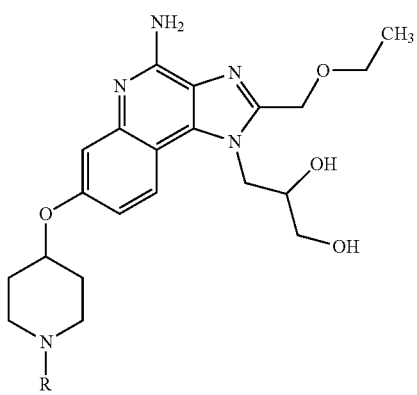

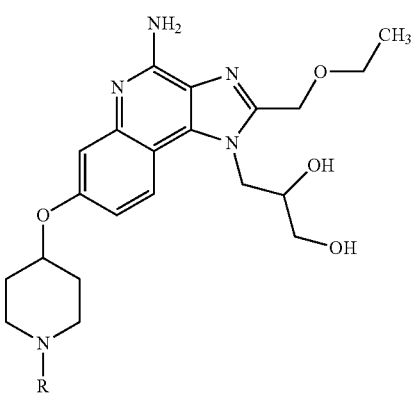

| Example | Reagent | R | Measured Mass (M + H) |
|---|---|---|---|
| 447 | Benzenesulfonyl chloride | phenylsulfonyl | 556.2224 |
| 448 | 1-Methylimidazole-4-sulfonyl chloride | 1-methylimidazol-4-ylsulfonyl | 560.2277 |
| 449 | Methyl isocyanate | C(O)NHCH₃ | 473.2537 |
| 450 | Ethyl isocyanate | C(O)NHCH₂CH₃ | 487.2658 |
| 451 | Isopropyl isocyanate | C(O)NHCH(CH₃)₂ | 501.2823 |
| 452 | Cyclopentyl isocyanate | C(O)NH-cyclopentyl | 527.2974 |

| Example | Reagent | R | Measured Mass (M + H) |
|---|---|---|---|
| 453 | Phenyl isocyanate | C(O)NHPh | 535.2666 |
| 454 | N,N-Dimethylcarbamoyl chloride | C(O)N(CH₃)₂ | 487.2687 |
| 455 | 1-Pyrrolidine-carbonyl chloride | C(O)-pyrrolidine | 513.2853 |
| 456 | 1-Piperidinecarbonyl chloride | C(O)-piperidine | 527.3002 |
| 457 | 4-Morpholinecarbonyl chloride | C(O)-morpholine | 529.2791 |

Examples 460-477

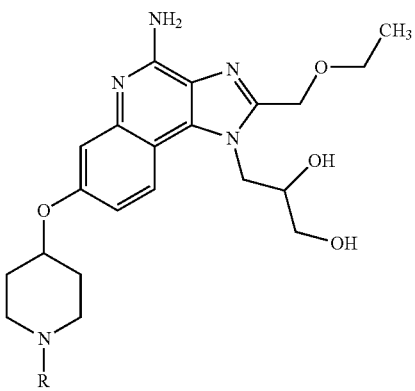

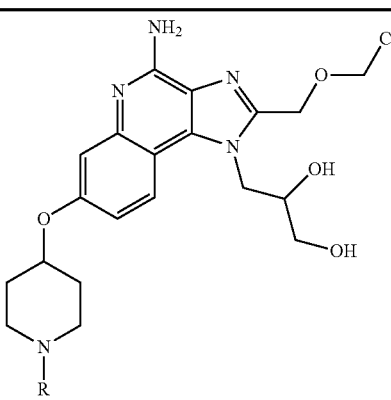

| Example | Reagent | R | Measured Mass (M + H) |
|---|---|---|---|
| 458 | 4-Methyl-1-piperazinecarbonyl chloride | ![acetyl-4-methylpiperazine] | 542.3113 |
| 459 | N-Methyl-N-phenylcarbamoyl chloride | ![N-methyl-N-phenylacetamide] | 549.2811 |

Examples 460-477

The free base of 3-[4-amino-2-(ethoxymethyl)-7-(piperidin-4-yloxy)-1H-imidazo[4,5-c]quinolin-1-yl]propane-1,2-diol dihydrochloride (prepared as described in Example 375) was prepared. An aldehyde or ketone (0.125 mmol, 1.25 equivalents) from the table below was added to a test tube containing 3-[4-amino-2-(ethoxymethyl)-7-(piperidin-4-yloxy)-1H-imidazo[4,5-c]quinolin-1-yl]propane-1,2-diol (42 mg, 0.10 mmol) in N,N-dimethylacetamide (1 mL). The test tubes were capped and shaken for 30 minutes at room temperature. Borane-pyridine complex (16 µL, 0.13 mmol) was added to each of the tubes. The test tubes were capped and shaken overnight at room temperature, then two drops of water were added to each test tube. The solvent was removed by vacuum centrifugation. The compounds were purified using the method described in Examples 376-386. The table below shows the aldehyde or ketone added to each test tube, the structure of the resulting compound, and the observed accurate mass for the isolated trifluoroacetate salt.

| Example | Reagent | R | Measured Mass (M + H) |
|---|---|---|---|
| 460 | None | H | 416.2328 |
| 461 | Cyclopropane-carboxaldehyde | cyclopropylmethyl | 470.2766 |
| 462 | Isobutyraldehyde | isobutyl | 472.2943 |
| 463 | Butyraldehyde | n-butyl | 472.2970 |
| 464 | Tetrahydrofuran-3-carboxaldehyde | (tetrahydrofuran-3-yl)methyl | 500.2865 |
| 465 | Benzaldehyde | benzyl | 506.2785 |
| 466 | Picolinaldehyde | (pyridin-2-yl)methyl | 507.2712 |
| 467 | 1-Methyl-2-imidazole-carboxaldehyde | (1-methyl-1H-imidazol-2-yl)methyl | 510.2865 |

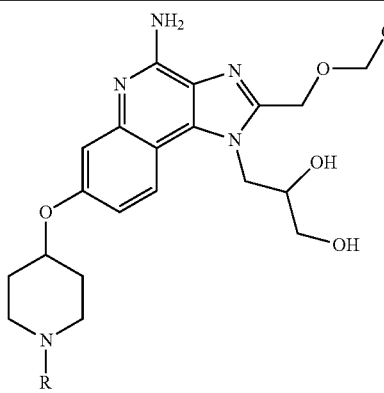

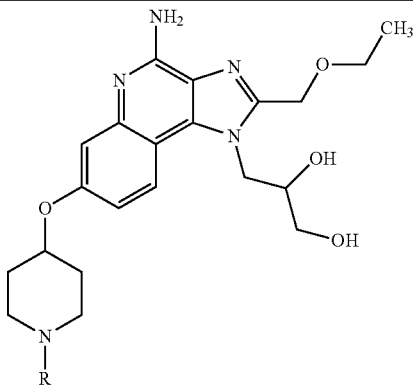

| Example | Reagent | R | Measured Mass (M + H) |
|---|---|---|---|
| 468 | m-Tolualdehyde | benzyl with 3-CH3 | 520.2944 |
| 469 | o-Tolualdehyde | benzyl with 2-CH3 | 520.2950 |
| 470 | p-Tolualdehyde | benzyl with 4-CH3 | 520.2921 |
| 471 | Phenylacetaldehyde | 2-phenylethyl | 520.2942 |
| 472 | 2-Fluorobenzaldehyde | benzyl with 2-F | 524.2708 |
| 473 | 3-Fluorobenzaldehyde | benzyl with 3-F | 524.2668 |

| Example | Reagent | R | Measured Mass (M + H) |
|---|---|---|---|
| 474 | 4-Fluorobenzaldehyde | benzyl with 4-F | 524.2665 |
| 475 | 3-Methoxybenzaldehyde | benzyl with 3-OCH3 | 536.2888 |
| 476 | 3-Chlorobenzaldehyde | benzyl with 3-Cl | 540.2387 |
| 477 | 1-Acetyl-4-piperidone | 1-acetyl-4-methylpiperidine | 541.3156 |

Examples 478-503

Part A

A mixture of 2-(ethoxymethyl)-1-propyl-1H-imidazo[4,5-c]quinolin-8-ol (prepared as described in Parts A-I of Example 2, 3.00 g, 10.5 mmol), 1-bromo-3-chloropropane (1.82 g, 11.6 mmol), and cesium carbonate (10.27 g, 31.53 mmol) in DMF (50 mL) was heated at 50° C. for 8 hours. The reaction mixture was allowed to cool to room temperature and was stirred over a weekend. The slurry was poured into a solution of sodium chloride (200 g) in water (800 mL). After 6 hours, a precipitate had formed that was isolated by filtration. The precipitate was dissolved in dichloromethane/ chloroform, dried over magnesium sulfate, and filtered. The filtrate was used in the next reaction.

Part B mCPBA (60% pure, 3.3 g, 11.5 mmol) was added in portions to the stirred filtrate from Part A at room temperature. The reaction mixture was stirred overnight. Concentrated ammonium hydroxide was added followed by p-toluenesulfonyl chloride (2.20 g, 11.5 mmol) in small portions. After 2 hours, 1% aqueous sodium carbonate was added and the mixture was stirred for 1 hour. The mixture was transferred to a separatory funnel and the layers were separated. The organic phase was washed with 1% aqueous sodium carbonate (2×75 mL). The aqueous phases were combined and extracted with dichloromethane (1×100 mL). The organic layers were dried over magnesium sulfate, filtered, and concentrated under reduced pressure. The crude product was purified by chromatography on a HORIZON HPFC system (silica gel, gradient elution with 0-25% CMA in chloroform) to provide 2.4 g of 8-(3-chloropropoxy)-2-(ethoxymethyl)-1-propyl-1H-imidazo[4,5-c]quinolin-4-amine.

Part C

An amine (0.15 mmol, 1.5 equivalents) from the table below was added to a test tube containing 8-(3-chloropropoxy)-2-(ethoxymethyl)-1-propyl-1H-imidazo[4,5-c]quinolin-4-amine (38 mg, 0.10 mmol) and potassium carbonate (55 mg, 0.40 mmol) in N,N-dimethylacetamide (1 mL). The test tubes were capped and heated at 70° C. for 16 hours, then at 85° C. for 6 hours. After the reaction mixtures were filtered, the solvent was removed by vacuum centrifugation. The compounds were purified using the method described in Examples 376-386. The table below shows the amine added to each test tube, the structure of the resulting compound, and the observed accurate mass for the isolated trifluoroacetate salt.

Examples 478-503

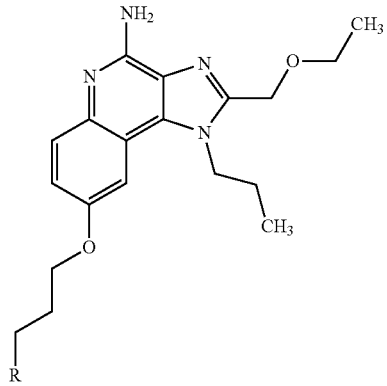

| Example | Reagent | R | Measured Mass (M + H) |
|---|---|---|---|
| 478 | None | ―Cl | 377.1718 |
| 479 | Piperidine | ―N(piperidinyl) | 426.2886 |
| 480 | 3-Methylpiperidine | ―N(3-methylpiperidinyl) | 440.3015 |
| 481 | 1-Methylpiperazine | ―N(4-methylpiperazinyl) | 441.3000 |

-continued
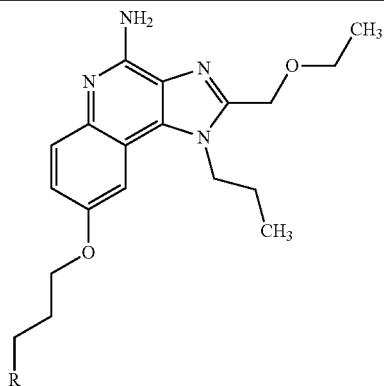
| Example | Reagent | R | Measured Mass (M + H) |
|---|---|---|---|
| 482 | 3-(Dimethylamino)pyrrolidine | *3-(dimethylamino)pyrrolidin-1-yl* | 455.3170 |
| 483 | N-Methylhomopiperazine | *4-methyl-1,4-diazepan-1-yl* | 455.3141 |
| 484 | 2-Piperidinemethanol | *2-(hydroxymethyl)piperidin-1-yl* | 456.2928 |
| 485 | 3-Azabicyclo[3.2.2]nonane | *3-azabicyclo[3.2.2]non-3-yl* | 466.3185 |
| 486 | Isonipecotamide | *4-carbamoylpiperidin-1-yl* | 469.2953 |
| 487 | Nipecotic acid | *3-carboxypiperidin-1-yl* | 470.2718 |

-continued
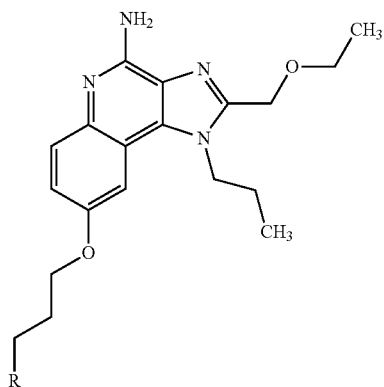
| Example | Reagent | R | Measured Mass (M + H) |
|---|---|---|---|
| 488 | N-(2-Hydroxyethyl)piperazine | 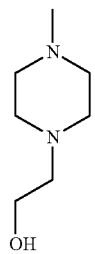 | 471.3096 |
| 489 | 1,2,3,4-Tetrahydroisoquinoline | 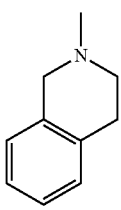 | 474.2879 |
| 490 | Decahydroisoquinoline | 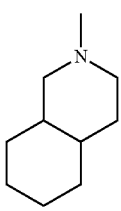 | 480.3345 |
| 491 | Decahydroquinoline | 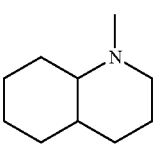 | 480.3343 |
| 492 | 1,3,3-Trimethyl-6-azabicyclo[3.2.1]octane | 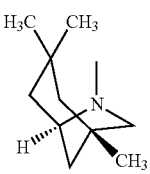 | 494.3507 |

-continued
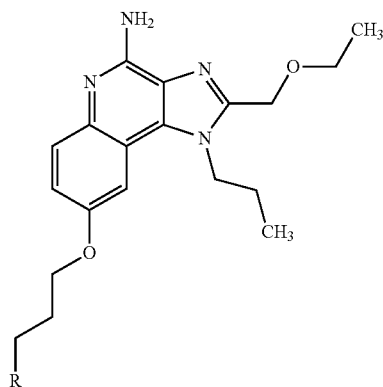
| Example | Reagent | R | Measured Mass (M + H) |
|---|---|---|---|
| 493 | 4-(1-Pyrrolidinyl)-piperidine | 1-(4-pyrrolidin-1-yl-piperidin-1-yl) | 495.3468 |
| 494 | 1-(2-Ethoxyethyl)piperazine | 4-(2-ethoxyethyl)piperazin-1-yl | 499.3405 |
| 495 | 2-Benzyl-2-imidazoline | 2-benzyl-4,5-dihydro-1H-imidazol-1-yl | 501.3005 |
| 496 | 4-Phenylpiperidine | 4-phenylpiperidin-1-yl | 502.3179 |

-continued
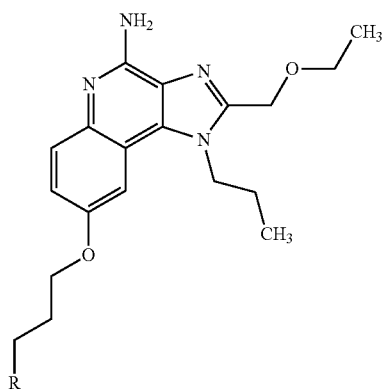
| Example | Reagent | R | Measured Mass (M + H) |
|---|---|---|---|
| 497 | 1-Phenylpiperazine | piperazine-N-phenyl | 503.3112 |
| 498 | 1-(2-Pyridyl)piperazine | piperazine-N-(2-pyridyl) | 504.3083 |
| 499 | 1-(4-Pyridyl)piperazine | piperazine-N-(4-pyridyl) | 504.3085 |
| 500 | 1-(2-Pyrimidyl)piperazine | piperazine-N-(2-pyrimidyl) | 505.3041 |

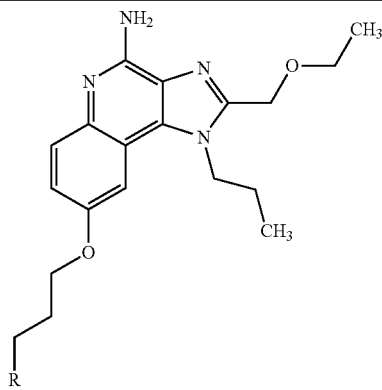

| Example | Reagent | R | Measured Mass (M + H) |
|---|---|---|---|
| 501 | 1-Cyclohexylpiperazine | *piperazine-N-cyclohexyl* | 509.3608 |
| 502 | 4-Piperidinopiperidine | *piperidine-N-piperidine* | 509.3599 |
| 503 | 1-[2-(2-Hydroxyethoxy)ethyl]piperazine | *piperazine-N-CH2CH2OCH2CH2OH* | 515.3372 |

Examples 504-522

Part A

A mixture of 4-amino-2-(ethoxymethyl)-1-propyl-1H-imidazo[4,5-c]quinolin-7-ol hydrochloride (prepared using a modification on the procedure described in Parts A and B of Example 51, 2.5 g, 7.4 mmol), 1-chloro-3-iodopropane (1.7 g, 8.2 mmol), and potassium carbonate (3.1 g, 22 mmol) in DMF (25 mL) was stirred overnight, then triethylamine (2 mL) was added and the reaction mixture was heated to 70° C. for 8 hours. The mixture was allowed to cool to room temperature and was stirred overnight. The mixture was poured into water (500 mL) and solid sodium hydroxide was added to adjust the mixture to pH 14. The mixture was extracted with chloroform (300 mL followed by 3×75 mL). The organic layers were thrown away and the aqueous layer was adjusted to pH 10 with 10% aqueous hydrochloric acid. A precipitate formed and was isolated by filtration. The solid was subjected to the initial reaction conditions, and this time methanol (25 mL) was added. After 3 hours at room temperature, the reaction mixture was heated at 90° C. and

243 potassium carbonate (1 g) and 1-chloro-3-bromopropane (1 mL) were added. After 3 hours, the reaction mixture was allowed to cool to room temperature, was filtered, and the methanol was removed under reduced pressure. The solution was poured into water (300 mL) and sodium chloride (200 g) was added, causing a precipitate to form within 30 minutes. After 1 hour, the precipitate was filtered, dissolved in a minimal amount of chloroform, and purified by chromatography on a HORIZON HPFC system (silica gel, gradient elution with 0-15% CMA in chloroform) to yield 900 mg of 7-(3-chloropropoxy)-2-(ethoxymethyl)-1-propyl-1H-imidazo[4,5-c]quinolin-4-amine.

Part B

An amine (0.2 mmol, 2.0 equivalents) from the table below was added to a test tube containing 7-(3-chloropropoxy)-2-(ethoxymethyl)-1-propyl-1H-imidazo[4,5-c]quinolin-4-amine (38 mg, 0.10 mmol) and potassium carbonate (55 mg, 0.40 mmol) in N,N-dimethylacetamide (1 mL). The test tubes were capped and heated at 90° C. for 10 hours. After the reaction mixtures were filtered, the solvent was removed by vacuum centrifugation. The compounds were purified using the method described in Examples 376-386. The table below shows the amine added to each test tube, the structure of the resulting compound, and the observed accurate mass for the isolated trifluoroacetate salt.

Examples 504-522

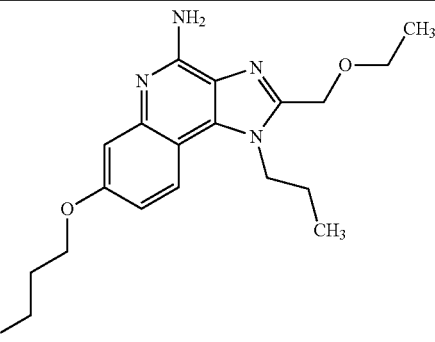

| Example | Reagent | R | Measured Mass (M + H) |
|---|---|---|---|
| 504 | Pyrrolidine | | 412.2679 |
| 505 | Piperidine | | 426.2837 |
| 506 | Morpholine | | 428.2685 |
| 507 | 4-Methylpiperidine | | 440.2992 |
| 508 | Hexamethyleneimine | | 440.2983 |
| 509 | 1-Methylpiperazine | | 441.2997 |
| 510 | 4-Hydroxypiperidine | | 442.2843 |
| 511 | Thiomorpholine | | 444.2455 |
| 512 | 3-(Dimethylamino)pyrrolidine | | 455.3094 |
| 513 | N-Methylhomopiperazine | | 455.3110 |
| 514 | 3-(Hydroxymethyl)piperidine | | 456.2964 |
| 515 | Isonipecotamide | | 469.2969 |

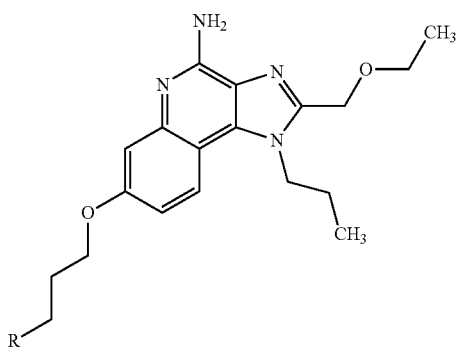

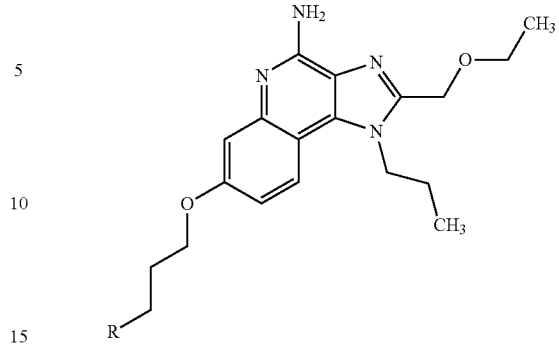

| Example | Reagent | R | Measured Mass (M + H) |
|---|---|---|---|
| 516 | Nipecotamide | | 469.2942 |
| 517 | 1-Acetylpiperazine | | 469.2945 |
| 518 | 4-Piperidineethanol | | 470.3167 |
| 519 | N-(2-Hydroxyethyl)piperazine | | 471.3084 |
| 520 | 1,2,3,4-Tetrahydroisoquinoline | | 474.2891 |
| 521 | Decahydroisoquinoline | | 480.3346 |
| 522 | 1-(2-Methoxyethyl)piperazine | 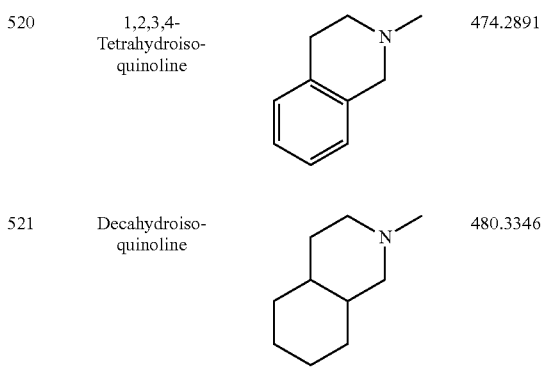 | 485.3240 |

Examples 523-550

Part A

A solution of methoxyacetyl chloride (7.0 g, 64.5 mmol) in dichloromethane (10 mL) was added dropwise to a stirred solution of 6-(benzyloxy)-$N^4$-propylquinoline-3,4-diamine (prepared as described in Parts A-F of Example 2, approximately 58.7 mmol) in dichloromethane (300 mL) at room temperature. After one hour, the solvent was removed under reduced pressure to yield a solid that was dissolved in ethanol (300 mL). After 2% aqueous potassium carbonate (100 mL) was added, the reaction was heated at reflux for 30 minutes, then stirred at room temperature overnight. The reaction mixture was concentrated under reduced pressure, then was partitioned between dichloromethane (300 mL) and 2% aqueous potassium carbonate (100 mL). The aqueous layer was extracted with dichloromethane (3×100 mL). The organic layers were combined, dried over magnesium sulfate, filtered, and concentrated under reduced pressure. The crude product was purified by chromatography (silica gel, sequential elution with 4% then 7% methanol in dichloromethane) to yield 18.2 g of a black solid that was used in the next step.

Part B mCPBA (60% pure, 15.7 g, 54.8 mmol) was added in small portions to a solution of the material from Part A (18.0 g, 49.8 mmol) in dichloromethane (200 mL). After the reaction was complete, 2% aqueous sodium carbonate was added and the mixture was stirred vigorously. An emulsion formed and chloroform and water were added. After two hours, the mixture was extracted multiple times with chloroform. The combined organic layers were dried over magnesium sulfate and filtered. The filtrate was used in the next step.

Part C

Trichloroacetyl isocyanate (6.5 mL, 54.8 mmol) was added slowly to the stirred filtrate from Part B. After 4 hours, additional isocyanate was added and the solution was stirred overnight. The reaction mixture was concentrated under reduced pressure and the residue was dissolved in dichloromethane (400 mL). Concentrated ammonium hydroxide (20 mL) was added and the mixture was stirred at room temperature for 1 hour, then 2% aqueous sodium carbonate (300 mL). The mixture was transferred to a separatory funnel and the layers were separated. The aqueous layer, an emulsion, was extracted multiple times with chloroform. The organic layers were combined, dried over magnesium sulfate, filtered, and concentrated under reduced pressure to yield a dark brown solid that was used in the next step.

Part D

A mixture of the material from Part C and 10% palladium on carbon in ethanol/methanol (600 mL) was hydrogenated on a Parr apparatus at 30 psi ($2.1 \times 10^5$ Pa) for 72 hours. The reaction mixture was filtered, and the filtrate was concentrated under reduced pressure. The resulting solid was treated with 2% aqueous sodium carbonate (300 mL), then concentrated hydrochloric acid was added to adjust to pH 1. After most of the solid had dissolved, the pH of the solution was adjusted to pH 7 with sodium carbonate, causing a precipitate to form. The mixture was stirred overnight. The solid was isolated by filtration and used in the next step without purification.

Part E

A mixture of the material from Part D (2.5 g, 8.7 mmol), 1-bromo-3-chloropropane (0.94 mL, 9.6 mmol), and cesium carbonate (5.7 g, 17.4 mmol) in DMF (50 mL) was stirred overnight at room temperature. Additional cesium carbonate (1 equivalent) was added and the mixture was heated to 50° C. overnight. The mixture was allowed to cool to room temperature and was poured into a solution of sodium chloride (250 g) in water (800 mL). After 20 minutes, a dark precipitate formed and was isolated by filtration. The solid was dissolved in chloroform, dried over magnesium sulfate, filtered, and concentrated. The crude product was purified by chromatography on a HORIZON HPFC system (silica gel, gradient elution with 0-30% of a 20% methanol in dichloromethane solution in dichloromethane) to yield 1.18 g of 8-(3-chloropropoxy)-2-(methoxymethyl)-1-propyl-1H-imidazo[4,5-c]quinolin-4-amine that contained some impurities.

Part F

An amine (0.15 mmol, 1.5 equivalents) from the table below was added to a test tube containing 8-(3-chloropropoxy)-2-(methoxymethyl)-1-propyl-1H-imidazo[4,5-c]quinolin-4-amine (36 mg, 0.10 mmol) and potassium carbonate (55 mg, 0.40 mmol) in N,N-dimethylacetamide (1 mL). The test tubes were capped and heated at 90° C. for 16 hours. After the reaction mixtures were filtered, the solvent was removed by vacuum centrifugation. The compounds were purified using the method described in Examples 376-386. The table below shows the amine added to each test tube, the structure of the resulting compound, and the observed accurate mass for the isolated trifluoroacetate salt.

Examples 523-550

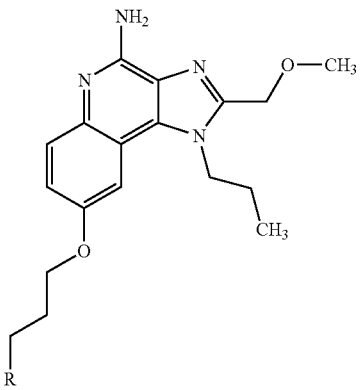

| Example | Reagent | R | Measured Mass (M + H) |
|---|---|---|---|
| 523 | None | Cl | 363.1563 |
| 524 | Pyrrolidine | pyrrolidinyl | 398.2574 |
| 525 | Piperidine | piperidinyl | 412.2709 |
| 526 | Morpholine | morpholinyl | 414.2532 |
| 527 | Thiazolidine | thiazolidinyl | 416.2142 |
| 528 | 3-Methylpiperidine | 3-methylpiperidinyl | 426.2871 |
| 529 | 4-Methylpiperidine | 4-methylpiperidinyl | 426.2856 |

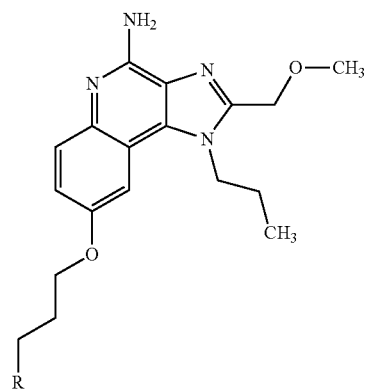
| Example | Reagent | R | Measured Mass (M + H) |
|---|---|---|---|
| 530 | Hexamethyleneimine | 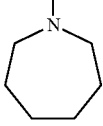 | 426.2835 |
| 531 | 1-Methylpiperazine | 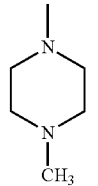 | 427.2804 |
| 532 | 3-Hydroxypiperidine | 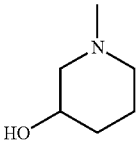 | 428.2652 |
| 533 | 4-Hydroxypiperidine | 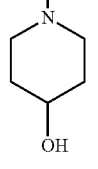 | 428.2681 |
| 534 | Thiomopholine | 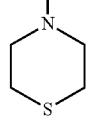 | 430.2297 |
| 535 | 3-(Dimethylamino)pyrrolidine | 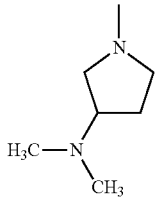 | 441.2975 |
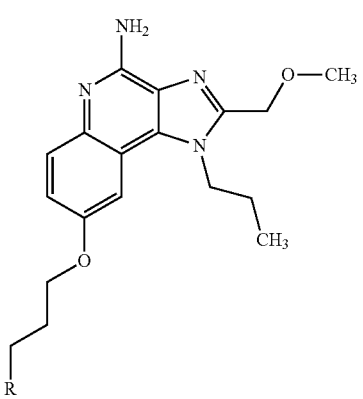
| Example | Reagent | R | Measured Mass (M + H) |
|---|---|---|---|
| 536 | N-Ethylpiperazine | 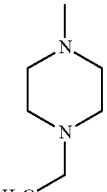 | 441.2952 |
| 537 | N-Methylhomopiperazine | 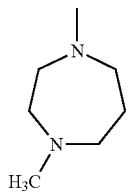 | 441.2940 |
| 538 | 2-Piperidinemethanol | 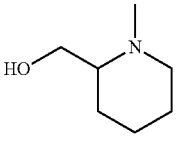 | 442.2831 |
| 539 | 3-(Hydroxymethyl)piperidine | 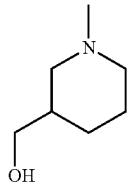 | 442.2821 |
| 540 | 4-(Hydroxymethyl)piperidine | 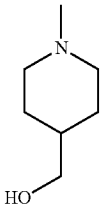 | 442.2847 |

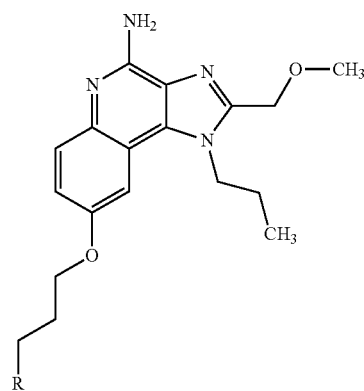
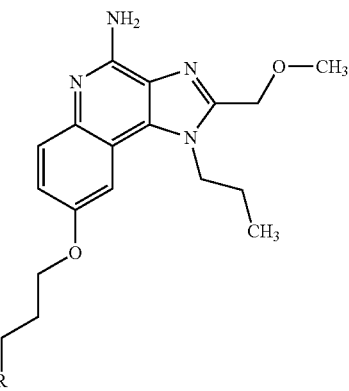
| Example | Reagent | R | Measured Mass (M + H) |
|---|---|---|---|
| 541 | Isonipecotamide | 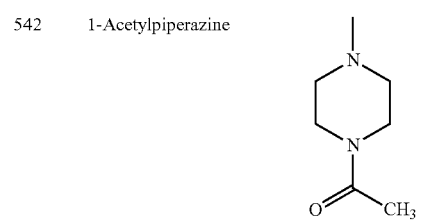 | 455.2816 |
| 542 | 1-Acetylpiperazine | 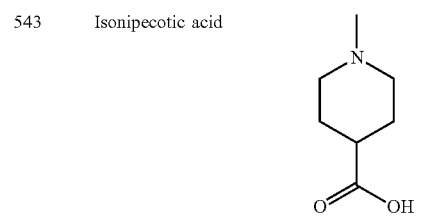 | 455.2813 |
| 543 | Isonipecotic acid | 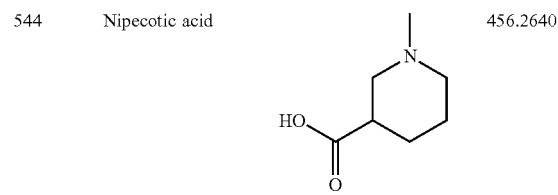 | 456.2655 |
| 544 | Nipecotic acid | | 456.2640 |
| 545 | 2-Piperidineethanol | 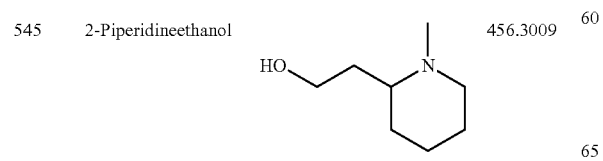 | 456.3009 |
| Example | Reagent | R | Measured Mass (M + H) |
|---|---|---|---|
| 546 | 4-Piperidineethanol | 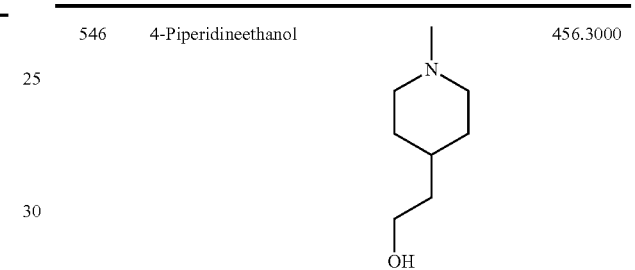 | 456.3000 |
| 547 | N-(2-Hydroxyethyl)piperazine | 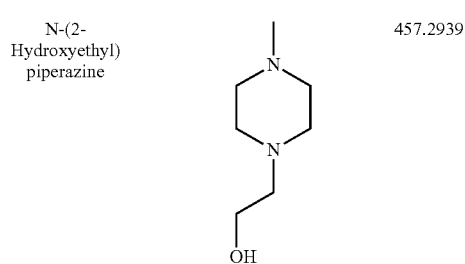 | 457.2939 |
| 548 | 2-Benzyl-2-imidazoline | 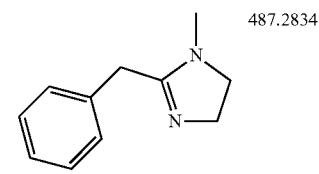 | 487.2834 |
| 549 | 4-Phenylpiperazine | 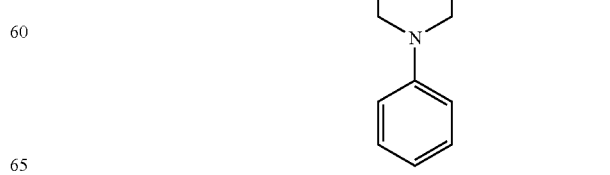 | 489.3026 |

-continued

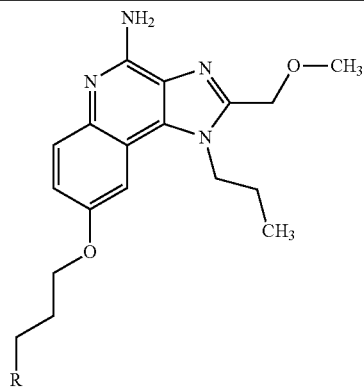

| Example | Reagent | R | Measured Mass (M + H) |
|---|---|---|---|
| 550 | 1-(2-Pyrimidyl)piperazine | | 491.2915 |

Example 551 tert-Butyl 2-{[4-amino-2-ethyl-1-(tetrahydro-2H-pyran-4-ylmethyl)-1H-imidazo[4,5-c]quinolin-7-yl]oxy}ethylcarbamate

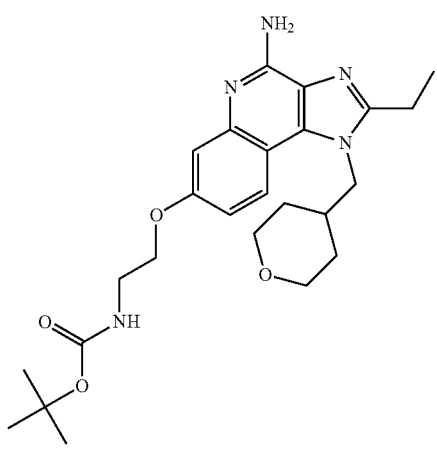 [SMILES: CCc1nc2c(N)nc3cc(OCCNC(=O)OC(C)(C)C)ccc3c2n1CC1CCOCC1]

Part A

Ammonium hydroxide (1 L) was added to a solution of methyl tetrahydro-2H-pyran-4-carboxylate (20 mL, 150 mmol) in methanol (500 mL), and the reaction was stirred overnight at ambient temperature. Additional ammonium hydroxide (500 mL) was added, and the reaction was stirred for four additional days. The methanol was removed under reduced pressure. Solid sodium chloride was added to the aqueous layer, which was extracted with chloroform (3×150 mL). The combined extracts were dried over sodium sulfate, filtered, and concentrated under reduced pressure to provide 11.4 g of tetrahydro-2H-pyran-4-carboxamide as a white solid.

Part B

A solution of tetrahydro-2H-pyran-4-carboxamide (11.4 g, 88.3 mmol) in THF (441 mL) was cooled to 0° C. Lithium aluminum hydride (10.0 g, 265 mmol) was added in six portions over a period of ten minutes. The reaction flask was purged with nitrogen between the additions. When the reaction mixture was no longer bubbling, it was heated at reflux for six hours. The reaction was then cooled to 0° C., and ethyl acetate was added dropwise until bubbling ceased. Methanol was then added dropwise until bubbling ceased. Water (10 mL), 15% aqueous sodium hydroxide (10 mL), and water (30 mL) were sequentially added. The organic fraction was decanted off, and the remaining gray solid was washed with chloroform. The combined organic fractions were dried over sodium sulfate, filtered, and concentrated under reduced pressure to provide tetrahydro-2H-pyran-4-ylmethylamine.

Part C 7-(Benzyloxy)-3-nitroquinolin-4-ol (12.3 g, 41.6 mmol) was slurried in DMF (83 mL). Phosphorous oxychloride (4.2 mL, 45 mmol) was added in one portion and the mixture was heated at 100° C. for 5 minutes. The solution was allowed to cool to 40° C. and was then poured into ice water (total volume 400 mL) resulting in a tan precipitate. The precipitate was filtered and washed with water. After drying, the solid was dissolved in dichloromethane and the residual water was separated. The organic fraction was dried over anhydrous sodium sulfate and anhydrous magnesium sulfate (about a 50/50 mixture). The organic fraction was filtered into a reaction flask (total volume of organic with 7-(benzyloxy)-3-chloro-4-nitroquinoline is about 425 mL). The flask was cooled to 8° C. and triethylamine (11.6 mL, 83.0 mmol) was added. (Tetrahydro-2H-pyran-4-yl)methylamine (6.0 g, 52 mmol) in dichloromethane (50 mL) was added dropwise to the mixture. The cooling bath was removed and the reaction was stirred for 16 hours. Water (200 mL) was added followed by stirring for 30 minutes. The layers were separated and the organic fraction was sequentially washed with saturated aqueous sodium chloride, dried over anhydrous sodium sulfate, filtered and concentrated under reduced pressure. Recrystallization from 2-propanol afforded 14.1 g of 7-(benzyloxy)-3-nitro-N-(tetrahydro-2H-pyran-4-ylmethyl)quinolin-4-amine as a yellow powder.

Part D 7-(Benzyloxy)-3-nitro-N-(tetrahydro-2H-pyran-4-ylmethyl)quinolin-4-amine (14.1 g, 35.6 mmol) and 5% platinum on carbon (2.0 g) were added to a Parr vessel. The solids were covered with acetonitrile (200 mL) and placed on a hydrogenator. The vessel was degassed three times, then charged with 50 psi (3.4×10$^5$ Pa) hydrogen and allowed to shake for 3 hours, replenishing the hydrogen as needed. After 6 hours, the catalyst was removed by filtration through CELITE filter agent. The CELITE was washed with acetonitrile until the filtrate ran clear (~300 mL). The solvent was evaporated to ½ volume under reduced pressure and cooled to 8° C. Propionyl chloride (3.15 mL, 35.6 mmol) was added dropwise to the solution over 3 minutes. The cooling bath was removed and the reaction was stirred for 16 hours. The resulting precipitate was filtered and washed with acetonitrile. Drying under vacuum for 1 hour afforded 14.2 g of N-{7-(benzyloxy)-4-[(tetrahydro-2H-pyran-4-ylmethyl)amino]quinolin-3-yl}propanamide dihydrochloride as a tan solid.

Part E

N-{7-(Benzyloxy)-4-[(tetrahydro-2H-pyran-4-ylmethyl)amino]quinolin-3-yl}propanamide dihydrochloride (14.2 g, 31.1 mmol) was slurried in ethanol (150 mL) and diluted with water (50 mL). Potassium carbonate (12.3 g, 89 mmol) in water (15 mL) was added and the reaction was stirred until dissolution (~30 minutes). The reaction was then heated to 60° C. for 16 hours. The ethanol was evaporated under reduced pressure and the remaining water was extracted with dichloromethane. The organic fraction was sequentially washed with water, followed by saturated aqueous sodium chloride, dried over anhydrous sodium sulfate, filtered and concentrated. Recrystallization from acetonitrile afforded 8.4 g of 7-(benzyloxy)-2-ethyl-1-(tetrahydro-2H-pyran-4-ylmethyl)-1H-imidazo[4,5-c]quinoline as a tan powder.

Part F 7-(Benzyloxy)-2-ethyl-1-(tetrahydro-2H-pyran-4-ylmethyl)-1H-imidazo[4,5-c]quinoline (8.3 g, 20.7 mmol) was added to a Parr vessel containing 10% palladium on carbon (1.5 g) wetted with acetonitrile. Methanol (160 mL) was added and the vessel was placed on the hydrogenator. The vessel was degassed three times and charged with 50 psi ($3.4\times10^5$ Pa) hydrogen. The vessel was allowed to shake for 16 hours, replenishing the hydrogen as needed. The catalyst was removed by filtration through glass fiber filter paper. The catalyst was washed with 3:1 chloroform/methanol. The filtrates were combined. Evaporation under reduced pressure afforded 6.1 g of 2-ethyl-1-(tetrahydro-2H-pyran-4-ylmethyl)-1H-imidazo[4,5-c]quinolin-7-ol as a gray solid.

Part G

The material was prepared using the general method described in Part A of Example 390. tert-Butyl 2-iodoethylcarbamate (5.26 g, 19.4 mmol added over 24 hours, then 1 g, 3.70 mmol after 72 hours), was used in lieu of t-butyl 3-iodopropylcarbamate. Purification via chromatography on a HORIZON HPFC system (gradient elution with 2-25% CMA in chloroform), followed by recrystallization from acetonitrile afforded 2.34 g of tert-butyl 2-{[2-ethyl-1-(tetrahydro-2H-pyran-4-ylmethyl)-1H-imidazo[4,5-c]quinolin-7-yl]oxy}ethylcarbamate as white flakes.

Part H tert-Butyl 2-{[2-ethyl-1-(tetrahydro-2H-pyran-4-ylmethyl)-1H-imidazo[4,5-c]quinolin-7-yl]oxy}ethylcarbamate (2.3 g, 5.06 mmol) was slurried in ethyl acetate (20 mL). 32% Peracetic acid in acetic acid (1.06 mL, 5.06 mmol) was added in one portion and the reaction was heated to 50° C. for 2 hours. Another 0.250 mL (1.19 mmol) peracetic acid solution was added and the reaction was stirred for 1 additional hour. Sodium metabisulfite (1.2 g, 6.33 mmol) in water (2.5 mL) was added over 3 minutes and the reaction was stirred for 30 minutes. The heat was removed and the reaction was brought to pH 10 with saturated aqueous sodium carbonate (~10 mL). The milky slurry was cooled in an ice bath and subsequently filtered. The solid was washed with water and dried for 1 hour. Roughly 2.0 g of tert-butyl 2-{[2-ethyl-5-oxido-1-(tetrahydro-2H-pyran-4-ylmethyl)-1H-imidazo[4,5-c]quinolin-7-yl]oxy}ethylcarbamate was isolated as an off-white solid with water still remaining.

Part I tert-Butyl 2-{[2-ethyl-5-oxido-1-(tetrahydro-2H-pyran-4-ylmethyl)-1H-imidazo[4,5-c]quinolin-7-yl]oxy}ethylcarbamate (wet from above) was slurried in dichloromethane (25 mL) and ammonium hydroxide (25 mL). p-Toluenesulfonyl chloride (0.810 g, 4.25 mmol) was added in one portion and the reaction was stirred for 16 hours. The layers were separated and the aqueous fraction was extracted with dichloromethane. The combined organic fractions were washed with water, then saturated aqueous sodium chloride. The organic fraction was dried over anhydrous sodium sulfate, filtered and concentrated. The material was purified by chromatography on a HORIZON HPFC system (silica gel, gradient elution with 2-20% CMA in chloroform) to afford 1.8 g of tert-butyl 2-{[4-amino-2-ethyl-1-(tetrahydro-2H-pyran-4-ylmethyl)-1H-imidazo[4,5-c]quinolin-7-yl]oxy}ethylcarbamate as a white foam. Recrystallization from acetonitrile of a small portion provided an analytical sample as a white solid, mp 200-201° C.

$^1$H NMR (300 MHz, DMSO-d$_6$) δ 7.92 (d, J=9.1 Hz, 1H), 7.05 (d, J=2.7 Hz, 1H), 7.02 (t, J=5.3 Hz, 1H), 6.90 (dd, J=9.0, 2.6 Hz, 1H), 6.38 (s, 2H), 4.39-4.36 (m, 2H), 4.04 (t, J=5.8 Hz, 2H), 3.84-3.79 (m, 2H), 3.34 (q, J=5.7 Hz, 2H), 3.21-3.08 (m, 2H), 2.91 (q, J=7.4 Hz, 2H), 2.14-1.97 (m, 1H), 1.54-1.36 (m, 4H), 1.39 (s, 9H), 1.36 (t, J=7.4 Hz, 3H);

$^{13}$C NMR (125 MHz, DMSO-d$_6$) δ 155.0, 155.7, 153.7, 152.0, 146.6, 132.9, 125.1, 121.2, 111.5, 109.1, 108.2, 77.7, 66.6, 66.2, 49.6, 35.7, 29.6, 28.2, 20.1, 12.1;

MS (APCI) m/z 470.3 (M+H)$^+$;

Anal. calcd for $C_{25}H_{35}N_5O_4$: C, 63.95; H, 7.51; N, 14.91. Found: C, 63.80; H, 7.54; N, 15.06.

Example 552

7-(2-Aminoethoxy)-2-ethyl-1-(tetrahydro-2H-pyran-4-ylmethyl)-1H-imidazo[4,5-c]quinolin-4-amine dihydrochloride

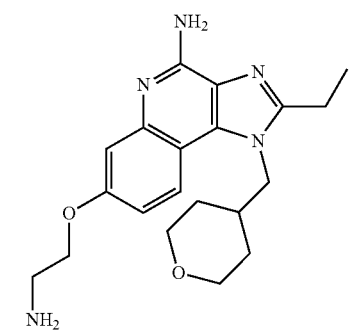 [SMILES: CCc1nc2c(N)nc3cc(OCCN)ccc3c2n1CC1CCOCC1]

tert-Butyl 2-{[4-amino-2-ethyl-1-(tetrahydro-2H-pyran-4-ylmethyl)-1H-imidazo[4,5-c]quinolin-7-yl]

oxy}ethylcarbamate (1.8 g, 3.83 mmol) was added to 4.0M ethanolic hydrogen chloride (13 mL) and the reaction was heated to 65° C. for 1 hour. The milky slurry solidified after 20 minutes. Ethanol (10 mL) was added to loosen the solid. After 1 hour, the heat was removed and the reaction was allowed to cool to ambient temperature. Filtration afforded 1.3 g of 7-(2-aminoethoxy)-2-ethyl-1-(tetrahydro-2H-pyran-4-ylmethyl)-1H-imidazo[4,5-c]quinolin-4-amine dihydrochloride as a white solid, mp 238° C., decomposition.

$^1$H NMR (300 MHz, DMSO-$d_6$) δ 14.24 (s, 1H), 8.75 (br s, 2H), 8.43 (br s, 3H), 8.20 (d, J=9.2 Hz, 1H), 7.36 (d, J=2.5 Hz, 1H), 7.26 (dd, J=9.1, 2.4 Hz, 1H), 4.50-4.47 (m, 2H), 4.36 (t, J=4.9 Hz, 2H), 3.85-3.81 (m, 2H), 3.36-3.23 (m, 2H), 3.22-3.07 (m, 2H), 2.99 (q, J=7.4 Hz, 2H), 2.13-1.94 (m, 1H), 1.59-1.40 (m, 4H), 1.40 (t, J=7.4 Hz, 3H);

$^{13}$C NMR (125 MHz, DMSO-$d_6$) δ 158.3, 157.4, 148.9, 135.5, 135.3, 123.5, 122.9, 114.0, 106.9, 102.1, 66.5, 64.7, 49.9, 38.1, 35.6, 29.4, 20.2, 11.6;

MS (ESI) m/z 370.2 (M+H)$^+$.

Example 553

2-Ethyl-7-(2-morpholin-4-yl-2-oxoethoxy)-1-(tetrahydro-2H-pyran-4-ylmethyl)-1H-imidazo[4,5-c]quinolin-4-amine

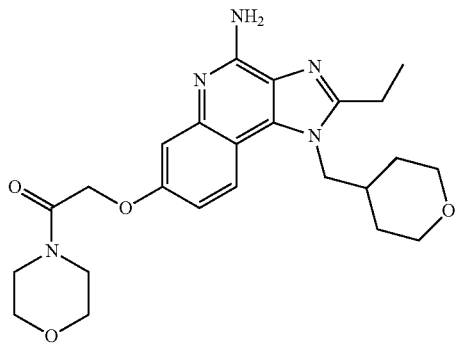 [SMILES: CCc1nc2c(N)nc3cc(OCC(=O)N4CCOCC4)ccc3c2n1CC1CCOCC1]

Part A mCPBA (2.0 g of 60%, 6.97 mmol) was added to a solution of 7-benzyloxy-2-ethyl-1-(tetrahydro-2H-pyran-4-ylmethyl)-1H-imidazo[4,5-c]quinoline (2.8 g, 6.97 mmol) in chloroform (50 mL). After 30 minutes an additional equivalent of mCPBA was added and the reaction mixture was stirred for an additional hour. Ammonium hydroxide (20 mL) was added and the reaction mixture was stirred for 10 minutes. p-Toluenesulfonyl chloride (1.33 g, 6.97 mmol) was added in a single portion and the reaction mixture was stirred for 16 hours. The layers were separated and the aqueous layer was extracted with dichloromethane (2×100 mL). The organics were combined, washed with water and brine, dried over sodium sulfate, filtered, and then concentrated under reduced pressure. The residue was purified by chromatography on a HORIZON HPFC system (40+M cartridge eluting with a gradient of 2 to 25% CMA in chloroform). The residue was combined with acetonitrile and allowed to stand overnight. A solid was isolated by filtration and rinsed with acetonitrile to provide 1.96 g of 7-benzyloxy-2-ethyl-1-(tetrahydro-2H-pyran-4-ylmethyl)-1H-imidazo[4,5-c]quinolin-4-amine as a tan solid.

Part B

A mixture of 7-benzyloxy-2-ethyl-1-(tetrahydro-2H-pyran-4-ylmethyl)-1H-imidazo[4,5-c]quinolin-4-amine (1.76 g, 4.23 mmol), palladium on carbon (1 g), and ethanol (50 mL) was shaken under hydrogen pressure (50 psi, 3.4×10$^5$ Pa) on a Parr apparatus overnight. The reaction mixture was diluted with dichloromethane (75 mL) and then filtered through a layer of CELITE filter agent. The filter cake was rinsed with 25% methanol in chloroform (400 mL). The combined filtrates were concentrated under reduced pressure to provide a white solid. This material was slurried with methanol, isolated by filtration, and dried under vacuum to provide 0.98 g of 4-amino-2-ethyl-1-(tetrahydro-2H-pyran-4-ylmethyl)-1H-imidazo[4,5-c]quinolin-7-ol.

Part C

A mixture of 4-amino-2-ethyl-1-(tetrahydro-2H-pyran-4-ylmethyl)-1H-imidazo[4,5-c]quinolin-7-ol (500 mg, 1.53 mmol), 2-bromo-1-(morpholin-4-yl)ethanone (351 mg, 1.69 mmol), cesium carbonate (1.5 g, 4.59 mmol) and anhydrous DMF was heated at 70° C. overnight. The reaction mixture was cooled, poured into water (350 mL), and then extracted with dichloromethane (2×100 mL). The combined organics were dried over magnesium sulfate, filtered, and then concentrated under reduced pressure. The residue was dissolved in dichloromethane and filtered. The filtrate was purified by chromatography on a HORIZON HPFC system (eluting with a gradient of 0 to 8% methanol in dichloromethane). The product was recrystallized from acetonitrile to provide 362 mg of 2-ethyl-7-(2-morpholin-4-yl-2-oxoethoxy)-1-(tetrahydro-2H-pyran-4-ylmethyl)-1H-imidazo[4,5-c]quinolin-4-amine as a white powder, mp 245-247° C. Anal. calcd for $C_{24}H_{31}N_5O_4$: C, 63.56; H, 6.89; N, 15.44. Found: C, 63.20; H, 6.78; N, 15.31.

Example 554

2-Methoxymethyl-8-(3-morpholin-4-ylpropoxy)-1-propyl-1H-imidazo[4,5-c]quinolin-4-amine

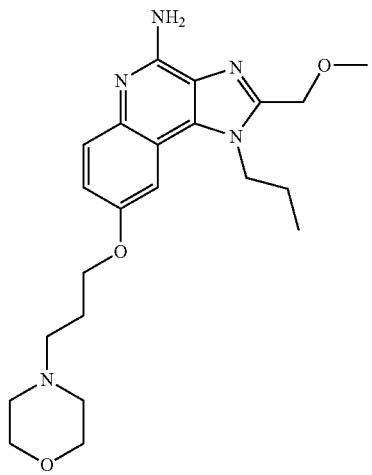 [SMILES: CCCn1c(COC)nc2c(N)nc3ccc(OCCCN4CCOCC4)cc3c21]

Part A

Cesium carbonate (5.7 g, 17.4 mmol, 2 eq) was added to a mixture of 8-hydroxy-2-methoxymethyl-1-propyl-1H-imidazo[4,5-c]quinolin-4-amine (2.5 g, 8.7 mmol, 1 eq), prepared as described in Examples 523-550 Parts A-D, 1-bromo-3-chloropropane (0.94 mL, 9.6 mmol, 1.1 eq), and 50 mL of N,N-dimethylformamide (DMF). The reaction mixture was stirred overnight. Analysis by HPLC indicated the reaction was incomplete. Additional cesium carbonate (2.85 g) was added to the reaction mixture and the mixture was heated to 50° C. overnight. Analysis by HPLC indicated the reaction was complete and the reaction mixture was poured into a brine solution (250 g of sodium chloride in 800 mL of deionized water). After 20 minutes, a dark brown/black material precipitated and was filtered. The solid material was dissolved in chloroform, dried over magnesium sulfate, and purified by chromatography on a HORIZON HPFC system (eluting with a gradient of methanol/dichloromethane (20:80) in dichloromethane from 0:100 to 30:70). The combined fractions were concentrated, dissolved in dichloromethane and methanol, and concentrated under reduced pressure to yield 1.18 g of 8-(3-chloropropoxy)-2-methoxymethyl-1-propyl-1H-imidazo[4,5-c]quinolin-4-amine.

Part B

Potassium carbonate (530 mg, 3.84 mmol), morpholine (92 mg, 1.06 mmol), and 8-(3-chloropropoxy)-2-methoxymethyl-1-propyl-1H-imidazo[4,5-c]quinolin-4-amine (350 mg, 0.96 mmol) were added to 15 mL of DMF and heated to 50° C. for 18 hours. Analysis by LC/MS indicated the presence of two peaks and the reaction mixture was cooled and poured into 500 mL of deionized water. After three hours, no precipitation was observed. Sodium chloride (250 g) was added to the mixture and the mixture was stirred vigorously overnight. The precipitate was collected by filtration, dissolved in dichloromethane, and purified by chromatography on a HORIZON HPFC system (eluting with a gradient of methanol/dichloromethane (20:80) in dichloromethane from 0:100 to 40:60). The resulting material was concentrated under reduced pressure, crystallized from acetonitrile, and dried under high vacuum to yield 36 mg of 2-methoxymethyl-8-(3-morpholin-4-ylpropoxy)-1-propyl-1H-imidazo[4,5-c]quinolin-4-amine as tan crystals, mp 193-196° C. Anal. calcd for $C_{22}H_{31}N_5O_3$: C, 63.90; H, 7.56; N, 16.94. Found: C, 63.58; H, 7.76; N, 17.28.

Example 555

3-{[4-Amino-2-(methoxymethyl)-1-propyl-1H-imidazo[4,5-c]quinolin-8-yl]oxy}propyl morpholine-4-carboxylate

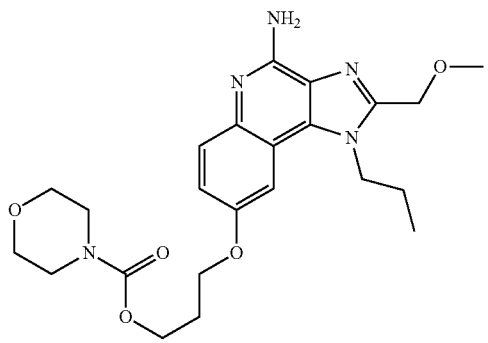 [SMILES: CCCn1c(COC)nc2c(N)nc3ccc(OCCCOC(=O)N4CCOCC4)cc3c21]

A second product was isolated after chromatographic purification of Example 554; 92 mg of 3-{[4-amino-2-(methoxymethyl)-1-propyl-1H-imidazo[4,5-c]quinolin-8-yl]oxy}propyl morpholine-4-carboxylate was isolated as pale yellow crystals, mp 173-174° C.

Anal. calcd for $C_{23}H_{31}N_5O_5$: C, 60.38; H, 6.83; N, 15.31. Found: C, 60.12; H, 7.09; N, 15.44.

Example 556

2-(Methoxymethyl)-8-(2-oxo-2-thiomorpholin-4-ylethoxy)-1-propyl-1H-imidazo[4,5-c]quinolin-4-amine

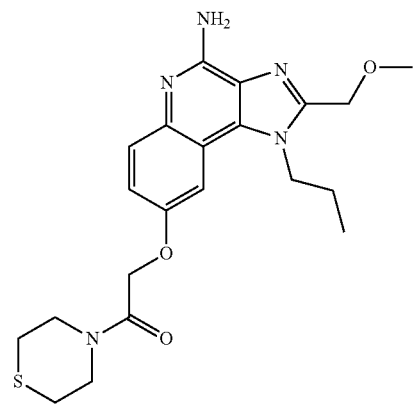 [SMILES: CCCn1c(COC)nc2c(N)nc3ccc(OCC(=O)N4CCSCC4)cc3c21]

Cesium carbonate (1.7 g, 5.22 mmol, 3 eq) was added to a mixture of 4-(bromoacetyl)thiomorpholine (468 mg, 2.09 mmol, 1.2 eq, prepared according to the method described in Part C of Example 30) and 8-hydroxy-2-methoxymethyl-1-propyl-1H-imidazo[4,5-c]quinolin-4-amine (500 mg, 1.74 mmol, 1.0 eq) in 20 mL of DMF. The reaction mixture was heated to 70° C. and maintained for 14 hours. The reaction mixture was then cooled to ambient temperature, filtered, diluted with 50 mL of dichloromethane, concentrated under reduced pressure, and filtered to afford crude material. The crude material was purified by chromatography on a HORIZON HPFC system (eluting with a gradient of methanol/dichloromethane (20:80) in dichloromethane from 0:100 to 40:60), concentrated under reduced pressure, and crystallized from acetonitrile to afford 231 mg of 2-(methoxymethyl)-8-(2-oxo-2-thiomorpholin-4-ylethoxy)-1-propyl-1H-imidazo[4,5-c]quinolin-4-amine as an off white solid, mp 214-216° C.

Anal. calcd for $C_{21}H_{27}N_5O_3S$: C, 58.72; H, 6.34; N, 16.30. Found: C, 58.60; H, 6.48; N, 16.41.

Example 557

2-(Methoxymethyl)-8-(2-morpholin-4-yl-2-oxoethoxy)-1-propyl-1H-imidazo[4,5-c]quinolin-4-amine

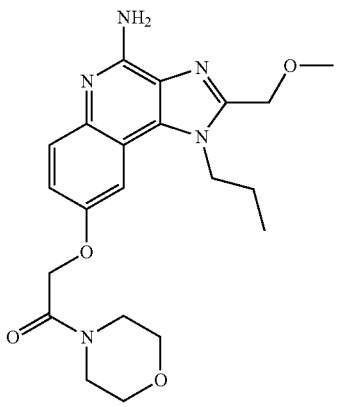 [SMILES: CCCn1c(COC)nc2c(N)nc3ccc(OCC(=O)N4CCOCC4)cc3c21]

Cesium carbonate (1.7 g, 5.25 mmol, 3 eq) was added to a mixture of 2-bromo-1-morpholin-4-yl-ethanone (400 mg, 1.92 mmol, 1.1 eq), 8-hydroxy-2-methoxymethyl-1-propyl-1H-imidazo[4,5-c]quinolin-4-amine (500 mg, 1.75 mmol, 1.0 eq), and anhydrous DMF. The reaction mixture was heated to 70° C. and maintained overnight. The reaction mixture was then cooled to ambient temperature, filtered, and concentrated under reduced pressure to yield a dark oil. The dark oil was dissolved in dichloromethane, filtered, purified by chromatography on a HORIZON HPFC system (eluting with a gradient of methanol/dichloromethane (20:80) in dichloromethane from 0:100 to 40:60), and crystallized from acetonitrile to afford 356 mg of 2-(methoxymethyl)-8-(2-morpholin-4-yl-2-oxoethoxy)-1-propyl-1H-imidazo[4,5-c]quinolin-4-amine as an off white powder, mp 201-204° C.

Anal. calcd for $C_{21}H_{27}N_5O_4$: C, 61.00; H, 6.58; N, 16.94. Found: C, 60.82; H, 6.51; N, 16.86.

Example 558

2-Methoxymethyl-8-(1-methylpiperidin-3-yl-methoxy)-1-propyl-1H-imidazo[4,5-c]quinolin-4-amine

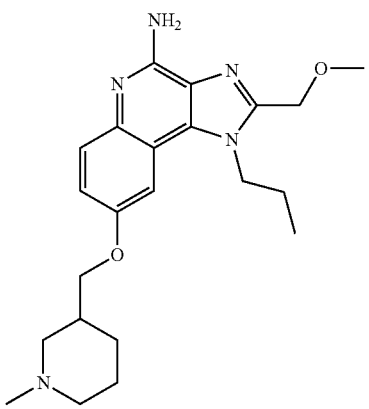

Potassium carbonate (1.48 g, 10.75 mmol), 3-chloromethyl-1-methyl-piperidine hydrochloride (483 mg, 2.62 mmol), sodium iodide (100 mg, 0.66 mmol), and 8-hydroxy-2-methoxymethyl-1-propyl-1H-imidazo[4,5-c]quinolin-4-amine (500 mg, 1.75 mmol) were combined in acetone and heated at reflux overnight. No desired product was detected and the reaction mixture was filtered. The filtrate was concentrated under reduced pressure, dissolved in DMF, and heated at 90° C. overnight. The reaction mixture was then cooled to ambient temperature, filtered, and concentrated under reduced pressure to provide a dark oil. The oil was dissolved in dichloromethane, filtered, purified by chromatography on a HORIZON HPFC system (eluted with a gradient of CMA: chloroform from 0:100 to 35:65), and crystallized from acetonitrile to afford 160 mg of 2-methoxymethyl-8-(1-methyl-piperidin-3-yl-methoxy)-1-propyl-1H-imidazo[4,5-c]quinolin-4-amine as a tan powder, mp 194-196° C.

Anal. calcd for $C_{22}H_{31}N_5O_2$: C, 66.47; H, 7.86; N, 17.62. Found: C, 66.27; H, 8.15; N, 17.74.

Example 559

2-Methoxymethyl-8-(2-piperidin-1-ylethoxy)-1-propyl-1H-imidazo[4,5-c]quinolin-4-amine

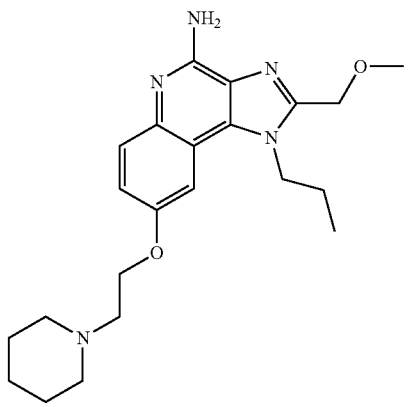 [SMILES: CCCn1c(COC)nc2c(N)nc3ccc(OCCN4CCCCC4)cc3c21]

Potassium carbonate (1.48 g, 10.75 mmol), N-(2-chloroethyl)-piperidine hydrochloride (483 mg, 2.62 mmol), sodium iodide (100 mg, 0.66 mmol), and 8-hydroxy-2-methoxymethyl-1-propyl-1H-imidazo[4,5-c]quinolin-4-amine (500 mg, 1.75 mmol) were combined in acetone as a slurry and heated at reflux overnight. The reaction mixture was cooled to ambient temperature and filtered. The filter cake was washed with acetone and the combined filtrate was concentrated under reduced pressure to afford a solid. The solid material was dissolved in dichloromethane and purified by chromatography on a HORIZON HPFC system (eluting with a gradient of CMA:chloroform from 0:100 to 40:60).

263

The resulting material was concentrated under reduced pressure and crystallized from acetonitrile to afford 175 mg of 2-methoxymethyl-8-(2-piperidin-1-ylethoxy)-1-propyl-1H-imidazo[4,5-c]quinolin-4-amine as tan crystals, mp 160-162° C. Anal. calcd for $C_{22}H_{31}N_5O_2 \cdot 0.33$ $CH_3CN \cdot 0.33$ $H_2O$: C, 65.18; H, 7.90; N, 17.82. Found: C, 65.18; H, 8.05; N, 18.10.

Example 560

7-[(1-Acetylpiperidin-4-yl)oxy]-2-(ethoxymethyl)-1-propyl-1H-imidazo[4,5-c]quinolin-4-amine

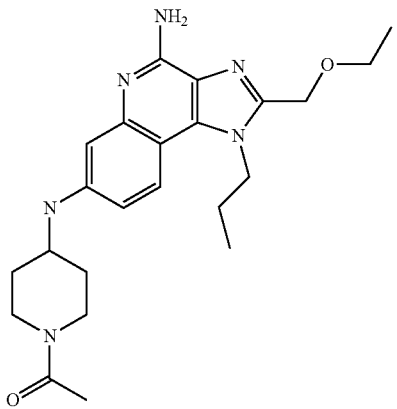 [SMILES: CCCn1c(COCC)nc2c(N)nc3cc(NC4CCN(C(C)=O)CC4)ccc3c21]

2-(Ethoxymethyl)-7-(piperidin-4-yloxy)-1-propyl-1H-imidazo[4,5-c]quinolin-4-amine (0.500 g, 1.3 mmol) was slurried in dichloromethane (13 mL). Acetic anhydride (0.122 mL, 1.3 mmol) was added dropwise to the slurry and the mixture was stirred for 36 hours. Saturated aqueous sodium carbonate (5 mL) was added and the reaction was stirred for 1 hour. The layers were separated and the organic fraction was purified by chromatography on a HORIZON HPFC system (silica gel, gradient elution with 1-22% CMA in chloroform). The resulting amorphous solid was triturated with boiling acetonitrile. Filtration afforded 0.270 g of 7-[(1-acetylpiperidin-4-yl)oxy]-2-(ethoxymethyl)-1-propyl-1H-imidazo[4,5-c]quinolin-4-amine as an off-white solid, mp 178-179.5° C.

$^1$H NMR (300 MHz, DMSO-$d_6$) δ 7.91 (d, J=9.0 Hz, 1H), 7.13 (d, J=2.6 Hz, 1H), 6.96 (dd, J=9.0, 2.6 Hz, 1H), 6.52 (s, 2H), 4.75 (s, 2H), 4.75-4.66 (m, 1H), 4.52-4.41 (m, 2H), 3.98-3.82 (m, 1H), 3.78-3.64 (m, 1H), 3.55 (q, J=7.0 Hz, 2H), 3.44-3.16 (m, 2H), 2.09-1.77 (m, 4H), 2.03 (s, 3H), 1.74-1.45 (m, 2H), 1.16 (t, J=7.0 Hz, 3H), 1.00 (t, J=7.3 Hz, 3H);

MS (APCI) m/z 426.2 (M+H)$^+$;

Anal. calcd for $C_{23}H_{31}N_5O_3$: C, 64.92; H, 7.34; N, 16.46. Found: C, 64.76; H, 7.64; N, 16.60.

Example 561

2-(Ethoxymethyl)-7-{[1-(methylsulfonyl)piperidin-4-yl]oxy}-1-propyl-1H-imidazo[4,5-c]quinolin-4-amine

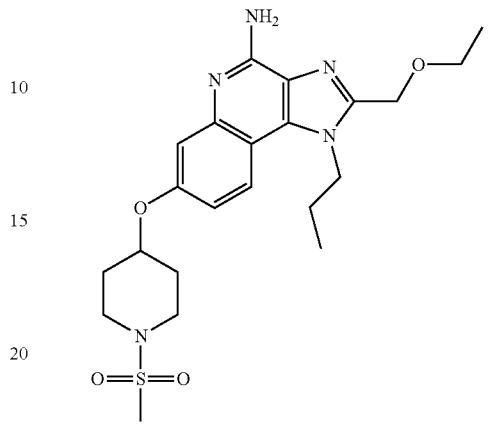

The general method described in Example 560 was followed using methanesulfonyl chloride (0.100 mL, 1.3 mmol) in lieu of acetic anhydride. The reaction time was reduced to 2 hours. Filtration from acetonitrile afforded 0.381 g of 2-(ethoxymethyl)-7-{[1-(methylsulfonyl)piperidin-4-yl]oxy}-1-propyl-1H-imidazo[4,5-c]quinolin-4-amine as a pale yellow solid, mp 215-217° C.

$^1$H NMR (300 MHz, DMSO-$d_6$) δ 7.92 (d, J=9.0 Hz, 1H), 7.13 (d, J=2.5 Hz, 1H), 6.97 (dd, J=9.0, 2.5 Hz, 1H), 6.53 (s, 2H), 4.75 (s, 2H), 4.72-4.62 (m, 1H), 4.53-4.41 (m, 2H), 3.55 (q, J=7.0 Hz, 2H), 3.46-3.32 (m, 2H), 3.23-3.08 (m, 2H), 2.92 (s, 3H), 2.14-1.99 (m, 2H), 1.94-1.71 (m, 4H), 1.16 (t, J=7.0 Hz, 3H), 1.00 (t, J=7.4 Hz, 3H);

$^{13}$C NMR (125 MHz, DMSO-$d_6$) δ 155.7, 152.3, 148.1, 147.0, 133.3, 125.0, 121.5, 112.5, 110.0, 109.0, 70.7, 65.3, 64.2, 46.7, 42.6, 34.4, 29.8, 23.0, 14.9, 10.7;

MS (APCI) m/z 462.3 (M+H)$^+$;

Anal. calcd for $C_{22}H_{31}N_5O_4S$: C, 57.25; H, 6.77; N, 15.17; % S, 6.95. Found: C, 57.14; H, 7.04; N, 15.48; % S, 6.77.

Example 562 tert-Butyl 2-{[4-amino-2-(ethoxymethyl)-1-(2-hydroxy-2-methylpropyl)-1H-imidazo[4,5-c]quinolin-7-yl]oxy}ethylcarbamate

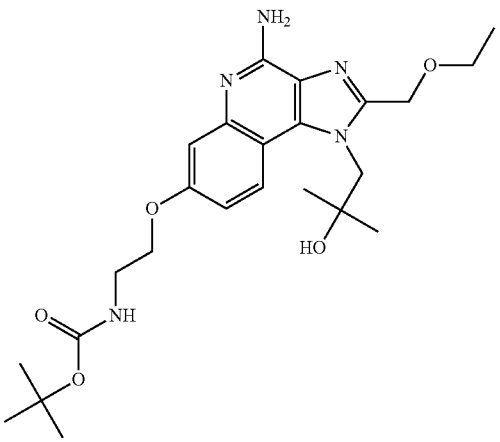 [SMILES: CCOCc1nc2c(N)nc3cc(OCCNC(=O)OC(C)(C)C)ccc3c2n1CC(C)(C)O]

A modification of the methods described in Parts A-I of Example 2 was used to prepare 2-(ethoxymethyl)-1-(2-hydroxy-2-methylpropyl)-1H-imidazo[4,5-c]quinolin-7-ol, with 3-benzyloxyaniline and 1-amino-2-methylpropan-2-ol used in lieu of 4-benzyloxyaniline and propylamine, respectively.

Part A 2-(Ethoxymethyl)-1-(2-hydroxy-2-methylpropyl)-1H-imidazo[4,5-c]quinolin-7-ol (4.0 g, 12.7 mmol) and cesium carbonate (6.20 g, 19.0 mmol) were slurried in DMF (100 mL). tert-Butyl 2-iodoethylcarbamate (4.12 g, 15.2 mmol) in DMF (27 mL) was added, and the mixture was heated to 65° C. under nitrogen. After 15 hours, the DMF was removed under reduced pressure. The residue was taken up in dichloromethane and washed repeatedly with water. The organic layer was dried over anhydrous sodium sulfate, filtered and evaporated under reduced pressure. The residue was purified by chromatography on a HORIZON HPFC system (silica gel, 2-30% CMA in chloroform) to afford, after evaporation of the solvent, 2.9 g of tert-butyl 2-{[2-(ethoxymethyl)-1-(2-hydroxy-2-methylpropyl)-1H-imidazo[4,5-c]quinolin-7-yl]oxy}ethylcarbamate as a tan foam.

Part B tert-Butyl 2-{[2-(ethoxymethyl)-1-(2-hydroxy-2-methylpropyl)-1H-imidazo[4,5-c]quinolin-7-yl]oxy}ethylcarbamate (2.9 g, 6.32 mmol) was dissolved in ethyl acetate (25 mL). 32% Peracetic acid in acetic acid (1.99 mL, 9.48 mmol) was added to the solution and the mixture was heated to 50° C. for 2 hours. Another 0.5 mL of the peracetic acid solution (2.37 mmol) was added and the reaction was stirred for 1 hour. A solution of sodium metabisulfite in water (1.5 g in 3.0 mL) was added in two portions and the reaction mixture was stirred for 10 minutes. The heat was then removed and the solution was brought to pH≈10 with saturated aqueous sodium carbonate (~15 mL). The resulting precipitate was filtered, washed with ethyl acetate (10 mL) and water (10 mL), and dried under vacuum to afford 2.8 g of tert-butyl 2-{[2-(ethoxymethyl)-1-(2-hydroxy-2-methylpropyl)-5-oxido-1H-imidazo[4,5-c]quinolin-7-yl]oxy}ethylcarbamate as a white paper-like solid with some water remaining.

Part C tert-Butyl 2-{[2-(ethoxymethyl)-1-(2-hydroxy-2-methylpropyl)-5-oxido-1H-imidazo[4,5-c]quinolin-7-yl]oxy}ethylcarbamate (2.8 g, 5.05 mmol) was dissolved in dichloromethane (35 mL) and ammonium hydroxide (25 mL). p-Toluenesulfonyl chloride (0.962 g, 5.05 mmol) was added in one portion and the reaction was stirred for 16 hours. The layers were separated and the aqueous fraction was extracted with dichloromethane. The organics were combined and evaporated under reduced pressure. The residue was purified by chromatography on a HORIZON HPFC system (silica gel, 2-25% CMA in chloroform) to provide 1.95 g of tert-butyl 2-{[4-amino-2-(ethoxymethyl)-1-(2-hydroxy-2-methylpropyl)-1H-imidazo[4,5-c]quinolin-7-yl]oxy}ethylcarbamate as white crystals.

$^1$H NMR (300 MHz, DMSO-$d_6$) δ 8.16 (d, J=9.1 Hz, 1H), 7.06-6.98 (m, 1H), 7.02 (d, J=2.6 Hz, 1H), 6.84 (dd, J=9.0, 2.6 Hz, 1H), 6.49 (s, 2H), 5.01-4.73 (m, 1H), 4.86 (s, 2H), 4.61 (br s, 2H), 4.04 (t, J=5.8 Hz, 2H), 3.50 (q, J=7.0 Hz, 2H), 3.39-3.27 (m, 2H), 1.39 (s, 9H), 1.16 (br s, 6H), 1.13 (t, J=7.0 Hz, 3H);

MS (ESI) m/z 474.3 (M+H)$^+$.

Example 563 tert-Butyl 4-{[4-amino-2-(ethoxymethyl)-1-(2-hydroxy-2-methylpropyl)-1H-imidazo[4,5-c]quinolin-7-yl]oxy}piperidine-1-carboxylate

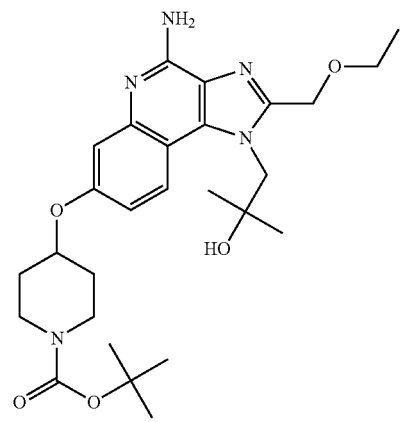 [SMILES: CCOCc1nc2c(N)nc3cc(OC4CCN(C(=O)OC(C)(C)C)CC4)ccc3c2n1CC(C)(C)O]

Part A 2-(Ethoxymethyl)-1-(2-hydroxy-2-methylpropyl)-1H-imidazo[4,5-c]quinolin-7-ol (3.31 g, 10.5 mmol), triphenylphosphine (3.43 g, 13.1 mmol) and tert-butyl 4-hydroxypiperidine-1-carboxylate (2.64 g, 13.1 mmol) were slurried in THF (105 mL) and cooled with an ice/water bath. Diisopropyl azodicarboxylate (2.58 mL, 13.1 mmol) was added dropwise. The cooling bath was removed and the reaction was stirred for 16 hours. The solvent was removed under reduced pressure and the residue was purified by chromatography on a HORIZON HPFC system (silica gel, gradient elution with 1-28% CMA in chloroform) to afford 3.32 g of tert-butyl 4-{[2-(ethoxymethyl)-1-(2-hydroxy-2-methylpropyl)-1H-imidazo[4,5-c]quinolin-7-yl]oxy}piperidine-1-carboxylate as a tan foam.

Part B

To a stirring solution of tert-butyl 4-{[2-(ethoxymethyl)-1-(2-hydroxy-2-methylpropyl)-1H-imidazo[4,5-c]quinolin-7-yl]oxy}piperidine-1-carboxylate (3.32 g, 6.66 mmol) in chloroform (70 mL) was added 3-chloroperoxybenzoic acid (2.29 g, 6.66 mmol, based on 50% purity). After 30 minutes, concentrated ammonium hydroxide (35 mL) was added and the reaction was stirred for 15 minutes. p-Toluenesulfonyl chloride (1.27 g, 6.66 mmol) was added in one portion and stirring was continued for 16 additional hours. The layers were separated and the organic fraction was washed with water, then saturated aqueous sodium chloride. The organic fraction was evaporated under reduced pressure and the residue was purified by chromatography on a HORIZON HPFC system (silica gel, gradient elution with 2-28% CMA in chloroform), followed by recrystallization from acetonitrile to afford 0.630 g of tert-butyl 4-{[4-amino-2-(ethoxymethyl)-1-(2-hydroxy-2-methylpropyl)-1H-imidazo[4,5-c]

quinolin-7-yl]oxy}piperidine-1-carboxylate as a tan crystalline solid, mp 214-215° C., decomposition.

$^1$H NMR (300 MHz, DMSO-d$_6$) δ 8.16 (d, J=9.1 Hz, 1H), 7.07 (d, J=2.6 Hz, 1H), 6.86 (dd, J=9.1, 2.6 Hz, 1H), 6.48 (s, 2H), 5.04-4.74 (m, 1H), 4.86 (s, 2H), 4.70-4.53 (m, 3H), 3.79-3.64 (m, 2H), 3.50 (q, J=7.0 Hz, 2H), 3.28-3.12 (m, 2H), 2.04-1.88 (m, 2H), 1.67-1.47 (m, 2H), 1.41 (s, 9H), 1.16 (br s, 6H), 1.13 (t, J=7.0 Hz, 3H);

MS (ESI) m/z 514.4 (M+H)$^+$;

Anal. calcd for C$_{27}$H$_{39}$N$_5$O$_5$: C, 63.14; H, 7.65; N, 13.63. Found: C, 62.79; H, 7.77; N, 13.41.

Example 564

1-[4-Amino-7-(1,3-dioxolan-2-ylmethoxy)-2-(2-methoxyethyl)-1H-imidazo[4,5-c]quinolin-1-yl]-2-methylpropan-2-ol

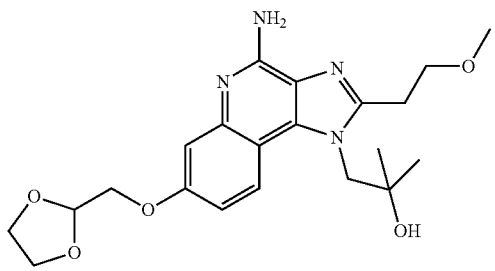 [SMILES: COCCc1nc2c(N)nc3cc(OCC4OCCO4)ccc3c2n1CC(C)(C)O]

[7-Benzyloxy-2-(2-methoxyethyl)-1H-imidazo[4,5-c]quinolin-1-yl]-2-methylpropan-2-ol was prepared according to a modification of the methods described in Parts A-H of Example 2, with 3-benzyloxyaniline, 1-amino-2-methylpropan-2-ol, and 3-methoxypropanoyl chloride used in lieu of 4-benzyloxyaniline, propylamine, and ethoxyacetyl chloride, respectively. The general methods described in Parts H through J of Example 1 were used to convert [7-benzyloxy-2-(2-methoxyethyl)-1H-imidazo[4,5-c]quinolin-1-yl]-2-methylpropan-2-ol to 4-amino-1-(2-hydroxy-2-methylpropyl)-2-(2-methoxyethyl)-1H-imidazo[4,5-c]quinolin-7-ol. A mixture of 4-amino-1-(2-hydroxy-2-methylpropyl)-2-(2-methoxyethyl)-1H-imidazo[4,5-c]quinolin-7-ol (375 mg, 1.13 mmol), 2-bromomethyl-1,3-dioxolane (208 mg, 1.24 mmol) and potassium carbonate (312 mg, 2.26 mmol) in DMF (15 mL) was heated at 70° C. overnight. The temperature was increased to 130° C. and additional 2-bromomethyl-1,3-dioxolane and potassium carbonate were added over 3 days. The reaction mixture was allowed to cool to room temperature, then was filtered to remove the solids. The filtrate was concentrated under reduced pressure and the residue was slurried in dichloromethane. Again, the solids were removed by filtration and the filtrate was concentrated under reduced pressure. Purification by chromatography on a HORIZON HPFC system (silica gel, gradient elution with 0-35% methanol/dichloromethane (20:80) in dichloromethane) followed by recrystallization from acetontrile provide 20 mg of 1-[4-amino-7-(1,3-dioxolan-2-ylmethoxy)-2-(2-methoxyethyl)-1H-imidazo[4,5-c]quinolin-1-yl]-2-methylpropan-2-ol as off white crystals, mp 131.0-136.0° C.

MS (APCI) m/z 417 (M+H)$^+$;

Anal. calcd for C$_{21}$H$_{28}$N$_4$O$_5$·0.58 H$_2$O: C, 59.08; H, 6.89; N, 13.12. Found: C, 59.08; H, 7.00; N, 13.18.

Example 565

8-[2-(1,1-Dioxidothiomorpholin-4-yl)-2-oxoethoxy]-2-(ethoxymethyl)-1-propyl-1H-imidazo[4,5-c]quinolin-4-amine

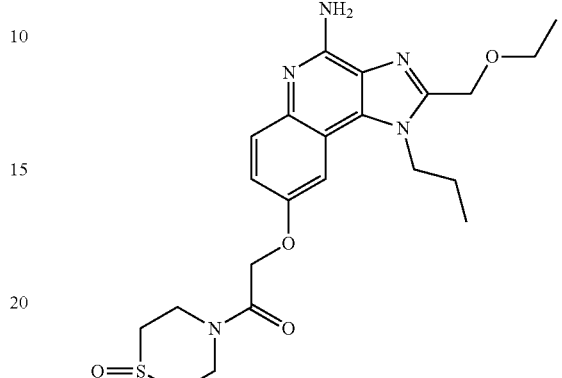

Part A

The synthesis of 2-(ethoxymethyl)-1-propyl-1H-imidazo[4,5-c]quinolin-8-ol is described in Parts A-I of Example 2. A mixture of 2-(ethoxymethyl)-1-propyl-1H-imidazo[4,5-c]quinolin-8-ol (1.0 g, 3.5 mmol), 4-(bromoacetyl)thiomorpholine (941 mg, 4.2 mmol, prepared from thiomorpholine according to the method described in Part C of Example 30), and cesium carbonate (3.4 g, 10.5 mmol) in DMF was heated at 70° C. for 6 hours, then at 50° C. overnight. The reaction was allowed to cool to room temperature and the solids were removed by filtration. The filtrate was concentrated under reduced pressure and the residue was treated with dichloromethane. More solids were removed by filtration. The filtrate was used in the next step.

Part B

The filtrate from Part A was diluted with dichloromethane (400 mL). mCPBA (60% pure, 3.50 g, 12.3 mmol) was added in portions to the stirred solution. After 5 hours, concentrated ammonium hydroxide (200 mL) was added in two portions. The mixture was stirred vigorously as p-toluenesulfonyl chloride (805 mg, 4.2 mmol) was added over 10 minutes. After 1 hour, the mixture was transferred to a separatory funnel and the layers were separated. The organic layer was washed with 1% aqueous sodium carbonate (2×100 mL). The aqueous layers were combined and extracted with chloroform (6×100 mL). The organic layers were combined, dried over magnesium sulfate, filtered, and concentrated under reduced pressure. The crude product was purified by chromatography on a HORIZON HPFC system (silica gel, gradient elution with 0-35% CMA in chloroform) then recrystallized from acetonitrile to provide 80 mg of 8-[2-(1,1-dioxidothiomorpholin-4-yl)-2-oxoethoxy]-2-(ethoxymethyl)-1-propyl-1H-imidazo[4,5-c]quinolin-4-amine as an off white solid, mp 223.0-225.0° C.

MS (APCI) m/z 476 (M+H)$^+$;

Anal. calcd for C$_{22}$H$_{29}$N$_5$O$_5$S: C, 55.56; H, 6.15; N, 14.73. Found: C, 55.45; H, 6.14; N, 15.08.

Example 566

2-(Ethoxymethyl)-8-(2-morpholin-4-yl-2-oxoethoxy)-1-propyl-1H-imidazo[4,5-c]quinolin-4-amine

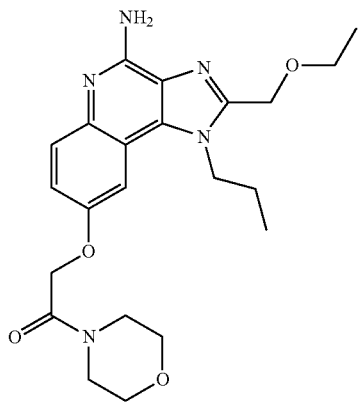 [SMILES: CCCn1c(COCC)nc2c(N)nc3ccc(OCC(=O)N4CCOCC4)cc3c21]

Part A mCPBA (60% pure, 27.5 g, 95.9 mmol) was added in small portions over a period of 20 minutes to 8-benzyloxy-2-(ethoxymethyl)-1-propyl-1H-imidazo[4,5-c]quinoline (30.0 g, 79.9 mmol, prepared in Parts A through H of Example 2) in dichloromethane (400 mL). After the reaction was stirred for two hours, it was washed with 1% aqueous sodium carbonate (3×100 mL). The combined aqueous washings were extracted with chloroform (200 mL), and the combined organic fractions were dried over magnesium sulfate and filtered. Trichloroacetyl isocyanate (18.0 g, 95.9 mmol) was added dropwise to the filtrate, and then the reaction was stirred overnight at ambient temperature. Concentrated ammonium hydroxide (100 mL) was slowly added, and the mixture was stirred at ambient temperature for 30 minutes. The organic layer was separated and washed with 1% aqueous sodium carbonate (2×100 mL). The combined aqueous fractions were extracted with chloroform (3×75 mL). The organic fractions were combined, dried over magnesium sulfate, filtered, and concentrated under reduced pressure to yield a dark semi-solid. The crude product was purified on silica gel (1 kg, eluting sequentially with 2% methanol in chloroform and 5% methanol in chloroform) to provide 22 g of 8-benzyloxy-2-(ethoxymethyl)-1-propyl-1H-imidazo[4,5-c]quinolin-4-amine as an off-white solid.

Part B

A dispersion of 8-benzyloxy-2-(ethoxymethyl)-1-propyl-1H-imidazo[4,5-c]quinolin-4-amine (22.0 g, 56.3 mmol) and 10% palladium on carbon (7.5 g) in 50:50 ethanol/methanol (300 mL) was shaken under hydrogen pressure on a Parr apparatus at 50 psi ($3.4 \times 10^5$ Pa) for three days. The reaction mixture was filtered to remove the catalyst, which was washed with hot ethanol/methanol (3 L). The filtrate was concentrated under reduced pressure. The resulting solid was triturated with methanol and isolated by filtration to provide 10.4 g of 4-amino-2-(ethoxymethyl)-1-propyl-1H-imidazo[4,5-c]quinolin-8-ol as an off-white solid.

Part C

Cesium carbonate (1.62 g, 5.00 mmol) was added to a solution of 2-bromo-1-morpholin-4-yl-ethanone (414 mg, 1.99 mmol), 4-amino-2-(ethoxymethyl)-1-propyl-1H-imidazo[4,5-c]quinolin-8-ol (500 mg, 1.66 mmol), and anhydrous DMF (20 mL). The reaction mixture was heated at 75° C. overnight, allowed to cool, and poured into deionized water (300 mL). The resulting mixture was stirred for 30 minutes and then extracted with chloroform (3×100 mL). The combined organic fractions were dried over magnesium sulfate, filtered, and concentrated under reduced pressure. The resulting solid was purified by chromatography on a HORIZON HPFC system (silica cartridge, eluting with a gradient of 0-35% methanol/dichloromethane (10:90) in dichloromethane). The resulting solid was recrystallized from acetonitrile to yield 333 mg of 2-(ethoxymethyl)-8-(2-morpholin-4-yl-2-oxoethoxy)-1-propyl-1H-imidazo[4,5-c]quinolin-4-amine as an off-white solid, mp 196-197° C. Anal. calcd for $C_{22}H_{29}N_5O_4$: C, 61.81; H, 6.84; N, 16.38. Found: C, 61.72; H, 6.86; N, 16.62.

Example 567

2-(Methoxymethyl)-8-[2-(1-methylpyrrolidin-2-yl)ethoxy]-1-propyl-1H-imidazo[4,5-c]quinolin-4-amine

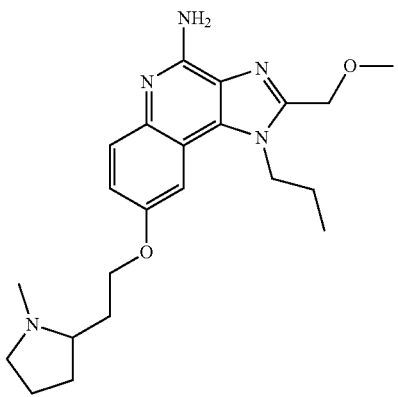 [SMILES: CCCn1c(COC)nc2c(N)nc3ccc(OCCC4CCCN4C)cc3c21]

Potassium carbonate (1.48 g, 10.75 mmol), 2-(2-chloroethyl)-1-methylpyrrolidine hydrochloride (483 mg, 2.62 mmol), sodium iodide (100 mg, 0.66 mmol), and 8-hydroxy-2-methoxymethyl-1-propyl-1H-imidazo[4,5-c]quinolin-4-amine (500 mg, 1.75 mmol) were combined in acetone and heated at reflux overnight. Additional 2-(2-chloroethyl)-1-methylpyrrolidine hydrochloride and potassium carbonate were added, and the reaction was heated at reflux overnight. The reaction mixture was then cooled to ambient temperature, filtered, and concentrated under reduced pressure. The residue was purified by chromatography on a HORIZON HPFC system (silica cartridge, eluting with a gradient of CMA: chloroform from 0:100 to 25:75) followed by recrystallization from acetonitrile to afford 105 mg of 2-methoxymethyl-8-[2-(1-methylpyrrolidin-2-yl)ethoxy]-1-propyl-1H-imidazo[4,5-c]quinolin-4-amine as an off-white solid, mp 155-157° C. Anal. calcd for $C_{22}H_{31}N_5O_2 \cdot 0.25H_2O$: C, 65.66; H, 7.90; N, 17.40. Found: C, 65.66; H, 8.24; N, 17.26.

Example 568

2-Ethyl-7-(2-morpholin-4-ylethoxy)-1-(tetrahydro-2H-pyran-4-ylmethyl)-1H-imidazo[4,5-c]quinolin-4-amine

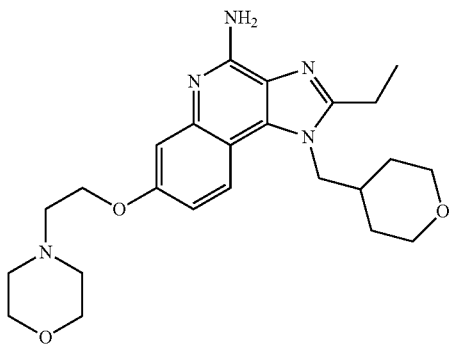 [SMILES: CCc1nc2c(N)nc3cc(OCCN4CCOCC4)ccc3c2n1CC1CCOCC1]

Cesium carbonate (1.41 g, 4.32 mmol) was added to a solution of 4-(2-chloroethyl)morpholine hydrochloride (348 mg, 1.87 mmol) and 4-amino-2-ethyl-1-(tetrahydro-2H-pyran-4-ylmethyl)-1H-imidazo[4,5-c]quinolin-7-ol (471 mg, 1.44 mmol, prepared in Parts A and B of Example 553) in anhydrous DMF (25 mL). The reaction mixture was heated at 75° C. overnight, allowed to cool, and poured into 1% aqueous sodium carbonate (300 mL). The resulting mixture was stirred for two hours and then extracted with chloroform (4×100 mL). The combined organic fractions were dried over magnesium sulfate, filtered, and concentrated under reduced pressure. The resulting solid was purified by chromatography on a HORIZON HPFC system (silica cartridge, eluting with a gradient of 0-40% methanol/dichloromethane (20:80) in dichloromethane). The resulting solid was recrystallized from acetonitrile and dried under vacuum to yield 393 mg of 2-ethyl-7-(2-morpholin-4-ylethoxy)-1-(tetrahydro-2H-pyran-4-ylmethyl)-1H-imidazo[4,5-c]quinolin-4-amine as an off-white solid, mp 230-232° C. Anal. calcd for $C_{24}H_{33}N_5O_3$: C, 65.58; H, 7.57; N, 15.93. Found: C, 65.48; H, 7.39; N, 15.91.

Example 569

2-(Ethoxymethyl)-1-propyl-8-(tetrahydrofuran-2-ylmethoxy)-1H-imidazo[4,5-c]quinolin-4-amine

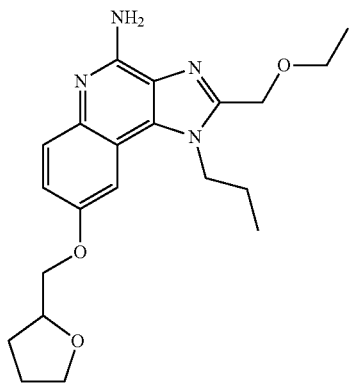 [SMILES: CCCn1c(COCC)nc2c(N)nc3ccc(OCC4CCCO4)cc3c21]

Cesium carbonate (1.62 g, 5.00 mmol) was added to a solution of tetrahydrofurfuryl bromide (330 mg, 1.99 mmol) and 4-amino-2-(ethoxymethyl)-1-propyl-1H-imidazo[4,5-c]quinolin-8-ol (500 mg, 1.66 mmol, prepared in Parts A and B of Example 566) in anhydrous DMF (20 mL). The reaction mixture was heated at 75° C. overnight, allowed to cool, and poured into deionized water (300 mL). After 30 minutes of stirring, a brown precipitate formed. Sodium chloride (100 g) was added, and the resulting mixture was stirred for three hours and then filtered. The isolated precipitate was purified by chromatography on a HORIZON HPFC system (silica cartridge, eluting with a gradient of 0-35% methanol/dichloromethane (10:90) in dichloromethane). The resulting solid was recrystallized from acetonitrile and dried under high vacuum to yield 429 mg of 2-(ethoxymethyl)-1-propyl-8-(tetrahydrofuran-2-ylmethoxy)-1H-imidazo[4,5-c]quinolin-4-amine as a fluffy, white solid, mp 178-179° C. Anal. calcd for $C_{21}H_{28}N_4O_3 \cdot 0.25\ H_2O$: C, 64.84; H, 7.39; N, 14.40. Found: C, 65.03; H, 7.75; N, 14.48.

Example 570

4-Amino-2-(ethoxymethyl)-1-propyl-1H-imidazo[4,5-c]quinolin-8-yl morpholine-4-carboxylate

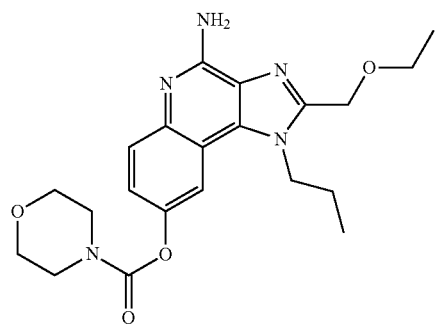 [SMILES: CCCn1c(COCC)nc2c(N)nc3ccc(OC(=O)N4CCOCC4)cc3c21]

Cesium carbonate (1.62 g, 5.00 mmol) was added to a solution of 4-amino-2-(ethoxymethyl)-1-propyl-1H-imidazo[4,5-c]quinolin-8-ol (500 mg, 1.66 mmol, prepared in Parts A and B of Example 566) in anhydrous DMF (30 mL). The reaction was stirred for ten minutes, and 4-morpholinecarbonyl chloride (275 mg, 1.83 g) was then added. The reaction was stirred overnight at ambient temperature and poured into deionized water (300 mL). The resulting mixture was stirred for one hour and then extracted with chloroform (3×100 mL). The combined organic fractions were concentrated under reduced pressure, and the resulting solid was purified by chromatography on a HORIZON HPFC system (silica cartridge, eluting with a gradient of 0-20% CMA in chloroform). The resulting solid was recrystallized from acetonitrile and dried under vacuum to yield 606 mg of 4-amino-2-(ethoxymethyl)-1-propyl-1H-imidazo[4,5-c]quinolin-8-yl morpholine-4-carboxylate as a white, crystalline solid, mp 193-196° C. Anal. calcd for $C_{21}H_{27}N_5O_4$: C, 61.00; H, 6.58; N, 16.94. Found: C, 61.01; H, 6.51; N, 17.21.

Example 571

8-(2-Azepan-1-ylethoxy)-2-(ethoxymethyl)-1-propyl-1H-imidazo[4,5-c]quinolin-4-amine

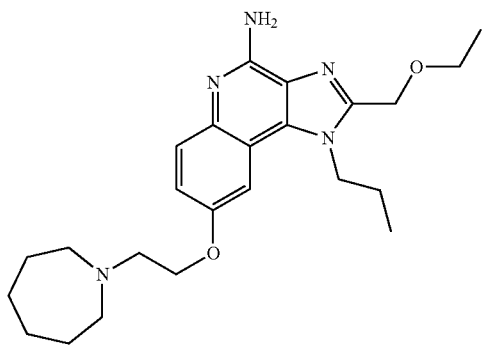 [SMILES: CCCn1c(COCC)nc2c(N)nc3ccc(OCCN4CCCCCC4)cc3c21]

The preparation and purification methods described in Part C of Example 566 were followed, using 1-(2-chloroethyl)azepane hydrochloride (395 mg, 1.99 mmol) in lieu of 2-bromo-1-morpholin-4-ylethanone, to provide 275 mg of 8-(2-azepan-1-ylethoxy)-2-(ethoxymethyl)-1-propyl-1H-imidazo[4,5-c]quinolin-4-amine as an off-white, crystalline solid, mp 146-148° C. Anal. calcd for $C_{24}H_{35}N_5O_2$: C, 67.74; H, 8.29; N, 16.46. Found: C, 67.49; H, 8.47; N, 16.43.

Examples 572-645

Part A

A reagent (0.11 mmol, 1.1 equivalents) from the table below was added to a test tube containing a solution of 7-(3-aminopropoxy)-2-(2-methoxyethyl)-1-propyl-1H-imidazo[4,5-c]quinolin-4-amine (36 mg, 0.10 mmol, prepared as described in Example 394) and triethylamine (0.028 mL, 0.20 mmol) in N,N-dimethylacetamide (1 mL). The test tubes were capped and shaken overnight at room temperature. The solvent was removed by vacuum centrifugation. The reaction mixtures were separated by solid-supported liquid-liquid extraction according to the following procedure. Each sample was dissolved in chloroform (1 mL) and loaded onto diatomaceous earth that had been treated with 600 µL of deionized water for 20 minutes. After ten minutes, chloroform (500 µL) was added to elute the product from the diatomaceous earth into a well of a collection plate. After an additional ten minutes, the process was repeated with additional chloroform (500 µL). The solvent was then removed by vacuum centrifugation.

Part B

Dichloromethane (1 mL) was added to test tubes containing the reaction mixtures from Part A, and the resulting mixtures were sonicated until all solids were dissolved. The resulting solutions were cooled to 0° C., and a solution of 1 M boron tribromide in dichloromethane (130 µL, 0.13 mmol) was added to each test tube, which was maintained at 0° C. for 30 minutes and then shaken on a vortexer for 2.5 hours. Methanol (0.5 mL) and 6 M aqueous hydrochloric acid (500 µL) were added to each test tube; each tube was shaken on a vortexer for 30 minutes. The volatiles were removed by vacuum centrifugation, and the compounds were purified by prepHPLC using the method described in Examples 376-386. The table below shows the reagent added to each test tube, the structure of the resulting compound, and the observed accurate mass for the isolated trifluoroacetate salt.

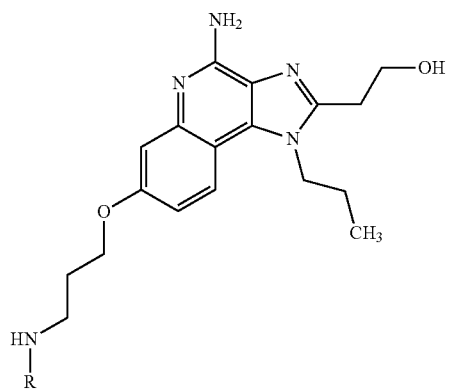

| Example | Reagent | R | Measured Mass (M + H) |
|---|---|---|---|
| 572 | None - starting material only | –H | 344.2116 |
| 573 | Propionyl chloride | 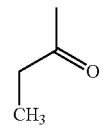 | 400.2354 |

-continued

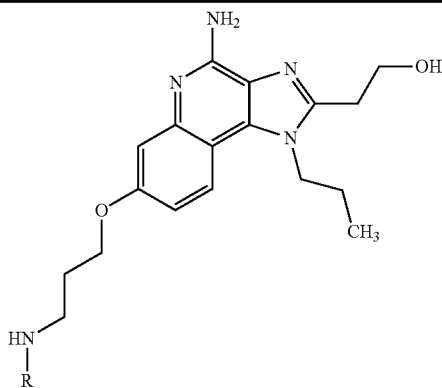

| Example | Reagent | R | Measured Mass (M + H) |
|---|---|---|---|
| 574 | Methyl chloroformate | methyl carbonate | 402.2151 |
| 575 | Cyclopropanecarbony chloride | cyclopropanecarbonyl | 412.2344 |
| 576 | Butyryl chloride | butyryl | 414.2487 |
| 577 | Isobutyryl chloride | isobutyryl | 414.2506 |
| 578 | Ethyl chloroformate | ethyl carbonate | 416.2283 |
| 579 | Methoxyacetyl chloride | hydroxyacetyl | 402.2147 |
| 580 | Cyclobutanecarbonyl chloride | cyclobutanecarbonyl | 426.2477 |
| 581 | Isovaleryl chloride | isovaleryl | 428.2657 |

-continued
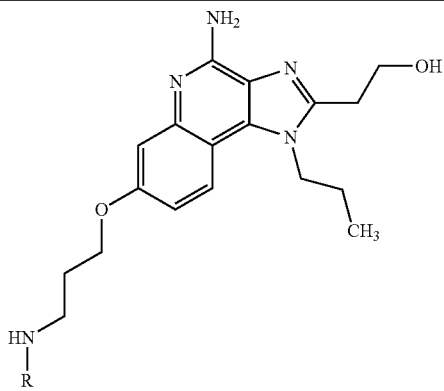
| Example | Reagent | R | Measured Mass (M + H) |
|---|---|---|---|
| 582 | Pivaloyl chloride | (CH₃)₃C-C(=O)- | 428.2662 |
| 583 | Cyclopentylacetyl chloride | cyclopentyl-C(=O)- | 440.2642 |
| 584 | Isobutyl chloroformate | (CH₃)₂CHCH₂-O-C(=O)- | 444.2586 |
| 585 | Benzoyl chloride | C₆H₅-C(=O)- | 448.2395 |
| 586 | Cyclohexanecarbonyl chloride | cyclohexyl-C(=O)- | 454.2772 |
| 587 | m-Toluoyl chloride | 3-CH₃-C₆H₄-C(=O)- | 462.2513 |
| 588 | o-Toluoyl chloride | 2-CH₃-C₆H₄-C(=O)- | 462.2517 |

-continued
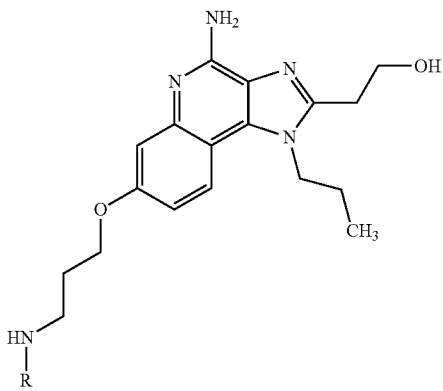
| Example | Reagent | R | Measured Mass (M + H) |
|---|---|---|---|
| 589 | p-Toluoyl chloride | | 462.2544 |
| 590 | Phenylacetyl chloride | | 462.2515 |
| 591 | 2-Fluorobenzoyl chloride | | 466.2296 |
| 592 | 4-Fluorobenzoyl chloride | | 466.2259 |
| 593 | 4-Cyanobenzoyl chloride | | 473.2291 |
| 594 | Cinnamoyl chloride | | 474.2477 |

-continued

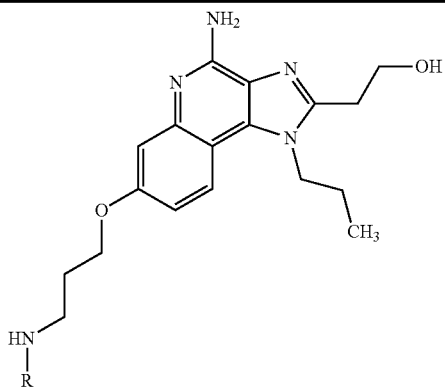

| Example | Reagent | R | Measured Mass (M + H) |
|---|---|---|---|
| 595 | Hydrocinnamoyl chloride | 3-phenylpropanoyl | 476.2686 |
| 596 | 2-Chlorobenzoyl chloride | 2-chlorobenzoyl | 482.1996 |
| 597 | 3-Chlorobenzoyl chloride | 3-chlorobenzoyl | 482.1943 |
| 598 | 4-Chlorobenzoyl chloride | 4-chlorobenzoyl | 482.1992 |
| 599 | Isonicotinoyl chloride hydrochloride | isonicotinoyl | 449.2347 |
| 600 | Nicotinoyl chloride hydrochloride | nicotinoyl | 449.2321 |
| 601 | Picolinoyl chloride hydrochloride | picolinoyl | 449.2292 |

-continued

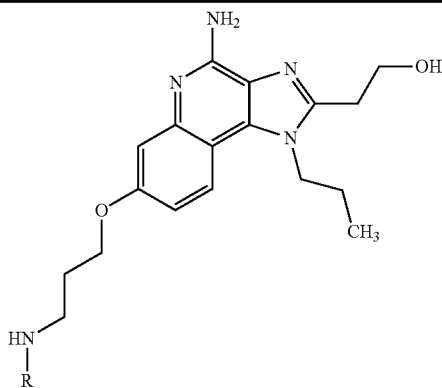

| Example | Reagent | R | Measured Mass (M + H) |
|---|---|---|---|
| 602 | trans-2-Phenyl-1-Cyclopropanecarbonyl chloride | (trans-2-phenylcyclopropanecarbonyl group) | 488.2635 |
| 603 | 4-Dimethylaminobenzoyl chloride | (4-dimethylaminobenzoyl group) | 491.2744 |
| 604 | 4-Chlorophenylacetyl chloride | (4-chlorophenylacetyl group) | 496.2112 |
| 605 | Methanesulfonyl chloride | (methanesulfonyl group) | 422.1879 |
| 606 | Ethanesulfonyl chloride | (ethanesulfonyl group) | 436.2013 |
| 607 | 1-Propanesulfonyl chloride | (1-propanesulfonyl group) | 450.2137 |
| 608 | Isopropylsulfonyl chloride | (isopropylsulfonyl group) | 450.2165 |

-continued

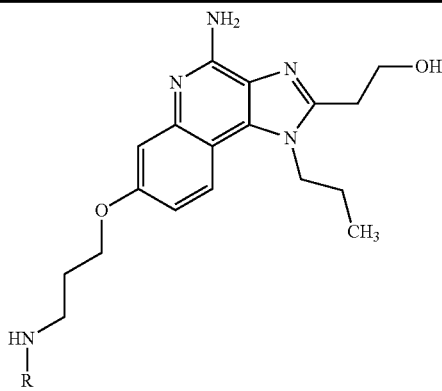

| Example | Reagent | R | Measured Mass (M + H) |
|---|---|---|---|
| 609 | Dimethylsulfamoyl chloride | H₃C–N(CH₃)–S(=O)₂– | 451.2091 |
| 610 | 1-Butanesulfonyl chloride | CH₃CH₂CH₂CH₂–S(=O)₂– | 464.2363 |
| 611 | Benzenesulfonyl chloride | C₆H₅–S(=O)₂– | 484.2063 |
| 612 | alpha-Toluenesulfonyl chloride | C₆H₅CH₂–S(=O)₂– | 498.2151 |
| 613 | 2-Methylbenzenesulfonyl chloride | 2-CH₃-C₆H₄–S(=O)₂– | 498.2155 |
| 614 | 4-Methylbenzenesulfonyl chloride | 4-CH₃-C₆H₄–S(=O)₂– | 498.2207 |
| 615 | 4-Fluorobenzenesulfonyl chloride | 4-F-C₆H₄–S(=O)₂– | 502.1945 |

-continued

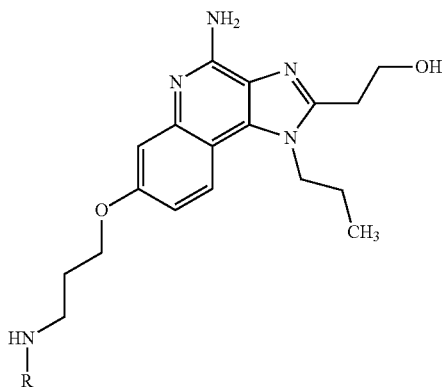

| Example | Reagent | R | Measured Mass (M + H) |
|---|---|---|---|
| 616 | beta-Styrenesulfonyl chloride | (2-phenylethenyl)sulfonyl | 510.2184 |
| 617 | 3,5-Dimethylbenzenesulfonyl chloride | (3,5-dimethylphenyl)sulfonyl | 512.2330 |
| 618 | 2-Chlorobenzenesulfonyl chloride | (2-chlorophenyl)sulfonyl | 518.1660 |
| 619 | 3-Chlorobenzenesulfonyl chloride | (3-chlorophenyl)sulfonyl | 518.1663 |
| 620 | 1-Naphthalenesulfonyl chloride | (naphthalen-1-yl)sulfonyl | 534.2173 |
| 621 | 2-Naphthalenesulfonyl chloride | (naphthalen-2-yl)sulfonyl | 534.2125 |

-continued
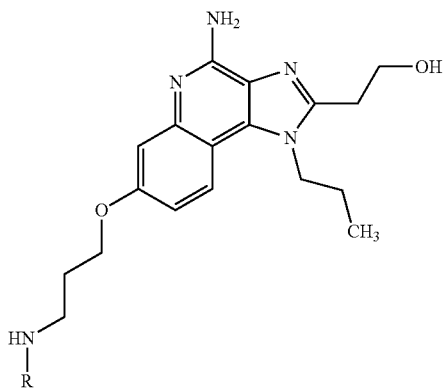
| Example | Reagent | R | Measured Mass (M + H) |
|---|---|---|---|
| 622 | 8-Quinolinesulfonyl chloride | | 535.2122 |
| 623 | 2-(Trifluoromethyl)benzenesulfonyl chloride | | 552.1940 |
| 624 | 3-(Trifluoromethyl)benzenesulfonyl chloride | | 552.1906 |
| 625 | 4-(Trifluoromethyl)benzenesulfonyl chloride | | 552.1903 |
| 626 | Ethyl isocyanate | | 415.2448 |
| 627 | N-Butyl isocyanate | | 443.2809 |

-continued
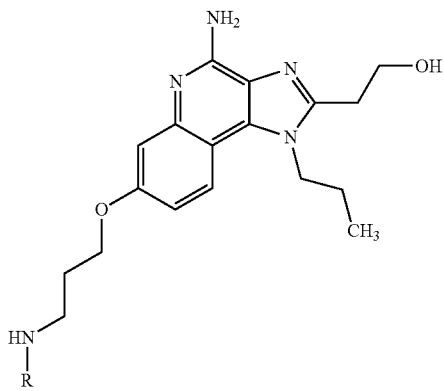
| Example | Reagent | R | Measured Mass (M + H) |
|---|---|---|---|
| 628 | sec-Butyl isocyanate | 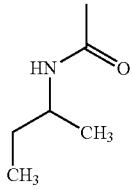 | 443.2796 |
| 629 | Cyclopentyl isocyanate | 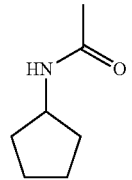 | 455.2740 |
| 630 | Pentyl isocyanate | 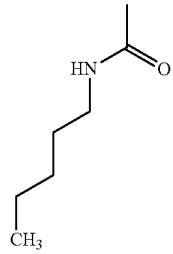 | 457.2888 |
| 631 | Phenyl isocyanate | 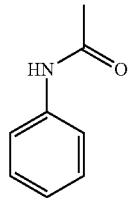 | 463.2447 |
| 632 | m-Tolyl isocyanate | 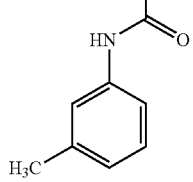 | 477.2644 |

-continued
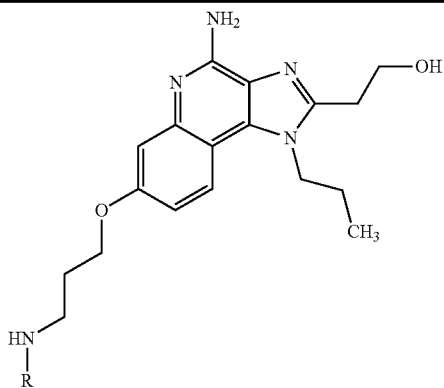
| Example | Reagent | R | Measured Mass (M + H) |
|---|---|---|---|
| 633 | o-Tolyl isocyanate | 2-methylphenyl-NHC(O)- | 477.2613 |
| 634 | p-Tolyl isocyanate | 4-methylphenyl-NHC(O)- | 477.2592 |
| 635 | 2,6-Dimethylphenyl isocyanate | 2,6-dimethylphenyl-NHC(O)- | 491.2792 |
| 636 | (R)-(+)-alpha-Methylbenzyl isocyanate | (R)-PhCH(CH₃)-NHC(O)- | 491.2758 |
| 637 | (S)-(−)-alpha-Methylbenzyl isocyanate | (S)-PhCH(CH₃)-NHC(O)- | 491.2758 |

-continued
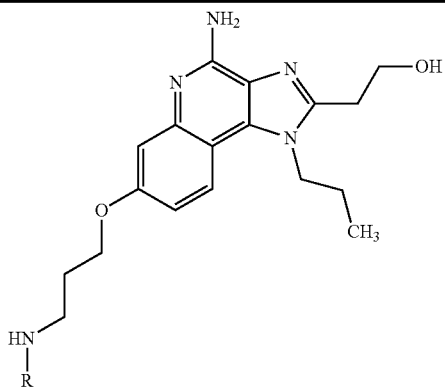
| Example | Reagent | R | Measured Mass (M + H) |
|---|---|---|---|
| 638 | 2-Phenyl ethylisocyanate | ![phenethyl urea] | 491.2752 |
| 639 | 2-(Thien-2-yl)ethyl isocyanate | ![thienylethyl urea] | 497.2327 |
| 640 | 4-Chlorophenyl isocyanate | ![4-chlorophenyl urea] | 497.2092 |
| 641 | trans-2-Phenylcyclopropyl isocyanate | ![trans-phenylcyclopropyl urea] | 503.2795 |
| 642 | N,N-Dimethylcarbamoyl chloride | ![N,N-dimethyl urea] | 415.2455 |

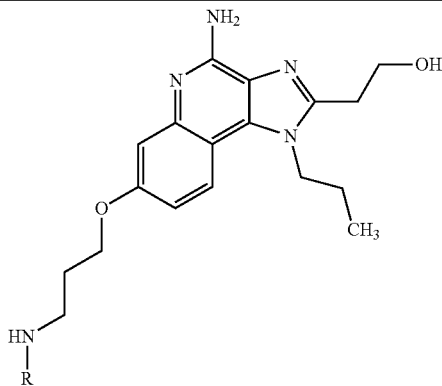

| Example | Reagent | R | Measured Mass (M + H) |
|---|---|---|---|
| 643 | 1-Piperidinecarbonyl chloride | | 455.2752 |
| 644 | 4-Methyl-1-piperazinecarbonyl chloride | | 470.2906 |
| 645 | N-Methyl-N-phenylcarbamoyl chloride | | 477.2604 |

Example 646

1-[4-Amino-2-(ethoxymethyl)-7-(2-morpholin-4-yl-2-oxoethoxy)-1H-imidazo[4,5-c]quinolin-1-yl]-2-methylpropan-2-ol

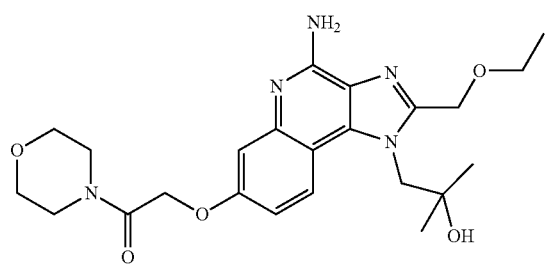 [SMILES: CCOCc1nc2c(N)nc3cc(OCC(=O)N4CCOCC4)ccc3c2n1CC(C)(C)O]

Part A

A modification of the methods described in Parts A-H of Example 2 was used to prepare 1-[7-(benzyloxy)-2-(ethoxymethyl)-1H-imidazo[4,5-c]quinolin-1-yl]-2-methyl-propan-2-ol, with 3-benzyloxyaniline and 1-amino-2-methylpropan-2-ol used in lieu of 4-benzyloxyaniline and propylamine, respectively. Modification on the methods described in steps M, N, and I of Example 2 were used to convert 1-[7-(benzyloxy)-2-(ethoxymethyl)-1H-imidazo[4,5-c]quinolin-1-yl]-2-methylpropan-2-ol into 4-amino-2-(ethoxymethyl)-1-(2-hydroxy-2-methylpropyl)-1H-imidazo[4,5-c]quinolin-7-ol.

Part B

A mixture of 4-amino-2-(ethoxymethyl)-1-(2-hydroxy-2-methylpropyl)-1H-imidazo[4,5-c]quinolin-7-ol (prepared as described above, 750 mg, 2.27 mmol), 4-(bromoacetyl)morpholine (565 mg, 2.72 mmol), and cesium carbonate (2.22 g, 6.81 mmol) in DMF (30 mL) was heated at 75° C. overnight. The reaction mixture was allowed to cool and was poured into water (300 mL). After 30 minutes, the solution was extracted with chloroform (6×75 mL). The organic layers were combined, dried over magnesium sulfate, filtered, and concentrated to dryness. The resulting solid was purified by chromatography on a HORIZON HPFC system (silica gel, gradient elution with 0-35% methanol/dichloromethane (1:10) in dichloromethane) The appropriate fractions were combined and concentrated to yield an off white solid that was slurried in boiling acetonitrile for 15 minutes. The slurry was allowed to cool with stirring. The solid was isolated by filtration and dried to yield 797 mg of 1-[4-amino-2-(ethoxymethyl)-7-(2-morpholin-4-yl-2-oxoethoxy)-1H-imidazo[4,5-c]quinolin-1-yl]-2-methylpropan-2-ol as an off-white solid, mp 209-211° C.

MS (ESI) m/z 458 (M+H)+;

Anal. calcd for $C_{23}H_3N_5O_5$: C, 60.38; H, 6.83; N, 15.31. Found: C, 60.25; H, 7.12; N, 15.50.

Example 647

1-[4-Amino-2-(ethoxymethyl)-7-(2-morpholin-4-ylethoxy)-1H-imidazo[4,5-c]quinolin-1-yl]-2-methylpropan-2-ol

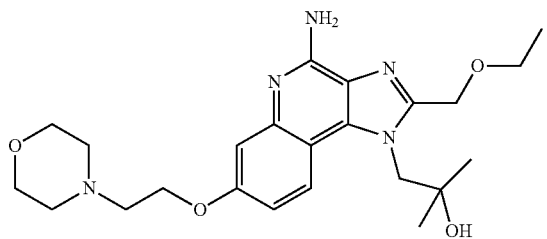 [SMILES: CCOCc1nc2c(N)nc3cc(OCCN4CCOCC4)ccc3c2n1CC(C)(C)O]

The general procedure described in Example 646 was used to convert 4-amino-2-(ethoxymethyl)-1-(2-hydroxy-2-methylpropyl)-1H-imidazo[4,5-c]quinolin-7-ol (prepared as described in Part A of Example 646, 750 mg, 2.27 mmol) into 1-[4-amino-2-(ethoxymethyl)-7-(2-morpholin-4-ylethoxy)-1H-imidazo[4,5-c]quinolin-1-yl]-2-methylpropan-2-ol with 4-(2-chloroethyl)morpholine hydrochloride (506 mg, 2.72 mmol) used in lieu of 4-(bromoacetyl)morpholine. The product was purified by chromatography on a HORIZON HPFC system (silica gel, gradient elution with 0-25% CMA in chloroform). The appropriate fractions were combined and concentrated to yield a white foam that was crystallized from acetontrile to provide 275 mg of 1-[4-amino-2-(ethoxymethyl)-7-(2-morpholin-4-ylethoxy)-1H-imidazo[4,5-c]quinolin-1-yl]-2-methylpropan-2-ol as an off-white crystalline solid, mp 161-163° C.

MS (ESI) m/z 444 (M+H)+;

Anal. calcd for $C_{23}H_{33}N_5O_4$: C, 62.28; H, 7.50; N, 15.79. Found: C, 62.15; H, 7.70; N, 16.01.

Example 648

2-(Ethoxymethyl)-7-(2-morpholin-4-yl-2-oxoethoxy)-1-propyl-1H-imidazo[4,5-c]quinolin-4-amine

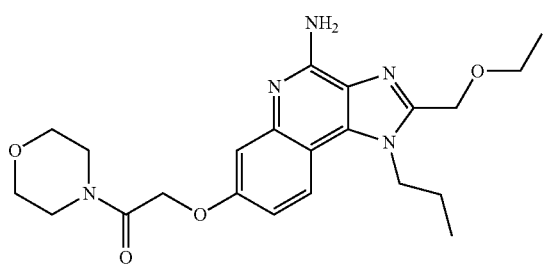 [SMILES: CCCn1c(COCC)nc2c(N)nc3cc(OCC(=O)N4CCOCC4)ccc3c21]

A modification on the procedure described in Example 646 was used to convert 4-amino-2-(ethoxymethyl)-1-propyl-1H-imidazo[4,5-c]quinolin-7-ol (prepared as described in Parts A and B of Example 51) into 2-(ethoxymethyl)-7-(2-morpholin-4-ylethoxy)-1-propyl-1H-imidazo[4,5-c]quinolin-4-amine. The reaction mixture was heated overnight then was poured slowly into water. After the mixture was stirred for 1 hour, a tan solid was isolated by filtration and recrystallized from acetonitrile to afford 2-(ethoxymethyl)-7-(2-morpholin-4-yl-2-oxoethoxy)-1-propyl-1H-imidazo[4,5-c]quinolin-4-amine as off-white crystals, mp 213° C.

MS (APCI) m/z 428 (M+H)+;

Anal. calcd for $C_{22}H_{29}N_5O_4$: C, 61.81; H, 6.84; N, 16.38. Found: C, 61.61; H, 7.17; N, 16.51.

Example 649

2-(Ethoxymethyl)-7-(2-morpholin-4-ylethoxy)-1-propyl-1H-imidazo[4,5-c]quinolin-4-amine

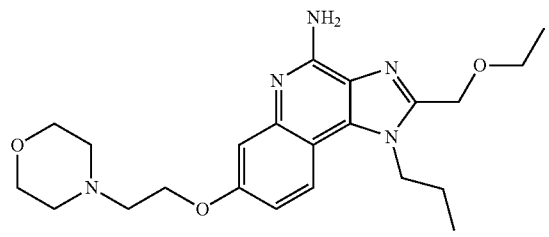 [SMILES: CCCn1c(COCC)nc2c(N)nc3cc(OCCN4CCOCC4)ccc3c21]

A modification on the procedure described in Example 647 was used to convert 4-amino-2-(ethoxymethyl)-1-propyl-1H-imidazo[4,5-c]quinolin-7-ol (prepared as described in Parts A and B of Example 51) into 2-(ethoxymethyl)-7-(2-morpholin-4-ylethoxy)-1-propyl-1H-imidazo[4,5-c]quinolin-4-amine. The reaction mixture was heated overnight and then was poured slowly into water. The mixture was stirred for 1 hour and a tan solid was isolated by filtration and recrystallized from acetonitrile to afford off-white crystals, mp 191-192° C.

MS (APCI) m/z 414.3 (M+H)+;

Anal. calcd for $C_{22}H_{31}N_5O_3$: C, 63.90; H, 7.56; N, 16.94. Found: C, 63.76; H, 7.48; N, 16.83.

Example 650

7-(2-Aminoethoxy)-2-ethyl-1-(tetrahydro-2H-pyran-4-ylmethyl)-1H-imidazo[4,5-c]quinolin-4-amine

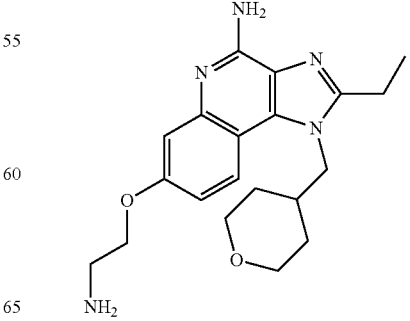

7-(2-Aminoethoxy)-2-ethyl-1-(tetrahydro-2H-pyran-4-ylmethyl)-1H-imidazo[4,5-c]quinolin-4-amine dihydrochloride (prepared as described in Example 552, 0.100 g) was dissolved in water (5 mL) and saturated aqueous sodium chloride (5 mL). The solution was brought to pH 13 with 50% aqueous sodium hydroxide and extracted with chloroform. The chloroform was washed successively with water and saturated aqueous sodium chloride, dried over anhydrous sodium sulfate, filtered and concentrated. The residue was recrystallized from acetonitrile to provide 0.065 g of 7-(2-aminoethoxy)-2-ethyl-1-(tetrahydro-2H-pyran-4-ylmethyl)-1H-imidazo[4,5-c]quinolin-4-amine as a white crystalline solid, mp 238° C. (decomposition).

$^1$H NMR (300 MHz, DMSO-$d_6$) δ 7.91 (d, J=9.0 Hz, 1H), 7.05 (d, J=2.6 Hz, 1H), 6.92 (dd, J=9.0, 2.6 Hz, 1H), 6.32 (s, 2H), 4.38-4.37 (m, 2H), 3.99 (t, J=5.8 Hz, 2H), 3.83-3.79 (m, 2H), 3.17-3.12 (m, 2H), 2.93-2.89 (m, 4H), 2.12-2.01 (m, 1H), 1.58-1.38 (m, 6H), 1.36 (t, J=7.4 Hz, 3H);

MS (ESI) m/z 370.2 (M+H)$^+$;

Anal. calcd for $C_{20}H_{27}N_5O_2$: C, 65.02; H, 7.37; N, 18.96. Found: C, 64.79; H, 7.32; N, 18.96.

Example 651

N-(2-{[4-Amino-2-ethyl-1-(tetrahydro-2H-pyran-4-ylmethyl)-1H-imidazo[4,5-c]quinolin-7-yl]oxy}ethyl)-N'-isopropylurea

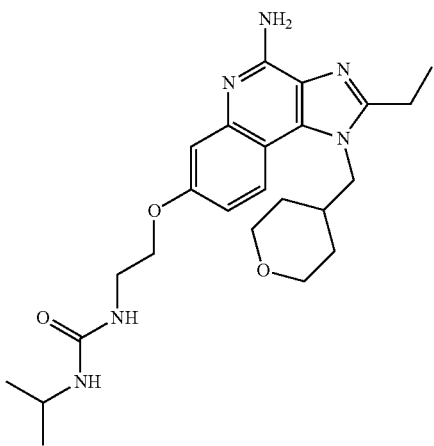 [SMILES: CCc1nc2c(N)nc3cc(OCCNC(=O)NC(C)C)ccc3c2n1CC1CCOCC1]

7-(2-Aminoethoxy)-2-ethyl-1-(tetrahydro-2H-pyran-4-ylmethyl)-1H-imidazo[4,5-c]quinolin-4-amine dihydrochloride (0.480 g, 1.03 mmol; prepared as in Example 552), dichloromethane (10 mL), and triethylamine (0.702 mL, 5.03 mmol) were combined and stirred for 10 minutes. Isopropyl isocyanate (0.101 mL, 1.03 mmol) was added dropwise and the reaction was stirred for 16 hours. Saturated aqueous sodium carbonate (~5 mL) was added and the reaction was stirred for 10 minutes. The layers were separated. The organic fraction was washed with water and then concentrated under reduced pressure. The resulting crude product was purified by chromatography on a HORIZON HPFC system (silica gel, gradient elution of 2-20% CMA in chloroform) followed by recrystallization from acetonitrile to provide 0.390 g of N-(2-{[4-amino-2-ethyl-1-(tetrahydro-2H-pyran-4-ylmethyl)-1H-imidazo[4,5-c]quinolin-7-yl]oxy}ethyl)-N-isopropylurea as a white solid, mp 223-225° C.

$^1$H NMR (300 MHz, DMSO-$d_6$) δ 7.92 (d, J=9.1 Hz, 1H), 7.06 (d, J=2.6 Hz, 1H), 6.92 (dd, J=9.0, 2.6 Hz, 1H), 6.38 (s, 2H), 5.95 (t, J=5.6 Hz, 1H), 5.83 (d, J=7.6 Hz, 1H), 4.39-4.36 (m, 2H), 4.03 (t, J=5.8 Hz, 2H), 3.84-3.79 (m, 2H), 3.73-3.62 (m, 1H), 3.45-3.36 (m, 2H), 3.21-3.09 (m, 2H), 2.91 (q, J=7.4 Hz, 2H), 2.13-1.97 (m, 1H), 1.56-1.36 (m, 4H), 1.36 (t, J=7.4 Hz, 3H), 1.03 (d, J=6.5 Hz, 6H);

$^{13}$C NMR (125 MHz, DMSO-$d_6$) δ 157.3, 157.0, 153.7, 152.0, 146.6, 132.9, 125.1, 121.2, 111.4, 109.2, 108.3, 67.2, 66.6, 49.6, 40.8, 38.7, 35.7, 29.6, 23.2, 20.1, 12.1;

MS (ESI) m/z 455.2 (M+H)$^+$;

Anal. calcd for $C_{24}H_{34}N_6O_3 \cdot 0.08H_2O \cdot 0.04CH_2Cl_2$: C, 62.85; H, 7.51; N, 18.29. Found: C, 62.72; H, 7.69; N, 18.16.

Example 652

N-(2-{[4-Amino-2-ethyl-1-(tetrahydro-2H-pyran-4-ylmethyl)-1H-imidazo[4,5-c]quinolin-7-yl]oxy}ethyl)acetamide

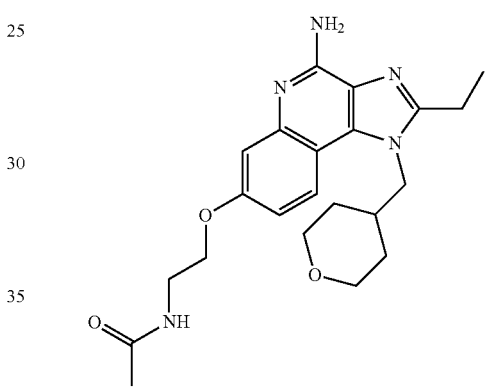

7-(2-Aminoethoxy)-2-ethyl-1-(tetrahydro-2H-pyran-4-ylmethyl)-1H-imidazo[4,5-c]quinolin-4-amine dihydrochloride (0.480 g, 1.03 mmol; prepared as in Example 552), dichloromethane (10 mL), and triethylamine (0.430 mL, 3.09 mmol) were combined and stirred for 10 minutes. Acetic anhydride (0.097 mL, 1.03 mmol) was added and the reaction was stirred for an additional 16 hours. The reaction mixture was purified by chromatography on a HORIZON HPFC system (silica gel, gradient elution with 2-20% CMA in chloroform). Fractions containing product were combined and concentrated. Trituration of the product in acetonitrile provided 0.319 g of N-(2-{[4-amino-2-ethyl-1-(tetrahydro-2H-pyran-4-ylmethyl)-1H-imidazo[4,5-c]quinolin-7-yl]oxy}ethyl)acetamide as fine white crystals, mp 165-167° C.

$^1$H NMR (300 MHz, DMSO-$d_6$) δ 8.12 (t, J=5.4 Hz, 1H), 7.92 (d, J=9.1 Hz, 1H), 7.06 (d, J=2.7 Hz, 1H), 6.92 (dd, J=9.0, 2.7 Hz, 1H), 6.40 (s, 2H), 4.39-4.37 (m, 2H), 4.07 (t, J=5.6 Hz, 2H), 3.84-3.79 (m, 2H), 3.45 (q, J=5.6 Hz, 2H), 3.20-3.08 (m, 2H), 2.91 (q, J=7.4 Hz, 2H), 2.13-1.98 (m, 1H), 1.84 (s, 3H), 1.54-1.34 (m, 4H), 1.36 (t, J=7.4 Hz, 3H);

$^{13}$C NMR (125 MHz, DMSO-$d_6$) δ 169.4, 157.0, 153.7, 152.0, 146.6, 133.0, 125.1, 121.2, 111.5, 109.2, 108.2, 66.6, 66.2, 49.6, 38.3, 35.7, 29.6, 22.5, 20.1, 12.1;

MS (APCI) m/z 412.2 (M+H)$^+$;

Anal. calcd for $C_{22}H_{29}N_5O_3 \cdot 0.33CH_3CN$: C, 64.03; H, 7.11; N, 17.56. Found: C, 63.67; H, 7.17; N, 17.41.

Example 653

N-(2-{[4-Amino-2-ethyl-1-(tetrahydro-2H-pyran-4-ylmethyl)-1H-imidazo[4,5-c]quinolin-7-yl]oxy}ethyl)methanesulfonamide

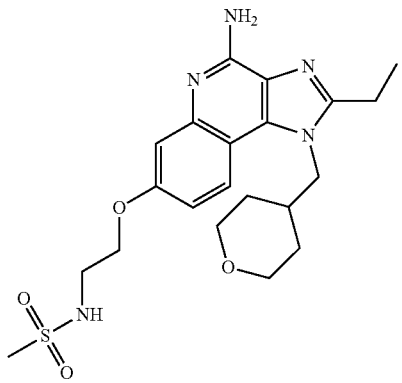 [SMILES: CCc1nc2c(N)nc3cc(OCCNS(C)(=O)=O)ccc3c2n1CC1CCOCC1]

7-(2-Aminoethoxy)-2-ethyl-1-(tetrahydro-2H-pyran-4-ylmethyl)-1H-imidazo[4,5-c]quinolin-4-amine dihydrochloride (0.450 g, 0.97 mmol; prepared as in Example 552), dichloromethane (10 mL), and triethylamine (0.418 mL, 3.00 mmol) were combined and then stirred for 10 minutes. Methanesulfonyl chloride (0.075 mL, 0.97 mmol) was added and the reaction was stirred for an additional 16 hours. The reaction mixture was purified by chromatography on a HORIZON HPFC system (silica gel, gradient elution with 2-20% CMA in chloroform) followed by recrystallization from acetonitrile to provide 0.173 g of N-(2-{[4-amino-2-ethyl-1-(tetrahydro-2H-pyran-4-ylmethyl)-1H-imidazo[4,5-c]quinolin-7-yl]oxy}ethyl)methanesulfonamide as white needles.

$^1$H NMR (300 MHz, DMSO-$d_6$) δ 7.93 (d, J=9.0 Hz, 1H), 7.31 (t, J=5.7 Hz, 1H), 7.07 (d, J=2.6 Hz, 1H), 6.93 (dd, J=9.0, 2.6 Hz, 1H), 6.40 (s, 2H), 4.44-4.34 (m, 2H), 4.12 (t, J=5.5 Hz, 2H), 3.87-3.77 (m, 2H), 3.44-3.35 (m, 2H), 3.21-3.08 (m, 2H), 2.98 (s, 3H), 2.91 (q, J=7.4 Hz, 2H), 2.12-1.98 (m, 1H), 1.55-1.34 (m, 4H), 1.36 (t, J=7.4 Hz, 3H);

$^{13}$C NMR (125 MHz, DMSO-$d_6$) δ 156.8, 153.8, 152.0, 146.5, 132.9, 125.1, 121.3, 111.4, 109.3, 108.2, 66.8, 66.6, 49.6, 41.9, 35.7, 29.6, 20.1, 12.1;

MS (APCI) m/z 448.2 (M+H)$^+$;

Anal. calcd for $C_{21}H_{29}N_5O_4S \cdot 1.5H_2O$: C, 53.15; H, 6.80; N, 14.76; S, 6.76. Found: C, 53.10; H, 6.53; N, 14.95; S, 6.75.

Example 654

1-[4-Amino-7-(2-aminoethoxy)-2-(ethoxymethyl)-1H-imidazo[4,5-c]quinolin-1-yl]-2-methylpropan-2-ol

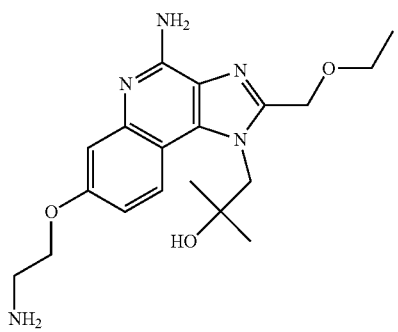 [SMILES: CCOCc1nc2c(N)nc3cc(OCCN)ccc3c2n1CC(C)(C)O]

Part A tert-Butyl 2-{[4-amino-2-(ethoxymethyl)-1-(2-hydroxy-2-methylpropyl)-1H-imidazo[4,5-c]quinolin-7-yl]oxy}ethylcarbamate (1.95 g, 4.12 mmol; prepared in Example 562) was slurried in 4.0 M ethanolic hydrogen chloride (15 mL). The reaction was heated at 65° C. for 1.75 hours during which time the starting material dissolved and a precipitate subsequently formed. The reaction mixture was cooled to ambient temperature and the solid was filtered, washed with ethanol, and dried to provide 1.49 g of 1-[4-amino-7-(2-aminoethoxy)-2-(ethoxymethyl)-1H-imidazo[4,5-c]quinolin-1-yl]-2-methylpropan-2-ol dihydrochloride as an off-white powder.

Part B

The filtrate from Part A was evaporated and the resulting residue was dissolved in water (5 mL) and saturated aqueous sodium chloride (5 mL). This solution was brought to pH 13 with 50% aqueous sodium hydroxide and extracted with chloroform. The chloroform was sequentially washed with water, saturated aqueous sodium chloride, dried over anhydrous sodium sulfate, filtered, and concentrated. Recrystallization from acetonitrile and drying provided 0.140 g of 1-[4-amino-7-(2-aminoethoxy)-2-(ethoxymethyl)-1H-imidazo[4,5-c]quinolin-1-yl]-2-methylpropan-2-ol as fine white crystals, mp 163-165° C.

$^1$H NMR (300 MHz, DMSO-$d_6$) δ 8.16 (d, J=9.1 Hz, 1H), 7.03 (d, J=2.7 Hz, 1H), 6.85 (dd, J=9.0, 2.7 Hz, 1H), 6.48 (s, 2H), 5.06-4.76 (m, 1H), 4.87 (s, 2H), 4.62 (br s, 2H), 3.99 (t, J=5.7 Hz, 2H), 3.50 (q, J=7.0 Hz, 2H), 2.91 (t, J=5.7 Hz, 2H), 1.60 (br s, 2H), 1.16 (br s, 6H), 1.13 (t, J=7.0 Hz, 3H);

$^{13}$C NMR (125 MHz, DMSO-$d_6$) δ 157.4, 152.2, 150.0, 147.1, 134.6, 124.7, 122.4, 111.0, 109.3, 107.9, 70.6, 70.0, 65.2, 64.9, 54.7, 41.0, 27.6, 15.0;

MS (ESI) m/z 374.22 (M+H)$^+$;

Anal. calcd for $C_{19}H_{27}N_5O_3 \cdot 0.3H_2O$: C, 60.24; H, 7.34; N, 18.49. Found: C, 60.42; H, 7.32; N, 18.76.

Example 655

N-(2-{[4-Amino-2-(ethoxymethyl)-1-(2-hydroxy-2-methylpropyl)-1H-imidazo[4,5-c]quinolin-7-yl]oxy}ethyl)-N'-isopropylurea

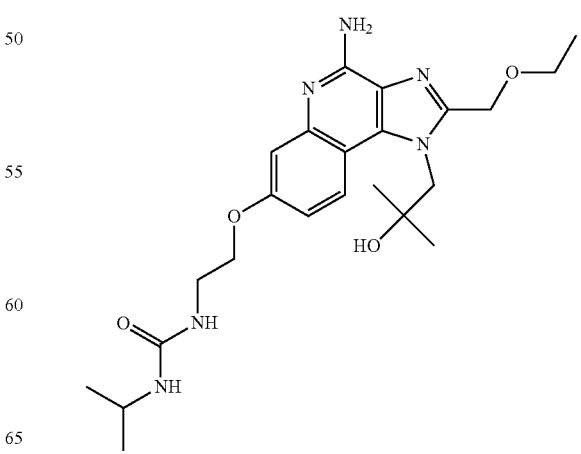

1-[4-Amino-7-(2-aminoethoxy)-2-(ethoxymethyl)-1H-imidazo[4,5-c]quinolin-1-yl]-2-methylpropan-2-ol dihydrochloride (prepared as described in Part A of Example 654, 0.466 g, 1.00 mmol), dichloromethane (10 mL), and triethylamine (0.418 mL, 3.0 mmol) were combined. The mixture was stirred for 10 minutes. Isopropyl isocyanate (0.097 mL, 1.00 mmol) was added and the reaction was stirred for 16 hours. Saturated aqueous sodium carbonate (~8 mL) was added and the layers were separated. The organic layer was concentrated and purified by chromatography on a HORIZON HPFC system (silica gel, gradient elution with 2-25% CMA in chloroform). The fractions containing product were combined and concentrated. Trituration of the product in dichloromethane, followed by filtration provided 0.319 g of N-(2-{[4-amino-2-(ethoxymethyl)-1-(2-hydroxy-2-methylpropyl)-1H-imidazo[4,5-c]quinolin-7-yl]oxy}ethyl)-N'-isopropylurea as an off-white powder.

$^1$H NMR (300 MHz, DMSO-$d_6$) δ 8.17 (d, J=9.1 Hz, 1H), 7.04 (d, J=2.6 Hz, 1H), 6.86 (dd, J=9.1, 2.6 Hz, 1H), 6.51 (s, 2H), 5.95 (t, J=5.6 Hz, 1H), 5.83 (d, J=7.7 Hz, 1H), 5.00-4.77 (m, 1H), 4.87 (s, 2H), 4.62 (br s, 2H), 4.02 (t, J=5.5 Hz, 2H), 3.77-3.59 (m, 1H), 3.50 (q, J=7.0 Hz, 2H), 3.43-3.37 (m, 2H), 1.16 (br s, 6H), 1.13 (t, J=7.0 Hz, 3H), 1.03 (d, J=6.5 Hz, 6H);

$^{13}$C NMR (125 MHz, DMSO-$d_6$) δ 157.3, 157.2, 152.3, 150.0, 147.1, 134.5, 124.8, 122.5, 110.8, 109.5, 108.0, 70.6, 67.2, 65.2, 64.9, 54.7, 40.8, 38.7, 27.6, 23.2, 15.0;

MS (ESI) m/z 459.2 (M+H)$^+$;

Anal. calcd for $C_{23}H_{34}N_6O_4 \cdot 2.0H_2O$: C, 55.86; H, 7.75; N, 16.99. Found: C, 55.63; H, 7.56; N, 16.94.

Example 656

1-[7-[(1-Acetylpiperidin-4-yl)oxy]-4-amino-2-(ethoxymethyl)-1H-imidazo[4,5-c]quinolin-1-yl]-2-methylpropan-2-ol

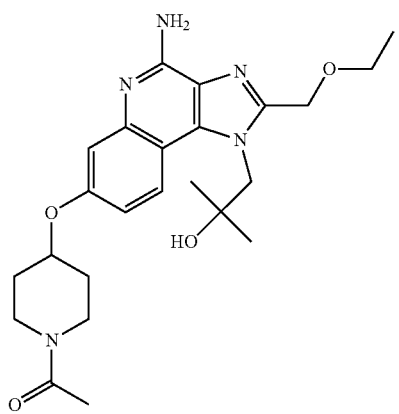 [SMILES: CCOCc1nc2c(N)nc3cc(OC4CCN(C(C)=O)CC4)ccc3c2n1CC(C)(C)O]

Part A tert-Butyl 4-{[4-amino-2-(ethoxymethyl)-1-(2-hydroxy-2-methylpropyl)-1H-imidazo[4,5-c]quinolin-7-yl]oxy}piperidine-1-carboxylate (0.580 g, 1.13 mmol; prepared in Example 563) was taken up in 4.0 M ethanolic hydrogen chloride (5 mL). The reaction was heated at 65° C. for 1 hour, and then cooled to ambient temperature. The ethanol was removed under reduced pressure and the residue was dissolved in water (3 mL) and saturated aqueous sodium chloride (7 mL). The solution was adjusted to pH 13 with 50% aqueous sodium hydroxide and then extracted with chloroform. The combined organic fractions were sequentially washed with water and saturated aqueous sodium chloride, dried over anhydrous sodium sulfate, filtered and concentrated. Trituration with acetonitrile yielded 0.467 g of 1-[4-amino-2-(ethoxymethyl)-7-(piperidin-4-yloxy)-1H-imidazo[4,5-c]quinolin-1-yl]-2-methylpropan-2-ol as an off-white solid.

Part B

1-[4-Amino-2-(ethoxymethyl)-7-(piperidin-4-yloxy)-1H-imidazo[4,5-c]quinolin-1-yl]-2-methylpropan-2-ol (from Part A) was slurried in dichloromethane (11 mL). Acetic anhydride (0.105 mL, 1.03 mmol) was added and the reaction was stirred for 16 hours. The reaction mixture was purified by chromatography on a HORIZON HPFC system (silica gel, gradient elution with 2-25% CMA in chloroform). The resulting solid was covered with diethyl ether for one week. Filtration of the solid provided 0.130 g of 1-[7-[(1-acetylpiperidin-4-yl)oxy]-4-amino-2-(ethoxymethyl)-1H-imidazo[4,5-c]quinolin-1-yl]-2-methylpropan-2-ol as red-tan crystals, mp 162-164° C.

$^1$H NMR (300 MHz, DMSO-$d_6$) δ 8.16 (d, J=9.1 Hz, 1H), 7.09 (d, J=2.5 Hz, 1H), 6.87 (dd, J=9.0, 2.5 Hz, 1H), 6.47 (s, 2H), 5.04-4.77 (m, 1H), 4.86 (s, 2H), 4.75-4.61 (m, 1H), 4.61 (br s, 2H), 3.98-3.82 (m, 1H), 3.79-3.63 (m, 1H), 3.50 (q, J=7.0 Hz, 2H), 3.43-3.14 (m, 2H), 2.02 (s, 3H), 2.02-1.87 (m, 2H), 1.74-1.44 (m, 2H), 1.16 (br s, 6H), 1.13 (t, J=7.0 Hz, 3H);

MS (APCI) m/z 456.3 (M+H)$^+$;

Anal. calcd for $C_{24}H_{33}N_5O_4$: C, 63.28; H, 7.30; N, 15.37. Found: C, 63.13; H, 7.63; N, 15.48.

Example 657

2-(Methoxymethyl)-1-propyl-8-[3-(4-pyridin-2-ylpiperazin-1-yl)propoxy]-1H-imidazo[4,5-c]quinolin-4-amine

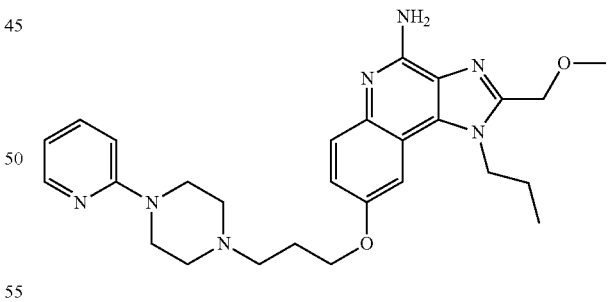

Part A 8-(3-Chloropropoxy)-2-(methoxymethyl)-1-propyl-1H-imidazo[4,5-c]quinolin-4-amine was prepared using a modification on the procedure described in Parts A-E of Examples 523-550. In the work-up of Part E, the reaction mixture was allowed to cool to room temperature and was poured into water. A pale brown solid, crude 8-(3-chloropropoxy)-2-(methoxymethyl)-1-propyl-1H-imidazo[4,5-c]quinolin-4-amine, was isolated by filtration and was used in the next step without purification.

Part B

A mixture of 8-(3-chloropropoxy)-2-(methoxymethyl)-1-propyl-1H-imidazo[4,5-c]quinolin-4-amine (0.20 g, 0.55 mmol, 1 equivalent), potassium carbonate (4 equivalents), and 1-(2-pyridyl)piperazine (1.1 equivalents) in DMF (5 mL) was heated at 70° C. overnight. The reaction mixture was allowed to cool to room temperature and was poured onto ice (50 g). After the mixture was stirred for 3 hours, a brown solid was isolated by filtration. The crude product was purified by chromatography on a HORIZON HPFC system (silica gel, gradient elution with 0-30% CMA in chloroform), followed by recrystallization from acetonitrile to afford 0.065 g of 2-(methoxymethyl)-1-propyl-8-[3-(4-pyridin-2-ylpiperazin-1-yl)propoxy]-1H-imidazo[4,5-c]quinolin-4-amine as off white crystals, mp 196-197° C.

MS (APCI) m/z 490 (M+H)$^+$;

Anal. calcd for $C_{27}H_{35}N_7O_2 \cdot 0.33 H_2O$: C, 65.44; H, 7.25; N, 19.78. Found: C, 65.42; H, 7.28; N, 19.63.

Examples 658-661

The general method described in Example 647 can be applied to prepare Examples 658-661, whose structure and names are shown in the table below, from 4-(2-chloroethyl)morpholine hydrochloride and the starting materials listed in the table below. The starting materials can be prepared using known methods. 4-Amino-2-(ethoxymethyl)-1-propyl-1H-imidazo[4,5-c]quinolin-8-ol can be prepared as described in Parts A-B of Example 566. 4-Amino-2-ethyl-1-(2-hydroxy-2-methylpropyl)-1H-imidazo[4,5-c]quinolin-7-ol can be prepared using the methods described in Parts A-J of Example 1, using 1-amino-2-methylpropan-2-ol in lieu of isobutylamine in Part E and triethyl orthopropionate in lieu of trimethyl orthobutyrate in Part G. 4-Amino-2-ethyl-1-(2-hydroxy-2-methylpropyl)-1H-imidazo[4,5-c]quinolin-8-ol can be prepared using the methods described in Parts A-J of Example 1, using 4-benzyloxyaniline in lieu of 3-benzyloxyaniline in Part A, 1-amino-2-methylpropan-2-ol in lieu of isobutylamine in Part E, and triethyl orthopropionate in lieu of trimethyl orthobutyrate in Part G. A modification of the methods described in Parts A-H, M, N, and I of Example 2 can be used to prepare 4-amino-2-(ethoxymethyl)-1-(2-hydroxy-2-methylpropyl)-1H-imidazo[4,5-c]quinolin-8-ol, with 1-amino-2-methylpropan-2-ol used in lieu of propylamine in Part E.

| Example | Structure | Name | Starting Material |
|---------|-----------|------|-------------------|
| 658 | 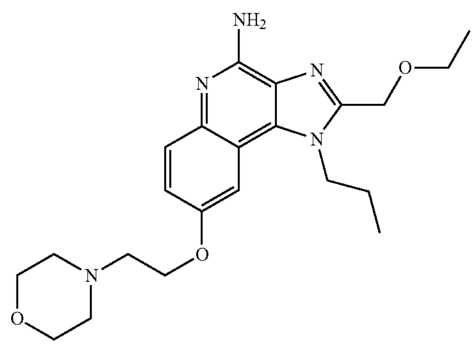 [SMILES: CCCn1c(COCC)nc2c(N)nc3ccc(OCCN4CCOCC4)cc3c21] | 2-(Ethoxymethyl)-8-(2-morpholin-4-ylethoxy)-1-propyl-1H-imidazo[4,5-c]quinolin-4-amine | 4-Amino-2-(ethoxymethyl)-1-propyl-1H-imidazo[4,5-c]quinolin-8-ol |
| 659 | 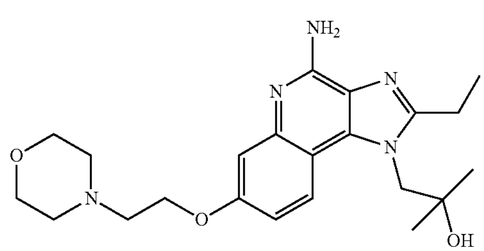 [SMILES: CCc1nc2c(N)nc3cc(OCCN4CCOCC4)ccc3c2n1CC(C)(C)O] | 1-[4-Amino-2-ethyl-7-(2-morpholin-4-ylethoxy)-1H-imidazo[4,5-c]quinolin-1-yl]-2-methylpropan-2-ol | 4-Amino-2-ethyl-1-(2-hydroxy-2-methylpropyl)-1H-imidazo[4,5-c]quinolin-7-ol |
| 660 | 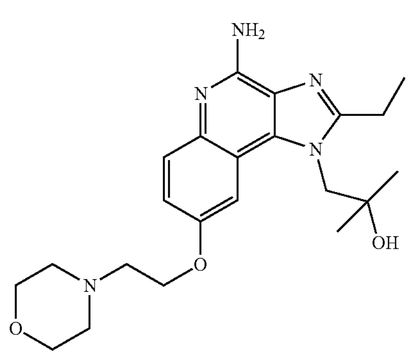 [SMILES: CCc1nc2c(N)nc3ccc(OCCN4CCOCC4)cc3c2n1CC(C)(C)O] | 1-[4-Amino-2-ethyl-8-(2-morpholin-4-ylethoxy)-1H-imidazo[4,5-c]quinolin-1-yl]-2-methylpropan-2-ol | 4-Amino-2-ethyl-1-(2-hydroxy-2-methylpropyl)-1H-imidazo[4,5-c]quinolin-8-ol |

| Example | Structure | Name | Starting Material |
|---|---|---|---|
| 661 | 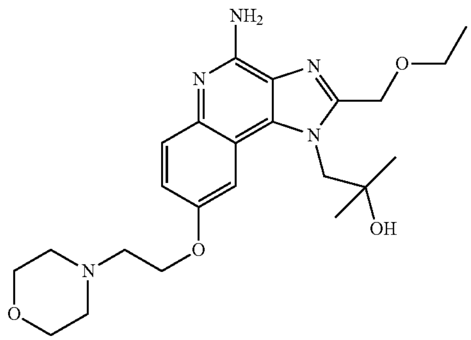 [SMILES: CCOCc1nc2c(N)nc3ccc(OCCN4CCOCC4)cc3c2n1CC(C)(C)O] | 1-[4-Amino-2-(ethoxymethyl)-8-(2-morpholin-4-ylethoxy)-1H-imidazo[4,5-c]quinolin-1-yl]-2-methylpropan-2-ol | 4-Amino-2-(ethoxymethyl)-1-(2-hydroxy-2-methylpropyl)-1H-imidazo[4,5-c]quinolin-8-ol |

Examples 662-664

The general method described in Example 646 can be applied to prepare Examples 662-664, whose structure and names are shown in the table below, from 4-(bromoacetyl)morpholine and the starting materials listed in the table below. The starting materials can be prepared using the methods described in Examples 658-661.

| Example | Structure | Name | Starting Material |
|---|---|---|---|
| 662 | 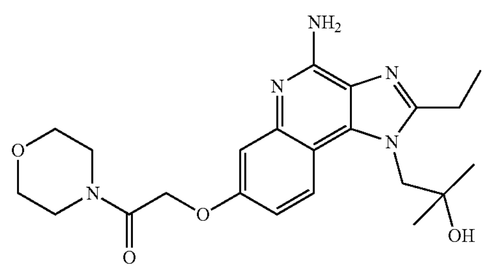 [SMILES: CCc1nc2c(N)nc3cc(OCC(=O)N4CCOCC4)ccc3c2n1CC(C)(C)O] | 1-[4-Amino-2-ethyl-7-(2-morpholin-4-yl-2-oxoethoxy)-1H-imidazo[4,5-c]quinolin-1-yl]-2-methylpropan-2-ol | 4-Amino-2-ethyl-1-(2-hydroxy-2-methylpropyl)-1H-imidazo[4,5-c]quinolin-7-ol |
| 663 | 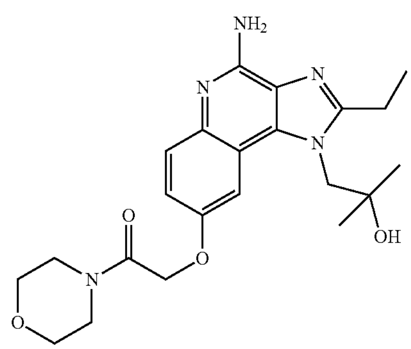 [SMILES: CCc1nc2c(N)nc3ccc(OCC(=O)N4CCOCC4)cc3c2n1CC(C)(C)O] | 1-[4-Amino-2-ethyl-8-(2-morpholin-4-yl-2-oxoethoxy)-1H-imidazo[4,5-c]quinolin-1-yl]-2-methylpropan-2-ol | 4-Amino-2-ethyl-1-(2-hydroxy-2-methylpropyl)-1H-imidazo[4,5-c]quinolin-8-ol |
| 664 | 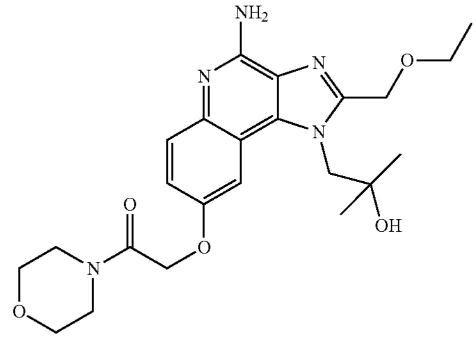 [SMILES: CCOCc1nc2c(N)nc3ccc(OCC(=O)N4CCOCC4)cc3c2n1CC(C)(C)O] | 1-[4-Amino-2-(ethoxymethyl)-8-(2-morpholin-4-yl-2-oxoethoxy)-1H-imidazo[4,5-c]quinolin-1-yl]-2-methylpropan-2-ol | 4-Amino-2-(ethoxymethyl)-1-(2-hydroxy-2-methylpropyl)-1H-imidazo[4,5-c]quinolin-8-ol |

Certain exemplary compounds, including some of those described above in the Examples, have the following Formula IIa, IIb, or IIc and the following $R_1$, $R_2$, and $R_3$ substituents, wherein each line of the table is matched with each of Formula IIa, IIb, or IIc to represent a specific embodiment of the invention.

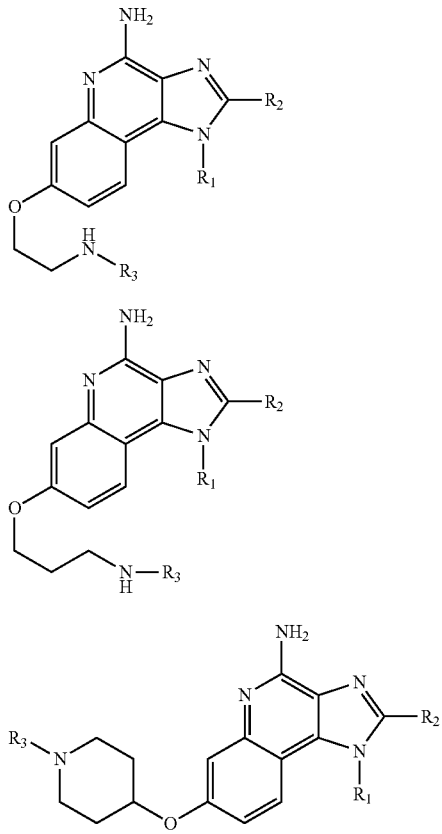

IIa
IIb
IIc

| $R_1$ | $R_2$ | $R_3$ |
|---|---|---|
| 2-methylpropyl | methyl | acetyl |
| 2-methylpropyl | methyl | isobutyryl |
| 2-methylpropyl | methyl | (isopropylamino)carbonyl |
| 2-methylpropyl | methyl | methylsulfonyl |
| 2-methylpropyl | methyl | morpholin-4-ylcarbonyl |
| 2-methylpropyl | ethyl | acetyl |
| 2-methylpropyl | ethyl | isobutyryl |
| 2-methylpropyl | ethyl | (isopropylamino)carbonyl |
| 2-methylpropyl | ethyl | methylsulfonyl |
| 2-methylpropyl | ethyl | morpholin-4-ylcarbonyl |
| 2-methylpropyl | n-propyl | acetyl |
| 2-methylpropyl | n-propyl | isobutyryl |
| 2-methylpropyl | n-propyl | (isopropylamino)carbonyl |
| 2-methylpropyl | n-propyl | methylsulfonyl |
| 2-methylpropyl | n-propyl | morpholin-4-ylcarbonyl |
| 2-methylpropyl | ethoxymethyl | acetyl |
| 2-methylpropyl | ethoxymethyl | isobutyryl |
| 2-methylpropyl | ethoxymethyl | (isopropylamino)carbonyl |
| 2-methylpropyl | ethoxymethyl | methylsulfonyl |
| 2-methylpropyl | ethoxymethyl | morpholin-4-ylcarbonyl |
| 2-methylpropyl | 2-hydroxyethyl | acetyl |
| 2-methylpropyl | 2-hydroxyethyl | isobutyryl |
| 2-methylpropyl | 2-hydroxyethyl | (isopropylamino)carbonyl |
| 2-methylpropyl | 2-hydroxyethyl | methylsulfonyl |
| 2-methylpropyl | 2-hydroxyethyl | morpholin-4-ylcarbonyl |
| 2-hydroxy-2-methylpropyl | methyl | acetyl |
| 2-hydroxy-2-methylpropyl | methyl | isobutyryl |
| 2-hydroxy-2-methylpropyl | methyl | (isopropylamino)carbonyl |
| 2-hydroxy-2-methylpropyl | methyl | methylsulfonyl |
| 2-hydroxy-2-methylpropyl | methyl | morpholin-4-ylcarbonyl |
| 2-hydroxy-2-methylpropyl | ethyl | acetyl |
| 2-hydroxy-2-methylpropyl | ethyl | isobutyryl |
| 2-hydroxy-2-methylpropyl | ethyl | (isopropylamino)carbonyl |
| 2-hydroxy-2-methylpropyl | ethyl | methylsulfonyl |
| 2-hydroxy-2-methylpropyl | ethyl | morpholin-4-ylcarbonyl |
| 2-hydroxy-2-methylpropyl | n-propyl | acetyl |
| 2-hydroxy-2-methylpropyl | n-propyl | isobutyryl |
| 2-hydroxy-2-methylpropyl | n-propyl | (isopropylamino)carbonyl |
| 2-hydroxy-2-methylpropyl | n-propyl | methylsulfonyl |
| 2-hydroxy-2-methylpropyl | n-propyl | morpholin-4-ylcarbonyl |
| 2-hydroxy-2-methylpropyl | ethoxymethyl | acetyl |
| 2-hydroxy-2-methylpropyl | ethoxymethyl | isobutyryl |
| 2-hydroxy-2-methylpropyl | ethoxymethyl | (isopropylamino)carbonyl |
| 2-hydroxy-2-methylpropyl | ethoxymethyl | methylsulfonyl |
| 2-hydroxy-2-methylpropyl | ethoxymethyl | morpholin-4-ylcarbonyl |
| 2-hydroxy-2-methylpropyl | 2-hydroxyethyl | acetyl |
| 2-hydroxy-2-methylpropyl | 2-hydroxyethyl | isobutyryl |
| 2-hydroxy-2-methylpropyl | 2-hydroxyethyl | (isopropylamino)carbonyl |
| 2-hydroxy-2-methylpropyl | 2-hydroxyethyl | methylsulfonyl |
| 2-hydroxy-2-methylpropyl | 2-hydroxyethyl | morpholin-4-ylcarbonyl |
| methyl | methyl | acetyl |
| methyl | methyl | isobutyryl |
| methyl | methyl | (isopropylamino)carbonyl |
| methyl | methyl | methylsulfonyl |
| methyl | methyl | morpholin-4-ylcarbonyl |
| methyl | ethyl | acetyl |
| methyl | ethyl | isobutyryl |
| methyl | ethyl | (isopropylamino)carbonyl |
| methyl | ethyl | methylsulfonyl |
| methyl | ethyl | morpholin-4-ylcarbonyl |
| methyl | n-propyl | acetyl |
| methyl | n-propyl | isobutyryl |
| methyl | n-propyl | (isopropylamino)carbonyl |
| methyl | n-propyl | methylsulfonyl |
| methyl | n-propyl | morpholin-4-ylcarbonyl |
| methyl | ethoxymethyl | acetyl |
| methyl | ethoxymethyl | isobutyryl |
| methyl | ethoxymethyl | (isopropylamino)carbonyl |
| methyl | ethoxymethyl | methylsulfonyl |
| methyl | ethoxymethyl | morpholin-4-ylcarbonyl |
| methyl | 2-hydroxyethyl | acetyl |
| methyl | 2-hydroxyethyl | isobutyryl |
| methyl | 2-hydroxyethyl | (isopropylamino)carbonyl |
| methyl | 2-hydroxyethyl | methylsulfonyl |
| methyl | 2-hydroxyethyl | morpholin-4-ylcarbonyl |
| n-propyl | methyl | acetyl |
| n-propyl | methyl | isobutyryl |
| n-propyl | methyl | (isopropylamino)carbonyl |
| n-propyl | methyl | methylsulfonyl |
| n-propyl | methyl | morpholin-4-ylcarbonyl |
| n-propyl | ethyl | acetyl |
| n-propyl | ethyl | isobutyryl |
| n-propyl | ethyl | (isopropylamino)carbonyl |
| n-propyl | ethyl | methylsulfonyl |
| n-propyl | ethyl | morpholin-4-ylcarbonyl |
| n-propyl | n-propyl | acetyl |
| n-propyl | n-propyl | isobutyryl |
| n-propyl | n-propyl | (isopropylamino)carbonyl |
| n-propyl | n-propyl | methylsulfonyl |
| n-propyl | n-propyl | morpholin-4-ylcarbonyl |
| n-propyl | ethoxymethyl | acetyl |
| n-propyl | ethoxymethyl | isobutyryl |
| n-propyl | ethoxymethyl | (isopropylamino)carbonyl |
| n-propyl | ethoxymethyl | methylsulfonyl |
| n-propyl | ethoxymethyl | morpholin-4-ylcarbonyl |
| n-propyl | 2-hydroxyethyl | acetyl |
| n-propyl | 2-hydroxyethyl | isobutyryl |
| n-propyl | 2-hydroxyethyl | (isopropylamino)carbonyl |
| n-propyl | 2-hydroxyethyl | methylsulfonyl |
| n-propyl | 2-hydroxyethyl | morpholin-4-ylcarbonyl |
| tetrahydro-2H-pyran-4-ylmethyl | methyl | acetyl |

-continued

| R₁ | R₂ | R₃ |
|---|---|---|
| tetrahydro-2H-pyran-4-ylmethyl | methyl | isobutyryl |
| tetrahydro-2H-pyran-4-ylmethyl | methyl | (isopropylamino)carbonyl |
| tetrahydro-2H-pyran-4-ylmethyl | methyl | methylsulfonyl |
| tetrahydro-2H-pyran-4-ylmethyl | methyl | morpholin-4-ylcarbonyl |
| tetrahydro-2H-pyran-4-ylmethyl | ethyl | acetyl |
| tetrahydro-2H-pyran-4-ylmethyl | ethyl | isobutyryl |
| tetrahydro-2H-pyran-4-ylmethyl | ethyl | (isopropylamino)carbonyl |
| tetrahydro-2H-pyran-4-ylmethyl | ethyl | methylsulfonyl |
| tetrahydro-2H-pyran-4-ylmethyl | ethyl | morpholin-4-ylcarbonyl |
| tetrahydro-2H-pyran-4-ylmethyl | n-propyl | acetyl |
| tetrahydro-2H-pyran-4-ylmethyl | n-propyl | isobutyryl |
| tetrahydro-2H-pyran-4-ylmethyl | n-propyl | (isopropylamino)carbonyl |
| tetrahydro-2H-pyran-4-ylmethyl | n-propyl | methylsulfonyl |
| tetrahydro-2H-pyran-4-ylmethyl | n-propyl | morpholin-4-ylcarbonyl |
| tetrahydro-2H-pyran-4-ylmethyl | ethoxymethyl | acetyl |
| tetrahydro-2H-pyran-4-ylmethyl | ethoxymethyl | isobutyryl |
| tetrahydro-2H-pyran-4-ylmethyl | ethoxymethyl | (isopropylamino)carbonyl |
| tetrahydro-2H-pyran-4-ylmethyl | ethoxymethyl | methylsulfonyl |
| tetrahydro-2H-pyran-4-ylmethyl | ethoxymethyl | morpholin-4-ylcarbonyl |
| tetrahydro-2H-pyran-4-ylmethyl | 2-hydroxyethyl | acetyl |
| tetrahydro-2H-pyran-4-ylmethyl | 2-hydroxyethyl | isobutyryl |
| tetrahydro-2H-pyran-4-ylmethyl | 2-hydroxyethyl | (isopropylamino)carbonyl |
| tetrahydro-2H-pyran-4-ylmethyl | 2-hydroxyethyl | methylsulfonyl |
| tetrahydro-2H-pyran-4-ylmethyl | 2-hydroxyethyl | morpholin-4-ylcarbonyl |

Certain exemplary compounds, including some of those described above in the Examples, have the following Formula IIIa or IIIb and the following R₁ and R₂ substituents, wherein each line of the table is matched with each of Formula IIIa or IIIb to represent a specific embodiment of the invention.

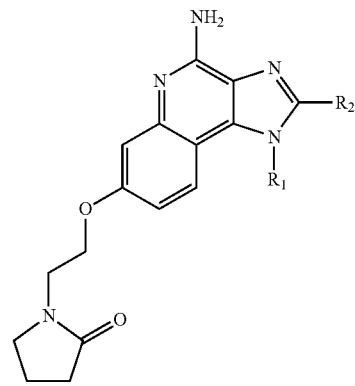

IIIa

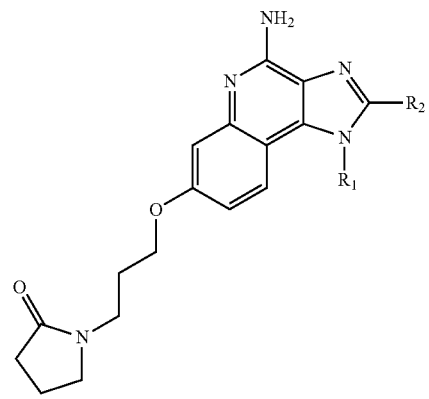

IIIb

| R₁ | R₂ |
|---|---|
| 2-methylpropyl | methyl |
| 2-methylpropyl | ethyl |
| 2-methylpropyl | n-propyl |
| 2-methylpropyl | ethoxymethyl |
| 2-methylpropyl | 2-hydroxyethyl |
| 2-hydroxy-2-methylpropyl | methyl |
| 2-hydroxy-2-methylpropyl | ethyl |
| 2-hydroxy-2-methylpropyl | n-propyl |
| 2-hydroxy-2-methylpropyl | ethoxymethyl |
| 2-hydroxy-2-methylpropyl | 2-hydroxyethyl |
| methyl | methyl |
| methyl | ethyl |
| methyl | n-propyl |
| methyl | ethoxymethyl |
| methyl | 2-hydroxyethyl |
| n-propyl | methyl |
| n-propyl | ethyl |
| n-propyl | n-propyl |
| n-propyl | ethoxymethyl |
| n-propyl | 2-hydroxyethyl |
| tetrahydro-2H-pyran-4-ylmethyl | methyl |
| tetrahydro-2H-pyran-4-ylmethyl | ethyl |
| tetrahydro-2H-pyran-4-ylmethyl | n-propyl |
| tetrahydro-2H-pyran-4-ylmethyl | ethoxymethyl |
| tetrahydro-2H-pyran-4-ylmethyl | 2-hydroxyethyl |

Certain exemplary compounds, including some of those described above in the Examples, have the following Formula VIa or VIb and the following R₁, R₂, and R₃ substituents, wherein each line of the table is matched with each of Formula VIa or VIb to represent a specific embodiment of the invention.

VIa

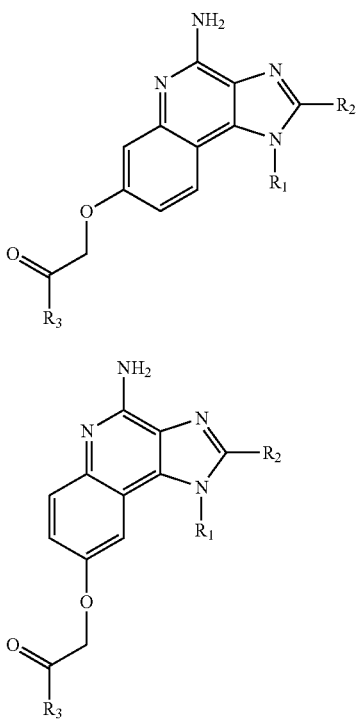

VIb

| R₁ | R₂ | R₃ |
|---|---|---|
| 2-methylpropyl | methyl | morpholin-4-yl |
| 2-methylpropyl | methyl | piperdin-1-yl |
| 2-methylpropyl | methyl | pyrrolidin-1-yl |
| 2-methylpropyl | ethyl | morpholin-4-yl |
| 2-methylpropyl | ethyl | piperdin-1-yl |
| 2-methylpropyl | ethyl | pyrrolidin-1-yl |
| 2-methylpropyl | n-propyl | morpholin-4-yl |
| 2-methylpropyl | n-propyl | piperdin-1-yl |
| 2-methylpropyl | n-propyl | pyrrolidin-1-yl |
| 2-methylpropyl | ethoxymethyl | morpholin-4-yl |
| 2-methylpropyl | ethoxymethyl | piperdin-1-yl |
| 2-methylpropyl | ethoxymethyl | pyrrolidin-1-yl |
| 2-methylpropyl | 2-hydroxyethyl | morpholin-4-yl |
| 2-methylpropyl | 2-hydroxyethyl | piperdin-1-yl |
| 2-methylpropyl | 2-hydroxyethyl | pyrrolidin-1-yl |
| 2-hydroxy-2-methylpropyl | methyl | morpholin-4-yl |
| 2-hydroxy-2-methylpropyl | methyl | piperdin-1-yl |
| 2-hydroxy-2-methylpropyl | methyl | pyrrolidin-1-yl |
| 2-hydroxy-2-methylpropyl | ethyl | morpholin-4-yl |
| 2-hydroxy-2-methylpropyl | ethyl | piperdin-1-yl |
| 2-hydroxy-2-methylpropyl | ethyl | pyrrolidin-1-yl |
| 2-hydroxy-2-methylpropyl | n-propyl | morpholin-4-yl |
| 2-hydroxy-2-methylpropyl | n-propyl | piperdin-1-yl |
| 2-hydroxy-2-methylpropyl | n-propyl | pyrrolidin-1-yl |
| 2-hydroxy-2-methylpropyl | ethoxymethyl | morpholin-4-yl |
| 2-hydroxy-2-methylpropyl | ethoxymethyl | piperdin-1-yl |
| 2-hydroxy-2-methylpropyl | ethoxymethyl | pyrrolidin-1-yl |
| 2-hydroxy-2-methylpropyl | 2-hydroxyethyl | morpholin-4-yl |
| 2-hydroxy-2-methylpropyl | 2-hydroxyethyl | piperdin-1-yl |
| 2-hydroxy-2-methylpropyl | 2-hydroxyethyl | pyrrolidin-1-yl |
| methyl | methyl | morpholin-4-yl |
| methyl | methyl | piperdin-1-yl |
| methyl | methyl | pyrrolidin-1-yl |
| methyl | ethyl | morpholin-4-yl |
| methyl | ethyl | piperdin-1-yl |
| methyl | ethyl | pyrrolidin-1-yl |
| methyl | n-propyl | morpholin-4-yl |
| methyl | n-propyl | piperdin-1-yl |
| methyl | n-propyl | pyrrolidin-1-yl |
| methyl | ethoxymethyl | morpholin-4-yl |
| methyl | ethoxymethyl | piperdin-1-yl |
| methyl | ethoxymethyl | pyrrolidin-1-yl |
| methyl | 2-hydroxyethyl | morpholin-4-yl |
| methyl | 2-hydroxyethyl | piperdin-1-yl |
| methyl | 2-hydroxyethyl | pyrrolidin-1-yl |
| n-propyl | methyl | morpholin-4-yl |
| n-propyl | methyl | piperdin-1-yl |
| n-propyl | methyl | pyrrolidin-1-yl |
| n-propyl | ethyl | morpholin-4-yl |
| n-propyl | ethyl | piperdin-1-yl |
| n-propyl | ethyl | pyrrolidin-1-yl |
| n-propyl | n-propyl | morpholin-4-yl |
| n-propyl | n-propyl | piperdin-1-yl |
| n-propyl | n-propyl | pyrrolidin-1-yl |
| n-propyl | ethoxymethyl | morpholin-4-yl |
| n-propyl | ethoxymethyl | piperdin-1-yl |
| n-propyl | ethoxymethyl | pyrrolidin-1-yl |
| n-propyl | 2-hydroxyethyl | morpholin-4-yl |
| n-propyl | 2-hydroxyethyl | piperdin-1-yl |
| n-propyl | 2-hydroxyethyl | pyrrolidin-1-yl |
| tetrahydro-2H-pyran-4-ylmethyl | methyl | morpholin-4-yl |
| tetrahydro-2H-pyran-4-ylmethyl | methyl | piperdin-1-yl |
| tetrahydro-2H-pyran-4-ylmethyl | methyl | pyrrolidin-1-yl |
| tetrahydro-2H-pyran-4-ylmethyl | ethyl | morpholin-4-yl |
| tetrahydro-2H-pyran-4-ylmethyl | ethyl | piperdin-1-yl |
| tetrahydro-2H-pyran-4-ylmethyl | ethyl | pyrrolidin-1-yl |
| tetrahydro-2H-pyran-4-ylmethyl | n-propyl | morpholin-4-yl |
| tetrahydro-2H-pyran-4-ylmethyl | n-propyl | piperdin-1-yl |
| tetrahydro-2H-pyran-4-ylmethyl | n-propyl | pyrrolidin-1-yl |
| tetrahydro-2H-pyran-4-ylmethyl | ethoxymethyl | morpholin-4-yl |
| tetrahydro-2H-pyran-4-ylmethyl | ethoxymethyl | piperdin-1-yl |
| tetrahydro-2H-pyran-4-ylmethyl | ethoxymethyl | pyrrolidin-1-yl |
| tetrahydro-2H-pyran-4-ylmethyl | 2-hydroxyethyl | morpholin-4-yl |
| tetrahydro-2H-pyran-4-ylmethyl | 2-hydroxyethyl | piperdin-1-yl |
| tetrahydro-2H-pyran-4-ylmethyl | 2-hydroxyethyl | pyrrolidin-1-yl |

Compounds of the invention were found to induce or inhibit cytokine biosynthesis when tested using the methods described below.

Cytokine Induction in Human Cells

Compounds of the invention have been found to modulate cytokine biosynthesis by inducing the production of interferon α and/or tumor necrosis factor α when tested using the method described below. Particular examples include, but are not limited to, the compounds of Examples 1-9, 11, 13-22, 26-37, 40-43, 45-134, 139, 143, 146-149, 151, 154-156, 160, 162-201, 204-206, 209, 210, 212, 214-216, 218-220, 222-224, 226-230, 233-256, 258-261, 263-278, 280-306, 308-320, 322-335, 338-355, 358, 359, 361, 364-373, 376-394, 397-405, 407-409, 411-414, and 418-422.

An in vitro human blood cell system is used to assess cytokine induction. Activity is based on the measurement of interferon (α) and tumor necrosis factor (α) (IFN and TNF, respectively) secreted into culture media as described by Testerman et al. in "Cytokine Induction by the Immunomodulators Imiquimod and S-27609", *Journal of Leukocyte Biology,* 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at $4\times10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (30-0.014 µM). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) by ELISA and for tumor necrosis factor (α) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by ORIGEN M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

TNF-α Inhibition in Mouse Cells

Certain compounds of the invention may modulate cytokine biosynthesis by inhibiting production of tumor necrosis factor α (TNF-α) when tested using the method described below. Particular examples, include but are not limited to, the compounds of Examples 134-136, 139, 142, 143, 146-151, 153, 155-161, 218-224, 226-242, 323-326, 328-333, 336, 337, 355-357, and 362.

The mouse macrophage cell line Raw 264.7 is used to assess the ability of compounds to inhibit tumor necrosis factor-α (TNF-α) production upon stimulation by lipopolysaccharide (LPS).

Single Concentration Assay:

Blood Cell Preparation for Culture

Raw cells (ATCC) are harvested by gentle scraping and then counted. The cell suspension is brought to $3\times10^5$ cells/mL in RPMI with 10% fetal bovine serum (FBS). Cell suspension (100 µL) is added to 96-well flat bottom sterile tissues culture plates (Becton Dickinson Labware, Lincoln Park, N.J.). The final concentration of cells is $3\times10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 µM. LPS (Lipopolysaccharide from *Salmonella typhimurium*, Sigma-Aldrich) is diluted with colorless RPMI to the $EC_{70}$ concentration as measured by a dose response assay.

Incubation

A solution of test compound (1 µl) is added to each well. The plates are mixed on a microtiter plate shaker for 1 minute and then placed in an incubator. Twenty minutes later the solution of LPS (1 µL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:

Blood Cell Preparation for Culture

Raw cells (ATCC) are harvested by gentle scraping and then counted. The cell suspension is brought to $4\times10^5$ cells/mL in RPMI with 10% FBS. Cell suspension (250 µL) is added to 48-well flat bottom sterile tissues culture plates (Costar, Cambridge, Mass.). The final concentration of cells is $1\times10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 µM. LPS (Lipopolysaccharide from *Salmonella typhimurium*, Sigma-Aldrich) is diluted with colorless RPMI to the $EC_{70}$ concentration as measured by dose response assay.

Incubation

A solution of test compound (200 µl) is added to each well. The plates are mixed on a microtiter plate shaker for 1 minute and then placed in an incubator. Twenty minutes later the solution of LPS (200 µL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. The present invention has been described with reference to several embodiments thereof. The foregoing illustrative embodiments and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention is intended to be limited only by the claims that follow.

What is claimed is:

1. A compound of the formula (II):

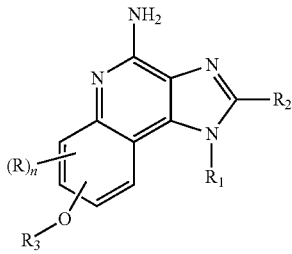

II wherein:
$R_3$ is selected from the group consisting of
—Z—Y—$R_4$,
—Z—Y—X—Y—$R_4$,
—Z—$R_5$,
—Z-Het,
—Z-Het'-$R_4$, and
—Z-Het'-Y—$R_4$;
Z is selected from the group consisting of alkylene, alkenylene, and alkynylene, wherein alkylene, alkenylene, and alkynylene can be optionally interrupted with one or more —O— groups;
R is selected from the group consisting of alkyl, alkoxy, hydroxy, halogen, and trifluoromethyl;
n is 0 or 1;
$R_1$ is selected from the group consisting of
—$R_4$,
—X—$R_4$,
—X—Y—$R_4$,
—X—Y—X—Y—$R_4$, and
—X—$R_5$;
$R_2$ is selected from the group consisting of hydrogen, alkyl, alkoxyalkylenyl, and hydroxyalkylenyl;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

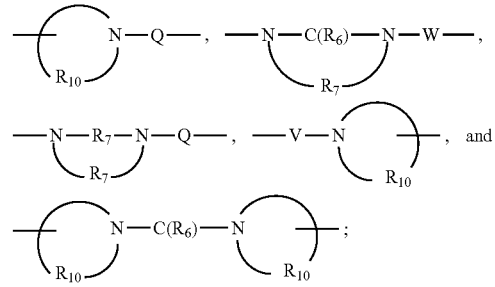

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
$R_5$ is selected from the group consisting of

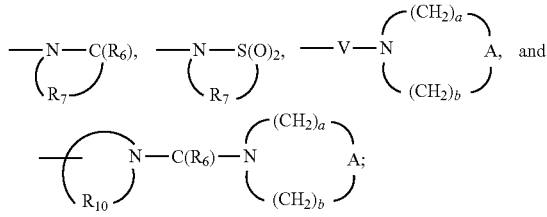

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, and —N($R_4$)—;
Het is a non-aromatic heterocyclyl that can be unsubstituted or substituted by one or more substituents independently selected from the group consisting of alkyl, alkoxy, haloalkyl, haloalkoxy, halogen, nitro, hydroxy, hydroxyalkyl, mercapto, cyano, aryloxy, arylalkyleneoxy, heteroaryloxy, heteroarylalkyleneoxy, heterocyclyl, hydroxyalkyleneoxyalkylenyl, amino, alkylamino, dialkylamino, (dialkylamino)alkyleneoxy, and oxo;

Het' is a non-aromatic heterocyclylene that can be unsubstituted or substituted by one or more substituents independently selected from the group consisting of alkyl, alkoxy, haloalkyl, haloalkoxy, halogen, nitro, hydroxy, hydroxyalkyl, mercapto, cyano, aryloxy, arylalkyleneoxy, heteroaryloxy, heteroarylalkyleneoxy, amino, alkylamino, dialkylamino, (dialkylamino)alkyleneoxy, and oxo;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

with the proviso that Z can also be a bond when:
R$_3$ is —Z-Het, —Z-Het'-R$_4$, or —Z-Het'-Y—R$_4$; or
R$_3$ is —Z—Y$_3$—R$_4$ or —Z—Y$_3$—X—Y$_3$—R$_4$, and Y$_3$ is selected from —S(O)$_{0-2}$—, —S(O)$_2$—N(R$_8$)—, —C(R$_6$)—, —C(R$_6$)—O—, —C(R$_6$)—N(R$_8$)—,

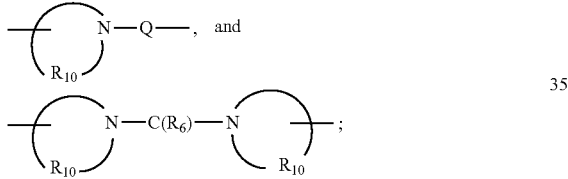

or

R$_3$ is —Z—R$_5$ and R$_5$ is

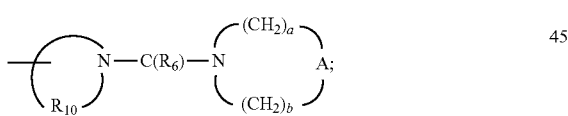

or a pharmaceutically acceptable salt thereof.

2. The compound or salt of claim 1, wherein R$_3$ is —Z—Y—R$_4$ or —Z—Y—X—Y—R$_4$.

3. The compound or salt of claim 1, wherein Y is selected from the group consisting of
—S(O)$_{0-2}$—
—C(O)—,
—C(O)—O—,
—O—C(O)—,
—N(R$_8$)-Q-,
—C(R$_6$)—N(R$_8$)—,

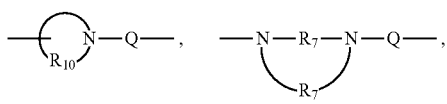

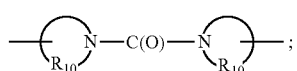

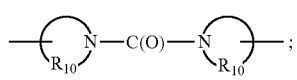

wherein Q is selected from the group consisting of a bond, —C(O)—, —C(O)—O—, —S(O)$_2$—, —C(R$_6$)—N(R$_8$)—W—, and —S(O)$_2$—N(R$_8$)—; W is selected from the group consisting of a bond, —C(O)—, and —S(O)$_2$—; R$_6$ is selected from the group consisting of =O or =S; R$_8$ is selected from the group consisting of hydrogen, C$_{1-4}$ alkyl, and alkoxyalkylenyl; and R$_{10}$ is selected from the group consisting of C$_{4-6}$ alkylene;

X is selected from the group consisting of alkylene, arylene, heterocyclylene, heteroarylene, and alkylene terminated with heteroarylene; and R$_4$ is selected from the group consisting of
hydrogen,
alkyl,
alkenyl,
aryl,
arylalkylenyl,
alkylheteroarylenyl,
heteroarylalkylenyl,
aryloxyalkylenyl,
heteroaryl, and
heterocyclyl,
wherein alkyl is unsubstituted or substituted by one or more substituents selected from the group consisting of hydroxy, alkoxy, and heterocyclyl, and wherein arylalkylenyl and heteroarylalkylenyl are unsubstituted or substituted by one or more substituents selected from the group consisting of alkyl, halogen, and alkoxy.

4. The compound or salt of claim 1, wherein R$_3$ is —Z-Het, —Z-Het'-R$_4$, or —Z-Het'-Y—R$_4$.

5. The compound or salt of claim 4, wherein Z is a bond.

6. The compound or salt of claim 4, wherein Het or Het' is selected from the group consisting of tetrahydropyranyl, tetrahydrofuranyl, 1,3-dioxolanyl, pyrrolidinyl, piperidinyl, morpholinyl, thiomorpholinyl, thiazolidinyl, aziridinyl, azepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and piperazinyl.

7. The compound or salt of claim 4, wherein Het is substituted by one or more substituents selected from the group consisting of alkyl, hydroxyl, hydroxyalkyl, hydroxyalkyleneoxyalkylenyl, diakylamino, and heterocyclyl; Y is selected from the group consisting of —C(O)—, —C(O)—O—, —C(O)—N(H)—, and —N(H)—C(O)—; and R$_4$ is selected from the group consisting of hydrogen and alkyl.

8. The compound or salt of claim 1, wherein Z is alkylene.

9. A compound of the formula (III):

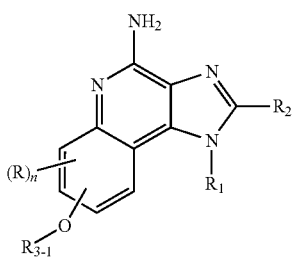

wherein:
$R_{3-1}$ is selected from the group consisting of
—Z—N($R_8$)—C($R_6$)—$R_4$,

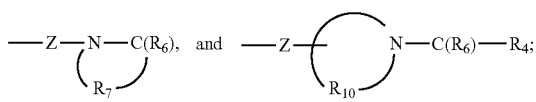

Z is selected from the group consisting of alkylene, alkenylene, and alkynylene, wherein alkylene, alkenylene, and alkynylene can be optionally interrupted with one or more —O— groups;
R is selected from the group consisting of alkyl, alkoxy, hydroxy, halogen, and trifluoromethyl;
n is 0 or 1;
$R_1$ is selected from the group consisting of
—$R_4$,
—X—$R_4$,
—X—Y—X—Y—$R_4$, and
—X—$R_5$;
$R_2$ is selected from the group consisting of hydrogen, alkyl, alkoxyalkylenyl, and hydroxyalkylenyl;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

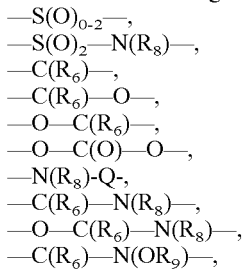

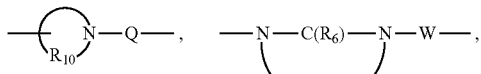

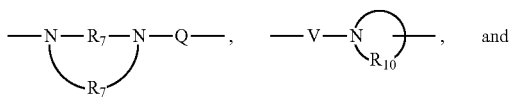
and

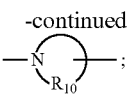

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
$R_5$ is selected from the group consisting of

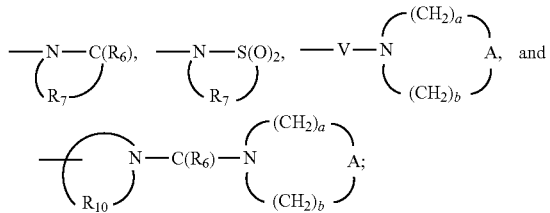

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, and —N($R_4$)—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≤7;
with the proviso that Z can also be a bond when $R_{3-1}$ is

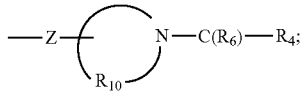

or a pharmaceutically acceptable salt thereof.

10. The compound or salt of claim 9, wherein $R_{3\text{-}1}$ is $-Z-N(R_8)-C(R_6)-R_4$.

11. A compound of the formula (IV):

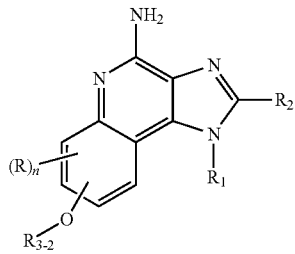

IV wherein:
$R_{3\text{-}2}$ is selected from the group consisting of
  $-Z-N(R_8)-S(O)_2-R_4$,
  $-Z-N(R_8)-S(O)_2-N(R_8)-R_4$,

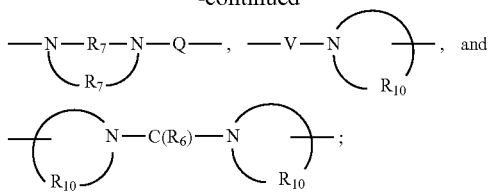

Z is selected from the group consisting of alkylene, alkenylene, and alkynylene, wherein alkylene, alkenylene, and alkynylene can be optionally interrupted with one or more —O— groups;
R is selected from the group consisting of alkyl, alkoxy, hydroxy, halogen, and trifluoromethyl;
n is 0 or 1;
$R_1$ is selected from the group consisting of
  $-R_4$,
  $-X-Y-R_4$,
  $-X-Y-X-Y-R_4$, and
  $-X-R_5$;
$R_2$ is selected from the group consisting of hydrogen, alkyl, alkoxyalkylenyl, and hydroxyalkylenyl;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of
  $-S(O)_{0\text{-}2}-$,
  $-S(O)_2-N(R_8)-$,
  $-C(R_6)-$,
  $-C(R_6)-O-$,
  $-O-C(R_6)-$,
  $-O-C(O)-O-$,
  $-N(R_8)-Q-$,
  $-C(R_6)-N(R_8)-$,
  $-O-C(R_6)-N(R_8)-$,
  $-C(R_6)-N(OR_9)-$,

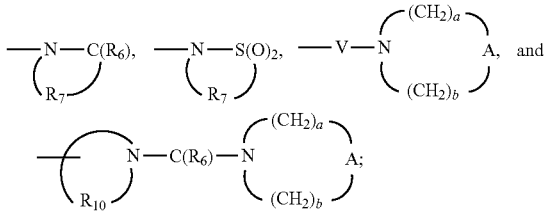

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
$R_5$ is selected from the group consisting of $R_6$ is selected from the group consisting of =O and =S;
$R_7$ is $C_{2\text{-}7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3\text{-}8}$ alkylene;
A is selected from the group consisting of —O—, —C(O)—, —S(O)_{0\text{-}2}—, and —N(R_4)—;
Q is selected from the group consisting of a bond, $-C(R_6)-$, $-C(R_6)-C(R_6)-$, $-S(O)_2-$, $-C(R_6)-N(R_8)-W-$, $-S(O)_2-N(R_8)-$, $-C(R_6)-O-$, and $-C(R_6)-N(OR_9)-$;
V is selected from the group consisting of $-C(R_6)-$, $-O-C(R_6)-$, $-N(R_8)-C(R_6)-$, and $-S(O)_2-$;
W is selected from the group consisting of a bond, —C(O)—, and —S(O)_2—; and
a and b are independently integers from 1 to 6 with the proviso that a+b is ≤7;
with the proviso that Z can also be a bond when $R_{3\text{-}2}$ is

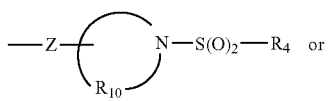 or

327

-continued

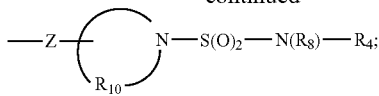

or a pharmaceutically acceptable salt thereof.

12. The compound or salt of claim 11, wherein $R_{3-2}$ is —Z—N($R_8$)—S(O)$_2$—$R_4$.

13. The compound or salt of claim 1, wherein n is 0.

14. The compound or salt of claim 1, wherein $R_1$ is selected from the group consisting of alkyl, arylalkylenyl, aryloxyalkylenyl, hydroxyalkyl, dihydroxyalkyl, alkylsulfonylalkylenyl, —X—Y—$R_4$, —X—$R_5$, and heterocyclylalkylenyl, wherein the heterocyclyl of the heterocyclylalkylenyl group is optionally substituted by one or more alkyl groups; wherein X is alkylene; Y is —N($R_8$)—C(O)—, —N($R_8$)—S(O)$_2$—, —N($R_8$)—C(O)—N($R_8$)—, or

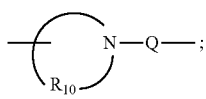

$R_4$ is alkyl, aryl, or heteroaryl; and $R_5$ is

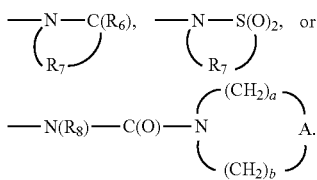

328

15. The compound or salt of claim 14, wherein $R_1$ is selected from the group consisting of alkyl, alkoxyalkylenyl, aminoalkylenyl, hydroxyalkylenyl, dihydroxyalkylenyl and alkyl substituted by a group selected from the group consisting of —NH—C(O)-alkyl, —NH—S(O)$_2$-alkyl, —NH—C(O)—NH-alkyl, —NH—C(O)—O-alkyl, phenoxy, tetrahydropyranyl, 1,1-dioxidoisothiazolidin-2-yl, and 2,2-dimethyl-1,3-dioxolan-4-yl.

16. The compound or salt of claim 14, wherein $R_1$ is selected from the group consisting of 2-hydroxy-2-methylpropyl, 2-methylpropyl, propyl, ethyl, methyl, 2,3-dihydroxypropyl, 2-phenoxyethyl, 4-[(methyl sulfonyl)amino]butyl, 2-methyl-2-[(methyl sulfonyl)amino]propyl, 2-(acetylamino)-2-methylpropyl, 2-{[(isopropylamino)carbonyl]amino}-2-methylpropyl, 4-{[(isopropylamino)carbonyl]amino}butyl, 4-(1,1-dioxidoisothiazolidin-2-yl)butyl, tetrahydro-2H-pyran-4-ylmethyl, and (2,2-dimethyl-1,3-dioxolan-4-yl)methyl.

17. The compound or salt of claim 1, wherein $R_1$ is $R_4$.

18. The compound or salt of claim 17, wherein $R_2$ is selected from the group consisting of hydrogen, methyl, ethyl, propyl, butyl, ethoxymethyl, methoxymethyl, 2-methoxyethyl, hydroxymethyl, and 2-hydroxyethyl.

19. A pharmaceutical composition comprising a therapeutically effective amount of a compound or salt of claim 1 in combination with a pharmaceutically acceptable carrier.

20. A method of inducing cytokine biosynthesis in an animal comprising administering an effective amount of a compound or salt of claim 1 to the animal.

* * * * *